United States Patent
Mansour

(10) Patent No.: US 10,246,444 B2
(45) Date of Patent: Apr. 2, 2019

(54) 1,2-DITHIOLANE AND DITHIOL COMPOUNDS USEFUL IN TREATING MUTANT EGFR-MEDIATED DISEASES AND CONDITIONS

(71) Applicant: Sabila Biosciences LLC, New City, NY (US)

(72) Inventor: Tarek Suhayl Mansour, New City, NY (US)

(73) Assignee: SABILA BIOSCIENCES LLC, New City, NY (US)

( * ) Notice: Subject to any disclaimer, the term of this patent is extended or adjusted under 35 U.S.C. 154(b) by 0 days.

(21) Appl. No.: 15/873,255

(22) Filed: Jan. 17, 2018

(65) Prior Publication Data
US 2018/0208584 A1    Jul. 26, 2018

Related U.S. Application Data

(60) Provisional application No. 62/448,981, filed on Jan. 21, 2017.

(51) Int. Cl.
C07D 409/14 (2006.01)
C07D 409/12 (2006.01)
C07D 215/44 (2006.01)
A61P 35/00 (2006.01)
C07D 401/12 (2006.01)

(52) U.S. Cl.
CPC ............ *C07D 409/12* (2013.01); *A61P 35/00* (2018.01); *C07D 215/44* (2013.01); *C07D 401/12* (2013.01); *C07D 409/14* (2013.01)

(58) Field of Classification Search
CPC .................................................... C07D 409/12
USPC ........................................................ 514/313
See application file for complete search history.

(56) References Cited

PUBLICATIONS

Antonello, Journal of Medicinal Chemistry (2006), 49(23), 6642-6645.*

* cited by examiner

*Primary Examiner* — Nizal S Chandrakumar
(74) *Attorney, Agent, or Firm* — Leason Ellis LLP

(57) ABSTRACT

Compositions of the invention comprise 1,2-dithiolane, dithiol and related compounds useful as therapeutic agents for the treatment and prevention of diseases and conditions associated with aberrant EGFR activity.

12 Claims, No Drawings

1,2-DITHIOLANE AND DITHIOL COMPOUNDS USEFUL IN TREATING MUTANT EGFR-MEDIATED DISEASES AND CONDITIONS

CROSS-REFERENCE TO RELATED APPLICATIONS

This application claims the benefit of priority under 35 U.S.C. Section 119(e) of U.S. Application Ser. No. 62/448,981, filed on Jan. 21, 2017, which is hereby incorporated by reference in its entirety.

FIELD OF INVENTION

The present invention is directed towards novel 1,2-dithiolane, dithiol and related compounds and pharmaceutical compositions comprising the compounds, which are useful for the treatment of mutant EGFR-mediated diseases or conditions, such as cancer, as well as other diseases and conditions associated with the modulation of mutant EGFR activity. The present invention is further directed towards methods of treatment of diseases or conditions associated with aberrant EGFR activity.

BACKGROUND OF THE INVENTION

Cancer is a major global problem. There are about 1.7 million of new cancer cases and about 580,000 deaths from cancer in the United States every year amounting to one in 4 deaths is due to cancer. Cancer can impact all organs and systems in the body including, but not limited to the genital system, which includes the prostate, the digestive system which includes the colon and the pancreas, the respiratory system that includes the lung and bronchus, the breast, the urinary system that includes bladder and kidney, the skin, blood (such as lymphoma, leukemia, myeloma), endocrine, oral cavity and pharynx, brain, soft tissue, bones, joints and eye (Siegel, R. et al., CA Cancer J. Clin. 2013, 63, 11-30).

The human genome encodes for 518 protein kinases of which 30 distinct targets have been developed in the clinic primarily for the treatment of cancer. However, deregulation of kinase functions has also been implicated in immunological diseases and disorders, neurological diseases and disorders, metabolic diseases and disorders and infectious disease. The utility of kinases as drug targets is driven by several factors which include their involvement in signal transduction pathways that are dependent on a phosphotransfer cascade to elicit a real physiological response (Zhang, J. et al., Nature, 2009, 9, 28-39). Approximately 100 are tyrosine kinases. These kinases regulate several physiological mechanisms including but not limited to cell proliferation, cell differentiation, cell migration, and cellular metabolism by transferring the ATP terminal phosphate to one or more tyrosine or serine residues of the protein substrates (Carmi, C. et. al., Biochem. Pharmcol. 2012, 84, 1388-1399).

The ErbB family of receptor tyrosine kinases and their ligands are important regulators of tumor cell proliferation, tumor angiogenesis and metastasis. (Gschwind, A. et. al., Nat. Rev. Cancer, 2004, 4, 361). There are four receptors in the ErbB family, EGFR (endothelial growth factor receptor), HER2, HER3 and HER4. EGFR plays a key role in signal transduction pathways controlling proliferation and apoptosis (Zhou, B-B S. et. al. Cancer Cell, 2006, 10, 39-50). Activation of the EGFR pathway results in downstream events stimulating five of the six hallmarks of cancer: 1) independence of growth signals 2) insensitivity to growth-inhibitory signals 3) resistance to apoptosis, 4) angiogenesis, and 5) metastasis. Thus, inhibition of EGFR signaling presents multiple opportunities for identifying novel therapeutic agents.

The identification of somatic mutations in the tyrosine kinase domain of EGFR resulted in ligand-independent gene activation that are associated with responses to small molecule inhibitors of EGFR. The vast majority of EGFR mutations (>90%) are either a deletion of a conserved sequence in exon 19 or a single point mutation in exon 21 at amino acid residue 858 (L858R) (Lynch, T. J. et. al. N. Engl. J. Med. 2004, 350, 2129-39; Paez, J. G. et. al. Science (Wash. D.C.), 2004, 304, 1497-50; Kosaka, T. et. al. Cancer Res. 2004, 64, 8919-23). These activating mutations result in ligand-independent tumor-cell dependence on EGFR signaling and simultaneously provide the means to inhibit the tumor growth and cancer progression. EGFR mutations are most common in non-smoking East Asian females and those with adenocarcinoma histology. Although other point and deletion mutations have been discovered, only two mutations, deletion in exon 19 and L858R mutation in exon 21, account for over 90% of all mutations. The frequency of mutations in Asia is estimated to be approximately 35%, almost 4 times that of the U.S.A.

There are two main types of inhibitors of receptor tyrosine kinases that have potential benefit for treatment of EGFR dependent tumors. The ATP competitive inhibitors which are reversible and have broad pan ErbB family activity particularly as EGFR and HER2 inhibitors. Non-ATP competitive inhibitors are either lysine-trapping or cysteine-trapping covalent inhibitors and have attracted intensive investigations (Barf, T. et. al. J. Med. Chem., 2012, 55, 6243-6262). The latter non-ATP class includes two sub classes: pan ErbB inhibitors such as neratinib, afatinib and pelitinib, or inhibitors with high activities against mutant EGFR enzymes compared to wild type enzymes such as AZD9291 (Butterworth, S. et. Al. PCT Int. Appl. (2013), WO 2013014448 A1 20130131) and CO-1686 as well as a few as multicomponent inhibitors with proapoptotic effects (Antonello, A. et. al. J. Med. Chem., 2005, 48, 28-31 ibid J. Med. Chem., 2006, 49, 6642-6645). Gefitinib and erlotinib are the leading targeted drugs inhibiting EGFR. Initially, gefitinib was approved as third-line therapy and in 2009 was granted European approval in EGFR-mutated NSCLC. Both drugs are now used as first-line therapy in mutant EGFR patients although gefitinib has superior tolerability and lower cost. Erlotinib is well positioned globally in maintenance therapy or refractory setting. Afatinib was approved in 2013 for late stage (metastatic) non-small cell lung cancer (NSCLC) patients whose tumors express specific types of (EGFR) gene mutations, as detected by an FDA-approved test. Neratinib, AZD9291, and rocilitinib (CO-1686) are also advancing in various clinical trials stages (Zhang, J. et. al. Nature, 2009, 9, 28-39; Bikker, J. et. al. J. Med. Chem. 2009, 52, 1493-1509). Afatinib, neratinib, rocilitinib, AZD9291, WZ4002 are irreversible inhibitors of EGFR targeting cysteine 797 in the ATP binding site.

Lung cancer is a disease in which the cell lining of lung tissue grows beyond control and leads to the formation of tumors. There are two main types of lung cancer; small cell lung cancer (SCLC) that accounts for about 15-20% of the total lung cancers and non-small cell lung cancer (NSCLC) that accounts for the rest. The common cause of lung cancer is exposure to tobacco smoke. Small cell lung cancer has very high metastasis and hence is inoperable. The survival rate for such a cancer is very low after diagnosis and has the highest mortality rate of all cancers. NSCLC is further categorized depending on the cell structure. It consists primarily of three types: 1) squamous cell carcinoma affecting the squamous epithelium, 2) adenocarcinoma affecting the glandular epithelium, and 3) the large cell carcinoma which is a heterogeneous group of neoplasm affecting the epithelial lining of the lung.

Non-small cell lung cancer is the most common type of lung cancer accounting for about 80-85% of all the lung cancers. The growth of this cancer is slower as compared to SCLC. Each type of NSCLC has different cancer cells and hence they grow and spread in different ways. The squamous cell cancer is the cancer of the squamous cells (thin and flat cells), accounting for about 30% of all NSCLC; adenocarcinoma is most common subtype of NSCLC, which develops at the edge of the lungs and in the cells in the airway, the most common type in never-smokers, having slow growth and does not typically cause symptoms in the early stages. The non-squamous cell cancers (large cell+adenocarcinomas) account for 40% of all lung cancers or about 50% of NSCLC (Siegelin, M. D. *Laboratory Investigation*, 2014, 94, 129-137). Cancers of the lung are aggressive and treatment remains a significant challenge. The estimated number of new cases of lung cancer in the U.S.A. is about 228,190 cases in 2013 in both male and female (Siegel, R. et. al. *CA Cancer J. Clin.* 2013, 63, 11-30). This is about 13% of all new cancer cases combined and estimated to be 1,660,290 in the U.S.A. which include prostate 239,590 case of prostate cancer and 232,340 cases of breast cancer. Lung cancer, however, has the highest mortality rate of all cancers.

There are mutations which have been identified in non-squamous NSCLC in three genes: EGFR, ALK and KRAS. The KRAS gene is downstream from EGFR and mutations in KRAS also conferred intrinsic resistance however, there are currently no drugs approved for KRAS mutations. The EML4-ALK fusion translocation oncogene carries a unique mutation resulting in maintenance of the malignant behavior of cancer cells. About 3-7% of all NSCLC patients carry this mutation (10-20% in adenocarcinomas). Crizotinib is an approved drug for the treatment of ALK+NSCLC. Analysis of Crizotinib treated ALK+ patients indicated that 50% of patients had ALK-dominant mutations while the rest were non-dominant mutations of which 31% were activating EGFR or KRAS mutations. These data suggests that one third of patients' resistance to Crizotinib would likely respond to EGFR or KRAS therapy (Kibble, A. et. al. Thompson Reuters report Spotlight on non-small-cell lung cancer: a new era in personalized care, 2013).

The majority of NSCLCs are diagnosed in patients with either localized advanced stage III (30-40%) or metastatic stage IV (40%) disease and will require some form of chemotherapy. Only a minority of NSCLCs are diagnosed when the disease is still in its localized early stages thus limiting the use of curative therapy such as surgery or radiation. Although the one-year survival rates for advanced NSCLC are about 40-45%, the five-year survival rate is less than 15%. A significant proportion of patients with lung cancer have an EGFR mutation: about 15% in the West and 30-40% in Asia.

Disease progression typically indicates that 50-70% of NSCLC patients will receive second-line therapy and about 25-30% will receive third-line regimen. For patients harboring EGFR or ALK mutations, the market is currently served by gefitinib, erlotinib, afatinib (EGFR) and crizotinib (ALK) agents. Gefitinib and erlotinib have moved into first-line therapy in patients with known EGFR mutations, although about 60% of these patients develop resistance to these drugs. The T790M mutation renders these drugs ineffective and occurs in about 50% of the mutant EGFR after treatment of gefitinib and erlotinib. There is, therefore, a need to develop novel therapeutic agents that are active against mutant EGFR especially the exon 19 and exon 21 mutations. There is also an unmet medical need to treat NSCLC disease and other EGFR associated pathological states effectively and without adverse side effects.

EGFR is dysregulated in glioblastoma multiforme, an aggressive malignant primary brain tumor, in addition to various tumors such as NSCLC, ovarian and breast cancers. In malignant neoplasms such as glioblastoma (GBM) which is the most common primary central nervous system tumor in adults, EGFR is overexpressed in about 40-50% of cases and almost 25% co-express the mutant EGFR subtype EGFRvIII (Loew, S. et. al. *Anti-Cancer Agents Med. Chem.*, 2009, 9, 703-715). This mutant is highly oncogenic and is generated from a deletion of exons 2 to 7 of the EGFR gene resulting in an in-frame deletion of 267 amino acids (Hatanpaa, K. J. et. al. *Neoplasia*, 2010, 12, 675-684). Studies of the activation of signaling events in GBM tumor cells revealed notable differences between wild type and EGFR mutant expressing cells. The wild-type EGF receptor signals through its canonical pathways whereas tumors expressing the mutant EGFR do not use these pathways suggesting a different role of mutant EGFR in GBM tumor biology (Zhu, H. et. al. *Proc. Natl. Acad. Sci. U.S.A.* 2009, 1-5, 5).

Mutant EGFR plays a role in resistance to EGFR tyrosine kinase inhibitors (TKIs). Analyses of samples of patients with glioblastoma treated with EGFR TKIs demonstrate that tumor cells reversibly upregulate or suppress mutant EGFR expression and that resistance to TKIs occurs after elimination of mutant EGFR from extrachromosomal DNA (Nathanson, D. A. et. al. *Science*, 2014, 343, 72-76).

Malignant peripheral nerve sheath tumors (MPNSTs) driven in part by hyperactive RAS and EGFR signaling are often incurable. In a specially developed xenografts model erlotinib demonstrated antiangiogeneic effects suggesting the potential use of new TKIs in this model. The present invention provides methods to meet these critical needs.

SUMMARY OF THE INVENTION

The present invention is directed to 1,2-dithiolane compounds and related dithiol compounds and their pharmaceutical compositions comprising the compounds and methods of using the compounds and pharmaceutical compositions for the treatment and/or prevention of mutant EGFR-mediated diseases or conditions such as cancer. The present invention is further directed towards methods of treatment of diseases or conditions associated with aberrant EGFR activity. Accordingly in one aspect this invention is directed to compounds of formula (I):

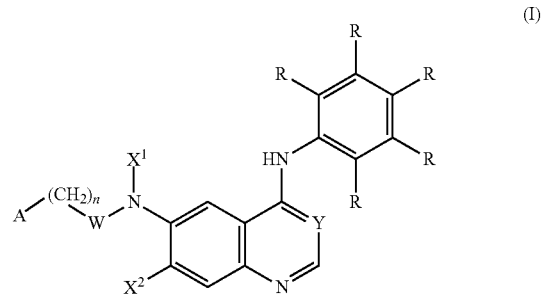

including enantiomers, diastereomers. hydrates, solvates, pharmaceutically acceptable salts, prodrugs and complexes thereof, wherein:

A is selected from the group consisting of

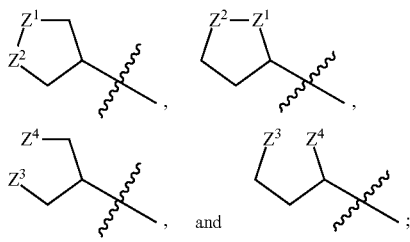

$Z^1$ is selected from the group consisting of S, SO, and $SO_2$;
$Z^2$ is selected from the group consisting of S, SO, and $SO_2$;
$Z^3$ is selected from the group consisting of SH, $SCOR^1$, $SO_2R^2$, and $SO_3H$;
$Z^4$ is selected from the group consisting of SH, $SCOR^1$, $SO_2R^2$, and $SO_3H$;
n=0, 1, 2, 3, or 4;
W is selected from the group consisting of CO and $SO_2$;
$X^1$ is selected from the group consisting of hydrogen, optionally substituted $C_{1-6}$ alkyl, and, optionally substituted $C_{1-6}$ alkoxy;
$X^2$ is selected from the group consisting of hydrogen, optionally substituted $C_{1-6}$ alkyl, $OR^3$,

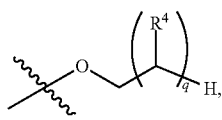

and the $C_{2-6}$ sugar alcohols ethylene glycol, glycerol, erythritol, threitol, arabitol, xylitol, ribitol, mannitol, galacitol frucitol, iditol, inositol, and sorbitol;

Y is selected from the group consisting of N and C—CN;
R is at each occurrence independently selected from the group consisting of hydrogen, $C_{1-6}$ alkyl, $C_{1-6}$ alkenyl, $C_{1-6}$ alkynyl, halogen, $C_{1-6}$ haloalkyl, $C_{3-7}$ cycloalkyl, cycloalkylalkyl, aryl, arylalkyl, heterocyclyl, heterocyclylalkyl, heteroaryl, heteroarylalkyl, alkoxyheteroarylalkyl,

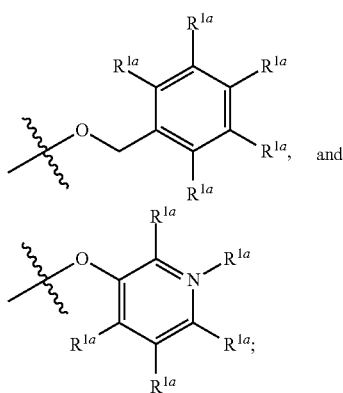

$R^{1a}$ is at each occurrence independently selected from the group consisting of hydrogen, halogen, $C_{1-6}$ alkyl, and $C_{1-6}$ alkoxy;

$R^1$ is at each occurrence independently selected from the group consisting of hydrogen, optionally substituted $C_{1-6}$ alkyl, and optionally substituted $C_{1-6}$ alkoxy;
$R^2$ is at each occurrence independently selected from the group consisting of hydrogen, optionally substituted $C_{1-6}$ alkyl, and optionally substituted $C_{1-6}$ alkoxy;
$R^3$ is an optionally substituted $C_{1-6}$ alkyl;
$R^4$ is at each occurrence independently selected from the group consisting of hydrogen, OH, and $OR^5$.
q=0, 1, 2, 3, 4, or 5;
$R^5$ is at each occurrence an optionally substituted $C_{1-6}$ alkyl;

Two $R^5$ substituents can be joined together with the atoms to which they are bound to form a 5 to 6 membered ring.

The present invention further relates to compositions comprising an effective amount of one or more compounds according to the present invention and an excipient.

The present invention also relates to a method for treating or preventing diseases that involve mutant EGFR, including, for example, cancer, non-small cell lung cancer, small cell lung cancer, glioblastoma multiforme, malignant peripheral nerve sheath tumors, said method comprising administering to a subject an effective amount of a compound or composition according to the present invention.

The present invention yet further relates to a method for treating or preventing diseases that involve mutant EGFR, including, for example, cancer, non-small cell lung cancer, small cell lung cancer, glioblastoma multiforme, malignant peripheral nerve sheath tumors, wherein said method comprises administering to a subject a composition comprising an effective amount of one or more compounds according to the present invention and an excipient.

The present invention also relates to a method for treating or preventing disease or conditions associated with mutant EGFR, and diseases that involve aberrant EGFR activity. Said methods comprise administering to a subject an effective amount of a compound or composition according to the present invention.

The present invention yet further relates to a method for treating or preventing disease or conditions associated with mutant EGFR, and diseases that involve aberrant EGFR activity, wherein said method comprises administering to a subject a composition comprising an effective amount of one or more compounds according to the present invention and an excipient.

The present invention also relates to a method for treating or preventing disease or conditions that involve aberrant EGFR activity. Said methods comprise administering to a subject an effective amount of a compound or composition according to the present invention.

The present invention yet further relates to a method for treating or preventing disease or conditions that involve with aberrant EGFR activity, wherein said method comprises administering to a subject a composition comprising an effective amount of one or more compounds according to the present invention and an excipient.

The present invention also relates to a method for treating or preventing disease or conditions associated with aberrant EGFR activity. Said methods comprise administering to a subject an effective amount of a compound or composition according to the present invention.

The present invention yet further relates to a method for treating or preventing disease or conditions associated with aberrant EGFR activity, wherein said method comprises administering to a subject a composition comprising an effective amount of one or more compounds according to the present invention and an excipient.

The present invention also relates to a method for treating or preventing cancer such as cancer of the lung, head and neck, colon, kidney, ovaries, prostate, and breast, cancers of the skin such as melanoma, and cancer of the blood such as leukemia, lymphoma and myeloma, said method comprises administering to a subject an effective amount of a compound or composition according to the present invention.

The present invention yet further relates to a method for treating or preventing cancer such cancer of the as lung, head and neck, colon, kidney, ovaries, prostate, and breast, cancers of the skin such as melanoma, and cancer of the blood such as leukemia, lymphoma, and myeloma, wherein said method comprises administering to a subject a composition comprising an effective amount of one or more compounds according to the present invention and an excipient.

The present invention also relates to a method for treating or preventing conditions associated with cancer of the lung, head and neck, colon, kidney, ovaries, prostate, and breast, cancers of the skin such as melanoma, and cancer of the blood such as leukemia, lymphoma. Said methods comprise administering to a subject an effective amount of a compound or composition according to the present invention.

The present invention also relates to a method for treating or preventing conditions associated with cancer of the lung, head and neck, colon, kidney, ovaries, prostate, and breast, cancers of the skin such as melanoma, and cancer of the blood such as leukemia, lymphoma. Said methods comprise administering to a subject an effective amount of a compound or composition according to the present invention and an excipient.

The present invention further relates to a process for preparing the EGFR inhibitors of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The EGFR inhibitors of the present invention are capable of treating and preventing diseases associated with mutant EGFR, for example cancer, non-small cell lung cancer, small cell lung cancer, glioblastoma multiforme, and malignant peripheral nerve sheath tumors. The EGFR inhibitors of the present invention are capable of treating and preventing diseases associated with aberrant EGFR activity. It has been discovered that inhibition of mutant EGFR activity will prevent tumor cell proliferation, tumor angiogenesis, and metastasis. It has further been discovered that inhibition of aberrant EGFR activity will prevent tumor cell proliferation, tumor angiogenesis, and metastasis. Without wishing to be limited by theory, it is believed that EGFR inhibitors of the present invention can ameliorate, abate, otherwise cause to be controlled, diseases associated with mutant EGFR. In addition, without wishing to be limited by theory, it is believed that EGFR inhibitors of the present invention can ameliorate, abate, otherwise cause to be controlled, diseases associated aberrant EGFR activity.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Arylalkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocyclyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d] thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

The term "cycloalkylalkyl" refers to the group -alkyl-cycloalkyl, where the alkyl and cycloalkyl groups are as defined herein. Cycloalkylalkyl groups of the present invention are optionally substituted. Non-limiting examples of cycloalkylalkyl groups include, for example, 1-cylcohexylethyl, 2-cyclohexylethyl, 1-cyclohexylpropyl, cyclopropylmethyl, 2-cyclopentylpropyl, and the like.

The term "heterocyclylalkyl" refers to the group -alkyl-heterocyclyl, where the alkyl and heterocyclyl groups are defined as herein. Heterocyclylalkyl groups of the present invention are optionally substituted. Non-limiting examples of heterocyclylalkyl group include, for example, 3-(4-piperidinyl)-propyl, 2-(4-morpholinyl)ethyl, 3-(1-pyrrolidinyl) propyl, 4-(oxiranyl)butyl, 4-(2-aziridinyl)butyl, and the like.

The term "heteroarylalkyl" refers to the group -alkyl-heteroaryl, where the alkyl and heteroaryl groups are defined as herein. Heteroarylalkyl groups of the present invention are optionally substituted. Non-limiting examples of heteroarylalkyl groups include, for example, 3-(4-pyridyl)propyl, 3-(2-pyridyl)propyl, 2-(2-imidazolyl)ethyl, 4-(1-imidazolyl)butyl, 2-(2-pyrrolyl)ethyl, 5-(2-furanyl)pentyl, and the like.

The term "alkoxyheteroarylalkyl" refers to the group -alkyl-heteroaryl-alkoxy, where the alkyl, heteroaryl, and alkoxy groups are defined herein. Alkoxyheteroarylalkyl groups of the present invention are optionally substituted. Non-limiting examples of alkoxyheteroarylalkyl include, for example, 3-(3-methoxy-4-pyridyl)propyl, 4-(2-methoxy-4-pyrimidinyl)butyl, 4-(4-ethoxythiopheneyl)butyl, 3-(6-propoxy-3-pyridinyl)propyl, and the like.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

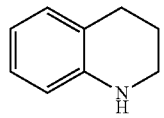

is, for the purposes of the present invention, considered a heterocyclic unit. 6,7-Dihydro-5H-cyclopentapyrimidine having the formula:

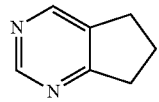

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

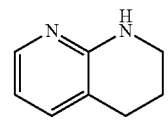

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^6$, —SR$^6$, —N(R$^6$)$_2$, —NR$^6$C(O)R$^6$, —SO$_2$R$^6$, —SO$_2$OR$^6$, —SO$_2$N(R$^6$)$_2$, —C(O)R$^6$, —C(O)OR$^6$, —C(O)N(R$^6$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^6$; wherein R$^6$, at each occurrence, independently is hydrogen, —OR$^7$, —SR$^7$, —C(O)R$^7$, —C(O)OR$^7$, —C(O)N(R$^7$)$_2$, —SO$_2$R$^7$, —S(O)$_2$OR$^7$, —N(R$^7$)$_2$, —NR$^7$C(O)R$^7$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^6$ units taken together with the atom(s) to which they are bound form an optionally substituted carbocycle or heterocycle wherein said carbocycle or heterocycle has 3 to 7 ring atoms; wherein R$^7$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^4$ units taken together with the atom(s) to which they are bound form an optionally substituted carbocycle or heterocycle wherein said carbocycle or heterocycle preferably has 3 to 7 ring atoms.

In some embodiments, the substituents are selected from i) —$OR^8$; for example, —OH, —$OCH_3$, —$OCH_2CH_3$, —$OCH_2CH_2CH_3$;

ii) —$C(O)R^8$; for example, —$COCH_3$, —$COCH_2CH_3$, —$COCH_2CH_2CH_3$;

iii) —$C(O)OR^8$; for example, —$CO_2CH_3$, —$CO_2CH_2CH_3$, —$CO_2CH_2CH_2CH_3$;

iv) —$C(O)N(R^8)_2$; for example, —$CONH_2$, —$CONHCH_3$, —$CON(CH_3)_2$;

v) —$N(R^8)_2$; for example, —$NH_2$, —$NHCH_3$, —$N(CH_3)_2$, —$NH(CH_2CH_3)$;

vi) halogen: —F, —Cl, —Br, and —I;

vii) —$CH_eX_g$; wherein X is halogen, m is from 0 to 2, e+g=3; for example, —$CH_2F$, —$CHF_2$, —$CF_3$, —$CCl_3$, or —$CBr_3$;

viii) —$SO_2R^8$; for example, —$SO_2H$; —$SO_2CH_3$; —$SO_2C_6H_5$;

ix) $C_1$-$C_6$ linear, branched, or cyclic alkyl;

x) Cyano xi) Nitro;

xii) $N(R^8)C(O)R^8$;

xiii) Oxo (=O);

xiv) Heterocycle; and xv) Heteroaryl, wherein each $R^8$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^8$ units can be taken together to form a ring comprising 3-7 ring atoms. In certain aspects, each $R^8$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the kinase inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, chiral separation by HPLC and asymmetric synthesis. The present teachings also encompass cis and trans isomers (Z and E) of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^4)_2$, each $R^4$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

Embodiments of the Invention

The kinase inhibitors of the present invention include all enantiomeric and diastereomeric forms and pharmaceutically accepted salts thereof having the formula:

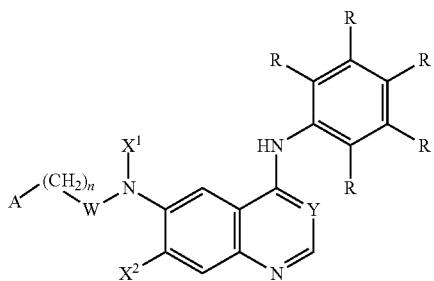

(I)

including hydrates, solvates, prodrugs and complexes thereof, wherein:
A is selected from the group consisting of

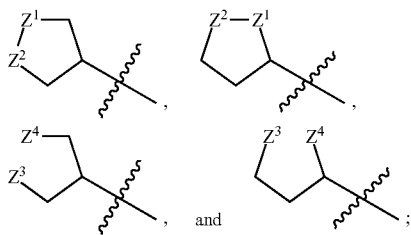

$Z^1$ is selected from the group consisting of S, SO, and $SO_2$;
$Z^2$ is selected from the group consisting of S, SO, and $SO_2$;
$Z^3$ is selected from the group consisting of SH, $SCOR^1$, $SO_2R^2$, and $SO_3H$;
$Z^4$ is selected from the group consisting of SH, $SCOR^1$, $SO_2R^2$, and $SO_3H$;
n=0, 1, 2, 3, 4;
W is selected from the group consisting of CO and $SO_2$;
$X^1$ is selected from the group consisting of hydrogen, optionally substituted $C_{1-6}$ alkyl, and, optionally substituted $C_{1-6}$ alkoxy;
$X^2$ is selected from the group consisting of hydrogen, optionally substituted $C_{1-6}$ alkyl, $OR^3$,

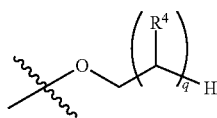

and the $C_{2-6}$ sugar alcohols such as ethylene glycol, glycerol, erythritol, threitol, arabitol, xylitol, ribitol, mannitol, galacitol frucitol, iditol, inositol, and sorbitol;
Y is selected from the group consisting of N and C—CN;
R is at each occurrence independently selected from the group consisting of hydrogen, $C_{1-6}$ alkyl, $C_{1-6}$ alkenyl, $C_{1-6}$ alkynyl, halogen, $C_{1-6}$ haloalkyl, $C_{3-7}$ cycloalkyl, cycloalkylalkyl, aryl, arylalkyl, heterocyclyl, heterocyclylalkyl, heteroaryl, heteroarylalkyl, alkoxyheteroarylalkyl,

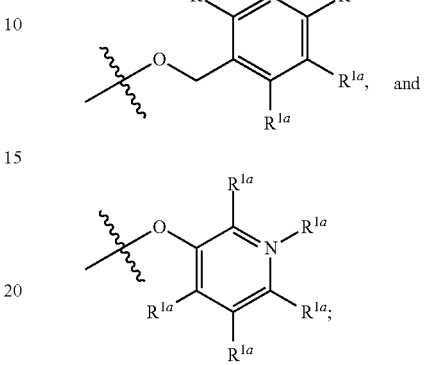

$R^{1a}$ is at each occurrence independently selected from the group consisting of hydrogen, halogen, $C_{1-6}$ alkyl, and $C_{1-6}$ alkoxy;
$R^1$ is at each occurrence independently selected from the group consisting of hydrogen, optionally substituted $C_{1-6}$ alkyl, and optionally substituted $C_{1-6}$ alkoxy;
$R^2$ is at each occurrence independently selected from the group consisting of hydrogen, optionally substituted $C_{1-6}$ alkyl, and optionally substituted $C_{1-6}$ alkoxy;
$R^3$ is an optionally substituted $C_{1-6}$ alkyl;
$R^4$ is at each occurrence independently selected from the group consisting of hydrogen, OH, and $OR^5$.
q=0, 1, 2, 3, 4, or 5;
$R^5$ is at each occurrence an optionally substituted $C_{1-6}$ alkyl;
Two $R^5$ substituents can be joined together with the atoms to which they are bound to form a 5 to 6 membered ring.

The compounds of the present invention include compounds having formula (II):

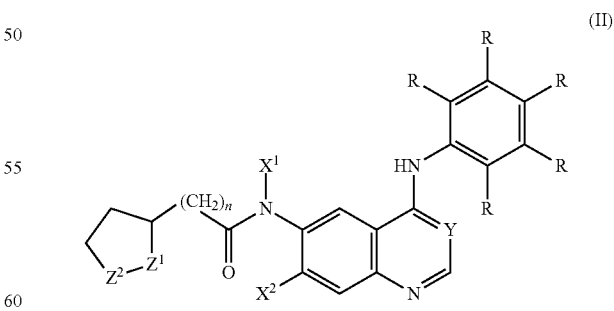

(II)

including enantiomers, diastereomers, hydrates, solvates, pharmaceutically acceptable salts, prodrugs and complexes thereof.

The compounds of the present invention include compounds having formula (III):

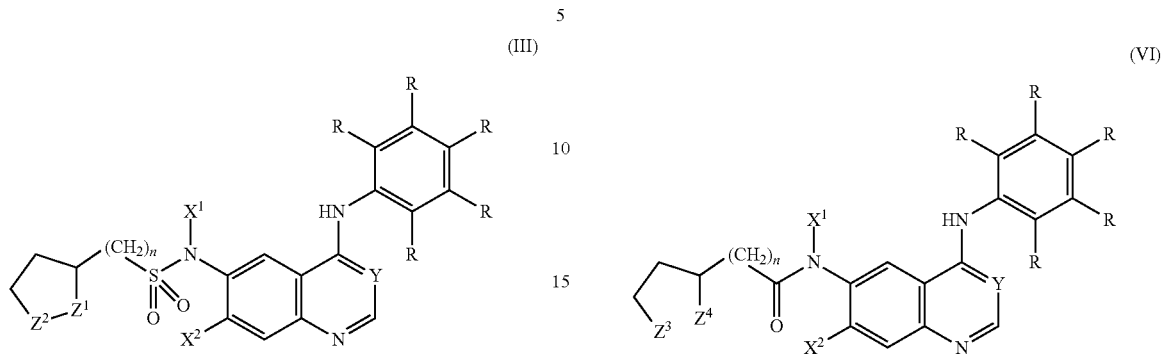

(III)

including enantiomers, diastereomers, hydrates, solvates, pharmaceutically acceptable salts, prodrugs and complexes thereof.

The compounds of the present invention include compounds having formula (IV):

(IV)

including enantiomers, diastereomers, hydrates, solvates, pharmaceutically acceptable salts, prodrugs and complexes thereof.

The compounds of the present invention include compounds having formula V):

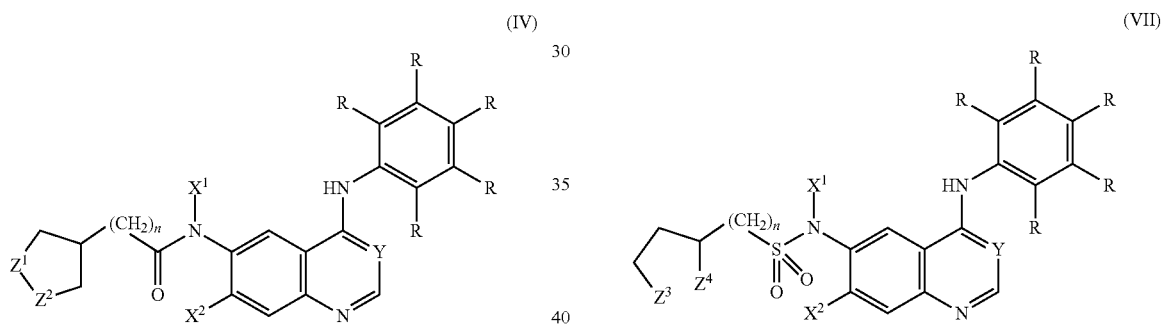

(V)

including enantiomers, diastereomers, hydrates, solvates, pharmaceutically acceptable salts, prodrugs and complexes thereof.

The compounds of the present invention include compounds having formula (VI):

(VI)

including enantiomers, diastereomers, hydrates, solvates, pharmaceutically acceptable salts, prodrugs and complexes thereof.

The compounds of the present invention include compounds having formula (VII):

(VII)

including enantiomers, diastereomers, hydrates, solvates, pharmaceutically acceptable salts, prodrugs and complexes thereof.

The compounds of the present invention include compounds having formula (VIII):

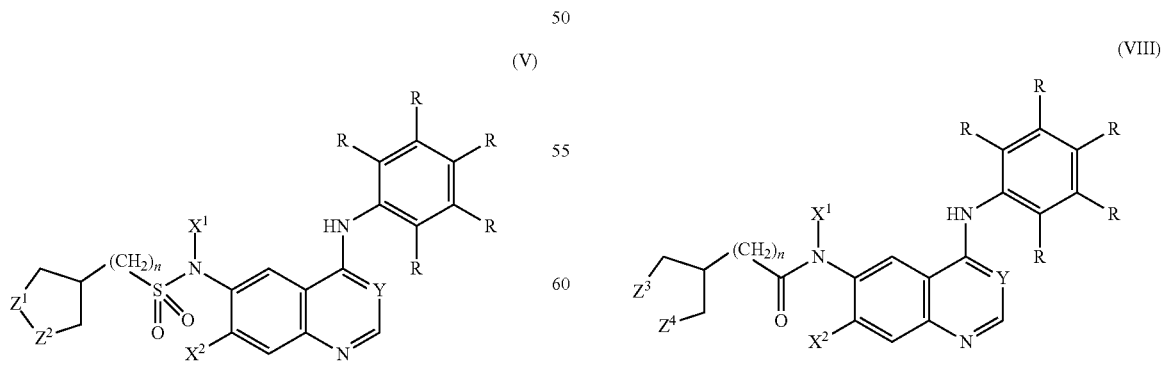

(VIII)

including enantiomers, diastereomers, hydrates, solvates, pharmaceutically acceptable salts, prodrugs and complexes thereof.

The compounds of the present invention include compounds having formula (IX):

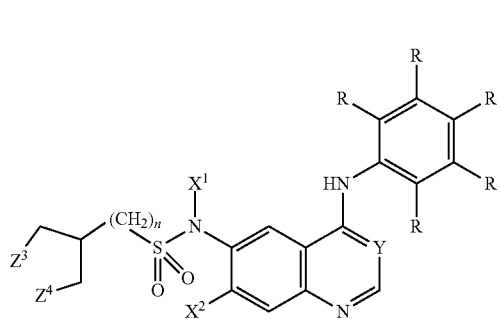

(IX)

including enantiomers, diastereomers, hydrates, solvates, pharmaceutically acceptable salts, prodrugs and complexes thereof.

In some embodiments A is

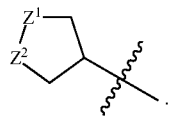

In some embodiments A is

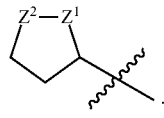

In some embodiments A is

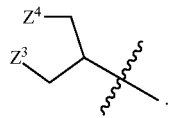

In some embodiments A is

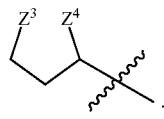

In some embodiments $Z^1$ is S.
In some embodiments $Z^1$ is SO.
In some embodiments $Z^1$ is $SO_2$.
In some embodiments $Z^2$ is S.
In some embodiments $Z^2$ is SO.
In some embodiments $Z^2$ is $SO_2$.
In some embodiments $Z^3$ is SH.
In some embodiments $Z^3$ is $SCOR^1$.
In some embodiments $Z^3$ is $SO_2R^2$.
In some embodiments $Z^3$ is $SO_3H$.
In some embodiments $Z^4$ is SH.
In some embodiments $Z^4$ is $SCOR^1$.
In some embodiments $Z^4$ is $SO_2R^2$.
In some embodiments $Z^3$ is $SO_3H$.
In some embodiments n is 0.
In some embodiments n is 1.
In some embodiments n is 2.
In some embodiments n is 3.
In some embodiments n is 4.
In some embodiments W is CO.
In some embodiments W is $SO_2$.
In some embodiments $X^1$ is hydrogen.
In some embodiments $X^1$ is optionally substituted $C_{1-6}$ alkyl.
In some embodiments $X^1$ is optionally substituted $C_{1-6}$ alkoxy.
In some embodiments $X^2$ is hydrogen.
In some embodiments $X^2$ is optionally substituted $C_{1-6}$ alkyl.
In some embodiments $X^2$ is optionally substituted $OR^3$.
In some embodiments $X^2$ is

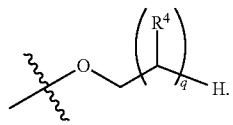

In some embodiments $X^2$ is selected from the group consisting of the $C_{2-6}$ sugar alcohols such as ethylene glycol, glycerol, erythritol, threitol, arabitol, xylitol, ribitol, mannitol, galacitol frucitol, iditol, inositol, and sorbitol.
In some embodiments Y is N.
In some embodiments Y is C—CN.
In some embodiments R is hydrogen.
In some embodiments R is $C_{1-6}$ alkyl
In some embodiments R is $C_{1-6}$ alkenyl
In some embodiments R is $C_{1-6}$ alkynyl
In some embodiments R is halogen
In some embodiments R is $C_{1-6}$ haloalkyl
In some embodiments R is $C_{3-7}$ cycloalkyl
In some embodiments R is cycloalkylalkyl
In some embodiments R is aryl.
In some embodiments R is arylalkyl.
In some embodiments R is heterocyclyl.
In some embodiments R is heterocyclylalkyl
In some embodiments R is heteroaryl.
In some embodiments R is heteroarylalkyl.
In some embodiments R is alkoxyheteroarylalkyl.
In some embodiments R is

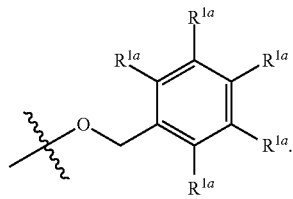

In some embodiments R is

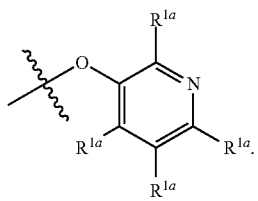

In some embodiments $R^{1a}$ is hydrogen.
In some embodiments $R^{1a}$ is halogen.
In some embodiments $R^{1a}$ is $C_{1-6}$ alkyl.
In some embodiments $R^{1a}$ is $C_{1-6}$ alkoxy.
In some embodiments $R^1$ is hydrogen.
In some embodiments $R^1$ is optionally substituted $C_{1-6}$ alkyl.
In some embodiments $R^1$ is optionally substituted $C_{1-6}$ alkoxy.
In some embodiments $R^2$ is hydrogen.
In some embodiments $R^2$ is optionally substituted $C_{1-6}$ alkyl.
In some embodiments $R^2$ is optionally substituted $C_{1-6}$ alkoxy.
In some embodiments $R^3$ is optionally substituted $C_{1-6}$ alkyl.
In some embodiments $R^4$ is hydrogen.
In some embodiments $R^4$ is OH.
In some embodiments $R^4$ is $OR^5$.
In some embodiments $R^5$ is optionally substituted $C_{1-6}$ alkyl.

In some embodiments two $R^5$ substituents can be joined together with the atoms to which they are bound to form a 5 membered ring.

In some embodiments two $R^5$ substituents can be joined together with the atoms to which they are bound to form a 6 membered ring.

In some embodiments q is 0.
In some embodiments q is 1.
In some embodiments q is 2.
In some embodiments q is 3.
In some embodiments q is 4.
In some embodiments q is 5.

Exemplary embodiments include compounds having the formula (X) or an enantiomer, diastereomer, hydrate, solvate, prodrug, complex, or pharmaceutically acceptable salt form thereof:

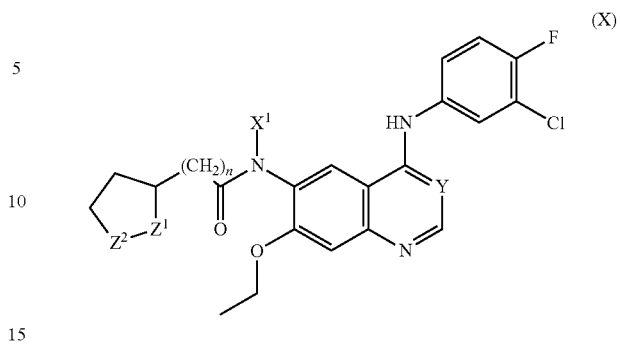

wherein non-limiting examples of $Z^1$, $Z^2$, n, $X^1$ and Y are defined herein below in Table 1.

TABLE 1

Exemplary compounds of the formula (X)

| Entry | $Z^1$ | $Z^2$ | n | $X^1$ | Y |
|---|---|---|---|---|---|
| 1 | S | S | 0 | H | C—CN |
| 2 | S | SO | 0 | H | C—CN |
| 3 | S | $SO_2$ | 0 | H | C—CN |
| 4 | SO | S | 0 | H | C—CN |
| 5 | SO | SO | 0 | H | C—CN |
| 6 | SO | $SO_2$ | 0 | H | C—CN |
| 7 | $SO_2$ | S | 0 | H | C—CN |
| 8 | $SO_2$ | SO | 0 | H | C—CN |
| 9 | $SO_2$ | $SO_2$ | 0 | H | C—CN |
| 10 | S | S | 1 | H | C—CN |
| 11 | S | SO | 1 | H | C—CN |
| 12 | S | $SO_2$ | 1 | H | C—CN |
| 13 | SO | S | 1 | H | C—CN |
| 14 | SO | SO | 1 | H | C—CN |
| 15 | SO | $SO_2$ | 1 | H | C—CN |
| 16 | $SO_2$ | S | 1 | H | C—CN |
| 17 | $SO_2$ | SO | 1 | H | C—CN |
| 18 | $SO_2$ | $SO_2$ | 1 | H | C—CN |
| 19 | S | S | 2 | H | C—CN |
| 20 | S | SO | 2 | H | C—CN |
| 21 | S | $SO_2$ | 2 | H | C—CN |
| 22 | SO | S | 2 | H | C—CN |
| 23 | SO | SO | 2 | H | C—CN |
| 24 | SO | $SO_2$ | 2 | H | C—CN |
| 25 | $SO_2$ | S | 2 | H | C—CN |
| 26 | $SO_2$ | SO | 2 | H | C—CN |
| 27 | $SO_2$ | $SO_2$ | 2 | H | C—CN |
| 28 | S | S | 3 | H | C—CN |
| 29 | S | SO | 3 | H | C—CN |
| 30 | S | $SO_2$ | 3 | H | C—CN |
| 31 | SO | S | 3 | H | C—CN |
| 32 | SO | SO | 3 | H | C—CN |
| 33 | SO | $SO_2$ | 3 | H | C—CN |
| 34 | $SO_2$ | S | 3 | H | C—CN |
| 35 | $SO_2$ | SO | 3 | H | C—CN |
| 36 | $SO_2$ | $SO_2$ | 3 | H | C—CN |
| 37 | S | S | 4 | H | C—CN |
| 38 | S | SO | 4 | H | C—CN |
| 39 | S | $SO_2$ | 4 | H | C—CN |
| 40 | SO | S | 4 | H | C—CN |
| 41 | SO | SO | 4 | H | C—CN |
| 42 | SO | $SO_2$ | 4 | H | C—CN |
| 43 | $SO_2$ | S | 4 | H | C—CN |
| 44 | $SO_2$ | SO | 4 | H | C—CN |
| 45 | $SO_2$ | $SO_2$ | 4 | H | C—CN |
| 46 | S | S | 0 | H | N |
| 47 | S | SO | 0 | H | N |
| 48 | S | $SO_2$ | 0 | H | N |
| 49 | SO | S | 0 | H | N |
| 50 | SO | SO | 0 | H | N |

TABLE 1-continued

Exemplary compounds of the formula (X)

| Entry | $Z^1$ | $Z^2$ | n | $X^1$ | Y |
|---|---|---|---|---|---|
| 51 | SO | $SO_2$ | 0 | H | N |
| 52 | $SO_2$ | S | 0 | H | N |
| 53 | $SO_2$ | SO | 0 | H | N |
| 54 | $SO_2$ | $SO_2$ | 0 | H | N |
| 55 | S | S | 1 | H | N |
| 56 | S | SO | 1 | H | N |
| 57 | S | $SO_2$ | 1 | H | N |
| 58 | SO | S | 1 | H | N |
| 59 | SO | SO | 1 | H | N |
| 60 | SO | $SO_2$ | 1 | H | N |
| 61 | $SO_2$ | S | 1 | H | N |
| 62 | $SO_2$ | SO | 1 | H | N |
| 63 | $SO_2$ | $SO_2$ | 1 | H | N |
| 64 | S | S | 2 | H | N |
| 65 | S | SO | 2 | H | N |
| 66 | S | $SO_2$ | 2 | H | N |
| 67 | SO | S | 2 | H | N |
| 68 | SO | SO | 2 | H | N |
| 69 | SO | $SO_2$ | 2 | H | N |
| 70 | $SO_2$ | S | 2 | H | N |
| 71 | $SO_2$ | SO | 2 | H | N |
| 72 | $SO_2$ | $SO_2$ | 2 | H | N |
| 73 | S | S | 3 | H | N |
| 74 | S | SO | 3 | H | N |
| 75 | S | $SO_2$ | 3 | H | N |
| 76 | SO | S | 3 | H | N |
| 77 | SO | SO | 3 | H | N |
| 78 | SO | $SO_2$ | 3 | H | N |
| 79 | $SO_2$ | S | 3 | H | N |
| 80 | $SO_2$ | SO | 3 | H | N |
| 81 | $SO_2$ | $SO_2$ | 3 | H | N |
| 82 | S | S | 4 | H | N |
| 83 | S | SO | 4 | H | N |
| 84 | S | $SO_2$ | 4 | H | N |
| 85 | SO | S | 4 | H | N |
| 86 | SO | SO | 4 | H | N |
| 87 | SO | $SO_2$ | 4 | H | N |
| 88 | $SO_2$ | S | 4 | H | N |
| 89 | $SO_2$ | SO | 4 | H | N |
| 90 | $SO_2$ | $SO_2$ | 4 | H | N |

Exemplary embodiments include compounds having the formula (XI) or an enantiomer, diastereomer, hydrate, solvate, prodrug, complex, or pharmaceutically acceptable salt form thereof:

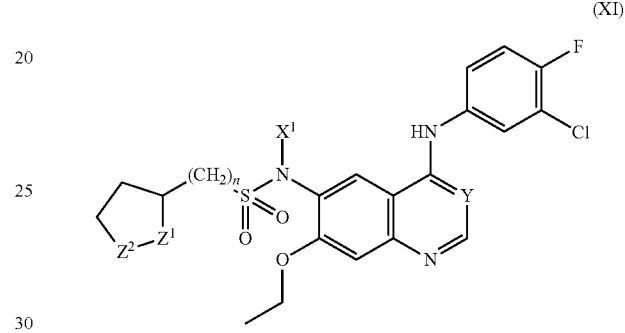

(XI)

wherein non-limiting examples of $Z^1$, $Z^2$, n, $X^1$ and Y are defined herein below in Table 2.

TABLE 2

Exemplary compounds of the formula (XI)

| Entry | $Z^1$ | $Z^2$ | N | $X^1$ | Y | Entry | $Z^1$ | $Z^2$ | n | $X^1$ | Y |
|---|---|---|---|---|---|---|---|---|---|---|---|
| 1 | S | S | 0 | H | C—CN | 25 | S | S | 0 | H | N |
| 2 | S | SO | 0 | H | C—CN | 26 | S | SO | 0 | H | N |
| 3 | S | $SO_2$ | 0 | H | C—CN | 27 | S | $SO_2$ | 0 | H | N |
| 4 | SO | S | 0 | H | C—CN | 28 | SO | S | 0 | H | N |
| 5 | $SO_2$ | S | 0 | H | C—CN | 29 | $SO_2$ | S | 0 | H | N |
| 6 | S | S | 1 | H | C—CN | 30 | S | S | 1 | H | N |
| 7 | S | SO | 1 | H | C—CN | 31 | S | SO | 1 | H | N |
| 8 | S | $SO_2$ | 1 | H | C—CN | 532 | S | $SO_2$ | 1 | H | N |
| 9 | SO | S | 1 | H | C—CN | 33 | SO | S | 1 | H | N |
| 10 | $SO_2$ | S | 1 | H | C—CN | 34 | $SO_2$ | S | 1 | H | N |
| 11 | S | S | 2 | H | C—CN | 35 | S | S | 2 | H | N |
| 12 | S | SO | 2 | H | C—CN | 36 | S | SO | 2 | H | N |
| 13 | S | $SO_2$ | 2 | H | C—CN | 37 | S | $SO_2$ | 2 | H | N |
| 14 | SO | S | 2 | H | C—CN | 38 | SO | S | 2 | H | N |
| 15 | $SO_2$ | S | 2 | H | C—CN | 39 | $SO_2$ | S | 2 | H | N |
| 16 | S | S | 3 | H | C—CN | 41 | S | S | 3 | H | N |
| 17 | S | SO | 3 | H | C—CN | 42 | S | SO | 3 | H | N |
| 18 | S | $SO_2$ | 3 | H | C—CN | 43 | S | $SO_2$ | 3 | H | N |
| 19 | SO | S | 3 | H | C—CN | 44 | SO | S | 3 | H | N |
| 20 | $SO_2$ | S | 3 | H | C—CN | 45 | $SO_2$ | S | 3 | H | N |
| 21 | S | S | 4 | H | C—CN | 46 | S | S | 4 | H | N |
| 22 | S | SO | 4 | H | C—CN | 47 | S | SO | 4 | H | N |
| 23 | S | $SO_2$ | 4 | H | C—CN | 48 | S | $SO_2$ | 4 | H | N |
| 24 | SO | S | 4 | H | C—CN | 49 | SO | S | 4 | H | N |
| 25 | $SO_2$ | S | 4 | H | C—CN | 50 | $SO_2$ | S | 4 | H | N |

Exemplary embodiments include compounds having the formula (XII) or an enantiomer, diastereomer, hydrate, solvate, prodrug, complex, or pharmaceutically acceptable salt form thereof:

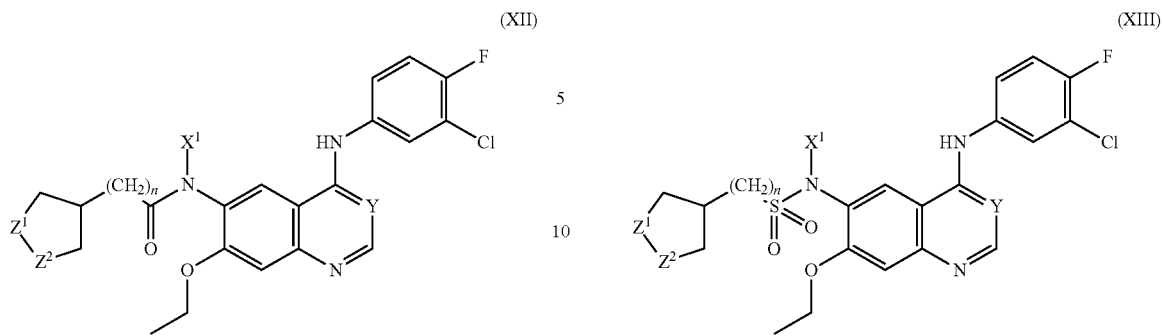

wherein non-limiting examples of $Z^1$, $Z^2$, n, $X^1$ and Y are defined herein below in Table 3.

wherein non-limiting examples of $Z^1$, $Z^2$, n, $X^1$ and Y are defined herein below in Table 4.

TABLE 3

Exemplary compounds of the formula (XII)

| Entry | $Z^1$ | $Z^2$ | N | $X^1$ | Y | Entry | $Z^1$ | $Z^2$ | n | $X^1$ | Y |
|---|---|---|---|---|---|---|---|---|---|---|---|
| 1 | S | S | 0 | H | C—CN | 46 | S | S | 0 | H | N |
| 2 | S | SO | 0 | H | C—CN | 47 | S | SO | 0 | H | N |
| 3 | S | $SO_2$ | 0 | H | C—CN | 48 | S | $SO_2$ | 0 | H | N |
| 4 | SO | S | 0 | H | C—CN | 49 | SO | S | 0 | H | N |
| 5 | SO | SO | 0 | H | C—CN | 50 | SO | SO | 0 | H | N |
| 6 | SO | $SO_2$ | 0 | H | C—CN | 51 | SO | $SO_2$ | 0 | H | N |
| 7 | $SO_2$ | S | 0 | H | C—CN | 52 | $SO_2$ | S | 0 | H | N |
| 8 | $SO_2$ | SO | 0 | H | C—CN | 53 | $SO_2$ | SO | 0 | H | N |
| 9 | $SO_2$ | $SO_2$ | 0 | H | C—CN | 54 | $SO_2$ | $SO_2$ | 0 | H | N |
| 10 | S | S | 1 | H | C—CN | 55 | S | S | 1 | H | N |
| 11 | S | SO | 1 | H | C—CN | 56 | S | SO | 1 | H | N |
| 12 | S | $SO_2$ | 1 | H | C—CN | 57 | S | $SO_2$ | 1 | H | N |
| 13 | SO | S | 1 | H | C—CN | 58 | SO | S | 1 | H | N |
| 14 | SO | SO | 1 | H | C—CN | 59 | SO | SO | 1 | H | N |
| 15 | SO | $SO_2$ | 1 | H | C—CN | 60 | SO | $SO_2$ | 1 | H | N |
| 16 | $SO_2$ | S | 1 | H | C—CN | 61 | $SO_2$ | S | 1 | H | N |
| 17 | $SO_2$ | SO | 1 | H | C—CN | 62 | $SO_2$ | SO | 1 | H | N |
| 18 | $SO_2$ | $SO_2$ | 1 | H | C—CN | 63 | $SO_2$ | $SO_2$ | 1 | H | N |
| 19 | S | S | 2 | H | C—CN | 64 | S | S | 2 | H | N |
| 20 | S | SO | 2 | H | C—CN | 65 | S | SO | 2 | H | N |
| 21 | S | $SO_2$ | 2 | H | C—CN | 66 | S | $SO_2$ | 2 | H | N |
| 22 | SO | S | 2 | H | C—CN | 67 | SO | S | 2 | H | N |
| 23 | SO | SO | 2 | H | C—CN | 68 | SO | SO | 2 | H | N |
| 24 | SO | $SO_2$ | 2 | H | C—CN | 69 | SO | $SO_2$ | 2 | H | N |
| 25 | $SO_2$ | S | 2 | H | C—CN | 70 | $SO_2$ | S | 2 | H | N |
| 26 | $SO_2$ | SO | 2 | H | C—CN | 71 | $SO_2$ | SO | 2 | H | N |
| 27 | $SO_2$ | $SO_2$ | 2 | H | C—CN | 72 | $SO_2$ | $SO_2$ | 2 | H | N |
| 28 | S | S | 3 | H | C—CN | 73 | S | S | 3 | H | N |
| 29 | S | SO | 3 | H | C—CN | 74 | S | SO | 3 | H | N |
| 30 | S | $SO_2$ | 3 | H | C—CN | 75 | S | $SO_2$ | 3 | H | N |
| 31 | SO | S | 3 | H | C—CN | 76 | SO | S | 3 | H | N |
| 32 | SO | SO | 3 | H | C—CN | 77 | SO | SO | 3 | H | N |
| 33 | SO | $SO_2$ | 3 | H | C—CN | 78 | SO | $SO_2$ | 3 | H | N |
| 34 | $SO_2$ | S | 3 | H | C—CN | 79 | $SO_2$ | S | 3 | H | N |
| 35 | $SO_2$ | SO | 3 | H | C—CN | 80 | $SO_2$ | SO | 3 | H | N |
| 36 | $SO_2$ | $SO_2$ | 3 | H | C—CN | 81 | $SO_2$ | $SO_2$ | 3 | H | N |
| 37 | S | S | 4 | H | C—CN | 82 | S | S | 4 | H | N |
| 38 | S | SO | 4 | H | C—CN | 83 | S | SO | 4 | H | N |
| 39 | S | $SO_2$ | 4 | H | C—CN | 84 | S | $SO_2$ | 4 | H | N |
| 40 | SO | S | 4 | H | C—CN | 85 | SO | S | 4 | H | N |
| 41 | SO | SO | 4 | H | C—CN | 86 | SO | SO | 4 | H | N |
| 42 | SO | $SO_2$ | 4 | H | C—CN | 87 | SO | $SO_2$ | 4 | H | N |
| 43 | $SO_2$ | S | 4 | H | C—CN | 88 | $SO_2$ | S | 4 | H | N |
| 44 | $SO_2$ | SO | 4 | H | C—CN | 89 | $SO_2$ | SO | 4 | H | N |
| 45 | $SO_2$ | $SO_2$ | 4 | H | C—CN | 90 | $SO_2$ | $SO_2$ | 4 | H | N |

Exemplary embodiments include compounds having the formula (XIII) or an enantiomer, diastereomer, hydrate, solvate, prodrug, complex, or pharmaceutically acceptable salt form thereof:

TABLE 4

Exemplary compounds of the formula (XIII)

| Entry | $Z^1$ | $Z^2$ | n | $X^1$ | Y |
|---|---|---|---|---|---|
| 1 | S | S | 0 | H | C—CN |
| 2 | S | SO | 0 | H | C—CN |
| 3 | S | $SO_2$ | 0 | H | C—CN |
| 4 | SO | S | 0 | H | C—CN |
| 5 | $SO_2$ | S | 0 | H | C—CN |
| 6 | S | S | 1 | H | C—CN |
| 7 | S | SO | 1 | H | C—CN |
| 8 | S | $SO_2$ | 1 | H | C—CN |
| 9 | SO | S | 1 | H | C—CN |
| 10 | $SO_2$ | S | 1 | H | C—CN |
| 11 | S | S | 2 | H | C—CN |
| 12 | S | SO | 2 | H | C—CN |
| 13 | S | $SO_2$ | 2 | H | C—CN |
| 14 | SO | S | 2 | H | C—CN |
| 15 | $SO_2$ | S | 2 | H | C—CN |
| 16 | S | S | 3 | H | C—CN |
| 17 | S | SO | 3 | H | C—CN |
| 18 | S | $SO_2$ | 3 | H | C—CN |
| 19 | SO | S | 3 | H | C—CN |
| 20 | $SO_2$ | S | 3 | H | C—CN |
| 21 | S | S | 4 | H | C—CN |
| 22 | S | SO | 4 | H | C—CN |
| 23 | S | $SO_2$ | 4 | H | C—CN |
| 24 | SO | S | 4 | H | C—CN |
| 25 | $SO_2$ | S | 4 | H | C—CN |
| 26 | S | S | 0 | H | N |
| 27 | S | SO | 0 | H | N |
| 28 | S | $SO_2$ | 0 | H | N |
| 29 | SO | S | 0 | H | N |
| 30 | $SO_2$ | S | 0 | H | N |
| 31 | S | S | 1 | H | N |
| 32 | S | SO | 1 | H | N |
| 33 | S | $SO_2$ | 1 | H | N |
| 34 | SO | S | 1 | H | N |
| 35 | $SO_2$ | S | 1 | H | N |
| 36 | S | S | 2 | H | N |
| 37 | S | SO | 2 | H | N |
| 38 | S | $SO_2$ | 2 | H | N |
| 39 | SO | S | 2 | H | N |
| 40 | $SO_2$ | S | 2 | H | N |
| 41 | S | S | 3 | H | N |
| 42 | S | SO | 3 | H | N |
| 43 | S | $SO_2$ | 3 | H | N |
| 44 | SO | S | 3 | H | N |
| 45 | $SO_2$ | S | 3 | H | N |
| 46 | S | S | 4 | H | N |
| 47 | S | SO | 4 | H | N |
| 48 | S | $SO_2$ | 4 | H | N |
| 49 | SO | S | 4 | H | N |
| 50 | $SO_2$ | S | 4 | H | N |

Exemplary embodiments include compounds having the formula (XIV) or an enantiomer, diastereomer, hydrate, solvate, prodrug, complex, or pharmaceutically acceptable salt form thereof:

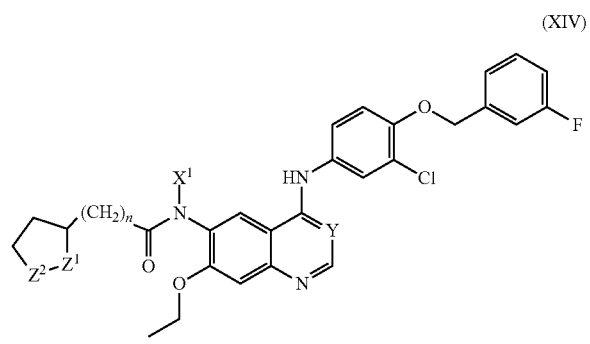

(XIV)

wherein non-limiting examples of $Z^1$, $Z^2$, n, $X^1$ and Y are defined herein below in Table 5.

TABLE 5

Exemplary compounds of the formula (XIV)

| Entry | $Z^1$ | $Z^2$ | n | $X^1$ | Y |
|---|---|---|---|---|---|
| 1 | S | S | 0 | H | C—CN |
| 2 | S | SO | 0 | H | C—CN |
| 3 | S | $SO_2$ | 0 | H | C—CN |
| 4 | SO | S | 0 | H | C—CN |
| 5 | SO | SO | 0 | H | C—CN |
| 6 | SO | $SO_2$ | 0 | H | C—CN |
| 7 | $SO_2$ | S | 0 | H | C—CN |
| 8 | $SO_2$ | SO | 0 | H | C—CN |
| 9 | $SO_2$ | $SO_2$ | 0 | H | C—CN |
| 10 | S | S | 1 | H | C—CN |
| 11 | S | SO | 1 | H | C—CN |
| 12 | S | $SO_2$ | 1 | H | C—CN |
| 13 | SO | S | 1 | H | C—CN |
| 14 | SO | SO | 1 | H | C—CN |
| 15 | SO | $SO_2$ | 1 | H | C—CN |
| 16 | $SO_2$ | S | 1 | H | C—CN |
| 17 | $SO_2$ | SO | 1 | H | C—CN |
| 18 | $SO_2$ | $SO_2$ | 1 | H | C—CN |
| 19 | S | S | 2 | H | C—CN |
| 20 | S | SO | 2 | H | C—CN |
| 21 | S | $SO_2$ | 2 | H | C—CN |
| 22 | SO | S | 2 | H | C—CN |
| 23 | SO | SO | 2 | H | C—CN |
| 24 | SO | $SO_2$ | 2 | H | C—CN |
| 25 | $SO_2$ | S | 2 | H | C—CN |
| 26 | $SO_2$ | SO | 2 | H | C—CN |
| 27 | $SO_2$ | $SO_2$ | 2 | H | C—CN |
| 28 | S | S | 3 | H | C—CN |
| 29 | S | SO | 3 | H | C—CN |
| 30 | S | $SO_2$ | 3 | H | C—CN |
| 31 | SO | S | 3 | H | C—CN |
| 32 | SO | SO | 3 | H | C—CN |
| 33 | SO | $SO_2$ | 3 | H | C—CN |
| 34 | $SO_2$ | S | 3 | H | C—CN |
| 35 | $SO_2$ | SO | 3 | H | C—CN |
| 36 | $SO_2$ | $SO_2$ | 3 | H | C—CN |
| 37 | S | S | 4 | H | C—CN |
| 38 | S | SO | 4 | H | C—CN |
| 39 | S | $SO_2$ | 4 | H | C—CN |
| 40 | SO | S | 4 | H | C—CN |
| 41 | SO | SO | 4 | H | C—CN |
| 42 | SO | $SO_2$ | 4 | H | C—CN |
| 43 | $SO_2$ | S | 4 | H | C—CN |
| 44 | $SO_2$ | SO | 4 | H | C—CN |
| 45 | $SO_2$ | $SO_2$ | 4 | H | C—CN |
| 46 | S | S | 0 | H | N |
| 47 | S | SO | 0 | H | N |
| 48 | S | $SO_2$ | 0 | H | N |
| 49 | SO | S | 0 | H | N |
| 50 | SO | SO | 0 | H | N |
| 51 | SO | $SO_2$ | 0 | H | N |
| 52 | $SO_2$ | S | 0 | H | N |
| 53 | $SO_2$ | SO | 0 | H | N |
| 54 | $SO_2$ | $SO_2$ | 0 | H | N |
| 55 | S | S | 1 | H | N |
| 56 | S | SO | 1 | H | N |
| 57 | S | $SO_2$ | 1 | H | N |
| 58 | SO | S | 1 | H | N |
| 59 | SO | SO | 1 | H | N |
| 60 | SO | $SO_2$ | 1 | H | N |
| 61 | $SO_2$ | S | 1 | H | N |
| 62 | $SO_2$ | SO | 1 | H | N |
| 63 | $SO_2$ | $SO_2$ | 1 | H | N |
| 64 | S | S | 2 | H | N |
| 65 | S | SO | 2 | H | N |
| 66 | S | $SO_2$ | 2 | H | N |
| 67 | SO | S | 2 | H | N |
| 68 | SO | SO | 2 | H | N |
| 69 | SO | $SO_2$ | 2 | H | N |
| 70 | $SO_2$ | S | 2 | H | N |
| 71 | $SO_2$ | SO | 2 | H | N |
| 72 | $SO_2$ | $SO_2$ | 2 | H | N |

TABLE 5-continued

Exemplary compounds of the formula (XIV)

| Entry | $Z^1$ | $Z^2$ | n | $X^1$ | Y |
|---|---|---|---|---|---|
| 73 | S | S | 3 | H | N |
| 74 | S | SO | 3 | H | N |
| 75 | S | $SO_2$ | 3 | H | N |
| 76 | SO | S | 3 | H | N |
| 77 | SO | SO | 3 | H | N |
| 78 | SO | $SO_2$ | 3 | H | N |
| 79 | $SO_2$ | S | 3 | H | N |
| 80 | $SO_2$ | SO | 3 | H | N |
| 81 | $SO_2$ | $SO_2$ | 3 | H | N |
| 82 | S | S | 4 | H | N |
| 83 | S | SO | 4 | H | N |
| 84 | S | $SO_2$ | 4 | H | N |
| 85 | SO | S | 4 | H | N |
| 86 | SO | SO | 4 | H | N |
| 87 | SO | $SO_2$ | 4 | H | N |
| 88 | $SO_2$ | S | 4 | H | N |
| 89 | $SO_2$ | SO | 4 | H | N |
| 90 | $SO_2$ | $SO_2$ | 4 | H | N |

Exemplary embodiments include compounds having the formula (XV) or an enantiomer, diastereomer, hydrate, solvate, prodrug, complex, or pharmaceutically acceptable salt form thereof:

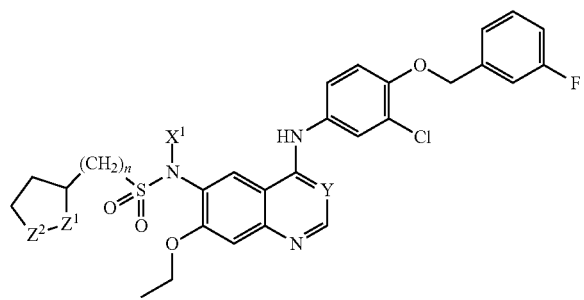

(XV)

wherein non-limiting examples of $Z^1$, $Z^2$, n, $X^1$ and Y are defined herein below in Table 6.

TABLE 6

Exemplary compounds of the formula (XV)

| Entry | $Z^1$ | $Z^2$ | n | $X^1$ | Y |
|---|---|---|---|---|---|
| 1 | S | S | 0 | H | C—CN |
| 2 | S | SO | 0 | H | C—CN |
| 3 | S | $SO_2$ | 0 | H | C—CN |
| 4 | SO | S | 0 | H | C—CN |
| 5 | $SO_2$ | S | 0 | H | C—CN |
| 6 | S | S | 1 | H | C—CN |
| 7 | S | SO | 1 | H | C—CN |
| 8 | S | $SO_2$ | 1 | H | C—CN |
| 9 | SO | S | 1 | H | C—CN |
| 10 | $SO_2$ | S | 1 | H | C—CN |
| 11 | S | S | 2 | H | C—CN |
| 12 | S | SO | 2 | H | C—CN |
| 13 | S | $SO_2$ | 2 | H | C—CN |
| 14 | SO | S | 2 | H | C—CN |
| 15 | $SO_2$ | S | 2 | H | C—CN |
| 16 | S | S | 3 | H | C—CN |
| 17 | S | SO | 3 | H | C—CN |
| 18 | S | $SO_2$ | 3 | H | C—CN |
| 19 | SO | S | 3 | H | C—CN |
| 20 | $SO_2$ | S | 3 | H | C—CN |
| 21 | S | S | 4 | H | C—CN |

TABLE 6-continued

Exemplary compounds of the formula (XV)

| Entry | $Z^1$ | $Z^2$ | n | $X^1$ | Y |
|---|---|---|---|---|---|
| 22 | S | SO | 4 | H | C—CN |
| 23 | S | $SO_2$ | 4 | H | C—CN |
| 24 | SO | S | 4 | H | C—CN |
| 25 | $SO_2$ | S | 4 | H | C—CN |
| 26 | S | S | 0 | H | N |
| 27 | S | SO | 0 | H | N |
| 28 | S | $SO_2$ | 0 | H | N |
| 29 | SO | S | 0 | H | N |
| 30 | $SO_2$ | S | 0 | H | N |
| 31 | S | S | 1 | H | N |
| 32 | S | SO | 1 | H | N |
| 33 | S | $SO_2$ | 1 | H | N |
| 34 | SO | S | 1 | H | N |
| 35 | $SO_2$ | S | 1 | H | N |
| 36 | S | S | 2 | H | N |
| 37 | S | SO | 2 | H | N |
| 38 | S | $SO_2$ | 2 | H | N |
| 39 | SO | S | 2 | H | N |
| 40 | $SO_2$ | S | 2 | H | N |
| 41 | S | S | 3 | H | N |
| 42 | S | SO | 3 | H | N |
| 43 | S | $SO_2$ | 3 | H | N |
| 44 | SO | S | 3 | H | N |
| 45 | $SO_2$ | S | 3 | H | N |
| 46 | S | S | 4 | H | N |
| 47 | S | SO | 4 | H | N |
| 48 | S | $SO_2$ | 4 | H | N |
| 49 | SO | S | 4 | H | N |
| 50 | $SO_2$ | S | 4 | H | N |

Exemplary embodiments include compounds having the formula (XVI) or an enantiomer, diastereomer, hydrate, solvate, prodrug, complex, or pharmaceutically acceptable salt form thereof:

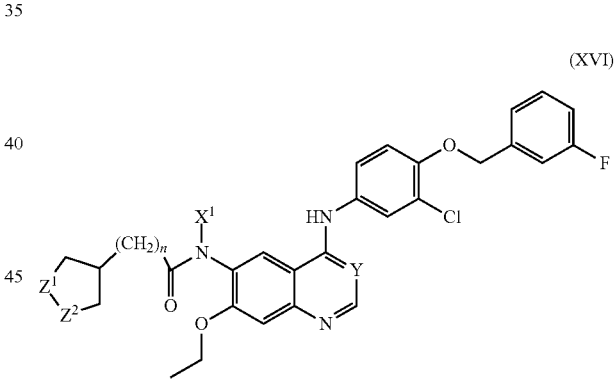

(XVI)

wherein non-limiting examples of $Z^1$, $Z^2$, n, $X^1$ and Y are defined herein below in Table 7.

TABLE 7

Exemplary compounds of the formula (XVI)

| Entry | $Z^1$ | $Z^2$ | n | $X^1$ | Y |
|---|---|---|---|---|---|
| 1 | S | S | 0 | H | C—CN |
| 2 | S | SO | 0 | H | C—CN |
| 3 | S | $SO_2$ | 0 | H | C—CN |
| 4 | SO | S | 0 | H | C—CN |
| 5 | SO | SO | 0 | H | C—CN |
| 6 | SO | $SO_2$ | 0 | H | C—CN |
| 7 | $SO_2$ | S | 0 | H | C—CN |
| 8 | $SO_2$ | SO | 0 | H | C—CN |
| 9 | $SO_2$ | $SO_2$ | 0 | H | C—CN |
| 10 | S | S | 1 | H | C—CN |

TABLE 7-continued

Exemplary compounds of the formula (XVI)

| Entry | $Z^1$ | $Z^2$ | n | $X^1$ | Y |
|---|---|---|---|---|---|
| 11 | S | SO | 1 | H | C—CN |
| 12 | S | $SO_2$ | 1 | H | C—CN |
| 13 | SO | S | 1 | H | C—CN |
| 14 | SO | SO | 1 | H | C—CN |
| 15 | SO | $SO_2$ | 1 | H | C—CN |
| 16 | $SO_2$ | S | 1 | H | C—CN |
| 17 | $SO_2$ | SO | 1 | H | C—CN |
| 18 | $SO_2$ | $SO_2$ | 1 | H | C—CN |
| 19 | S | S | 2 | H | C—CN |
| 20 | S | SO | 2 | H | C—CN |
| 21 | S | $SO_2$ | 2 | H | C—CN |
| 22 | SO | S | 2 | H | C—CN |
| 23 | SO | SO | 2 | H | C—CN |
| 24 | SO | $SO_2$ | 2 | H | C—CN |
| 25 | $SO_2$ | S | 2 | H | C—CN |
| 26 | $SO_2$ | SO | 2 | H | C—CN |
| 27 | $SO_2$ | $SO_2$ | 2 | H | C—CN |
| 28 | S | S | 3 | H | C—CN |
| 29 | S | SO | 3 | H | C—CN |
| 30 | S | $SO_2$ | 3 | H | C—CN |
| 31 | SO | S | 3 | H | C—CN |
| 32 | SO | SO | 3 | H | C—CN |
| 33 | SO | $SO_2$ | 3 | H | C—CN |
| 34 | $SO_2$ | S | 3 | H | C—CN |
| 35 | $SO_2$ | SO | 3 | H | C—CN |
| 36 | $SO_2$ | $SO_2$ | 3 | H | C—CN |
| 37 | S | S | 4 | H | C—CN |
| 38 | S | SO | 4 | H | C—CN |
| 39 | S | $SO_2$ | 4 | H | C—CN |
| 40 | SO | S | 4 | H | C—CN |
| 41 | SO | SO | 4 | H | C—CN |
| 42 | SO | $SO_2$ | 4 | H | C—CN |
| 43 | $SO_2$ | S | 4 | H | C—CN |
| 44 | $SO_2$ | SO | 4 | H | C—CN |
| 45 | $SO_2$ | $SO_2$ | 4 | H | C—CN |
| 46 | S | S | 0 | H | N |
| 47 | S | SO | 0 | H | N |
| 48 | S | $SO_2$ | 0 | H | N |
| 49 | SO | S | 0 | H | N |
| 50 | SO | SO | 0 | H | N |
| 51 | SO | $SO_2$ | 0 | H | N |
| 52 | $SO_2$ | S | 0 | H | N |
| 53 | $SO_2$ | SO | 0 | H | N |
| 54 | $SO_2$ | $SO_2$ | 0 | H | N |
| 55 | S | S | 1 | H | N |
| 56 | S | SO | 1 | H | N |
| 57 | S | $SO_2$ | 1 | H | N |
| 58 | SO | S | 1 | H | N |
| 59 | SO | SO | 1 | H | N |
| 60 | SO | $SO_2$ | 1 | H | N |
| 61 | $SO_2$ | S | 1 | H | N |
| 62 | $SO_2$ | SO | 1 | H | N |
| 63 | $SO_2$ | $SO_2$ | 1 | H | N |
| 64 | S | S | 2 | H | N |
| 65 | S | SO | 2 | H | N |
| 66 | S | $SO_2$ | 2 | H | N |
| 67 | SO | S | 2 | H | N |
| 68 | SO | SO | 2 | H | N |
| 69 | SO | $SO_2$ | 2 | H | N |
| 70 | $SO_2$ | S | 2 | H | N |
| 71 | $SO_2$ | SO | 2 | H | N |
| 72 | $SO_2$ | $SO_2$ | 2 | H | N |
| 73 | S | S | 3 | H | N |
| 74 | S | SO | 3 | H | N |
| 75 | S | $SO_2$ | 3 | H | N |
| 76 | SO | S | 3 | H | N |
| 77 | SO | SO | 3 | H | N |
| 78 | SO | $SO_2$ | 3 | H | N |
| 79 | $SO_2$ | S | 3 | H | N |
| 80 | $SO_2$ | SO | 3 | H | N |
| 81 | $SO_2$ | $SO_2$ | 3 | H | N |
| 82 | S | S | 4 | H | N |
| 83 | S | SO | 4 | H | N |
| 84 | S | $SO_2$ | 4 | H | N |
| 85 | SO | S | 4 | H | N |
| 86 | SO | SO | 4 | H | N |
| 87 | SO | $SO_2$ | 4 | H | N |
| 88 | $SO_2$ | S | 4 | H | N |
| 89 | $SO_2$ | SO | 4 | H | N |
| 90 | $SO_2$ | $SO_2$ | 4 | H | N |

Exemplary embodiments include compounds having the formula (XVII) or an enantiomer, diastereomer, hydrate, solvate, prodrug, complex, or pharmaceutically acceptable salt form thereof:

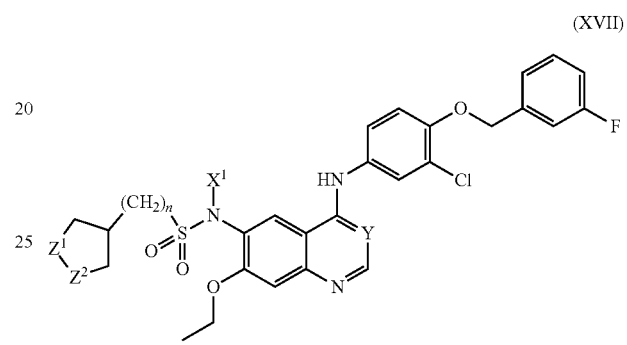

(XVII)

wherein non-limiting examples of $Z^1$, $Z^2$, n, $X^1$ and Y are defined herein below in Table 8.

TABLE 8

Exemplary compounds of the formula (XVII)

| Entry | $Z^1$ | $Z^2$ | n | $X^1$ | Y |
|---|---|---|---|---|---|
| 1 | S | S | 0 | H | C—CN |
| 2 | S | SO | 0 | H | C—CN |
| 3 | S | $SO_2$ | 0 | H | C—CN |
| 4 | SO | S | 0 | H | C—CN |
| 5 | $SO_2$ | S | 0 | H | C—CN |
| 6 | S | S | 1 | H | C—CN |
| 7 | S | SO | 1 | H | C—CN |
| 8 | S | $SO_2$ | 1 | H | C—CN |
| 9 | SO | S | 1 | H | C—CN |
| 10 | $SO_2$ | S | 1 | H | C—CN |
| 11 | S | S | 2 | H | C—CN |
| 12 | S | SO | 2 | H | C—CN |
| 13 | S | $SO_2$ | 2 | H | C—CN |
| 14 | SO | S | 2 | H | C—CN |
| 15 | $SO_2$ | S | 2 | H | C—CN |
| 16 | S | S | 3 | H | C—CN |
| 17 | S | SO | 3 | H | C—CN |
| 18 | S | $SO_2$ | 3 | H | C—CN |
| 19 | SO | S | 3 | H | C—CN |
| 20 | $SO_2$ | S | 3 | H | C—CN |
| 21 | S | S | 4 | H | C—CN |
| 22 | S | SO | 4 | H | C—CN |
| 23 | S | $SO_2$ | 4 | H | C—CN |
| 24 | SO | S | 4 | H | C—CN |
| 25 | $SO_2$ | S | 4 | H | C—CN |
| 26 | S | S | 0 | H | N |
| 27 | S | SO | 0 | H | N |
| 28 | S | $SO_2$ | 0 | H | N |
| 29 | SO | S | 0 | H | N |
| 30 | $SO_2$ | S | 0 | H | N |
| 31 | S | S | 1 | H | N |
| 32 | S | SO | 1 | H | N |
| 33 | S | $SO_2$ | 1 | H | N |
| 34 | SO | S | 1 | H | N |
| 35 | $SO_2$ | S | 1 | H | N |

TABLE 8-continued

Exemplary compounds of the formula (XVII)

| Entry | $Z^1$ | $Z^2$ | n | $X^1$ | Y |
|---|---|---|---|---|---|
| 36 | S | S | 2 | H | N |
| 37 | S | SO | 2 | H | N |
| 38 | S | $SO_2$ | 2 | H | N |
| 39 | SO | S | 2 | H | N |
| 40 | $SO_2$ | S | 2 | H | N |
| 41 | S | S | 3 | H | N |
| 42 | S | SO | 3 | H | N |
| 43 | S | $SO_2$ | 3 | H | N |
| 44 | SO | S | 3 | H | N |
| 45 | $SO_2$ | S | 3 | H | N |
| 46 | S | S | 4 | H | N |
| 47 | S | SO | 4 | H | N |
| 48 | S | $SO_2$ | 4 | H | N |
| 49 | SO | S | 4 | H | N |
| 50 | $SO_2$ | S | 4 | H | N |

Exemplary embodiments include compounds having the formula (XVIII) or an enantiomer, diastereomer, hydrate, solvate, prodrug, complex, or pharmaceutically acceptable salt form thereof:

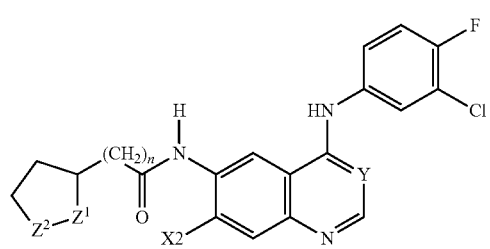

(XVIII)

wherein non-limiting examples of $Z^1$, $Z^2$, n, $X^1$ and Y are defined herein below in Table 9.

TABLE 9

Exemplary compounds of the formula (XVIII)

| Entry | $Z^1$ | $Z^2$ | n | $X^2$ | Y |
|---|---|---|---|---|---|
| 1 | S | S | 0 | $OCHOHCH_2OH$ | C—CN |
| 2 | S | SO | 0 | $OCHOHCH_2OH$ | C—CN |
| 3 | S | $SO_2$ | 0 | $OCHOHCH_2OH$ | C—CN |
| 4 | SO | S | 0 | $OCHOHCH_2OH$ | C—CN |
| 5 | $SO_2$ | S | 0 | $OCHOHCH_2OH$ | C—CN |
| 6 | S | S | 1 | $OCHOHCH_2OH$ | C—CN |
| 7 | S | SO | 1 | $OCHOHCH_2OH$ | C—CN |
| 8 | S | $SO_2$ | 1 | $OCHOHCH_2OH$ | C—CN |
| 9 | SO | S | 1 | $OCHOHCH_2OH$ | C—CN |
| 10 | $SO_2$ | S | 1 | $OCHOHCH_2OH$ | C—CN |
| 11 | S | S | 2 | $OCHOHCH_2OH$ | C—CN |
| 12 | S | SO | 2 | $OCHOHCH_2OH$ | C—CN |
| 13 | S | $SO_2$ | 2 | $OCHOHCH_2OH$ | C—CN |
| 14 | SO | S | 2 | $OCHOHCH_2OH$ | C—CN |
| 15 | $SO_2$ | S | 2 | $OCHOHCH_2OH$ | C—CN |
| 16 | S | S | 0 | $OCHOHCH_2OH$ | N |
| 17 | S | SO | 0 | $OCHOHCH_2OH$ | N |
| 18 | S | $SO_2$ | 0 | $OCHOHCH_2OH$ | N |
| 19 | SO | S | 0 | $OCHOHCH_2OH$ | N |
| 20 | $SO_2$ | S | 0 | $OCHOHCH_2OH$ | N |
| 21 | S | S | 1 | $OCHOHCH_2OH$ | N |
| 22 | S | SO | 1 | $OCHOHCH_2OH$ | N |
| 23 | S | $SO_2$ | 1 | $OCHOHCH_2OH$ | N |
| 24 | SO | S | 1 | $OCHOHCH_2OH$ | N |
| 25 | $SO_2$ | S | 1 | $OCHOHCH_2OH$ | N |
| 26 | S | S | 2 | $OCHOHCH_2OH$ | N |
| 27 | S | SO | 2 | $OCHOHCH_2OH$ | N |
| 28 | S | $SO_2$ | 2 | $OCHOHCH_2OH$ | N |
| 29 | SO | S | 2 | $OCHOHCH_2OH$ | N |
| 30 | $SO_2$ | S | 2 | $OCHOHCH_2OH$ | N |

Exemplary embodiments include compounds having the formula (XIX) or an enantiomer, diastereomer, hydrate, solvate, prodrug, complex, or pharmaceutically acceptable salt form thereof:

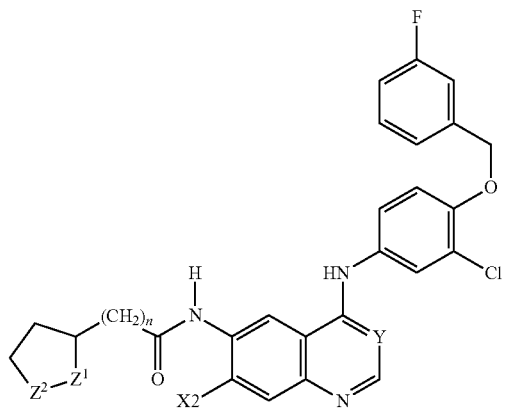

(XIX)

Wherein non-limiting examples of $Z^1$, $Z^2$, n, and $X^2$ are defined herein below in Table 10.

TABLE 10

Exemplary compounds of the formula (XIX)

| Entry | $Z^1$ | $Z^2$ | n | $X^2$ | Y |
|---|---|---|---|---|---|
| 1 | S | S | 0 | $OCHOHCH_2OH$ | C—CN |
| 2 | S | SO | 0 | $OCHOHCH_2OH$ | C—CN |
| 3 | S | $SO_2$ | 0 | $OCHOHCH_2OH$ | C—CN |
| 4 | SO | S | 0 | $OCHOHCH_2OH$ | C—CN |
| 5 | $SO_2$ | S | 0 | $OCHOHCH_2OH$ | C—CN |
| 6 | S | S | 1 | $OCHOHCH_2OH$ | C—CN |
| 7 | S | SO | 1 | $OCHOHCH_2OH$ | C—CN |
| 8 | S | $SO_2$ | 1 | $OCHOHCH_2OH$ | C—CN |
| 9 | SO | S | 1 | $OCHOHCH_2OH$ | C—CN |
| 10 | $SO_2$ | S | 1 | $OCHOHCH_2OH$ | C—CN |
| 11 | S | S | 2 | $OCHOHCH_2OH$ | C—CN |
| 12 | S | SO | 2 | $OCHOHCH_2OH$ | C—CN |
| 13 | S | $SO_2$ | 2 | $OCHOHCH_2OH$ | C—CN |
| 14 | SO | S | 2 | $OCHOHCH_2OH$ | C—CN |
| 15 | $SO_2$ | S | 2 | $OCHOHCH_2OH$ | C—CN |
| 16 | S | S | 0 | $OCHOHCH_2OH$ | N |
| 17 | S | SO | 0 | $OCHOHCH_2OH$ | N |
| 18 | S | $SO_2$ | 0 | $OCHOHCH_2OH$ | N |
| 19 | SO | S | 0 | $OCHOHCH_2OH$ | N |
| 20 | $SO_2$ | S | 0 | $OCHOHCH_2OH$ | N |
| 21 | S | S | 1 | $OCHOHCH_2OH$ | N |
| 22 | S | SO | 1 | $OCHOHCH_2OH$ | N |
| 23 | S | $SO_2$ | 1 | $OCHOHCH_2OH$ | N |
| 24 | SO | S | 1 | $OCHOHCH_2OH$ | N |
| 25 | $SO_2$ | S | 1 | $OCHOHCH_2OH$ | N |
| 26 | S | S | 2 | $OCHOHCH_2OH$ | N |
| 27 | S | SO | 2 | $OCHOHCH_2OH$ | N |
| 28 | S | $SO_2$ | 2 | $OCHOHCH_2OH$ | N |
| 29 | SO | S | 2 | $OCHOHCH_2OH$ | N |
| 30 | $SO_2$ | S | 2 | $OCHOHCH_2OH$ | N |

Exemplary embodiments include compounds having the formula (XX) or an enantiomer, diastereomer, hydrate, solvate, prodrug, complex, or pharmaceutically acceptable salt form thereof:

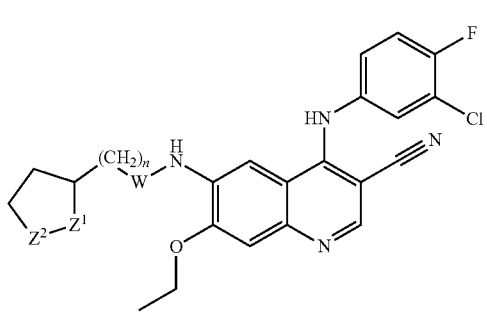

(XX)

Exemplary embodiments include compounds having the formula (XXI) or an enantiomer, diastereomer, hydrate, solvate, prodrug, complex, or pharmaceutically acceptable salt form thereof:

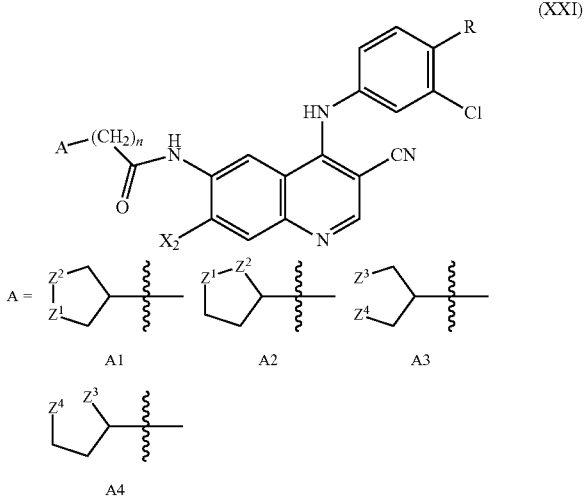

(XXI)

wherein non-limiting examples of $Z^1$, $Z^2$, n, and W are defined herein below in Table 11.

TABLE 11

Exemplary compounds of the formula (XX)

| Entry | $Z^1$ | $Z^2$ | n | W | Name |
|---|---|---|---|---|---|
| 1 | S | SO | 1 | CO | N-(4-((3-chloro-4-fluorophenyl)amino)-3-cyano-7-ethoxyquinolin-6-yl)-2-(1-oxido-1,2-dithiolan-3-yl)acetamide |
| 2 | SO | S | 1 | CO | N-(4-((3-chloro-4-fluorophenyl)amino)-3-cyano-7-ethoxyquinolin-6-yl)-2-(2-oxido-1,2-dithiolan-3-yl)acetamide |
| 3 | S | $SO_2$ | 1 | CO | N-(4-((3-chloro-4-fluorophenyl)amino)-3-cyano-7-ethoxyquinolin-6-yl)-2-(1,1-dioxido-1,2-dithiolan-3-yl)acetamide |
| 4 | SO | SO | 1 | CO | N-(4-((3-chloro-4-fluorophenyl)amino)-3-cyano-7-ethoxyquinolin-6-yl)-2-(1,2-dioxido-1,2-dithiolan-3-yl)acetamide |
| 5 | $SO_2$ | S | 1 | CO | N-(4-((3-chloro-4-fluorophenyl)amino)-3-cyano-7-ethoxyquinolin-6-yl)-2-(2,2-dioxido-1,2-dithiolan-3-yl)acetamide |
| 6 | SO | $SO_2$ | 1 | CO | N-(4-((3-chloro-4-fluorophenyl)amino)-3-cyano-7-ethoxyquinolin-6-yl)-2-(1,1,2-trioxido-1,2-dithiolan-3-yl)acetamide |
| 7 | $SO_2$ | SO | 1 | CO | N-(4-((3-chloro-4-fluorophenyl)amino)-3-cyano-7-ethoxyquinolin-6-yl)-2-(1,2,2-trioxido-1,2-dithiolan-3-yl)acetamide |
| 8 | $SO_2$ | $SO_2$ | 1 | CO | N-(4-((3-chloro-4-fluorophenyl)amino)-3-cyano-7-ethoxyquinolin-6-yl)-2-(1,1,2,2-tetroxido-1,2-dithiolan-3-yl)acetamide |
| 9 | S | S | 2 | CO | N-(4-((3-chloro-4-fluorophenyl)amino)-3-cyano-7-ethoxyquinolin-6-yl)-3-(1,2-dithiolan-3-yl)propanamide |
| 10 | S | S | 3 | CO | N-(4-((3-chloro-4-fluorophenyl)amino)-3-cyano-7-ethoxyquinolin-6-yl)-4-(1,2-dithiolan-3-yl)butanamide |
| 11 | S | S | 4 | CO | N-(4-((3-chloro-4-fluorophenyl)amino)-3-cyano-7-ethoxyquinolin-6-yl)-5-(1,2-dithiolan-3-yl)pentanamide |
| 12 | S | S | 0 | $SO_2$ | N-(4-((3-chloro-4-fluorophenyl)amino)-3-cyano-7-ethoxyquinolin-6-yl)-1,2-dithiolane-3-sulfonamide |
| 13 | S | S | 1 | $SO_2$ | N-(4-((3-chloro-4-fluorophenyl)amino)-3-cyano-7-ethoxyquinolin-6-yl)-1-(1,2-dithiolan-3-yl)methanesulfonamide |
| 14 | S | SO | 1 | $SO_2$ | N-(4-((3-chloro-4-fluorophenyl)amino)-3-cyano-7-ethoxyquinolin-6-yl)-1-(1-oxido-1,2-dithiolan-3-yl)methanesulfonamide |
| 15 | S | $SO_2$ | 1 | $SO_2$ | N-(4-((3-chloro-4-fluorophenyl)amino)-3-cyano-7-ethoxyquinolin-6-yl)-1-(1,1-dioxido-1,2-dithiolan-3-yl)methanesulfonamide |
| 16 | $SO_2$ | S | 1 | $SO_2$ | N-(4-((3-chloro-4-fluorophenyl)amino)-3-cyano-7-ethoxyquinolin-6-yl)-1-(2,2-dioxido-1,2-dithiolan-3-yl)methanesulfonamide |
| 17 | S | S | 2 | $SO_2$ | N-(4-((3-chloro-4-fluorophenyl)amino)-3-cyano-7-ethoxyquinolin-6-yl)-2-(1,2-dithiolan-3-yl)ethane-1-sulfonamide |
| 18 | S | S | 3 | $SO_2$ | N-(4-((3-chloro-4-fluorophenyl)amino)-3-cyano-7-ethoxyquinolin-6-yl)-3-(1,2-dithiolan-3-yl)propane-1-sulfonamide |
| 19 | S | S | 4 | $SO_2$ | N-(4-((3-chloro-4-fluorophenyl)amino)-3-cyano-7-ethoxyquinolin-6-yl)-4-(1,2-dithiolan-3-yl)butane-1-sulfonamide | wherein non-limiting examples of A, $Z^1$, $Z^2$, $Z^3$, $Z^4$, $X^2$, n, and R are defined herein below in Table 12.

TABLE 12

Exemplary compounds of the formula (XXI)

| Entry | Example | A | $Z^1$ | $Z^2$ | $Z^3$ | $Z^4$ | n | $X^2$ | R |
|---|---|---|---|---|---|---|---|---|---|
| 1 | 29 | A3 | | | SCOCH$_3$ | SCOCH$_3$ | 0 | OCH$_2$CH$_3$ | F |
| 2 | 30 | A3 | | | SH | SH | 0 | OCH$_2$CH$_3$ | F |
| 3 | 31 | A1 | S | S | | | 0 | OCH$_2$CH$_3$ | F |
| 4 | 32 | A1 | S | S | | | 0 | OCH$_2$CH$_3$ | F |
| 5 | 33 | A2 | S | S | | | 0 | OCH$_2$CH$_3$ | F |
| 6 | 34 | A3 | | | SCOCH$_3$ | SCOCH$_3$ | 0 | OCH$_2$CH$_3$ | 3-F-benzyloxy |
| 7 | 35 | A3 | | | SH | SH | 0 | OCH$_2$CH$_3$ | 3-F-benzyloxy |
| 8 | 36 | A1 | S | S | | | 0 | OCH$_2$CH$_3$ | 3-F-benzyloxy |
| 9 | 37 | A1 | S | S | | | 0 | OCH$_2$CH$_3$ | 3-F-benzyloxy |
| 10 | 38 | A4 | | | SBn | SBn | 0 | OCH$_2$CH$_3$ | F |
| 11 | 39 | A2 | S | S | | | 1 | OCH$_2$CH$_3$ | F |
| 12 | 40 | A2 | S | S | | | 1 | OCH$_2$CH$_3$ | 3-F-benzyloxy |
| 13 | 41 | A2 | S | S | | | 2 | OCH$_2$CH$_3$ | F |
| 14 | 42 | A2 | S | S | | | 4 | OCH$_2$CH$_3$ | F |
| 15 | 43 | A2 | S | S | | | 4 | OCH$_2$CH$_3$ | F |
| 16 | 44 | A2 | S | S | | | 4 | OCH$_2$CH$_3$ | 3-F-benzyloxy |
| 17 | 79 | A2 | S | S | | | 1 | 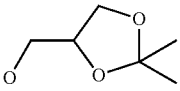 | 3-F-benzyloxy |
| 18 | 80 | A2 | S | S | | | 1 | 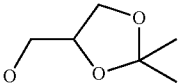 | 3-F-benzyloxy |
| 19 | 84 | A2 | S | S | | | 1 | 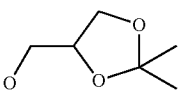 | 3-F-benzyloxy |
| 20 | 81 | A2 | S | S | | | 1 | 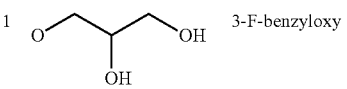 | 3-F-benzyloxy |
| 21 | 82 | A2 | S | S | | | 1 | 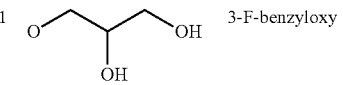 | 3-F-benzyloxy |
| 22 | 83 | A2 | S | S | | | 1 | 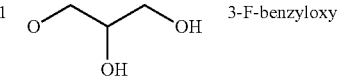 | 3-F-benzyloxy |
| 23 | 85 | A2 | S | S | | | 1 | 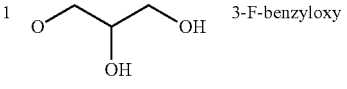 | 3-F-benzyloxy |
| 24 | 86 | A2 | S | S | | | 1 | 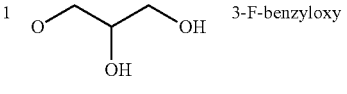 | 3-F-benzyloxy |
| 25 | 87 | A2 | SO | S | | | 1 | 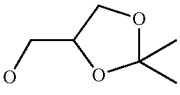 | 3-F-benzyloxy |
| 26 | 88 | A2 | SO | S | | | 1 | 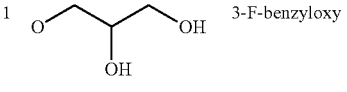 | 3-F-benzyloxy |
| 27 | 89 | A1 | S | S | | | 1 | 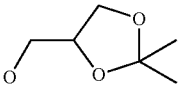 | 3-F-benzyloxy |

TABLE 12-continued

Exemplary compounds of the formula (XXI)

| Entry | Example | A | $Z^1$ | $Z^2$ | $Z^3$ | $Z^4$ | n | $X^2$ | R |
|---|---|---|---|---|---|---|---|---|---|
| 28 | 91 | A1 | S | S | | | 1 | 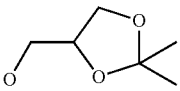 | 3-F-benzyloxy |
| 29 | 90 | A1 | S | S | | | 1 | 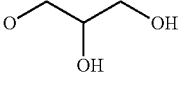 | 3-F-benzyloxy |
| 30 | 92 | A1 | S | S | | | 1 | 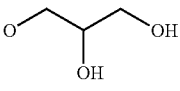 | 3-F-benzyloxy |
| 31 | 55 | A2 | S | S | | | 1 | H | 3-methyl-methylpy-oxyaniline |
| 32 | 56 | A3 | | | $SCOCH_3$ | $SCOCH_3$ | 0 | H | 3-methyl-methylpy-oxyaniline |
| 33 | 57 | A1 | S | S | | | 0 | H | 3-methyl-methylpy-oxyaniline |
| 34 | 60 | A3 | | | $SCOCH_3$ | $SCOCH_3$ | 1 | H | 3-F-benzyloxy |
| 35 | 61 | A1 | S | S | | | 0 | H | 3-F-benzyloxy |
| 36 | 62 | A2 | S | S | | | 0 | H | 3-F-benzyloxy |
| 37 | 93 | A1 | | | $SCOCH_3$ | $SCOCH_3$ | 0 | 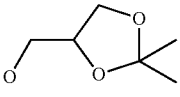 | 3-F-benzyloxy |
| 38 | 94 | A1 | | | $SCOCH_3$ | $SCOCH_3$ | 0 | 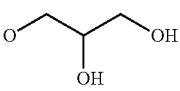 | 3-F-benzyloxy |
| 39 | 95 | A1 | S | S | | | 0 | 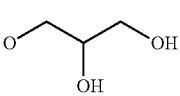 | 3-F-benzyloxy |
| 40 | 96 | A1 | | | $SCOCH_3$ | $SCOCH_3$ | 2 | 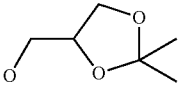 | 3-F-benzyloxy |
| 41 | | A1 | | | $SCOCH_3$ | $SCOCH_3$ | | 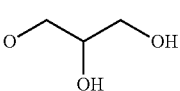 | 3-F-benzyloxy |
| 42 | | A1 | S | S | | | | 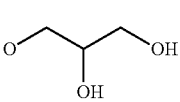 | 3-F-benzyloxy |

Exemplary embodiments include compounds having the formula (XXII) or an enantiomer, diastereomer, hydrate, solvate, prodrug, complex, or pharmaceutically acceptable salt form thereof:

(XXII)

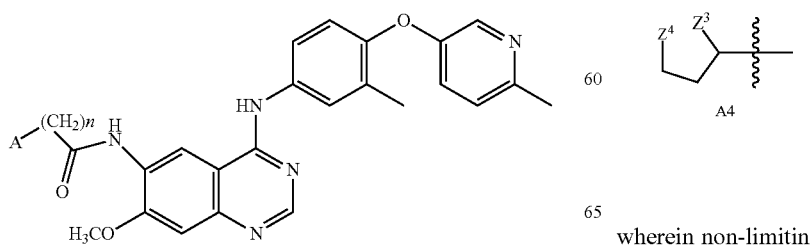

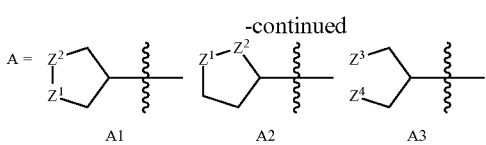

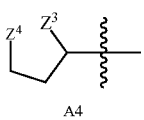

wherein non-limiting examples of A, $Z^1$, $Z^2$, $Z^3$, $Z^4$, $X^2$, n, and R are defined herein below in Table 12.

TABLE 13

Exemplary compounds of the formula (XXII)

| Entry | Example | A  | $Z^1$ | $Z^2$ | $Z^3$  | $Z^4$  | n |
|-------|---------|----|-------|-------|--------|--------|---|
| 1     | 103     | A3 |       |       | SCOCH₃ | SCOCH₃ | 0 |
| 2     | 104     | A1 | S     | S     |        |        | 0 |
| 3     | 105     | A2 | S     | S     |        |        | 1 |

Exemplary embodiments include compounds having the formula (XX) or an enantiomer, diastereomer, hydrate, solvate, prodrug, complex, or pharmaceutically acceptable salt form thereof:

(XXIII)

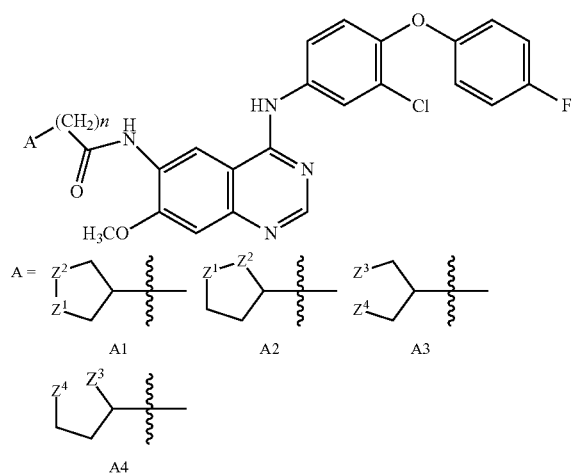

wherein non-limiting examples of A, $Z^1$, $Z^2$, $Z^3$, $Z^4$, $X^2$, n, and R are defined herein below in Table 14.

TABLE 14

Exemplary compounds of the formula (XXIII)

| Entry | Example | A  | $Z^1$ | $Z^2$ | $Z^3$  | $Z^4$  | n |
|-------|---------|----|-------|-------|--------|--------|---|
| 1     | 108     | A2 | S     | S     |        |        | 1 |
| 2     | 109     | A3 |       |       | SCOCH₃ | SCOCH₃ | 0 |
| 3     | 110     | A1 | S     | S     |        |        | 0 |

For the purposes of demonstrating the manner in which the compounds of the present invention are named and referred to herein, the compound having the formula:

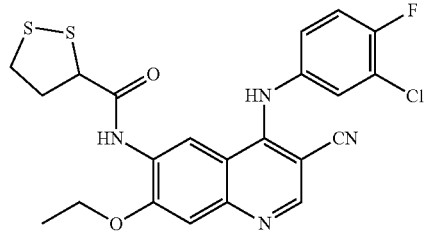 [SMILES: CCOc1cc2ncc(C#N)c(Nc3ccc(F)c(Cl)c3)c2cc1NC(=O)C1CCSS1]

has the chemical name N-(4-((3-chloro-4-fluorophenyl)amino)-3-cyano-7-ethoxyquinolin-6-yl)-1,2-dithiolane-3-carboxamide.

For the purposes of demonstrating the manner in which the compounds of the present invention are named and referred to herein, the compound having the formula:

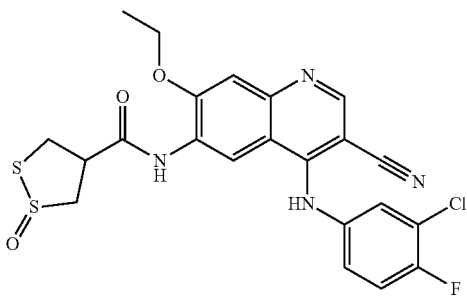 [SMILES: CCOc1cc2ncc(C#N)c(Nc3ccc(F)c(Cl)c3)c2cc1NC(=O)C1CSS(=O)C1]

has the chemical name N-(4-((3-chloro-4-fluorophenyl)amino)-3-cyano-7-ethoxyquinolin-6-yl)-1,2-dithiolane-4-carboxamide-1-oxide.

For the purposes of demonstrating the manner in which the compounds of the present invention are named and referred to herein, the compound having the formula:

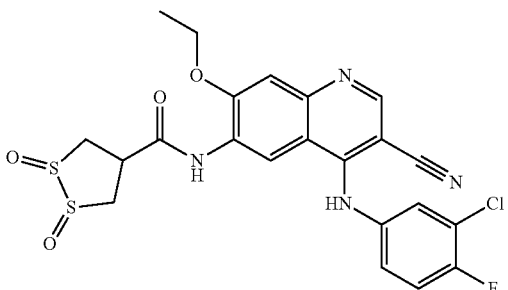

has the chemical name N-(4-((3-chloro-4-fluorophenyl)amino)-3-cyano-7-ethoxyquinolin-6-yl)-1,2-dithiolane-4-carboxamide 1,2-dioxide.

For the purposes of demonstrating the manner in which the compounds of the present invention are named and referred to herein, the compound having the formula:

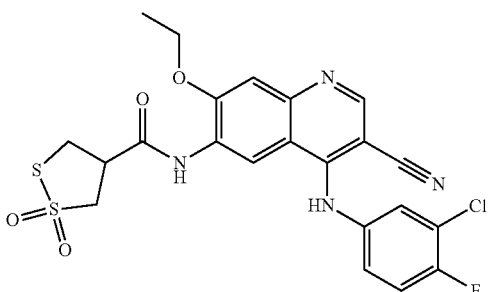

has the chemical name N-(4-((3-chloro-4-fluorophenyl)amino)-3-cyano-7-ethoxyquinolin-6-yl)-1,2-dithiolane-4-carboxamide 1,1-dioxide.

For the purposes of demonstrating the manner in which the compounds of the present invention are named and referred to herein, the compound having the formula:

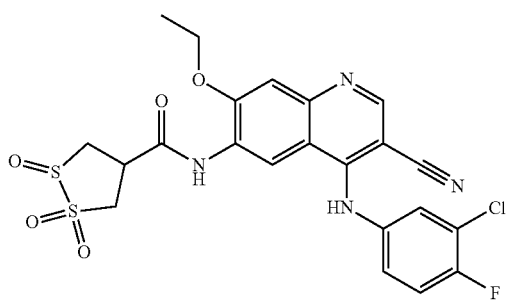 [SMILES: CCOc1cc2ncc(C#N)c(Nc3ccc(F)c(Cl)c3)c2cc1NC(=O)C1CS(=O)S(=O)(=O)C1]

has the chemical name N-(4-((3-chloro-4-fluorophenyl) amino)-3-cyano-7-ethoxyquinolin-6-yl)-1,2-dithiolane-4-carboxamide 1,1,2-trioxide For the purposes of demonstrating the manner in which the compounds of the present invention are named and referred to herein, the compound having the formula:

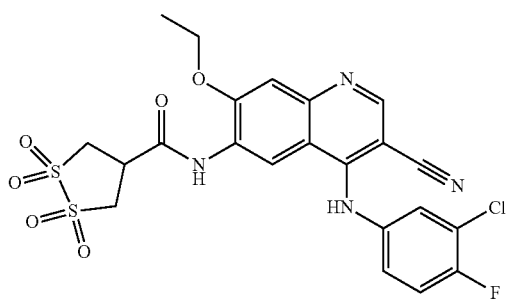 [SMILES: CCOc1cc2ncc(C#N)c(Nc3ccc(F)c(Cl)c3)c2cc1NC(=O)C1CS(=O)(=O)S(=O)(=O)C1]

has the chemical name N-(4-((3-chloro-4-fluorophenyl) amino)-3-cyano-7-ethoxyquinolin-6-yl)-1,2-dithiolane-4-carboxamide 1,1,2,2-tetraoxide.

For the purposes of demonstrating the manner in which the compounds of the present invention are named and referred to herein, the compound having the formula:

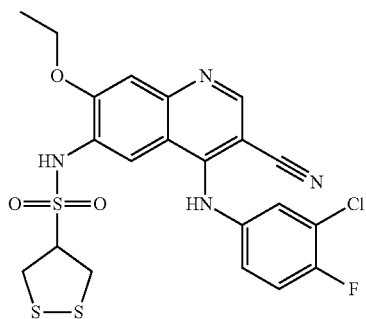 [SMILES: CCOc1cc2ncc(C#N)c(Nc3ccc(F)c(Cl)c3)c2cc1NS(=O)(=O)C1CSSC1]

has the chemical name N-(4-((3-chloro-4-fluorophenyl) amino)-3-cyano-7-ethoxyquinolin-6-yl)-1,2-dithiolane-4-sulfonamide.

For the purposes of demonstrating the manner in which the compounds of the present invention are named and referred to herein, the compound having the formula:

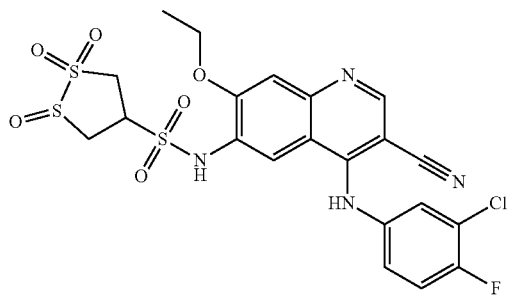 [SMILES: CCOc1cc2ncc(C#N)c(Nc3ccc(F)c(Cl)c3)c2cc1NS(=O)(=O)C1CS(=O)S(=O)(=O)C1]

has the chemical name N-(4-((3-chloro-4-fluorophenyl) amino)-3-cyano-7-ethoxyquinolin-6-yl)-1,2-dithiolane-4-sulfonamide 1,1,2-trioxide.

For the purposes of the present invention, a compound depicted by the racemic formula, for example:

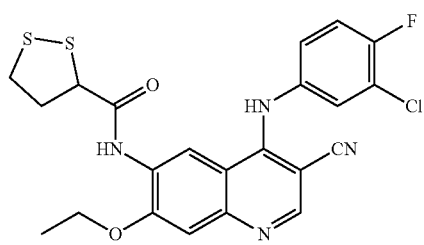 [SMILES: CCOc1cc2ncc(C#N)c(Nc3ccc(F)c(Cl)c3)c2cc1NC(=O)C1CCSS1]

will stand equally well for either of the two enantiomers having the formula:

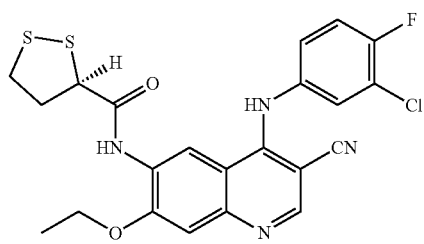 [SMILES: CCOc1cc2ncc(C#N)c(Nc3ccc(F)c(Cl)c3)c2cc1NC(=O)[C@H]1CCSS1]

or the formula:

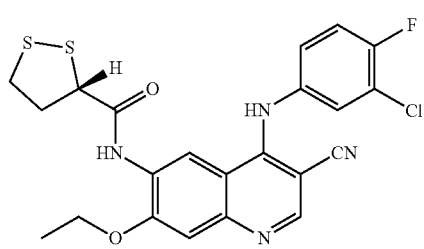 [SMILES: CCOc1cc2ncc(C#N)c(Nc3ccc(F)c(Cl)c3)c2cc1NC(=O)[C@@H]1CCSS1]

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

It will also be appreciated by those of skilled in the art, may be administered to a mammal and thereafter metabolized in the body to form compounds of the invention which are pharmacologically active. Such derivatives may therefore be described as "prodrugs". All prodrugs of compounds of formula (I) are included within the scope of this invention.

It is understood that one skilled in the art would be able to make compounds of the invention by similar methods as shown below, or by methods known to one skilled in the art. It is also understood that one skilled in the art would be able to make in a similar manner as described below other compounds of formula (I) not specifically illustrated below by using appropriate starting components and modifying the parameters of the synthesis as needed. In general, starting materials may be obtained from sources such as Sigma Aldrich, TCI and the like, or synthesized according to sources known to those of skill in the art (see Smith, M. B. and J. March, *Advanced Organic Chemistry: Reactions, Mechanisms and Structure*, 5$^{th}$ edition (Wiley, December 2000).

Combination Therapy

In another embodiment of the invention, a compound of the disclosure may be combined with one or more additional compounds of the disclosure for the treatment of EGFR-mediated disease and conditions. The compound of the disclosure may be administered simultaneously, sequentially or separately with the one or more additional compounds of the disclosure for the treatment of EGFR-mediated disease and conditions. In a further embodiment of the invention, a compound of the disclosure may be combined with one or more additional compounds of the disclosure and an excipient for the treatment of EGFR-mediated disease and conditions.

In another embodiment of the invention, a compound of the disclosure may be combined with an anti-cancer agent for the treatment of EGFR-mediated disease and conditions. The compound of the disclosure may be administered simultaneously, sequentially or separately with for the treatment of EGFR-mediated disease and conditions. Said anti-cancer agents include tyrosine kinase inhibitors such as erlotinib, neratinib, dacomitinib, afatinib, pelitinib, gefitinib, crizotinib, rociletinib, osimertinib, HM61713, AST-1306, WZ4002, and the like. Said anti-cancer agents also include Phosphatidylinositol 3-kinase (PI3K) inhibitors such as wortmannin, demethoxyviridin, LY294002, Perifosine, Idelalisib, PX-866, IPI-145, BAY 80-6946, BEZ235, RP6530, TGR 1202, SF1126, INK1117, GDC-0941, BKM120, XL147, XL765, Palomid 529, GSK1059615, ZSTK474, PWT33597, IC87114, TG100-115, CAL263, RP6503, PI-103, GNE-477, CUDC-907, AEZS-136, and the like, AKT inhibitors such as MK 2206, MKC-1, GSK 690693, FPA 124, AT7867, GDC-0068, ALM301, AZD5363, KP372-1 and the like, mTor inhibitors such as rapamycin, everolimus, temsirolimus, ridaforolimus, sirolimus, AZD8055, XL388, KU-0063794, GDC-0349, WYE-354, GSK1059615, PP242, Palomid 529, OSI-027, PF-05212384, WAY-600, WYE-125132, WYE-687, AZD2014, INK 128, Torin 1, Torin 2 and the like, c-Met inhibitors such as SU11274, K252a, PHA-665752, PHA-66752, PF-2341066, BMS-777607, JNJ-38877605, PF-04217903, MK-2461, GSK 1363089, AMG-458, Tivantinib, INCB28060, Cabozantinib, Foretinib, and the like, vascular endothelial growth factor (VEGF) monoclonal antibodies such as bevacizumab, ranibizumab, and the like, epidermal growth factor receptor (EGFR) inhibitor such as gefitinib, erlotinib, and the like, epidermal growth factor receptor (EGFR) monoclonal antibodies such as cetuximab, panitumumab and the like, Wnt pathway inhibitors such as XAV939 and the like, bioactive flavolignans such as silibinin and the like, DNA methylation inhibitors such as 5-aza-2'-deoxycytidine and the like, platinum based anticancer agents such as carboplatin, cisplatin, and the like. Said anti-cancer agents also include paclitaxel, gemcitabine, docetaxel, vinorelbine, irinotecan, pemetrexed, and the like, dual anti-cancer therapies such as carboplatin/paclitaxel, carboplatin/gemcitabine, carboplatin/docetaxel, carboplatin/vinorelbine, carboplatin/irinotecan, carboplatin/pemetrexed, cisplatin/paclitaxel, cisplatin/gemcitabine, cisplatin/docetaxel, cisplatin/vinorelbine, cisplatin/irinotecan, cisplatin/pemetrexed, and the like. Said anti-cancer agents also includes autophagy inducing agents such as imatinib and the like, Rexinoids or retinoid x receptor selective ligands such as baroxetene and the like, Cyclooxygenase-2 inhibitor such as rofecoxib and the like, Src family kinases and Bcr-Abl inhibitor such as bosulif and the like, and Recombinant adenoviral vector TRAIL protein.

In another embodiment of the invention, a compound of the disclosure may be combined with radiation therapy for the treatment of EGFR-mediated disease and conditions.

Kits of Parts

The present invention also provides kits that contain a pharmaceutical composition which includes one or more compounds of the invention. The kit also includes instructions for the use of the pharmaceutical composition for modulating the activity of EGFR, for the treatment of cancer, as well as other utilities as disclosed herein. Preferably, a commercial package will contain one or more unit doses of the pharmaceutical composition.

Preparation of the Compounds of the Invention

The present invention further relates to a process for preparing the compounds of the disclosure.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in Schemes 1-32.

Scheme 1

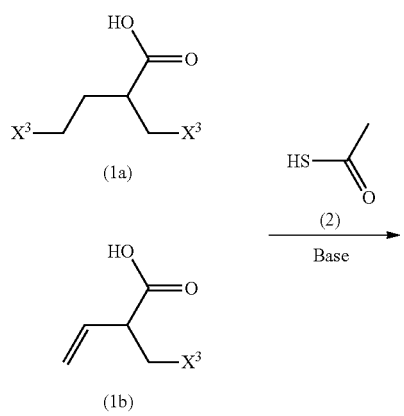

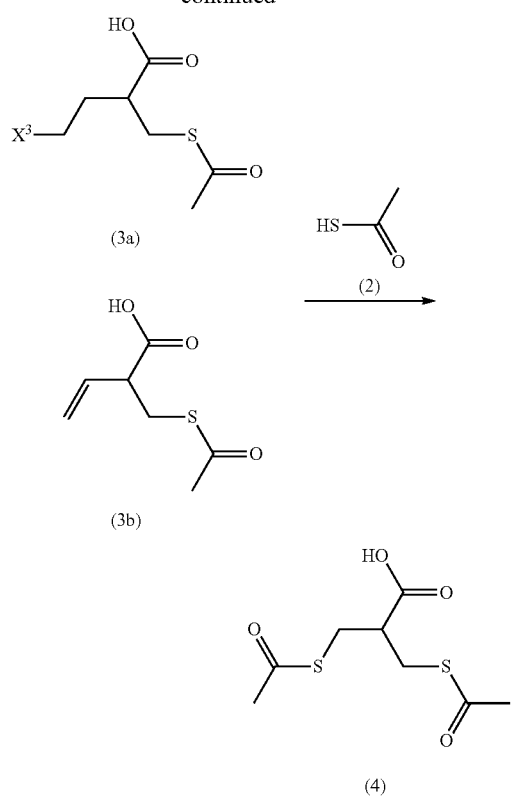

A compound of formula (1a) or (1b), a known compound or compound prepared by known methods wherein $X^3$ is a leaving group as chlorine, bromine, iodine, mesylate, tosylate, and the like, is reacted with a compound of the formula (2) in a solvent such as methanol, ethanol, isopropanol, water, N,N-dimethylformamide, N,N-dimethylacetamide, tetrahydrofuran, 1,4-dioxane, and the like in the presence of a base such as sodium carbonate, cesium carbonate, lithium carbonate, potassium carbonate, potassium hydroxide, sodium hydroxide, lithium hydroxide, and the like to provide a compound of the formula (3a or 3b). A compound of the formula (3a or 3b) is reacted with a compound of the formula (2), optionally in a solvent such as methanol, ethanol, isopropanol, water, N,N-dimethylformamide, N,N-dimethylacetamide, tetrahydrofuran, 1,4-dioxane, and the like, optionally with heating, optionally with microwave irradiation to provide a compound of the formula (4).

Scheme 2

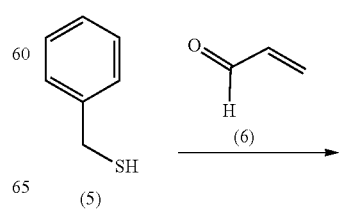

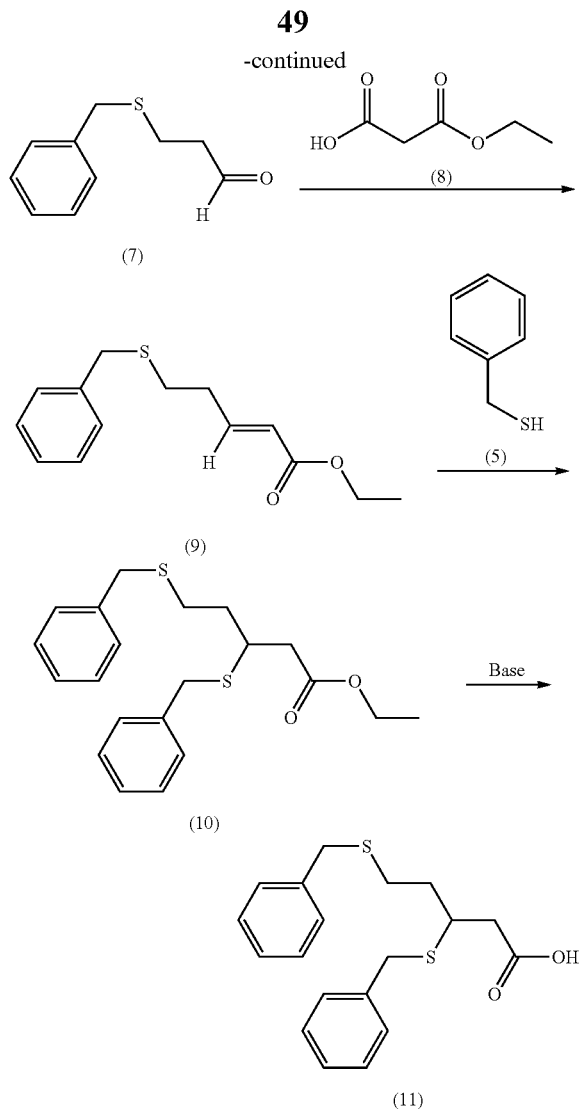

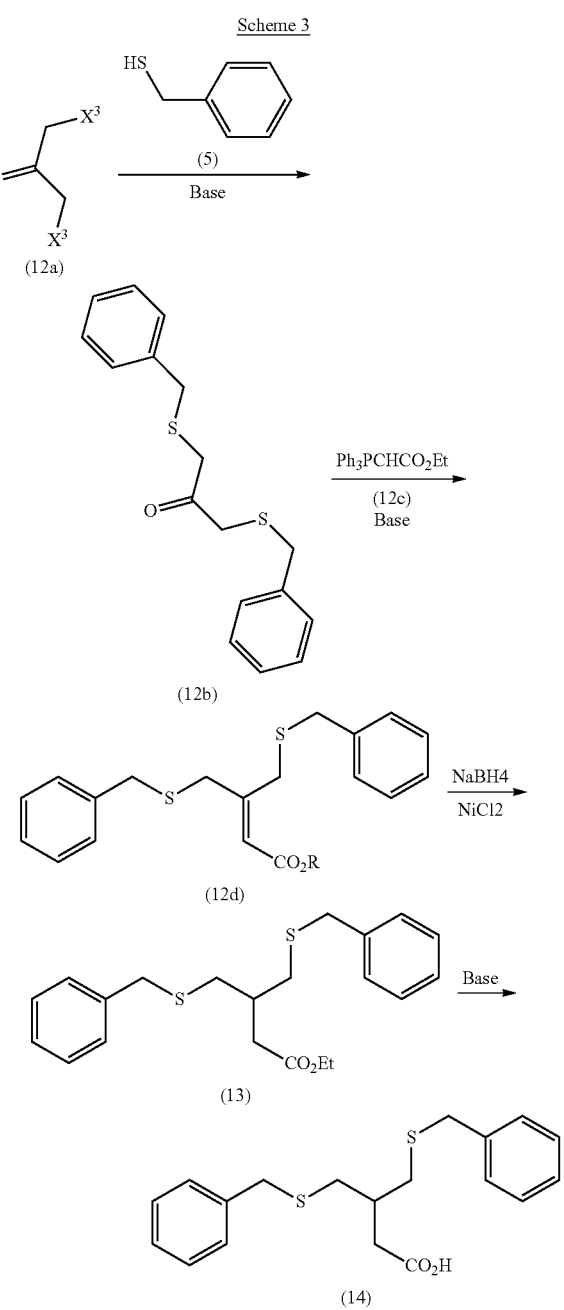

ine, diisopropylethylamine, and the like, optionally in a solvent such as methanol, ethanol, isopropanol, water, N,N-dimethylformamide, N,N-dimethylacetamide, tetrahydrofuran, 1,4-dioxane, and the like, optionally with heating, optionally with microwave irradiation to provide a compound of the formula (10). A compound of the formula (10) is reacted with a base such as sodium carbonate, cesium carbonate, lithium carbonate, potassium carbonate, potassium hydroxide, sodium hydroxide, lithium hydroxide, and the like, in the presence of a solvent such as methanol, ethanol, isopropanol, water, N,N-dimethylformamide, N,N-dimethylacetamide, tetrahydrofuran, 1,4-dioxane, and the like, optionally with heating, optionally with microwave irradiation to provide a compound of the formula (11).

A compound of the formula (5), a known compound or compound prepared by known methods, is reacted with a compound of the formula (6) in a solvent such as methylene chloride, chloroform, 1,2-dichloroethane, tetrahydrofuran, 1,4-dioxane, N,N-dimethylformamide, and the like, optionally with heating, optionally with microwave irradiation to provide a compound of the formula (7). A compound of the formula (7) is reacted with a compound of the formula (8), a known compound or compound prepared by known methods, in the presence of a base such as pyridine, 2,6-lutidine, triethylamine, diisopropylethylamine, and the like, in the presence of piperidine, optionally in a solvent such as methanol, ethanol, isopropanol, water, N,N-dimethylformamide, N,N-dimethylacetamide, tetrahydrofuran, 1,4-dioxane, and the like, optionally with heating, optionally with microwave irradiation. The resulting product is then reacted with an acid such as hydrochloric acid, sulfuric acid, trifluoroacetic acid, and the like, optionally in a solvent such as methanol, ethanol, isopropanol, water, N,N-dimethylformamide, N,N-dimethylacetamide, tetrahydrofuran, 1,4-dioxane, and the like, to provide a compound of the formula (9). A compound of the formula (9) is reacted with a compound of the formula (5), a known compound or compound prepared by known methods, in the presence of a base such as a base such as piperidine, pyridine, 2,6-lutidine, triethylam- A compound of the formula (12a), a known compound or compound prepared by known methods wherein $X^3$ is a leaving group such as chlorine, bromine, iodine, tosylate, mesylate, and the like, is reacted with a compound of the formula (5), a known compound or compound prepared by known methods, in the presence of a base such as sodium methoxide, sodium ethoxide, lithium methoxide, lithium ethoxide, lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like in the presence of a solvent such as methanol, ethanol, methylene chloride, chloroform, 1,2-dichloroethane, tetrahydrofuran, 1,4-dioxane, N,N-dimethylformamide, and the like, optionally with heating, optionally with microwave irradiation to provide a compound of the formula (12b). A compound of the formula (12b) is reacted with a compound of the formula (12c), a known compound such as triphenyl phosphine ylide or compound prepared by known methods, referred to as a Wittig reagent or a Wittig Schlosser reagent in the presence of a base such as phenyl lithium, lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like, optionally in the presence of a solvent such as, tetrahydrofuran, 1,4-dioxane, toluene, benzene, HMPA and the like, optionally with heating, optionally with microwave irradiation to provide a compound of the formula (12d) or under olefination conditions employing reagents such as Corey-Chaykovsky, Horner-Wadsworth-Emmons, Julia-Lythgoe, Petersen, Tebbe, Kauffmann, titanium-zinc methylation reagents. The alkene bond in a compound of formula (12d) is selectively reduced by sodium borohydride or sodium cyanoborohydride or hydrogen with a catalyst or the like, reagents optionally in the presence of a solvent such as methanol, ethanol, tetrahydrofuran, 1,4-dioxane and the like, optionally with heating, optionally in the presence of a metal solid such as nickel halide, cobalt halide, manganese halide and the like to provide a compound of formula (13). A compound of formula (13) is hydrolyzed under basic conditions such as sodium hydroxide, potassium hydroxide, lithium hydroxide, lithium methoxide, sodium methoxide, sodium ethoxide, potassium methoxide, lithium t-butoxide, sodium t-butoxide, potassium t-butoxide or the like to provide a compound of formula (14).

Scheme 4

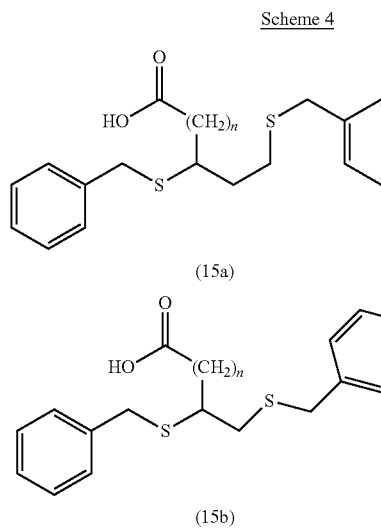

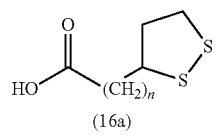

(16a)

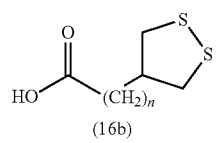

(16b)

A compound of the formula (15a or 15b), a known compound or compound prepared by known methods, is reacted with sodium in the presence of ammonia, optionally in the presence of a solvent such as toluene, benzene, methylene chloride, 1,2-dichloroethane, tetrahydrofuran, 1,4-dioxane, and the like. The resulting product is then reacted with an oxidant such as oxygen, in the a solvent such as methanol, ethanol, isopropanol, water, tetrahydrofuran, 1,4-dioxane, DMSO and the like to provide a compound of the formula (16a or 16b).

Scheme 5

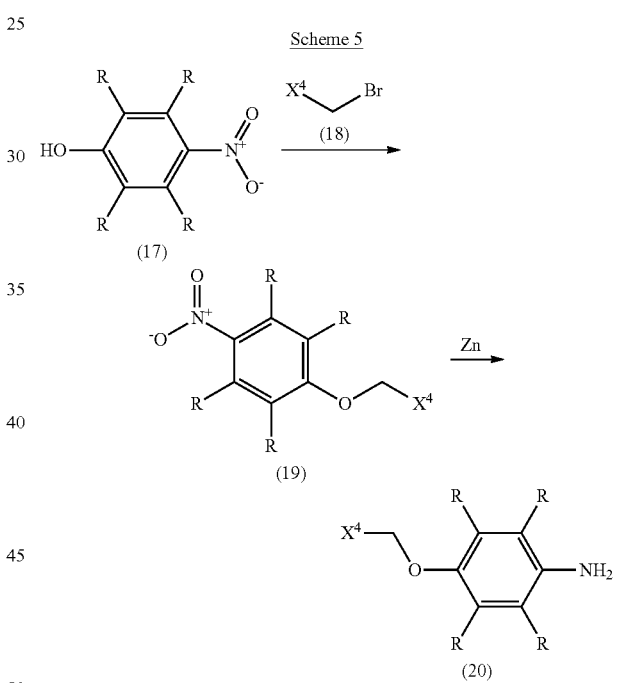

A compound of the formula (17), a known compound or compound prepared by known methods, is reacted with a compound of the formula (18), a known compound or a compound prepared by known methods wherein $X^4$ is selected from a group consisting of an optionally substituted aryl and an optionally substituted heteroaryl, in the presence of a base such as sodium carbonate, cesium carbonate, lithium carbonate, potassium carbonate, potassium hydroxide, sodium hydroxide, lithium hydroxide, and the like in a solvent such as methanol, ethanol, isopropanol, acetone, acetonitrile, tetrahydrofuran, 1,4-dioxane, methylene chloride, 1,2-dichloroethane, and the like, optionally with heating, optionally with microwave irradiation to provide a compound of the formula (19). A compound of the formula (19) is reacted with zinc in the presence of ammonium chloride in the presence of a solvent such as methanol, ethanol, isopropanol, acetone, acetonitrile, tetrahydrofuran, 1,4-dioxane, methylene chloride, 1,2-dichloroethane, and the like, optionally with heating, optionally with microwave irradiation to provide a compound of the formula (20).

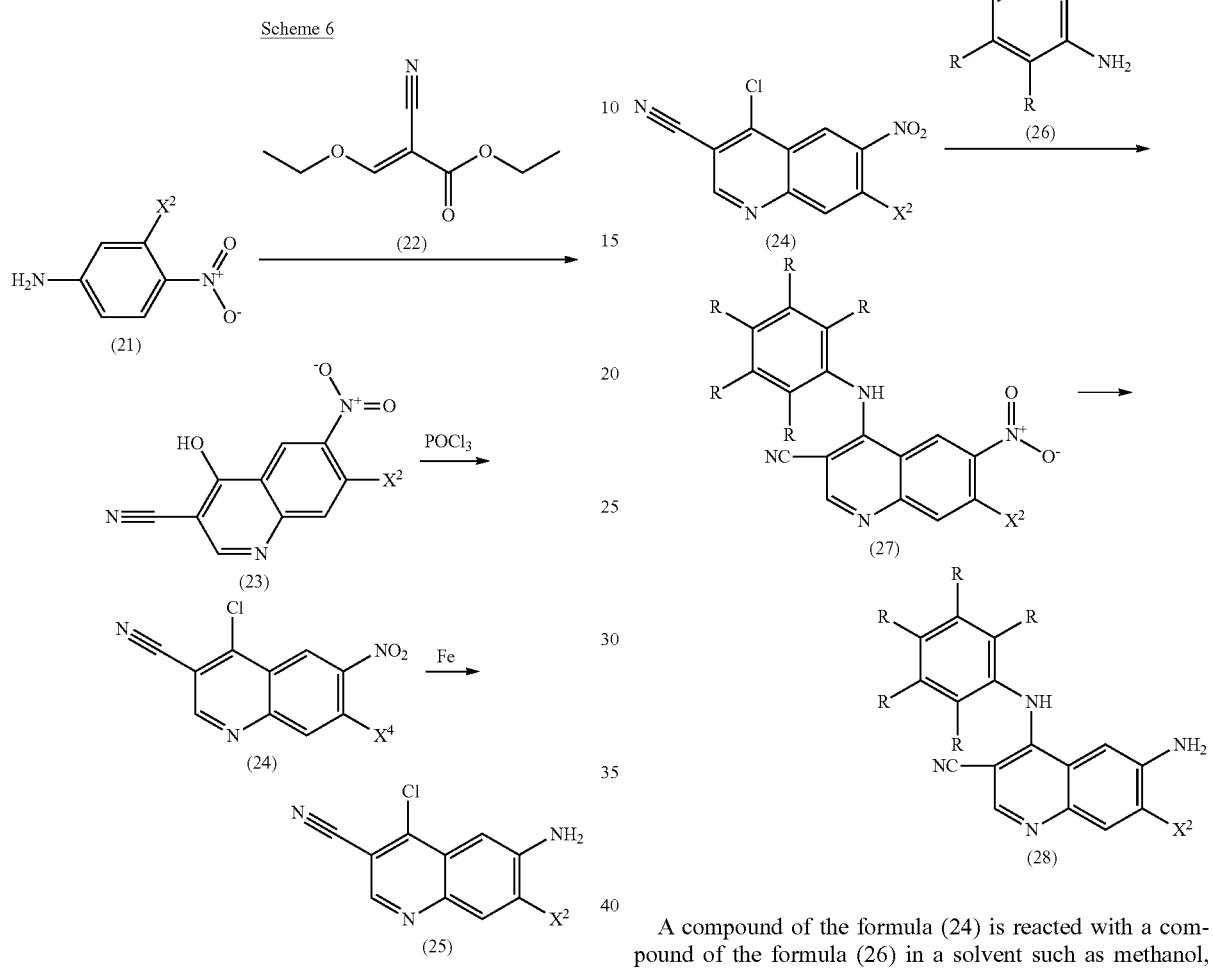

A compound of the formula (21), a known compound or compound prepared by known methods, is reacted with a compound of the formula (22) in the presence of solvent such as ethanol, methanol, tetrahydrofuran, 1,4-dioxane, toluene, benzene, and the like, optionally with heating, optionally with microwave irradiation. The resulting material is then heated in a solvent such as Dowtherm, biphenyl, diphenyl oxide, and the like, optionally with microwave irradiation to provide a compound of the formula (23). A compound of the formula (23) is reacted with phosphorous oxychloride optionally in the presence of a solvent such as tetrahydrofuran, 1,4-dioxane, toluene, benzene, 1,2-dichloroethane and the like, optionally with heating, optionally with microwave irradiation to provide a compound of the formula (24). A compound of the formula (24) is reacted with iron in the presence of an acid such as acetic acid, hydrochloric acid, sulfuric acid, and the like, optionally with heating, optionally with microwave irradiation to provide a compound of the formula (25).

A compound of the formula (24) is reacted with a compound of the formula (26) in a solvent such as methanol, ethanol, isopropanol, N,N-dimethylformamide, N,N-dimethylacetamide, tetrahydrofuran, 1,4-dioxane, and the like optionally with heating, optionally with microwave irradiation to provide a compound of the formula (27). A compound of the formula (27) was reacted with platinum on carbon doped with nitrogen in a solvent such as methanol, ethanol, isopropanol, tetrahydrofuran, 1,4-dioxane, and the like to provide a compound of the formula (28).

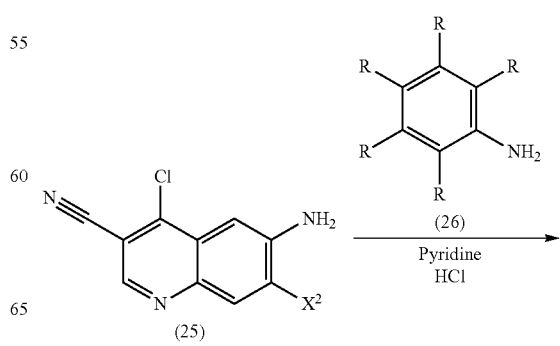

-continued

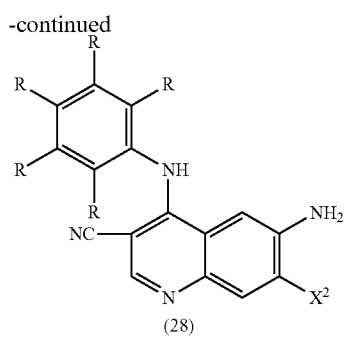
(28)

A compound of the formula (25) is reacted with a compound of the formula (26) in a solvent such as methanol, ethanol, isopropanol, N,N-dimethylformamide, N,N-dimethylacetamide, tetrahydrofuran, 1,4-dioxane, and the like in the presence of pyridine hydrochloride, optionally with heating, optionally with microwave irradiation to provide a compound of the formula (28).

Scheme 9

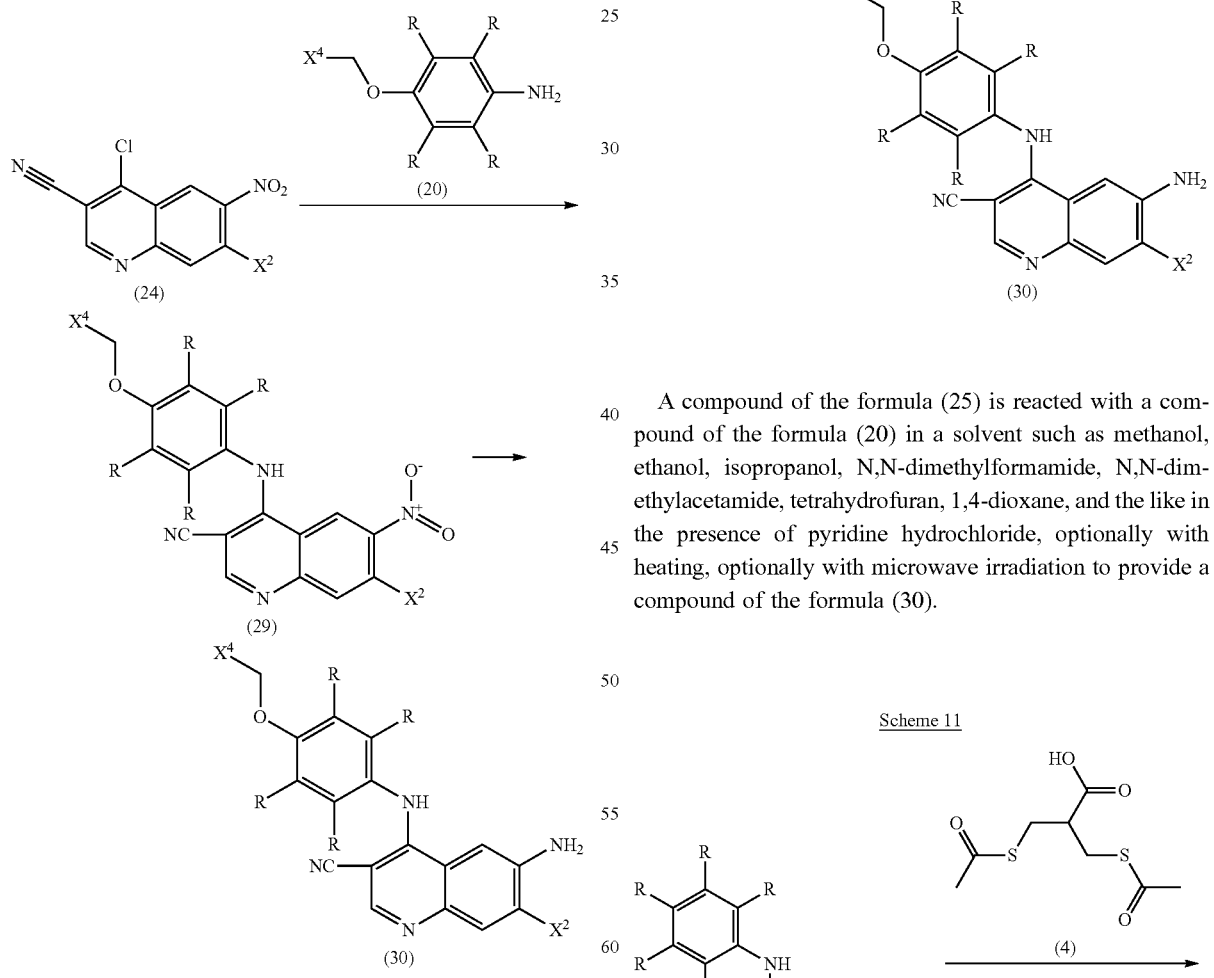

A compound of the formula (24) is reacted with a compound of the formula (20) in a solvent such as methanol, ethanol, isopropanol, N,N-dimethylformamide, N,N-dimethylacetamide, tetrahydrofuran, 1,4-dioxane, and the like optionally with heating, optionally with microwave irradiation to provide a compound of the formula (29). A compound of the formula (29) was reacted with platinum on carbon doped with nitrogen in a solvent such as methanol, ethanol, isopropanol, tetrahydrofuran, 1,4-dioxane, and the like to provide a compound of the formula (30).

Scheme 10

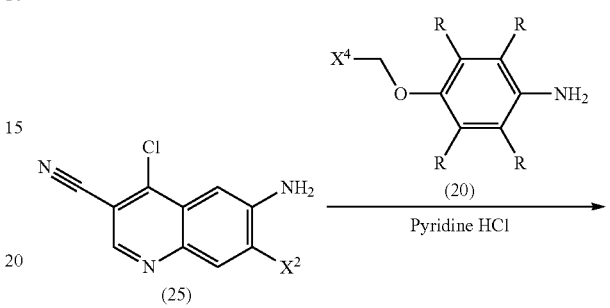

A compound of the formula (25) is reacted with a compound of the formula (20) in a solvent such as methanol, ethanol, isopropanol, N,N-dimethylformamide, N,N-dimethylacetamide, tetrahydrofuran, 1,4-dioxane, and the like in the presence of pyridine hydrochloride, optionally with heating, optionally with microwave irradiation to provide a compound of the formula (30).

Scheme 11

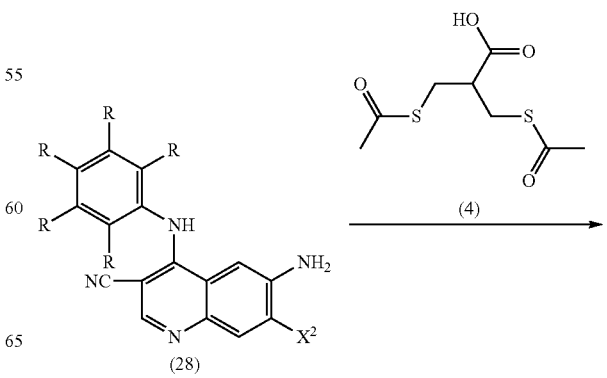

-continued

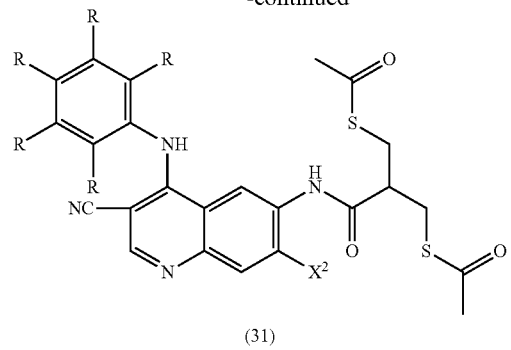
(31)

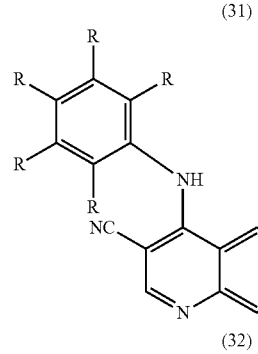
(32)

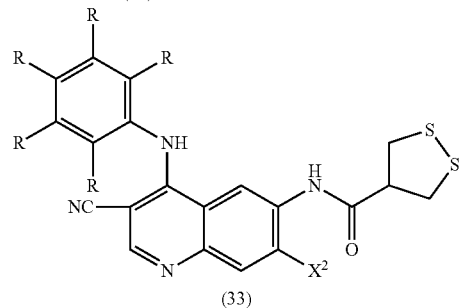
(33)

A compound of the formula (28) is reacted with a compound of the formula (4) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyluronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (31). A compound of the formula (31) is reacted with a hydride reagent such as sodium borohydride, lithium borohydride, sodium cyanoborohydride and the like in the presence of a solvent such as N-methylpyrrolidone, N,N-dimethylformamide, N,N-dimethylacetamide, tetrahydrofuran, 1,4-dioxane, and the like, optionally with heating, optionally with microwave irradiation to provide a compound of the formula (32). A compound of the formula (32) is heated in a solvent such as dimethylsulfoxide, N-methylpyrrolidone, N,N-dimethylformamide, N,N-dimethylacetamide, and the like to provide a compound of the formula (33).

Scheme 12

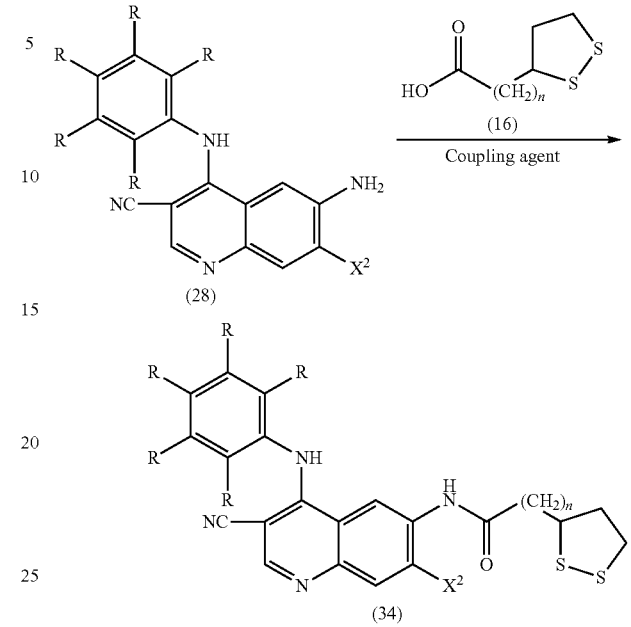
(28)
(34)

A compound of the formula (28) is reacted with a compound of the formula (16) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyluronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (34).

Scheme 13

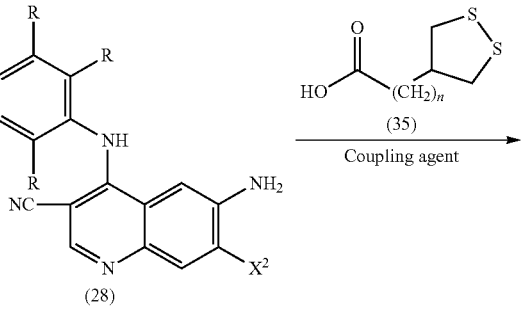
(28)

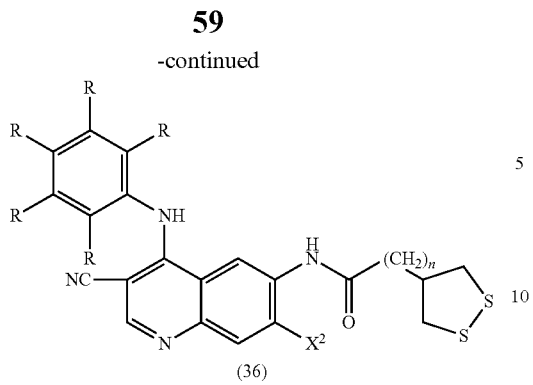
(36)

A compound of the formula (28) is reacted with a compound of the formula (35) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyluronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (36).

Scheme 14

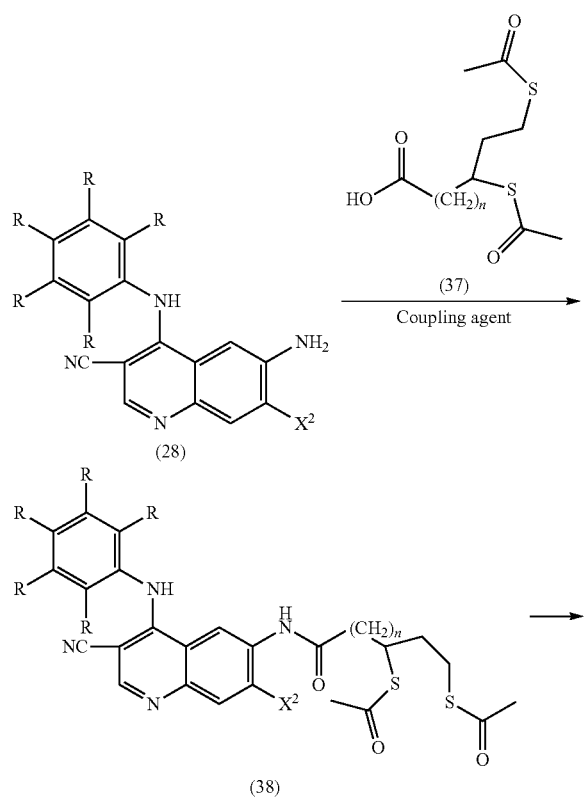

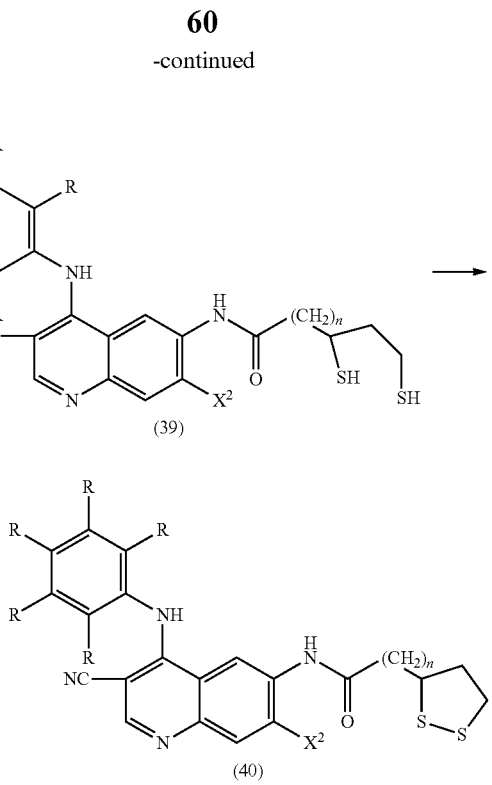

A compound of the formula (28) is reacted with a compound of the formula (37) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyluronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (38). A compound of the formula (38) is reacted with a hydride reagent such as sodium borohydride, lithium borohydride, sodium cyanoborohydride and the like in the presence of a solvent such as N-methylpyrrolidone, N,N-dimethylformamide, N,N-dimethylacetamide, tetrahydrofuran, 1,4-dioxane, and the like, optionally with heating, optionally with microwave irradiation to provide a compound of the formula (39). A compound of the formula (39) is heated in a solvent such as dimethylsulfoxide, N-methylpyrrolidone, N,N-dimethylformamide, N,N-dimethylacetamide, and the like to provide a compound of the formula (40).

Scheme 15

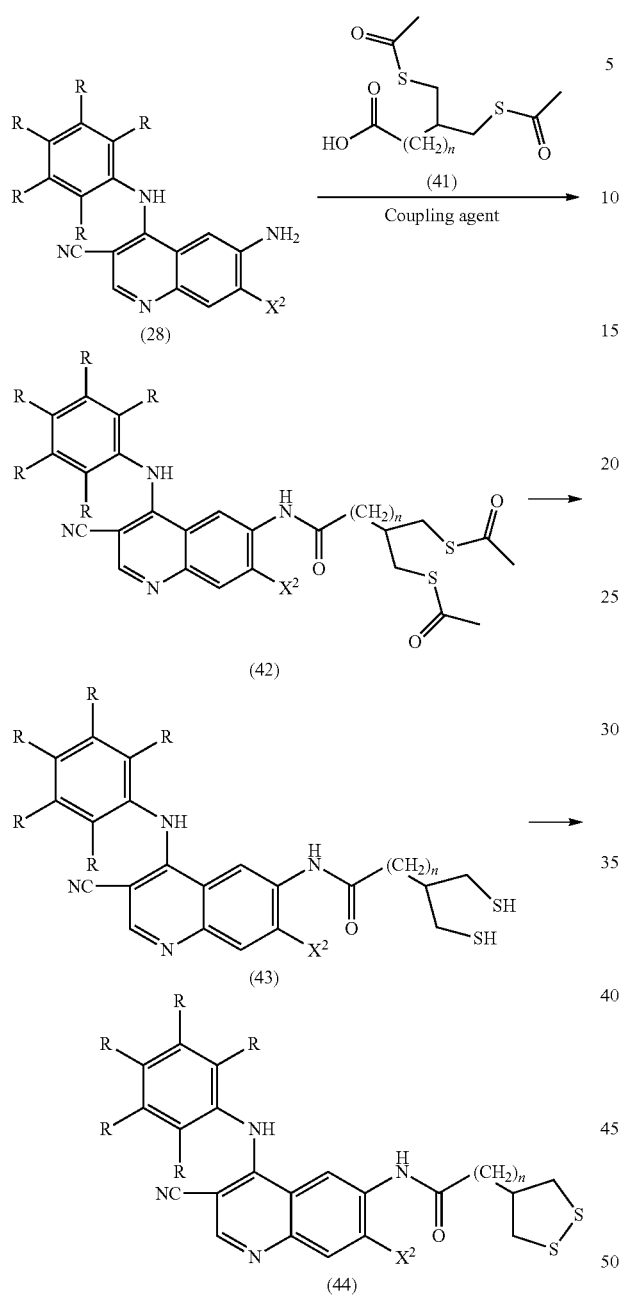

A compound of the formula (28) is reacted with a compound of the formula (41) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyluronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (42). A compound of the formula (42) is reacted with a hydride reagent such as sodium borohydride, lithium borohydride, sodium cyanoborohydride and the like in the presence of a solvent such as N-methylpyrrolidone, N,N-dimethylformamide, N,N-dimethylacetamide, tetrahydrofuran, 1,4-dioxane, and the like, optionally with heating, optionally with microwave irradiation to provide a compound of the formula (43). A compound of the formula (43) is heated in a solvent such as dimethylsulfoxide, N-methylpyrrolidone, N,N-dimethylformamide, N,N-dimethylacetamide, and the like to provide a compound of the formula (44).

Scheme 16

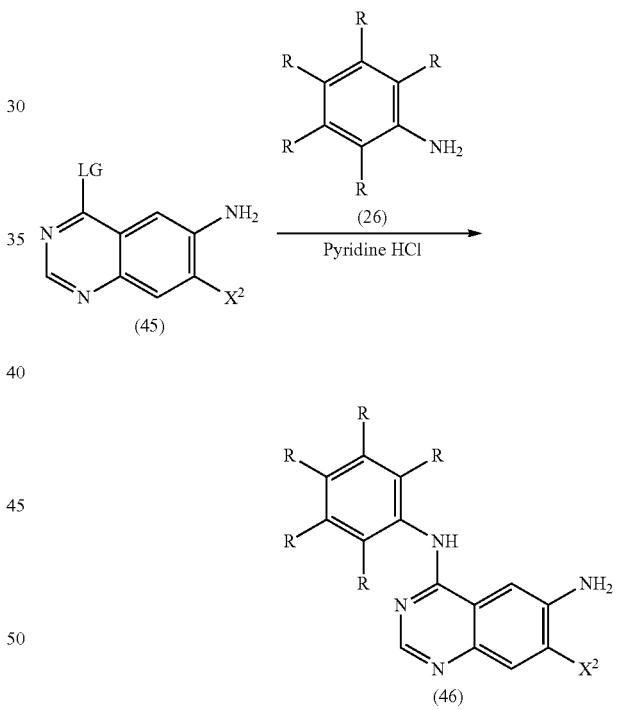

A compound of the formula (45), a known compound of a compound prepared by known methods wherein LG is a leaving group such as chlorine, bromine, iodine, mesylate, tosylate and the like, is reacted with a compound of the formula (26) in a solvent such as methanol, ethanol, isopropanol, N,N-dimethylformamide, N,N-dimethylacetamide, tetrahydrofuran, 1,4-dioxane, and the like in the presence of pyridine hydrochloride, optionally with heating, optionally with microwave irradiation to provide a compound of the formula (46).

Scheme 17

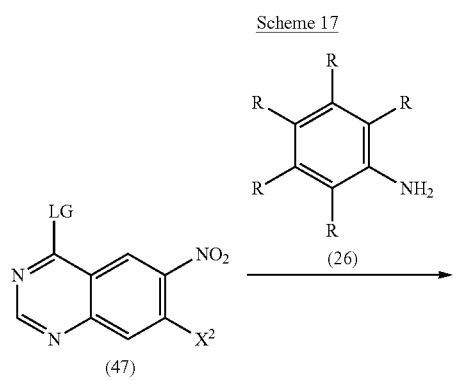

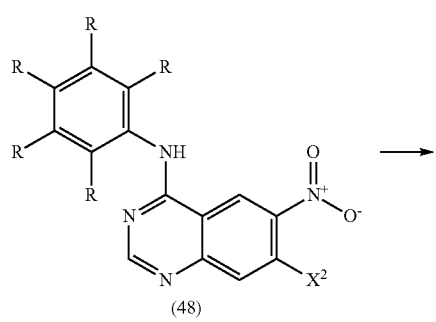

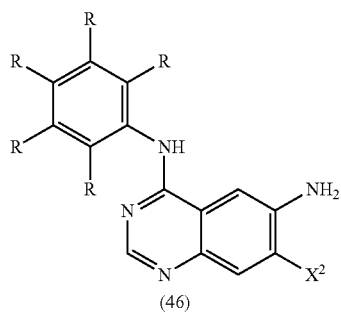

A compound of the formula (47), a known compound of a compound prepared by known methods wherein LG is a leaving group such as chlorine, bromine, iodine, mesylate, tosylate and the like, is reacted with a compound of the formula (26) in a solvent such as methanol, ethanol, isopropanol, N,N-dimethylformamide, N,N-dimethylacetamide, tetrahydrofuran, 1,4-dioxane, and the like optionally with heating, optionally with microwave irradiation to provide a compound of the formula (48). A compound of the formula (48) was reacted with platinum on carbon doped with nitrogen in a solvent such as methanol, ethanol, isopropanol, tetrahydrofuran, 1,4-dioxane, and the like to provide a compound of the formula (46).

Scheme 18

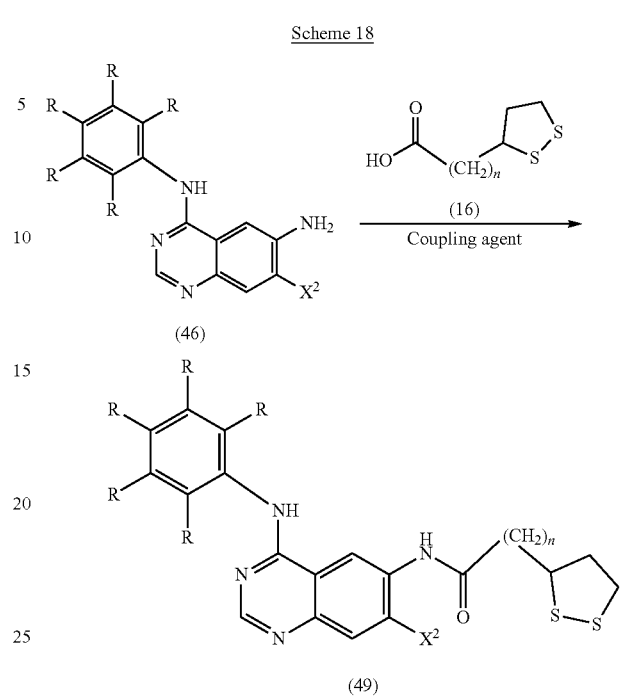

A compound of the formula (46) is reacted with a compound of the formula (16) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyluronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (49).

Scheme 19

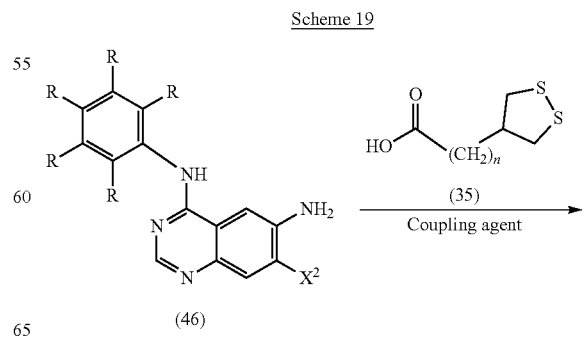

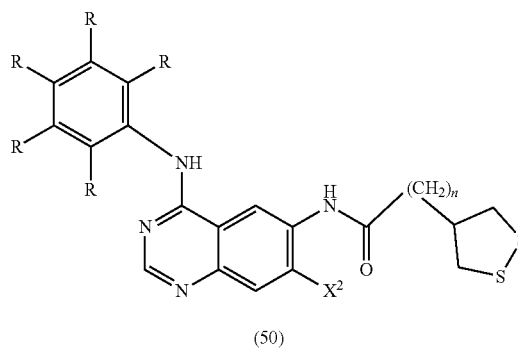

(50)

A compound of the formula (46) is reacted with a compound of the formula (35) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (50).

Scheme 20

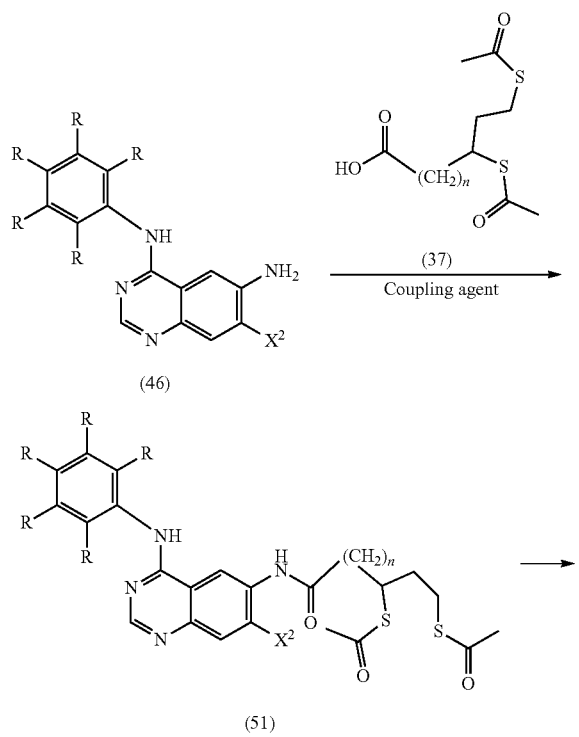

(46)

(51)

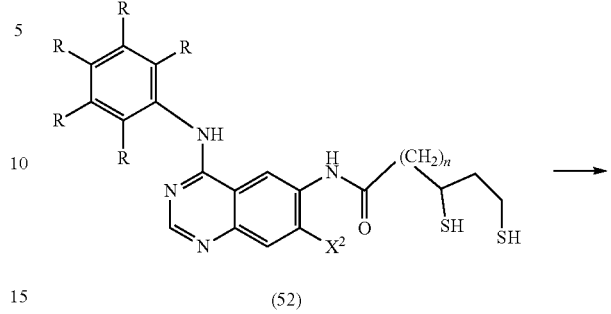

(52)

(53)

A compound of the formula (46) is reacted with a compound of the formula (37) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidino-phosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (51). A compound of the formula (51) is reacted with a hydride reagent such as sodium borohydride, lithium borohydride, sodium cyanoborohydride and the like in the presence of a solvent such as N-methylpyrrolidone, N,N-dimethylformamide, N,N-dimethylacetamide, tetrahydrofuran, 1,4-dioxane, and the like, optionally with heating, optionally with microwave irradiation to provide a compound of the formula (52). A compound of the formula (52) is heated in a solvent such as dimethylsulfoxide, N-methylpyrrolidone, N,N-dimethylformamide, N,N-dimethylacetamide, and the like to provide a compound of the formula (53).

Scheme 21

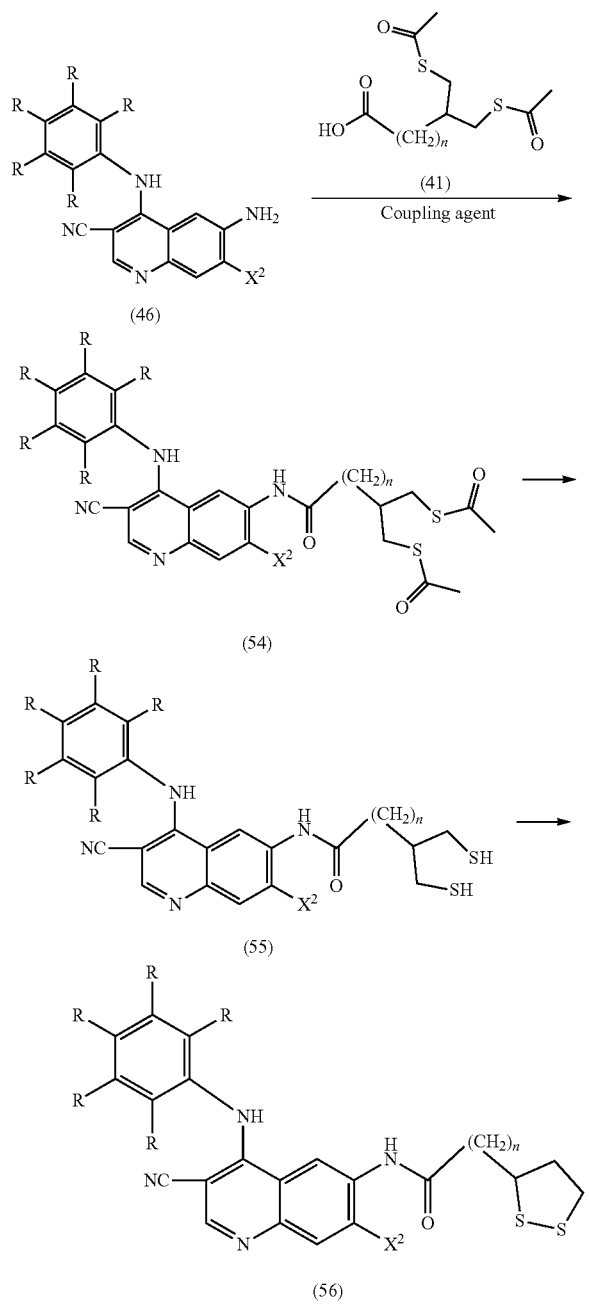

Scheme 22

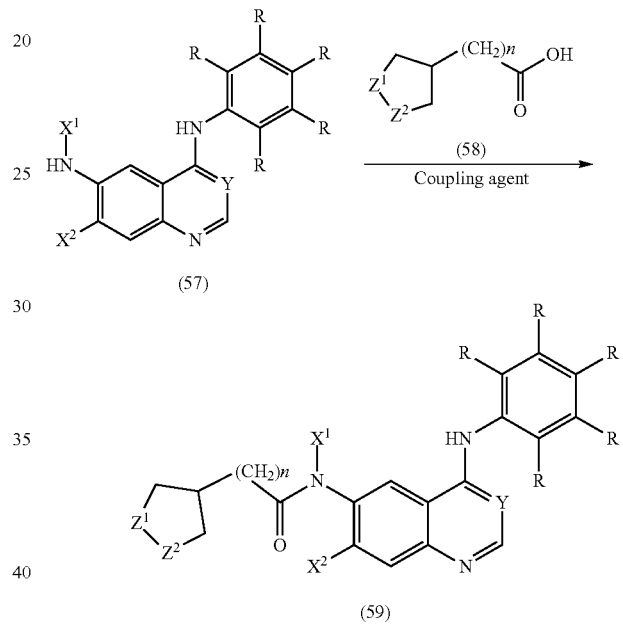

A compound of the formula (46) is reacted with a compound of the formula (41) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (54). A compound of the formula (54) is reacted with a hydride reagent such as sodium borohydride, lithium borohydride, sodium cyanoborohydride and the like in the presence of a solvent such as N-methylpyrrolidone, N,N-dimethylformamide, N,N-dimethylacetamide, tetrahydrofuran, 1,4-dioxane, and the like, optionally with heating, optionally with microwave irradiation to provide a compound of the formula (55). A compound of the formula (55) is heated in a solvent such as dimethylsulfoxide, N-methylpyrrolidone, N,N-dimethylformamide, N,N-dimethylacetamide, and the like to provide a compound of the formula (56).

A compound of the formula (57) is reacted with a compound of the formula (58), a known compound or compound prepared by known methods, in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N', N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (59).

Scheme 23

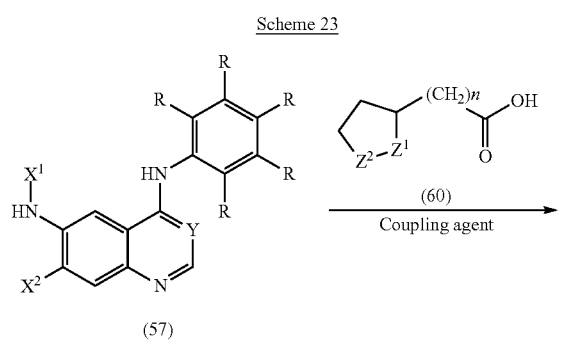

(57)

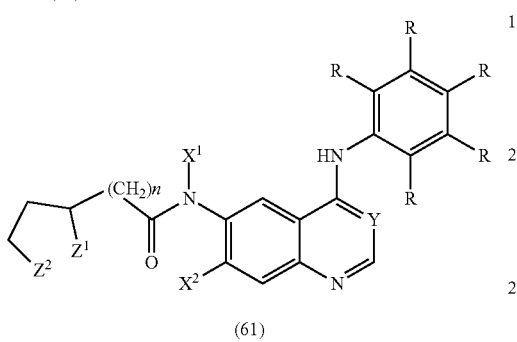

(61)

A compound of the formula (57) is reacted with a compound of the formula (60), a known compound or compound prepared by known methods, in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (61).

Scheme 24

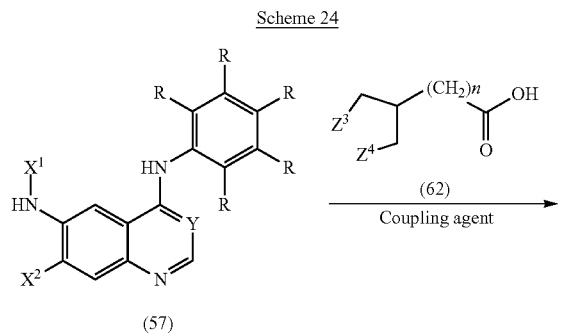

(57)

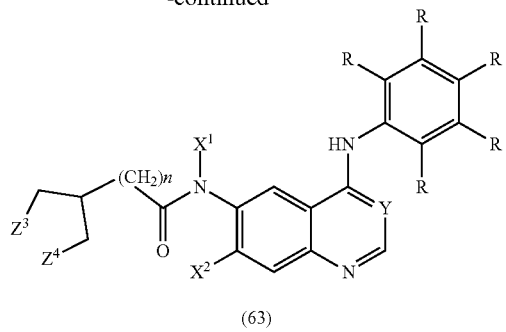

(63)

A compound of the formula (57) is reacted with a compound of the formula (62), a known compound or compound prepared by known methods, in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (63).

Scheme 25

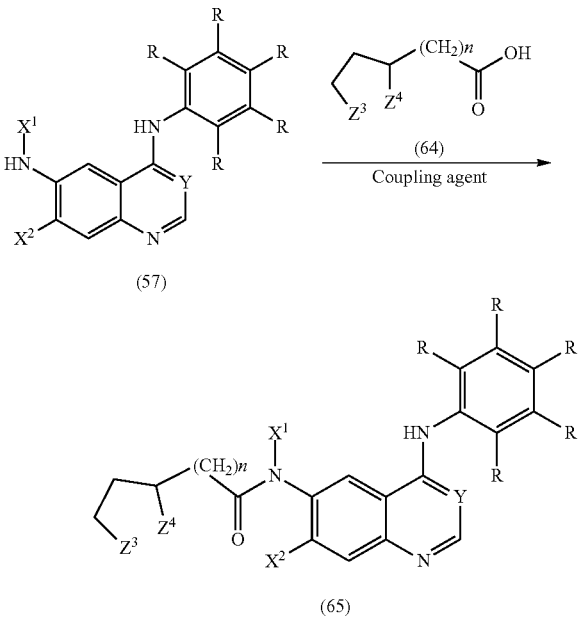

A compound of the formula (57) is reacted with a compound of the formula (64), a known compound or compound prepared by known methods, in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (65).

furan, ether, 1,4-dioxane, acetone, acetonitrile, N,N-dimethylformamide, and the like, optionally with heating, optionally with microwave irradiation to provide compounds of the formula (67), (68), (69), (70), (71), (72), and (73). Alternatively, a formula of the compound (66) is reacted with an oxidoreductase such as Baeyer-Villiger monooxygenase, cytochrome P450 2C9, cytochrome P450 2C19, cytochrome P450 3A4 and, in a solvent such as water, methanol, ethanol, isopropanol, acetonitrile, acetone, and the like, optionally with heating, optionally with microwave irradiation to provide compounds of the formula (67), (68), (69), (70), (71), (72), and (73). Alternatively, a compound of the formula (66) is reacted with hydrogen peroxide in the presence titanium (IV) isopropoxide-diethyltartarate,

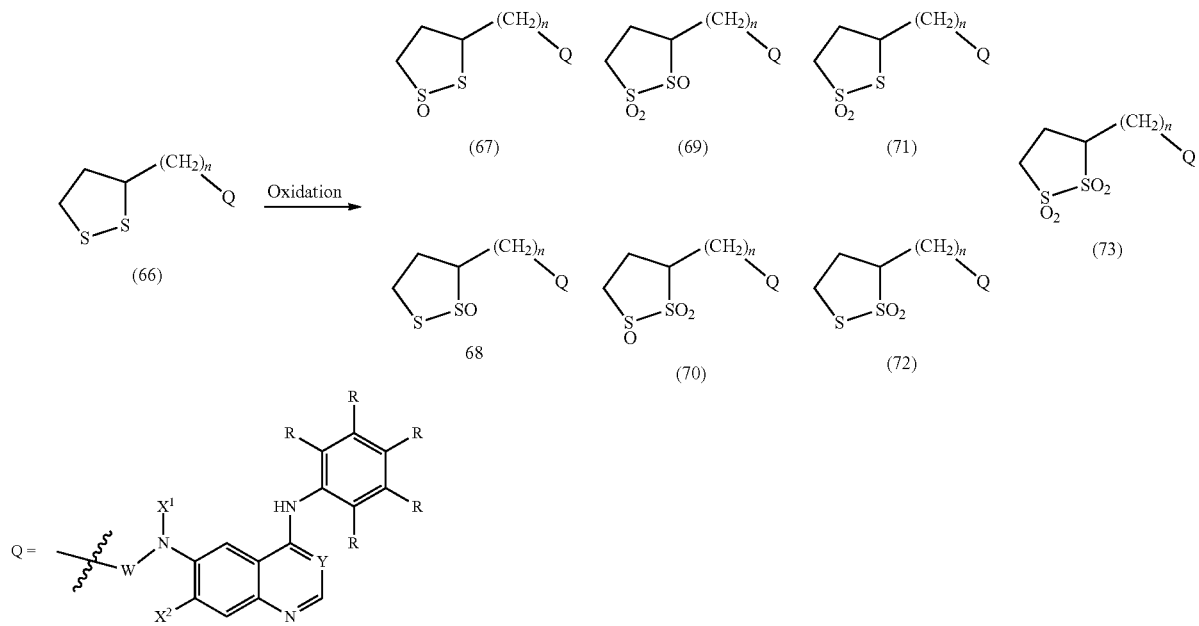

A compound of the formula (66) is reacted with an oxidizing agent such as m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, and the like, in the presence of a solvent such as tetrahydrofuran, ether, 1,4-dioxane, acetone, acetonitrile, methanol, ethanol, isopropanol, water, and the like, optionally with heating, optionally with microwave irradiation to provide compounds of the formula (67), (68), (69), (70), (71), (72), and (73). Alternatively, a formula of the compound (66) is reacted with a sulfoxide such as diphenyl sulfoxide, dimethyl sulfoxide, and the like, in the presence of a rhenium catalyst such as ReOCl$_3$(PPh$_3$)$_2$, and the like, in a solvent such as methylene chloride, 1,2-dichloroethane, chloroform, tetrahydrofuran, ether, 1,4-dioxane, acetone, acetonitrile, and the like, optionally with heating, optionally with microwave irradiation to provide compounds of the formula (67), (68), (69), (70), (71), (72), and (73). Alternatively, a formula of the compound (66) is reacted with a urea hydrogen peroxide complex in the presence of a rhenium catalyst such as ReOCl$_3$(PPh$_3$)$_2$, and the like, in a solvent such as methylene chloride, 1,2-dichloroethane, chloroform, tetrahydrooptionally in the presence of an amino alcohol such as 2-amino-3-phenylpropan-1-ol, 2-amino-4-methylpentan-1-ol, 2-amino-4-(methylthio)butan-1-ol, 2-aminopropan-1-ol, and the like, in a solvent such as methylene chloride, 1,2-dichloroethane, chloroform, tetrahydrofuran, ether, 1,4-dioxane, acetone, acetonitrile, N,N-dimethylformamide, and the like optionally with heating, optionally with microwave irradiation to provide compounds of the formula (67), (68), (69), (70), (71), (72), and (73). Alternatively, a compound of the formula of the compound (66) is electrochemically oxidized optionally in the presence of a buffer solution such as a sodium phosphate solution, a potassium phosphate solution, and the like to provide compounds of the formula (67), (68), (69), (70), (71), (72), and (73). Alternatively, a compound of the formula of the compound (66) is photochemically oxidized in a solvent such as methylene chloride, 1,2-dichloroethane, chloroform, tetrahydrofuran, ether, 1,4-dioxane, acetone, acetonitrile, N,N-dimethylformamide, water, methanol, ethanol, isopropanol, and the like, optionally with heating, optionally with microwave irradiation to provide compounds of the formula (67), (68), (69), (70), (71), (72), and (73). It is understood that one skilled in the art would readily understand that the ratio of products (67) through (73) will be controlled by the amount of oxidant added and would adjust the amount of oxidant accordingly to produce the desired ration of products.

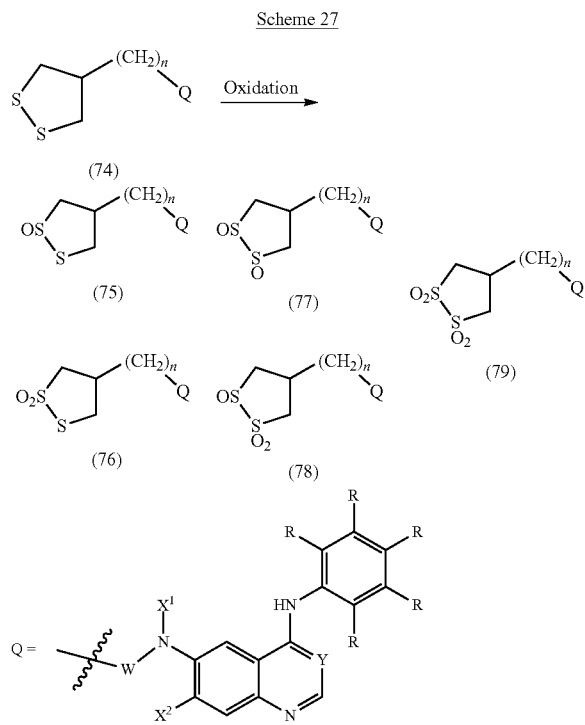

Scheme 27

A compound of the formula (74) is reacted with an oxidizing agent such as m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, and the like, in the presence of a solvent such as tetrahydrofuran, ether, 1,4-dioxane, acetone, acetonitrile, methanol, ethanol, isopropanol, water, and the like, optionally with heating, optionally with microwave irradiation to provide compounds of the formula (75), (76), (77), (78), and (79). Alternatively, a formula of the compound (74) is reacted with a sulfoxide such as diphenyl sulfoxide, dimethyl sulfoxide, and the like, in the presence of a rhenium catalyst such as ReOCl$_3$(PPh$_3$)$_2$, and the like, in a solvent such as methylene chloride, 1,2-dichloroethane, chloroform, tetrahydrofuran, ether, 1,4-dioxane, acetone, acetonitrile, and the like, optionally with heating, optionally with microwave irradiation to provide compounds of the formula (75), (76), (77), (78), and (79). Alternatively, a formula of the compound (74) is reacted with a urea hydrogen peroxide complex in the presence of a rhenium catalyst such as ReOCl$_3$ (PPh$_3$)$_2$, and the like, in a solvent such as methylene chloride, 1,2-dichloroethane, chloroform, tetrahydrofuran, ether, 1,4-dioxane, acetone, acetonitrile, N,N-dimethylformamide, and the like, optionally with heating, optionally with microwave irradiation to provide compounds of the formula (75), (76), (77), (78), and (79). Alternatively, a formula of the compound (74) is reacted with an oxidoreductase such as Baeyer-Villiger monooxygenase, cytochrome P450 2C9, cytochrome P450 2C19, cytochrome P450 3A4 and, in a solvent such as water, methanol, ethanol, isopropanol, acetonitrile, acetone, and the like, optionally with heating, optionally with microwave irradiation to provide compounds of the (75), (76), (77), (78), and (79). Alternatively, a compound of the formula (74) is reacted with hydrogen peroxide in the presence titanium (IV) isopropoxide-diethyltartarate, optionally in the presence of an amino alcohol such as 2-amino-3-phenylpropan-1-ol, 2-amino-4-methylpentan-1-ol, 2-amino-4-(methylthio)butan-1-ol, 2-aminopropan-1-ol, and the like, in a solvent such as methylene chloride, 1,2-dichloroethane, chloroform, tetrahydrofuran, ether, 1,4-dioxane, acetone, acetonitrile, N,N-dimethylformamide, and the like optionally with heating, optionally with microwave irradiation to provide compounds of the formula (75), (76), (77), (78), and (79). Alternatively, a compound of the formula of the compound (74) is electrochemically oxidized optionally in the presence of a buffer solution such as a sodium phosphate solution, a potassium phosphate solution, and the like to provide compounds of the formula (75), (76), (77), (78), and (79). Alternatively, a compound of the formula of the compound (74) is photochemically oxidized in a solvent such as methylene chloride, 1,2-dichloroethane, chloroform, tetrahydrofuran, ether, 1,4-dioxane, acetone, acetonitrile, N,N-dimethylformamide, water, methanol, ethanol, isopropanol, and the like, optionally with heating, optionally with microwave irradiation to provide compounds of the formula (75), (76), (77), (78), and (79). It is understood that one skilled in the art would readily understand that the ratio of products (75) through (79) will be controlled by the amount of oxidant added and would adjust the amount of oxidant accordingly to produce the desired ration of products.

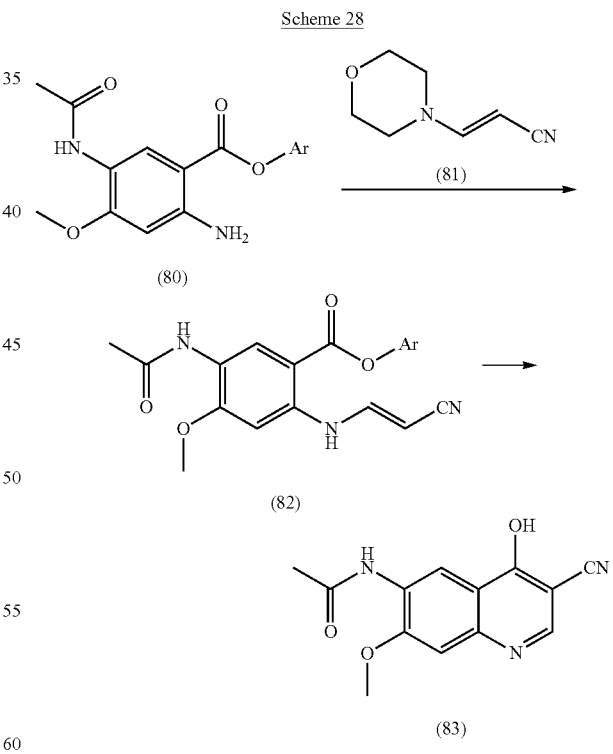

Scheme 28

A compound of the formula (80), a known compound or a compound prepared by known means wherein Ar is an optionally substituted aryl ring, is reacted with a compound of the formula (81) in the presence of on an acid such as acetic acid, formic acid, trifluoroacetic acid, hydrochloric acid, and the like, optionally in a solvent such as methanol, ethanol, isopropanol, water, N,N-dimethylformamide, N,N-dimethylacetamide, tetrahydrofuran, 1,4-dioxane, and the like, optionally with heating, optionally with microwave irradiation to provide a compound of the formula (82). A compound of the formula (82) is reacted a base such as sodium methoxide, sodium ethoxide, lithium methoxide, lithium ethoxide, lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like in the presence of a solvent such as methanol, ethanol, methylene chloride, chloroform, 1,2-dichloroethane, tetrahydrofuran, 1,4-dioxane, N,N-dimethylformamide, dimethylsulfoxide, and the like, optionally with heating, optionally with microwave irradiation to provide a compound of the formula (83).

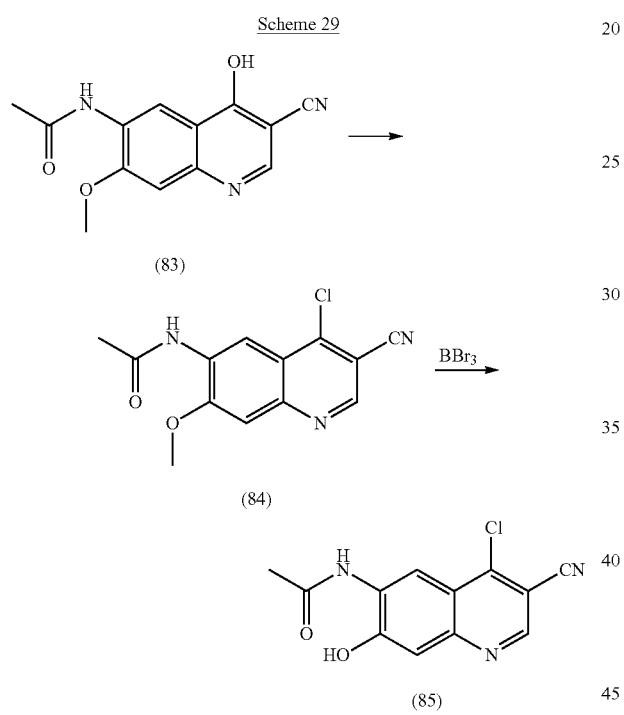

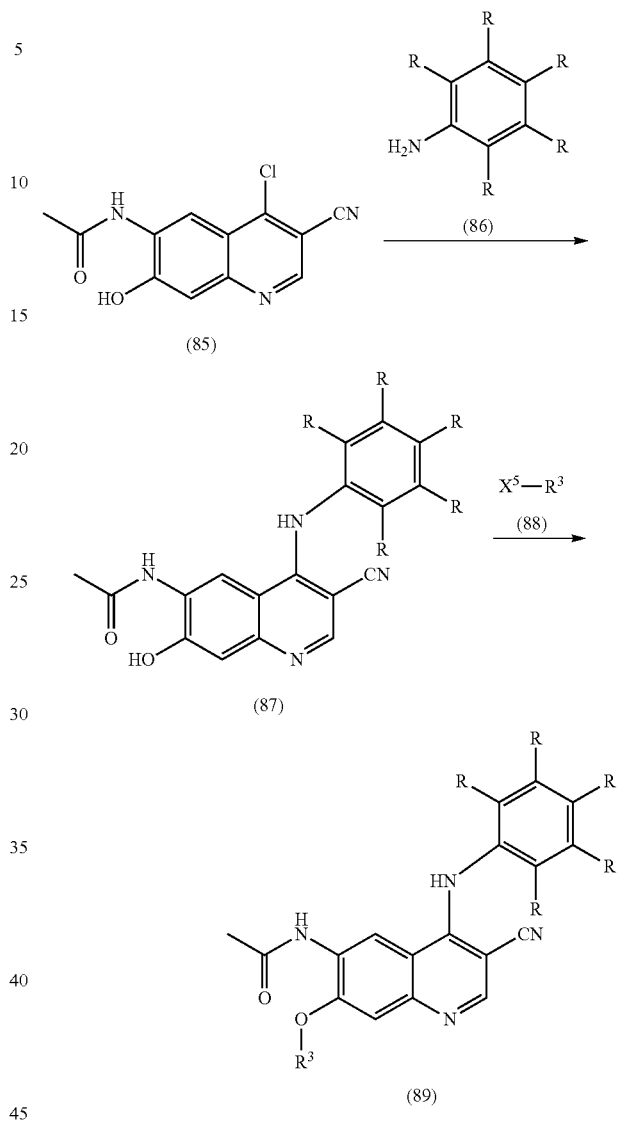

A compound of the formula (83) is reacted with phosphorous oxychloride or thionyl chloride in the presence of a base such as pyridine, 2,6-lutidine, triethylamine, diisopropylethylamine, and the like, optionally in the presence of a solvent such as N,N-dimethylformamide, N,N-dimethylacetamide, tetrahydrofuran, 1,4-dioxane, toluene, methylene chloride, 1,2-dichloroethane, chloroform, and the like, optionally with heating, optionally with microwave irradiation to provide a compound of the formula (84). A compound of the formula (84) is reacted with boron tribromide in the presence of a solvent such as N,N-dimethylformamide, N,N-dimethylacetamide, tetrahydrofuran, 1,4-dioxane, toluene, methylene chloride, 1,2-dichloroethane, chloroform, and the like, optionally with heating, optionally with microwave irradiation to provide a compound of the formula (85).

A compound of the formula (85) is reacted with a compound of the formula (86) in a solvent such as methanol, ethanol, isopropanol, N,N-dimethylformamide, N,N-dimethylacetamide, tetrahydrofuran, 1,4-dioxane, and the like optionally with heating, optionally with microwave irradiation to provide a compound of the formula (87). A compound of the formula (87) is reacted with a compound of the formula (88), a known compound or a compound prepared by known methods wherein $X^5$ is a leaving group such as chlorine, bromine, iodine, mesylate, tosylate, and the like, in the presence of a base such as sodium carbonate, cesium carbonate, lithium carbonate, potassium carbonate, potassium hydroxide, sodium hydroxide, lithium hydroxide, and the like, in a solvent such as as N,N-dimethylformamide, N,N-dimethylacetamide, tetrahydrofuran, 1,4-dioxane, toluene, methylene chloride, 1,2-dichloroethane, chloroform, and the like, optionally with heating, optionally with microwave irradiation to provide a compound of the formula (89).

Scheme 31

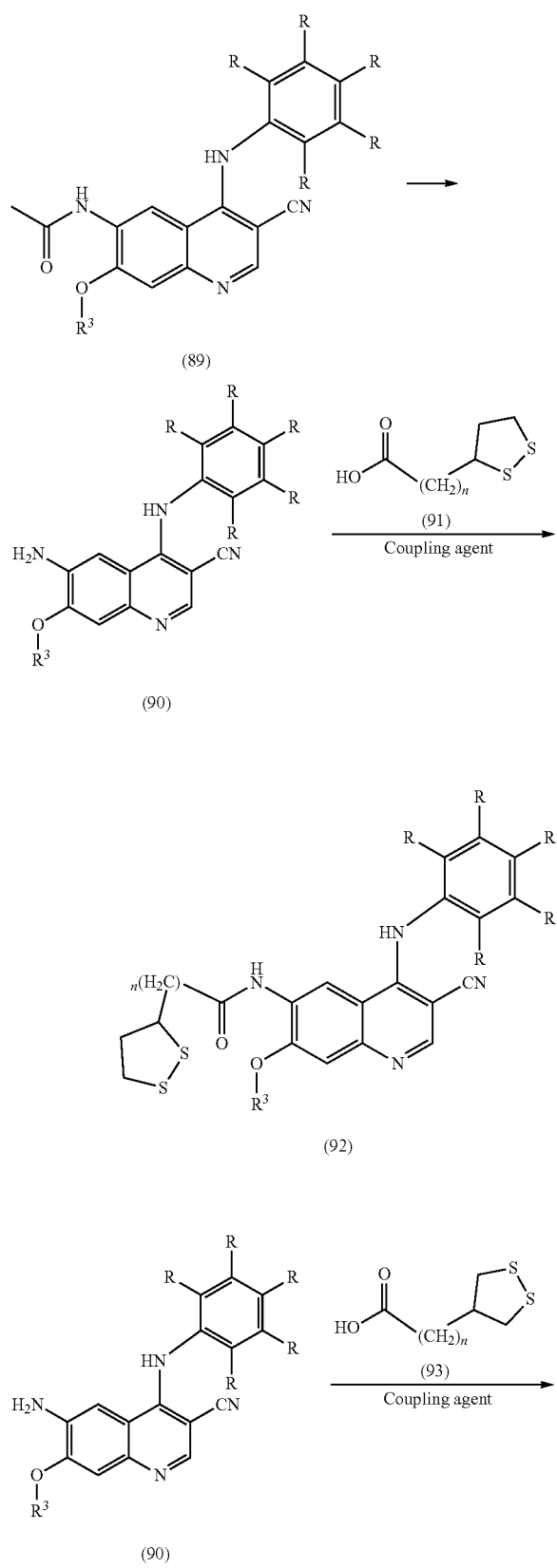
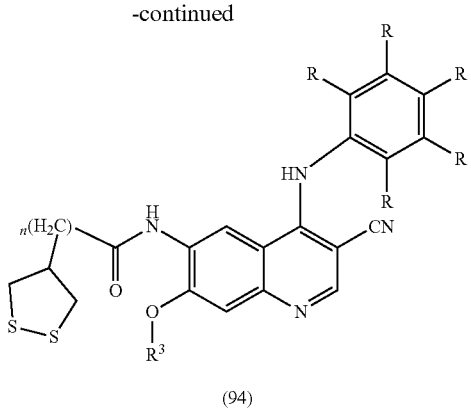

A compound of the formula (89) is reacted with a base such as potassium hydroxide, sodium hydroxide, lithium hydroxide, and the like, in a solvent such as methanol, ethanol, isopropanol, N,N-dimethylformamide, N,N-dimethylacetamide, tetrahydrofuran, 1,4-dioxane, and the like optionally with heating, optionally with microwave irradiation to provide a compound of the formula (90). A compound of the formula (90) is reacted with a compound of the formula (91) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (92). Alternatively, a compound of the formula (90) is reacted with a compound of the formula (93) in a solvent such as N-methylpyrrolidone, N,N-dimethylformamide, N,N-dimethylacetamide, tetrahydrofuran, 1,4-dioxane, and the like, the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (94).

Scheme 32

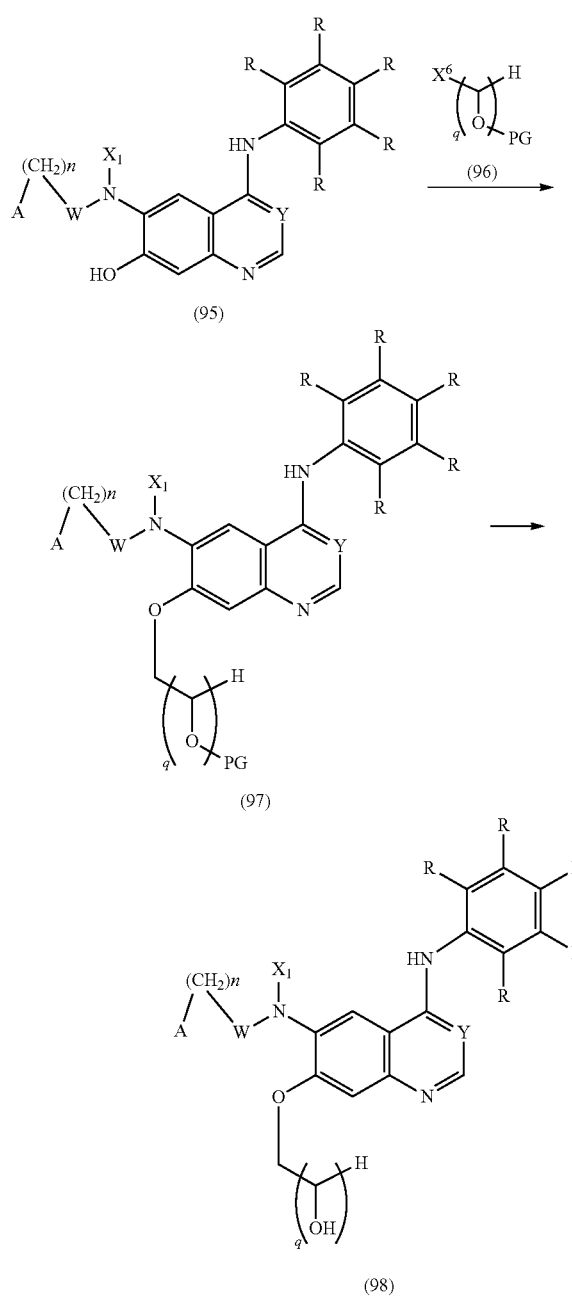

A compound of the formula (95) is reacted with a compound of the formula (96), a known compound or a compound prepared by known methods wherein $X^6$ is a leaving group such as chlorine, bromine, iodine, mesylate, tosylate, and the like and PG is a protecting group, in the presence of a base such as sodium carbonate, cesium carbonate, lithium carbonate, potassium carbonate, potassium hydroxide, sodium hydroxide, lithium hydroxide, and the like, in a solvent such as as N,N-dimethylformamide, N,N-dimethylacetamide, tetrahydrofuran, 1,4-dioxane, toluene, methylene chloride, 1,2-dichloroethane, chloroform, and the like, optionally with heating, optionally with microwave irradiation to provide a compound of the formula (97). A compound of the formula (97) is reacted with an acid such as acetic acid, trifluoroacetic acid, hydrochloric acid, and the like, in the presence of a solvent such as methanol, ethanol, methylene chloride, chloroform, 1,2-dichloroethane, tetrahydrofuran, 1,4-dioxane, N,N-dimethylformamide, dimethylsulfoxide, and the like, optionally with heating, optionally with microwave irradiation to provide a compound of the formula (98). Alternatively, a compound of the formula (97) is reacted with hydrogen in the presence of a palladium catalyst such as palladium on carbon, palladium acetate, palladium bis(triphenylphosphine) dichloride, palladium tetrakis(triphenylphosphine), bis(acetonitrile) dichloropalladium [1,1'-bis(diphenylphosphino), ferrocene]dichloropalladium, and the like, in the presence of a solvent such as methanol, ethanol, methylene chloride, chloroform, 1,2-dichloroethane, tetrahydrofuran, 1,4-dioxane, N,N-dimethylformamide, dimethylsulfoxide, and the like, to provide a compound of the formula (98). Alternatively, A compound of the formula (97) is reacted with a base such as piperidine, triethylamine, N,N-diisopropyl ethylamine, and the like, in the presence of a solvent such as methanol, ethanol, methylene chloride, chloroform, 1,2-dichloroethane, tetrahydrofuran, 1,4-dioxane, N,N-dimethylformamide, dimethylsulfoxide, and the like, optionally with heating, optionally with microwave irradiation to provide a compound of the formula (98).

The following examples are directed to the preparations of intermediates used to prepare compounds of formula (I) and compounds (I) of this invention are provided as a guide to assist in the practice of this invention.

Example 1: 2-((Acetylthio)methyl)acrylic acid

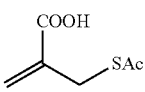

To a stirred suspension of 2-(bromomethyl)acrylic acid (8.0 g, 49 mmol) in water (160 mL) was added a solution of $Na_2CO_3$ (9 g in 32 mL of water) in small portions at 0° C. To the resulting solution was added thiolacetic acid (3.5 mL) and stirred at 0° C. for 30 minutes. The solution was acidified with concentrated hydrochloric acid to pH 1. The residue was extracted with ethyl acetate (3×500 ml). The combined extracts were dried over anhydrous $Na_2SO_4$ and evaporated to dryness to furnish the desired crude product. The pure product was obtained by column chromatography on silica gel (100-200 mesh) eluting with 5% (v/v) ethyl acetate in hexanes as a white solid (3.7 g, yield 47%). $^1$H-NMR (300 MHz, $CDCl_3$): δ 8.35 (bs, 1H), 6.40 (s, 1H), 6.03 (s, 1H), 3.80 (s, 2H), 2.34 (s, 3H).

Example 2:
3-(Acetylthio)-2-((acetylthio)methyl)propanoic acid

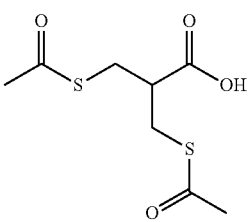

Method A. A mixture of 2-((acetylthio)methyl)acrylic acid (3.50 g, 21.9 mmol) in thiolacetic acid (3.1 mL) was stirred at room temperature for 16 hours. The reaction mixture was concentrated at reduced pressure to remove the thiolacetic acid and purified by column chromatography on silica gel (100-200 mesh) eluting with 10% (v/v) ethyl acetate in hexanes to produce the product as colorless liquid (2.3 g, yield 45%). $^1$H-NMR (300 MHz, CDCl$_3$): δ 7.27 (bs, 1H), 3.24-3.14 (m, 4H), 2.93-2.89 (m, 1H), 2.35 (s, 6H).

Method B. A mixture of 3-bromo-2-(bromomethyl)propanoic acid (12.0 g, 48.9 mmol) in 46 mL water containing 3.2 g of KOH was cooled to 0° C. Thioacetic acid (7.5 mL, 102 mmol) was added dropwise and the resultant solution was stirred for 5 minutes before the slow addition of a solution containing 6.8 g of KOH in 61 mL water. The reaction mixture was heated for 12 hours at 110° C. then cooled to 0° C. and carefully acidified with 4N HCl to reach pH 2. It was then extracted with ethyl acetate (3×200 mL) and the combined extracts were dried over anhydrous Na$_2$SO$_4$, filtered and concentrated to give an oil which was purified by column chromatography on silica gel (100-200 mesh) eluting with 10% (v/v) ethyl acetate in hexane to produce the title compound as colorless liquid (5.0 g, yield 43.4%). $^1$H-NMR (CDCl$_3$): δ 6.0-5.0 (s, br, 1H), 3.26-3.18 (m, 4H), 2.92-2.83 (m, 1H), 2.35 (s, 6H).

Example 3: 3-Benzylsulfanyl-propionaldehyde

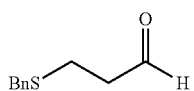

To a solution of benzylmercaptan (6.80 mL, 101 mmol) in dichloromethane (150 mL) was added acrolein (9.45 mL, 80.0 mmol) dropwise at 0° C. The resulting solution was allowed to warm up to room temperature and stirred for 2 hours. Dichloromethane was evaporated in vacuo and the residue was purified by flash column chromatography (silica gel, Ethyl acetate:hexanes, 2:98) to afford the desired compound as colorless liquid (13 g, yield 91%). $^1$H-NMR (300 MHz, DMSO-d6): δ 9.60 (s, 1H, CHO), 7.32-7.22 (m, 5H), 3.74 (s, 2H), 2.71-2.60 (m, 4H).

Example 4: 5-Benzylsulfanyl-pent-2-enoic acid ethyl ester

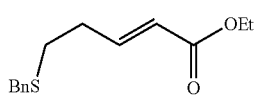

To a mixture of 3-benzylsulfanyl-propionaldehyde (13.0 g, 72.0 mmol) and monoethylmalonate (8.53 g, 72.0 mmol) in pyridine (26 mL) was added piperidine (0.32 mL) and heated to 135° C. for 2 hours. The reaction mixture was cooled to room temperature, poured into ice-cold water (200 mL) and acidified to pH 2 with 6N HCl. The aqueous layer was extracted with ethyl acetate (3×500 mL). The combined organic extracts were washed with water (200 mL) and brine (100 mL), then dried (Na$_2$SO$_4$), filtered and evaporated in vacuo. The residue was purified by flash column chromatography (silica gel, ethyl acetate:hexanes, 4:96) to afford the title compound as colorless liquid (13 g, yield 45%). $^1$H-NMR (300 MHz, DMSO-d6): δ 7.33-7.21 (m, 5H), 6.87-6.81 (dt, 1H, J=6.8 Hz and 13.6 Hz), 5.90-5.54 (dt, 1H, J=1.7 Hz and 3.4 Hz), 4.16-4.04 (m, 2H), 3.74-3.72 (s, 2H), 2.58-2.50 (m, 2H), 2.49-2.40 (m, 2H), 1.24-1.20 (m, 3H); MS (ES) m/e 251 [M+H]$^+$.

Example 5: 3,5-Bis-benzylsulfanyl-pentanoic acid ethyl ester

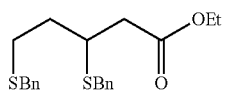

To a solution of 5-benzylsulfanyl-pent-2-enoic acid ethyl ester (8.0 g, 32 mmol) in piperidine (16.0 mL, 160 mmol) was added benzylmercaptan (4.0 g, 32 mmol) dropwise at room temperature and stirred overnight. The reaction mixture was poured into ice cold-water (500 mL) and acidified to pH 2 with 6N HCl. The aqueous layer was extracted with Ethyl acetate (3×500 mL). The combined organic extracts were washed with water (100 mL) and brine (100 mL), then dried (Na$_2$SO$_4$), filtered and evaporated in vacuo. The residue was purified by flash column chromatography (silica gel, Ethyl acetate:hexanes, 4:96) to afford the title compound as colorless oil (8.0 g, yield 67%). $^1$H-NMR (300 MHz, DMSO-d6): δ 7.32-7.22 (m, 10H), 4.07-4.02 (m, 2H), 3.72 (s, 2H), 3.67 (s, 2H), 3.02 (m, 1H), 2.58-2.56 (dd, 2H, J=6.8, 8.4 Hz), 2.54-2.42 (m, 2H), 1.78-1.71 (m, 2H), 1.18-1.15 (t, 3H, J=7.2 Hz); MS (ES) m/e 375 [M+H]$^+$.

Example 6: 3,5-Bis(benzylthio)pentanoic acid

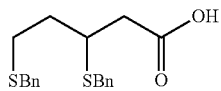

To a mixture of 3,5-bis-benzylsulfanyl-pentanoic acid ethyl ester (1.00 g, 26.7 mmol) in ethanol (4 mL) was added 10 mL of 10% NaOH and heated at 50° C. for 1 hours. The reaction mixture was cooled to room temperature followed by evaporation of ethanol. The residue was diluted with water and extracted with diethyl ether (3×70 mL). The combined aqueous extracts were acidified with 6N HCl and extracted with Ethyl acetate (3×400 mL). The combined organic extracts were washed with water (100 mL) and brine (100 mL), then dried (Na$_2$SO$_4$) and evaporated in vacuo to afford the title compound (0.9 g, yield 92%). $^1$H-NMR (300, MHz, DMSO-d6): δ 12.26 (s, 1H), 7.32-7.20 (m, 10H), 3.73 (s, 2H), 3.67 (s, 2H), 3.03 (m, 1H), 2.49-2.40 (m, 2H), 1.79-1.69 (m, 2H); MS (ES) m/e 347 [M+H]$^+$.

Example 7: 2-(1,2-Dithiolan-3-yl)acetic acid

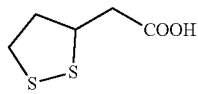

Sodium (2.60 g, 113 mmol) was added in small portions to liquid ammonia at −78° C. This solution was stirred while a solution of 3,5-bis(benzylthio)pentanoic acid (7.70 g, 22.3 mmol) in toluene (20 mL) was added dropwise during a 5 minute period. At the end of the addition, small pieces of sodium were added to maintain a permanent blue color for 30 min. The blue color was discharged with ammonium chloride and ammonia was allowed to evaporate overnight. After removal of ammonia, 200 mL of water and 150 mL of toluene were added. A rapid stream of oxygen was bubbled through the solution causing a color change from reddish to pale yellow for 2 hours. The solution was acidified and extracted with ethyl acetate (3×500 mL). The combined extracts were washed with water, dried over anhydrous $Na_2SO_4$, filtered and concentrated at reduced pressure to give the desired product as a semi solid compound (2.2 g, yield 61%). $^1$H-NMR (300 MHz, $CDCl_3$): δ 12.00 (m, 1H), 2.76 (m, 1H), 2.60-2.35 (m, 4H), 2.02-1.98 (m, 2H); MS (ES) m/e 163 [M−H]$^+$.

Example 8: Ethyl 3-bromo-2-(bromomethyl)propanoate

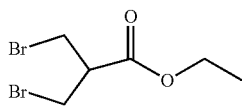

To a stirred solution of 3-bromo-2-(bromomethyl)propanoic acid (0.5 g, 2.04 mmol) in ethanol (10 mL) was added catalytic amount of concentrated $H_2SO_4$ and heated to reflux for 12 hours. The reaction mixture was then cooled and concentrated under reduced pressure and the residue was then poured into water and made basic by the addition of a solution of saturated $NaHCO_3$. The solution was extracted with diethyl ether (2×50 mL) and the organic extracts were washed with water, dried over anhydrous $Na_2SO_4$, filtered and concentrated at reduced pressure to afford the title compound (0.4 g, 72%). $^1$H NMR ($CDCl_3$): δ 4.19 (m, 2H), 3.73-3.62 (m, 4H), 3.11-3.08 (m, 1H), 1.26 (t, J=7.6 Hz, 3H), Example 9: Ethyl 3-(benzylthio)-2-((benzylthio)methyl)propanoate

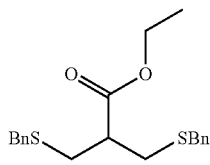

To a stirred solution of Ethyl 3-bromo-2-(bromomethyl) propanoate (350 mg, 1.28 mmol) in ethanol (5 mL) at 0° C. was added phenylmethanethiol (318 mg, 2.56 mmol) and KOH (150 mg, 2.69 mmol). The solution was stirred at room temperature for 2 hours, then it was poured into cold water and extracted with ethyl acetate (2×100 mL). The combined organic layers were dried over anhydrous $Na_2SO_4$, filtered and concentrated to give an oil which was purified by column chromatography eluting with 4-5% ethyl acetate in hexanes to give the title compound 0.2 g (43%). $^1$H NMR 400 MHz (DMSO-d6) δ 7.34-7.22 (m, 10H), 4.11-4.05 (q, J=7.2 Hz, 2H), 3.71 (s, 4H), 2.77-2.73 (m, 1H), 2.62-2.49 (m, 4H), 1.20 (t, J=7.2 Hz, 3H); LCMS m/e: 361 [M+1]$^+$.

Example 10: 3-Benzylthio-2-((benzylthio)methyl)propanoic acid

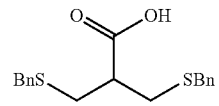

To a mixture of ethyl 3-(benzylthio)-2-((benzylthio) methyl)propanoate (100 mg, 0.28 mmol) in ethanol (2 mL) was added 10% NaOH (2 mL) and heated at 50° C. for 1 hour. The reaction mixture was then cooled to room temperature and ethanol was evaporated. The resultant solution was diluted with water and extracted with diethyl ether (10 mL). The aqueous solution was acidified with 6N HCl and extracted with chloroform (3×50 mL). The combined organic extracts were washed with water (50 mL), brine (50 mL) and then dried over $Na_2SO_4$, filtered and concentrated in vacuum to afford the title compound (70 mg, yield 78%). $^1$H NMR (DMSO-d6): δ 12.5 (s, 1H), 7.32-7.20 (m, 10H), 4.11 (m, 1H), 3.73 (s, 4H), 2.52-2.50 (m, 2H); LCMS (ES) m/e 333 [M+1]$^+$.

Example 11: 1,2-Dithiolane-4-carboxylic acid

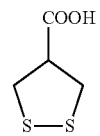

Sodium (0.87 g, 37.1 mmol) was added in small portions to liquid ammonia (30 mL) at −78° C. This solution was stirred while a solution of 3-benzylthio-2-((benzylthio) methylpropanoic acid (2.5 g, 7.53 mmol) in toluene (25 mL) was added dropwise during a period of 5 minutes. At the end of the reaction, small pieces of sodium were added to maintain a permanent blue color for 30 minutes. The blue color was discharged with ammonium chloride and ammonia was allowed to evaporate overnight. After removal of the ammonia, 200 ml of water and 150 ml of toluene were added and the aqueous layer was extracted with diethyl ether (100 mL). To the aqueous layer was added 1% ferric chloride (1 mL) and a rapid stream of oxygen was bubbled through the solution gradually causing changing from reddish color to pale yellow color in a period of 2 hours. The solution was acidified and extracted with chloroform (3×500 mL). The combined extract were washed with water, dried over anhydrous $Na_2SO_4$, filtered and concentrated at reduced pressure to give the desired product (1.0 g, yield 89%). $^1$H NMR ($CDCl_3$): δ 3.74 (m, 1H), 3.52-3.33 (m, 4H); MS (ES) m/e 163 [M−1]$^+$.

Example 12: 1,3-Bis-(benzylthio)propan-2-one

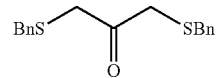

To a stirred solution of 1,3-dichloropropan-2-one (10.0 g, 78.8 mmol) in ethanol (150 mL) at 0° C. was slowly added phenylmethanethiol (19.6 g, 157.6 mmol) and KOH (9.27 g, 165.4 mmol) and stirring continued at room temperature for 2 hours. The reaction mixture was then poured into water and extracted with ethyl acetate (2×500 mL). The combined organic layer was dried over anhydrous $Na_2SO_4$, filtered and concentrated to afford a crude oil which was purified by column chromatography eluting with 3-4% ethyl acetate in hexanes to give 10.5 g (44%). LCMS m/e: 303 [M+1]$^+$.

Example 13: Ethyl 4-(benzylthio)-3-((benzylthio)methyl)but-2-enoate

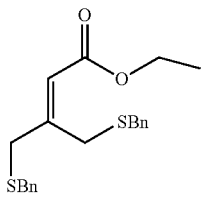

A mixture of 1,3-bis (benzylthio)propan-2-one (10.0 g, 33.1 mmol) and ethyl 2-(triphenyl-1$^5$-phosphanylidene)acetate (17.3 g, 49.7 mmol) in toluene (100 mL) was heated to 120° C. for 12 hours. After cooling, the reaction mixture was concentrated to give an oil which was purified by column chromatography eluting with 3-4% ethyl acetate in hexanes to give 10.0 g (81%) of the title compound. $^1$H NMR 400 MHz (DMSO-d6) δ 7.33-7.20 (m, 10H), 5.85 (s, 1H), 4.10-4.02 (m, 2H), 3.80 (s, 4H), 3.67 (d, J=8.4 Hz, 4H), 1.21 (t, J=7.6 Hz, 3H; LCMS m/e: 373 [M+1]$^+$.

Example 14: Ethyl 4-(benzylthio)-3-((benzylthio)methyl)butanoate

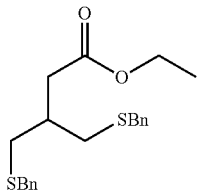

To a stirred solution of ethyl 4-(benzylthio)-3-((benzylthio)methyl)but-2-enoate (500 mg, 1.34 mmol) in tetrahydrofuran (1 mL) and methanol (4 mL) at 0° C. was added $NiCl_2.6H_2O$ (318 mg, 1.34 mmol) followed by careful addition of $NaBH_4$ (209 mg). The solution was further stirred for room temperature for 2 hours and then was filtered through celite. The filtrate was concentrated and the desired product 1.75 g (35%). was isolated by column chromatography eluting with 3-4% ethyl acetate in hexanes. $^1$H NMR 400 MHz (DMSO-d6) δ 7.32-7.21 (m, 10H), 4.05 (q, J=6.8 Hz, 2H), 3.67 (s, 4H), 2.53 (m, 2H), 2.45 (m, 4H), 2.18 (m, 1H), 1.71 (m, 3H); LCMS m/e: 375 [M+1]$^+$.

Example 15: 4-(Benzylthio)-3-((benzylthio)methyl)butanoic acid

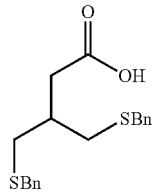

To a mixture of ethyl 4-(benzylthio)-3-((benzylthio)methyl)butanoate (3.5 g, 9.35 mmol) in ethanol (35 mL) was added 10% NaOH (35 mL) and the solution heated to 50° C. for 1 hour. The reaction mixture was then to room temperature and ethanol was evaporated. The resultant solution was diluted with water and extracted with diethyl ether (200 mL). The combined aqueous extracts were acidified with 6N HCl and extracted with chloroform (3×400 mL). The combined organic extracts were washed with water (100 mL) and brine (100 mL), then dried over $Na_2SO_4$, filtered and concentrated in vacuum to afford the title compound (3.0 g, yield 93%). LCMS m/e: 347 [M+1]$^+$.

Example 16: 2-(1,2-Dithiolan-4-yl)acetic acid

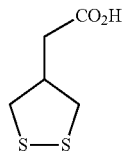

Sodium (0.9 g, 39.13 mmol) was added in small portions to liquid ammonia (50 mL) at −78° C. This solution was stirred while a solution of 4-(benzylthio)-3-((benzylthio)methyl)butanoic acid (3.0 g, 8.67 mmol) in toluene (25 mL) was added dropwise during a period of 5 minutes. At the end of the addition, small pieces of sodium were added to maintain a permanent blue color for 30 minutes. The blue color was discharged upon the addition of ammonium chloride and ammonia was allowed to evaporate overnight. After removal of the ammonia, 200 ml of water and 150 ml of toluene were added and a rapid stream of oxygen was bubbled through the solution such that the reddish color changed to pale yellow in 2 hours. The solution was carefully acidified and extracted with chloroform (3×500 mL). The combined extracts were washed with water, dried over anhydrous $Na_2SO_4$, filtered and concentrated at reduced pressure to give the desired product as a solid compound (1.2 g, yield 85%). $^1$H NMR (DMSO-d6): δ 12.29 (s, 1H), 3.31 (m, 2H), 2.93 (m, 3H), 2.44 (m, 2H), 1H); LCMS m/e: 163 [M−1]$^+$.

Example 17: 3-(1,2-Dithiolan-3-yl)propanoic acid

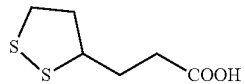

To a solution of 5-(2-chloroethyl)dihydrofuran-2(3H)-one (14.9 g, 100 mmol) in 20 mL of ethanol was slowly added a solution containing 2.4 g of sodium in 40 mL of ethanol followed by a slow addition of a solution of benzymercaptan (12.4 g, 100 mmol). After stirring for 1 hours at room temperature, the mixture was refluxed for 4 hours, cooled and poured into 120 mL of cold water and acidified with 10% HCl and then extracted with ether. The combined ether extracts were dried over sodium sulfate, filtered and concentrated to give 5-(2-(benzylthio)ethyl)dihydrofuran-2 (3H)-one (15 g, 63%). $^1$H-NMR (300 MHz, DMSO-d6): δ 7.40 (d, 2H), 7.30-7.25 (m, 3H), 4.21 (tt, 1H), 3.65 (s, 2H), 2.60 (t, 2H), 2.35-2.25 (m 2H), 2.15 (m, 1H), 1.92 (m, 1H), 1.88 (m, 1H).

A solution of sodium benzylthioate prepared from 6.2 g of benzymercaptan (50 mmol) and 1.1 g of sodium (48 mmol) in 30 mL of ethanol was evaporated to remove ethanol. Toluene (60 mL) and 5-(2-(benzylthio)ethyl)dihydrofuran-2(3H)-one (11.8 g, 50.0 mmol) were slowly added and the mixture was refluxed for 1.5 hours. Toluene was then evaporated and the residue was heated at 170-90° for 2 hours cooled and dissolved in 50 mL of water, acidified with 10% HCl, and extracted with ether. The combined ether layers were dried over anhydrous $Na_2SO_4$, filtered and evaporated to give 4,6-bis(benzylthio)hexanoic acid (10 g, 55%) as a solid. $^1$H-NMR (DMSO-d6): δ 7.40 (d, 4H), 7.30-7.25 (m, 6H), 3.71 (s, 2H), 3.65 (s, 2H), 2.60 (t, 2H), 2.33 (m, 3H), 1.97 (dq, 2H), 1.86 (dq, 3H).

To a solution of 150 mL of liquid ammonia containing a few mg of sodium, was slowly added a solution of 10.8 g (30.0 mmol) of 4,6-bis(benzylthio)hexanoic acid in 40 mL of toluene. This solution was allowed to stand overnight and then extracted with 50 mL cold water. The aqueous extracts were combined and acidified with 10% HCl and extracted with chloroform. The organic extracts were washed with 10% iodine-KI solution, dried over sodium sulfate and filtered to give to give 3.0 g (56%) of 3-(1,2-dithiolan-3-yl) propanoic acid. $^1$H-NMR (300 MHz, DMSO-d6): δ 2.48-2.50 (m, 2H), 2.33 (m, 3H), 1.96 (m, 1H), 1.70-1.81 (m, 3H).

Example 18:
2-Chloro-1-((3-fluorobenzyl)oxy)-4-nitrobenzene

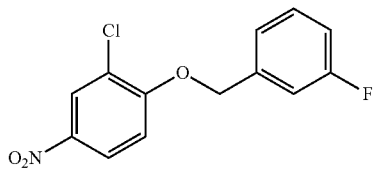

A mixture of 2-chloro-4-nitrophenol (2.00 g, 11.6 mmol), m-fluorobenzylbromide (2.60 g, 13.8 mmol), $K_2CO_3$ (3.19 g, 23.1 mmol) and acetone (50 mL) was stirred at 30° C. for 12 hours. The resulting mixture was filtered and washed with acetone. The filtrate was concentrated to give the crude product which was washed with petroleum ether and dried to produce the product as a yellow solid (2.80 g, yield 87.5%). $^1$H-NMR (300 MHz, DMSO-d6): δ 8.35 (d, J=2.8 Hz, 1H), 8.25 (dd, $J_1$=9.6 Hz, $J_2$=2.8 Hz, 1H), 7.49-7.45 (m, 2H), 7.31-7.34 (m, 2H), 7.20-7.21 (m, 1H), 3.32 (s, 2H); MS (ES) m/e 280 [M−H]$^+$.

Example 19:
3-Chloro-4-((3-fluorobenzyl)oxy)aniline

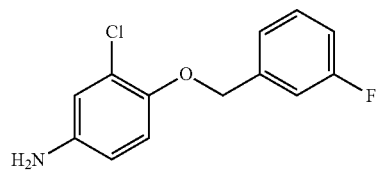 [SMILES: O=[N+]([O-])c1ccc(OCc2cccc(F)c2)c(Cl)c1]

To a stirred mixture of 2-chloro-1-((3-fluorobenzyl)oxy)-4-nitrobenzene (2.80 g, 9.96 mmol) and zinc (6.51 g, 99.6 mmol) in methanol (30 mL) at 0° C., was added $NH_4Cl$ (6.88 g, 129 mmol) slowly portion-wise (exothermic reaction). To this solution, water (15 mL) was added dropwise at 0° C. The reaction mixture was heated to 60° C. and stirred for 2 hours. The reaction mixture was filtered through celite and concentrated under vacuum. The residue was extracted with ethyl acetate (3×200 ml) and the combined organic layers were dried over anhydrous $Na_2SO_4$ and evaporated to dryness to furnish the desired crude product. The pure product was obtained by column chromatography over silica gel (100-200 mesh size) as a stationary phase and 40% (v/v) Ethyl acetate in petroleum ether as eluent to give the product as a brown solid (1.6 g, yield 64%). $^1$H-NMR (300 MHz, DMSO-d6): δ 7.44-7.40 (m, 1H), 7.23-7.14 (m, 1H), 6.90 (d, J=8.8 Hz, 1H), 6.64 (d, J=2.4 Hz, 1H), 6.46 (dd, $J_1$=8.8 Hz, $J_2$=2.4 Hz, 1H), 5.03 (m, 2H), 4.94 (s, 2H); MS (ES) m/e 252 [M+H]$^+$.

Example 20:
4-Hydroxy-6-nitro-7-ethoxyquinoline-3-carbonitrile

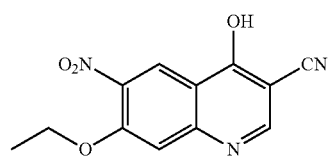 [SMILES: CCOc1cc2ncc(C#N)c(O)c2cc1[N+](=O)[O-]]

A mixture of 19.6 g (108 mmol) of 3-ethoxy-4-nitroaniline and 25.7 (152 mmol) of ethyl (ethoxymethylene)cyanoacetate in 70 mL of toluene was refluxed for 14 hours. After cooling the reaction mixture in an ice bath, the product was filtered and washed with three portions of ether and dried over sodium sulfate, filtered and evaporated in vacuo to give 31.4 g (102 mmol) of 3-ethoxy-4-nitro-1-aminomethylene ethyl cyanoacetate. This material was added as a solid to refluxing Dowtherm under nitrogen with mechanical stirring for 1.5 hours. The thick reaction mixture was diluted with 2 L of ether filtered and washed with cold ether to give 20 g of the title compound as an off white solid m.p. 244-247° C.; $^1$H-NMR (400 MHz, DMSO-d6): δ 8.75 (br, 1H), 8.52 (s, 1H), 7.25 (s, 1H), 4.29 (q, 2H, J=6.8 Hz), 1.41 (t, 3H, J=6.8 Hz); MS (ES) m/e 259.8 [M+H]$^+$

Example 21: 4-Chloro-6-nitro-7-ethoxynitroquinoline-3-carbonitrile

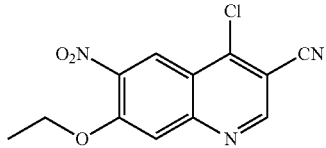 [SMILES: CCOc1cc2ncc(C#N)c(Cl)c2cc1[N+](=O)[O-]]

A mixture of 20 g (77 mmol) of 4-hydroxy-7-ethoxy-6-nitroquinoline-3-carbonitrile was refluxed with 120 mL of POCl$_3$ under N$_2$ for 2 hours. The mixture was cooled to room temperature and excess POCl$_3$ was removed in vacuo. The residue was then cooled in an ice bath and 500 mL of CH$_2$Cl$_2$ was slowly added to dissolve the residue. The resulting solution was added to a flask containing 250 mL of ice-cold saturated K$_2$CO$_3$ and stirred for 30 minutes. The organic layer was extracted, washed, dried over MgSO$_4$ and evaporated to give 18 g (86%) of the title compound as an off-white solid mp 200-202° C.; $^1$H NMR (400 MHz, DMSO-d6): δ 9.28 (bs, 1H), 8.85 (s, 1H), 7.91 (s, 1H), 4.46 (q, J=6.8 Hz, 2H), 1.41 (t, J=8 Hz, 3H); MS (ES) m/e 277.7 [M+H]$^+$.

Example 22: 4-Chloro-6-amino-7-ethoxyquinoline-3-carbonitrile

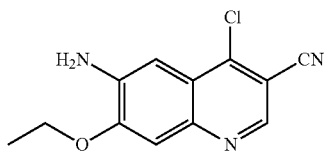 [SMILES: CCOc1cc2ncc(C#N)c(Cl)c2cc1N]

A 4.60 g (16.6 mmol) of 4-chloro-7-ethoxy-6-nitroquinoline-3-carbonitrile in 130 mL of methanol was brought to reflux with stirring. To this was added 6.50 g of iron powder suspended in 70 mL of acetic acid and reflux was continued for 2 hours. The reaction mixture was filtered hot and left to crystallize to produce 4 g of the acetate salt. This was suspended into 700 mL of ethyl acetate and 300 mL of saturated KHCO$_3$. The aqueous phase was extracted twice with 500 mL of Ethyl acetate and the organic phases were combined, dried over sodium sulfate and evaporated to a volume of about 100 mL. This solution was allowed to crystallize to yield 2.7 (60%) of the desired compound. $^1$H NMR (400 MHz, DMSO-d6): δ 9.28 (bs, 1H), 8.85 (s, 1H), 7.91 (s, 1H), 4.46 (q, J=6.8 Hz, 2H), 1.41 (t, J=6.8 Hz, 3H); MS (ES) m/e 237.7 [M+H]$^+$

Example 23: 4-((3-Chloro-4-fluorophenyl)amino)-6-nitro-7-ethoxyquinoline-3-carbonitrile

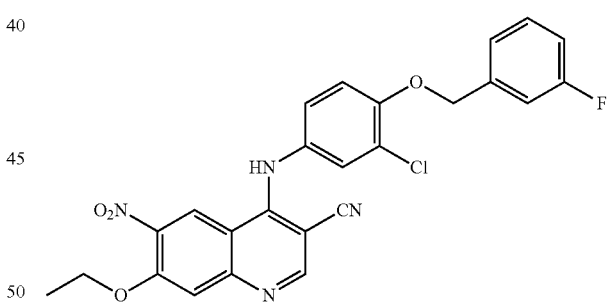

A solution of 13.4 g (48.3 mmol) of 4-chloro-6-nitro-7-ethoxyquinoline-3-carbonitrile and 7.03 g (48.3 mmol) of 3-chloro-4-fluoroaniline in 450 mL of 2-propanol was refluxed under N$_2$ for 3.5 h. TLC (Ethyl acetate:hexanes, 1:1) indicated complete consumption of starting material. The solution was allowed to stand overnight at room temperature, filtered and the washed with 2-propanol to give 19 g (94%) of the title compound as a yellow HCl salt. $^1$H NMR (400 MHz, DMSO-d6): δ 10.6 (bs, 1H), 9.52 (s, 1H), 8.74 (s, 1H), 8.54 (dd, 1H, J=2.1, 9.0 Hz), 8.07 (m, 1H), 7.67 (m, 1H), 7.45 (m, 1H), 4.42 (q, J=7.05 Hz, 2H), 1.28 (t, J=7.05 Hz, 3H); MS (ES) m/e 387 [M+H]$^+$.

Example 24: 4-((3-Chloro-4-((3-fluorobenzyl)oxy)phenyl)amino)-6-nitro-7-ethoxyquinoline-3-carbonitrile A solution of 6.70 g (24.2 mmol) of 4-chloro-6-nitro-7-ethoxyquinoline-3-carbonitrile and 4.36 g (24.8 mmol) of 3-chloro-4-((3-fluorobenzyl)oxyphenylamino) in 45 mL of 2-propanol was refluxed under N$_2$ for 3.5 hours. TLC (Ethyl acetate:hexanes, 1:1) indicated complete consumption of starting material. The solution was allowed to stand overnight at room temperature, filtered and the washed with 2-propanol to give 7.3 g (90%) of the title compound as a yellow HCl salt: $^1$H NMR (400 MHz, DMSO-d6): δ10.59 (bs, 1H), 8.8 (s, 1H), 7.7 (m, 1H), 7.59-7.51 (m, 3H), 7.35-7.31 (m, 5H), 7.29-7.19 (m, 1H), 6.01 (bs, 2H), 5.30 (s, 2H), 4.2 (q, J=7.6 Hz, 2H), 1.28 (t, J=7.6 Hz, 3H); MS (ES) m/e 463 [M+H]$^+$.

Example 25: 4-((3-Chloro-4-fluorophenyl)amino)-6-amino-7-ethoxyquinoline-3-carbonitrile

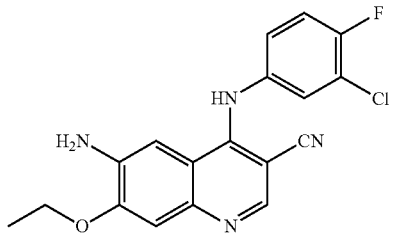 [SMILES: CCOc1cc2ncc(C#N)c(Nc3ccc(F)c(Cl)c3)c2cc1N]

To solution of 4-chloro-6-amino-7-ethoxyquinoline-3-carbonitrile (1.7 g, 7.2 mmol) in 2-propanol (75 mL) was added 3-chloro-4-fluoroaniline (1.29 g, 8.80 mmol) followed by pyridine HCl (1.19 g, 10.0 mmol) and refluxed for 6 hours. The reaction mixture was allowed to cool to room temperature overnight. A yellow solid precipitated out, filtered, washed with isopropanol (10 mL) and dried under vacuum to afford the title compound as a yellow solid (2.30 g, yield 90.2%). $^1$H NMR (400 MHz, DMSO-d6): δ 10.7 (bs, 1H), 7.8 (s, 1H), 7.7 (m, 1H), δ 7.6-7.4 (m, 4H), 6.0 (br, 2H), 4.2 (q, J=7.05 Hz, 2H), 1.28 (t, J=7.05 Hz, 3H); MS (ES) m/e 357 [M+H]$^+$.

Example 26: 4-((3-Chloro-4-fluorophenyl)amino)-6-amino-7-ethoxyquinoline-3-carbonitrile

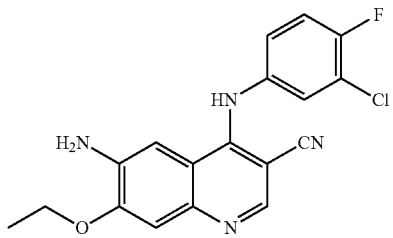 [SMILES: CCOc1cc2ncc(C#N)c(Nc3ccc(F)c(Cl)c3)c2cc1N]

To solution of 4-(3-chloro-4-fluorophenylamino)-6-nitro-7-ethoxyquinoline-3-carbonitrile (0.90 g, 2.16 mmol) in methyl-t-butylether/tetrahydrofuran (15 mL) was treated with an aqueous solution of saturated sodium bicarbonate at room temperature for 20 minutes. The organic layer was separated and the aqueous layer was extracted with tetrahydrofuran. The combined organic layer was dried over Na$_2$SO$_4$ and concentrated to give the free base which was dissolved in 120 mL of tetrahydrofuran:ethanol (5:1) solution and a catalyst 700 mg (Pt-5% N-2.5% on carbon) was slowly added. The mixture was stirred at room temperature for 1 hour followed by addition of another batch of the catalyst (700 mg) three times. The mixture was then filtered and concentrated in vacuo to give 600 mg (78.0%) of the desired compound. $^1$H NMR (400 MHz, DMSO-d6): δ 10.7 (bs, 1H), 7.8 (s, 1H), 7.7 (m, 1H), 7.6-7.4 (m, 4H), 6.0 (bs, 2H), 4.2 (q, J=7.05 Hz, 2H), 1.28 (t, J=7.05 Hz, 3H); MS (ES) m/e 357 [M+H].

Example 27: 4-((3-Chloro-4-((3-fluorobenzyl)oxy)phenyl)amino)-6-amino-7-ethoxyquinoline-3-carbonitrile

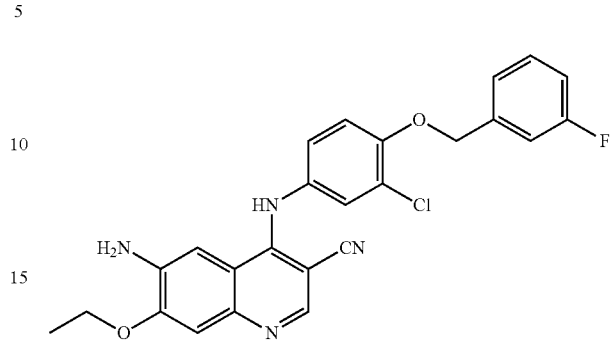

To solution of 4-chloro-6-amino-7-ethoxyquinoline-3-carbonitrile (0.5 g, 0.002 mmol) in 2-propanol (50 mL) was added 3-chloro-4-((3-fluorobenzyl)oxy)aniline (0.6 g 0.002 mmol) followed by pyridine HCl (0.3 g, 0.002 mmol) and refluxed the reaction mixture for 6 hours. The reaction mixture was allowed to cool to room temperature resulting in the formation of a yellow precipitate. The precipitated yellow solid was filtered, washed with isopropanol (10 mL) and dried under vacuum to afford the title compound as yellow solid (0.7 g, yield 75%). $^1$H-NMR (400 MHz, DMSO-d6): δ 10.59 (bs, 1H), 8.8 (s, 1H), 7.7 (m, 1H), 7.59-7.51 (m, 3H), 7.35-7.31 (m, 5H), 7.29-7.19 (m, 1H), 6.01 (bs, 2H), 5.30 (s, 2H), 4.2 (q, J=7.6 Hz, 2H), 1.28 (t, J=7.6 Hz, 3H); MS (ES) m/e 463 [M+H]$^+$.

Example 28: 4-((3-Chloro-4-((3-fluorobenzyl)oxy)phenyl)amino)-6-amino-7-ethoxyquinoline-3-carbonitrile

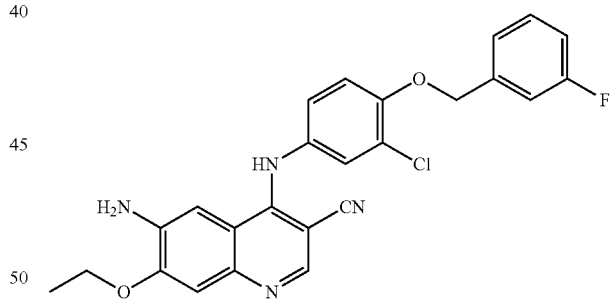

To solution of 4-(3-chlorophenyl-4-fluorobenzyloxyphenylamino)-6-nitro-7-ethoxyquinoline-3-carbonitrile (2.0 g, 3.8 mmol) in methyl-t-butylether/tetrahydrofuran (50 mL) was treated with an aqueous solution of saturated sodium bicarbonate at room temperature for 20 minutes. The organic layer was separated and the aqueous layer was extracted with tetrahydrofuran. The combined organic layer was dried over Na$_2$SO$_4$ filtered, and concentrated to give the free base which was dissolved in 120 mL of tetrahydrofuran:ethanol (5:1) solution and a catalyst 700 mg (Pt-5% N-2.5% on carbon) was then slowly added. The mixture was stirred at room temperature for 1 hour followed by addition of another batch of the catalyst (700 mg) three times. The mixture was then filtered and concentrated in vacuo to give 1.2 g (68%) of the desired compound. $^1$H NMR (400 MHz, DMSO-d6):

δ 10.59 (bs, 1H), 8.80 (s, 1H), 7.70 (m, 1H), 7.59-7.51 (m, 3H), 7.35-7.31 (m, 5H), 7.29-7.19 (m, 1H), 6.01 (bs, 2H), 5.30 (s, 2H), 4.20 (q, J=7.6 Hz, 2H), 1.28 (t, 3H, J=7.6 Hz); MS (ES) m/e 463 [M+H]⁺.

Example 29: S,S'-(2-((4-((3-Chloro-4-fluorophenyl) amino)-3-cyano-7-ethoxyquinolin-6-yl)carbamoyl) propane-1,3-diyl)diethanethioate

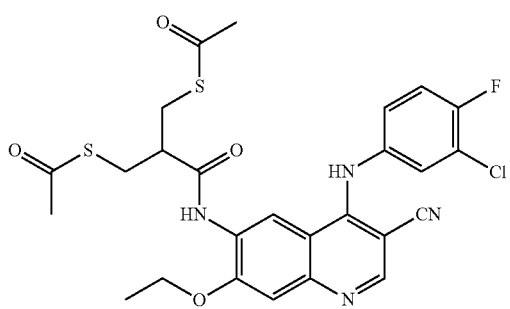 [SMILES: CCOc1cc2ncc(C#N)c(Nc3ccc(F)c(Cl)c3)c2cc1NC(=O)C(CSC(C)=O)CSC(C)=O]

To a mixture of 6-amino-4-((3-chloro-4-fluorophenyl) amino)-7-ethoxyquinoline-3-carbonitrile (0.10 g, 0.28 mmol) and 3-(acetylthio)-2-((acetylthio)methyl)propanoic acid (0.13 g, 0.56 mmol) in N-methylpyrrolidone (5 mL) was added 1-(3-dimethylaminopropyl)-3-ethylcarbodiimide hydrochloride (0.48 g, 2.5 mmol) and heated the reaction mixture at 70° C. for 24 hours. The reaction mixture was cooled, poured into water and a few drops of brine were added and stirred for 20 minutes. The resultant solid was filtered, dried under vacuum and purified by column chromatography on silica gel (100-200 mesh) eluting with 1-2% (v/v) methanol in dichloromethane to produce the desired product as pale brown solid (50 mg, yield 32%). ¹H-NMR (400 MHz, DMSO-d6): δ 10.02 (s, 1H), 9.58 (s, 1H), 8.81 (s, 1H), 8.64 (s, 1H), 7.51-7.41 (m, 3H), 7.30 (m, 1H), 4.30 (q, J=6.8 Hz, 2H), 3.17-3.10 (m, 5H), 2.34 (s, 6H), 1.47 (t, J=6.8 Hz, 3H); MS (ES) m/e 575 [M+H]⁺.

Example 30: N-(4-((3-Chloro-4-fluorophenyl) amino)-3-cyano-7-ethoxyquinolin-6-yl)-3-mercapto-2-(mercaptomethyl)propanamide

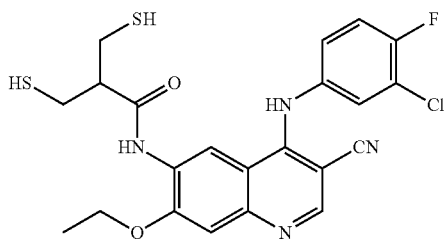 [SMILES: CCOc1cc2ncc(C#N)c(Nc3ccc(F)c(Cl)c3)c2cc1NC(=O)C(CS)CS]

To a solution of S,S'-(2-((4-((3-chloro-4-fluorophenyl) amino)-3-cyano-7-ethoxyquinolin-6-yl)carbamoyl)propane-1,3-diyl)diethanethioate (50 mg, 0.087 mmol) in N,N-dimethylacetamide (5 mL) was added NaBH₄ (14 mg, 0.37 mmol) and stirred the reaction mixture at room temperature for 2 hours. The reaction mixture was poured into water, acidified with citric acid and a few drops of brine were added and stirred for 20 minutes. The resultant solid was filtered, dried under vacuum to give the desired crude product as pale brown solid (38 mg). The obtained product was used in the next step without further purification. LC-MS (ES) m/e 491 [M+H]⁺.

Example 31: N-(4-((3-Chloro-4-fluorophenyl) amino)-3-cyano-7-ethoxyquinolin-6-yl)-1,2-dithiolane-4-carboxamide

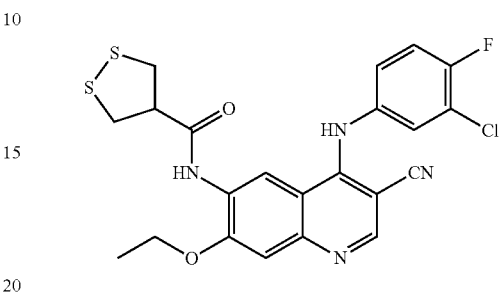

A mixture of N-(4-((3-chloro-4-fluorophenyl)amino)-3-cyano-7-ethoxyquinolin-6-yl)-3-mercapto-2-(mercaptomethyl)propanamide (36 mg, 0.073 mmol) in DMSO (5 mL) was heated at 120° C. with stirring for 5 hours. The mixture was cooled and poured into water. The aqueous mixture extracted with ethyl acetate (3×300 mL). The extracts were washed with water, dried over anhydrous Na₂SO₄, filtered and concentrated at reduced pressure. The pure product was obtained by column chromatography on silica gel (100-200 mesh) eluting with 1% (v/v) methanol in dichloromethane to produce as pale brown solid (6.0 mg, yield 17%). ¹H-NMR 400 MHz, (DMSO-d6): δ 9.76 (s, 1H), 9.66 (s, 1H), 8.81 (s, 1H), 8.83 (s, 1H), 7.43-7.41 (m, 3H), 7.39 (m, 1H), 4.30 (q, J=6.8 Hz, 2H), 3.58-3.53 (m, 1H), 3.31-3.28 (m, 4H), 1.47 (t, J=6.8 Hz, 3H); MS (ES) m/e 489 [M+H]⁺.

Example 32: N-(4-((3-Chloro-4-fluorophenyl) amino)-3-cyano-7-ethoxyquinolin-6-yl)-1,2-dithiolane-4-carboxamide

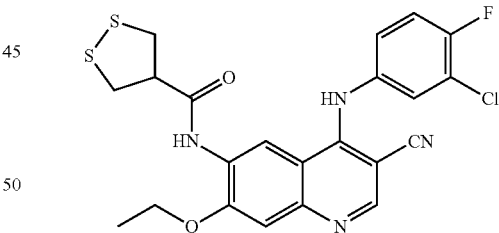

To a mixture of 6-amino-4-((3-chloro-4-fluorophenyl) amino)-7-ethoxyquinoline-3-carbonitrile (0.36 g, 1.07 mmol) and asparagusic acid (1,2-dithiolan-4-carboxylic acid) (0.17 g, 1.1 mmol) in N-methylpyrrolidone (6 mL) was added 1-(3-dimethylaminopropyl)-3-ethylcarbodiimide hydrochloride (0.58 g, 3.1 mmol) stirred for 2 hours at room temperature under dark condition. The mixture was cooled, poured into water and extracted with ethyl acetate (3×300 mL). The combined extracts were washed with water, dried over anhydrous Na₂SO₄, filtered and concentrated at reduced pressure. The pure product was obtained by column chromatography on silica gel (100-200 mesh) eluting with 2-3% (v/v) methanol in dichloromethane to produce the title compound as a yellow solid (0.15 g, yield 30%).

$^1$H-NMR 400 MHz (DMSO-d6): δ 9.76 (s, 1H), 9.66 (s, 1H), 8.81 (s, 1H), 8.83 (s, 1H), 7.43-7.41 (m, 3H), 7.39 (m, 1H), 4.30 (q, J=6.8 Hz, 2H), 3.58-3.53 (m, 1H), 3.31-3.28 (m, 4H), 1.47 (t, J=6.8 Hz, 3H); MS (ES) m/e 489 [M+H]$^+$.

Example 33: N-(4-((3-Chloro-4-fluorophenyl)amino)-3-cyano-7-ethoxyquinolin-6-yl)-1,2-dithiolane-3-carboxamide

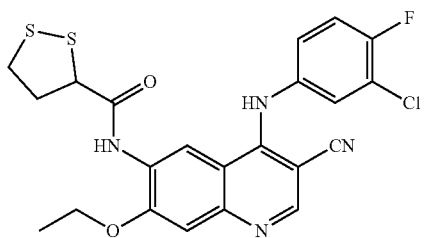 [SMILES: CCOc1cc2ncc(C#N)c(Nc3ccc(F)c(Cl)c3)c2cc1NC(=O)C1CCSS1]

To a mixture of 6-amino-4-((3-chloro-4-fluorophenyl)amino)-7-ethoxyquinoline-3-carbonitrile (0.36 g, 1.07 mmol) and commercially available 1,2-dithiolan-3-carboxylic acid (0.17 g, 1.1 mmol) in N-methylpyrrolidone (6 mL) was added 1-(3-dimethylaminopropyl)-3-ethylcarbodiimide hydrochloride (0.58 g, 3.1 mmol) stirred for 2 hours at room temperature under dark condition. The mixture was cooled, poured into water and extracted with ethyl acetate (3×300 mL). The combined extracts were washed with water, dried over anhydrous Na$_2$SO$_4$, filtered and concentrated at reduced pressure. The pure product was obtained by column chromatography on silica gel (100-200 mesh) eluting with 2-3% (v/v) methanol in dichloromethane to produce the title compound as a yellow solid (0.15 g, yield 30%). $^1$H-NMR 400 MHz (DMSO-d6): δ 9.96 (s, 1H), 9.76 (s, 1H), 8.58 (s, 1H), 7.91 (s, 1H), 7.43 (s, 1H), 7.38 (s, 1H), 7.39-7.25 (m, 2H), 4.20 (q, J=6.8 Hz, 2H), 3.58 (t, 1H), 2.59-2.36 (m, 3H), 2.11 (m, 1H), 1.37 (t, J=6.8 Hz, 3H).

Example 34: S,S'-(2-((4-(3-Chloro-4-((3-fluorobenzyl)oxy)phenyl)amino)-3-cyano-7-ethoxyquinolin-6-yl)carbomoyl)propane-1,3-diyl)diethanethioate

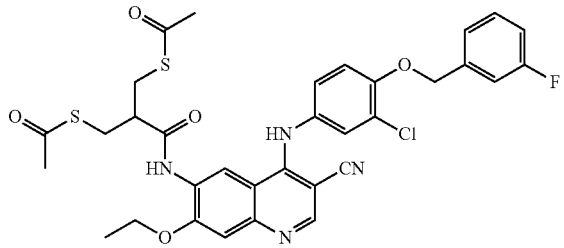 [SMILES: CCOc1cc2ncc(C#N)c(Nc3ccc(OCc4cccc(F)c4)c(Cl)c3)c2cc1NC(=O)C(CSC(C)=O)CSC(C)=O]

To a mixture of 6-amino-4-((3-chloro-4-((3-fluorobenzyl)oxy)phenyl)amino)-7-ethoxyquinoline-3-carbonitrile (0.20 g, 0.43 mmol) and 3-(acetylthio)-2-((acetylthio)methyl)propanoic acid (0.30 g, 1.3 mmol) in N-methylpyrrolidone (5 mL) was added 1-(3-dimethylaminopropyl)-3-ethylcarbodiimide hydrochloride (0.74 g, 3.9 mmol). The reaction mixture was heated at 70° C. for 24 hours. The reaction mixture was then cooled, poured into water and a few drops of brine were added and stirred for 20 minutes. The resultant solution was filtered and the solid was dried under vacuum and purified by column chromatography on silica gel (100-200 mesh) eluting with 1-2% (v/v) methanol in dichloromethane to produce the desired product as pale brown solid (45 mg, yield 26%). $^1$H-NMR 400 MHz (DMSO-d6): δ 9.59 (s, 1H), 9.36 (s, 1H), 8.82 (s, 1H), 8.46 (s, 1H), 7.49-7.18 (m, 9H), 5.25 (s, 2H), 4.30 (q, J=6.8 Hz, 2H), 3.11-3.01 (m, 5H), 2.34 (s, 6H), 1.47 (t, J=6.8 Hz, 3H); MS (ES) m/e 681 [M+H]$^+$.

Example 35: N-(4-((3-Chloro-4-((3-fluorobenzyl)oxy)phenyl)amino)-3-cyano-7-ethoxyquinolin-6-yl)-3-mercapto-2-(mercaptomethyl)propanamide

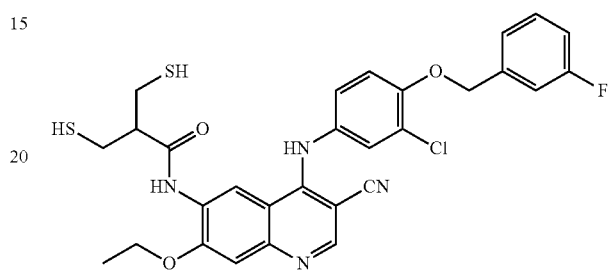

To a solution of S,S'-(2-((4-((3-chloro-4-((3-fluorobenzyl)oxy)phenyl)amino)-3-cyano-7-ethoxyquinolin-6-yl)carbomoyl)propane-1,3-diyl)diethanethioate (45 mg, 0.066 mmol) in N,N-dimethylacetamide (5 ml) was added NaBH$_4$ (5.0 mg, 0.13 mmol) and stirred at room temperature for 2 hours. The reaction mixture was poured into cold water, acidified with citric acid and a few drops of brine were added and stirred for 20 minutes. The solution was filtered and the resultant solid was dried under vacuum to give the desired crude product as pale brown solid (38 mg). The product obtained was used in the next step without further purification. LC-MS (ES) m/e 597 [M+H]$^+$.

Example 36: N-(4-((3-Chloro-4-((3-fluorobenzyl)oxy)phenyl)amino)-3-cyano-7-ethoxyquinolin-6-yl)-1,2-dithiolane-4-carboxamide

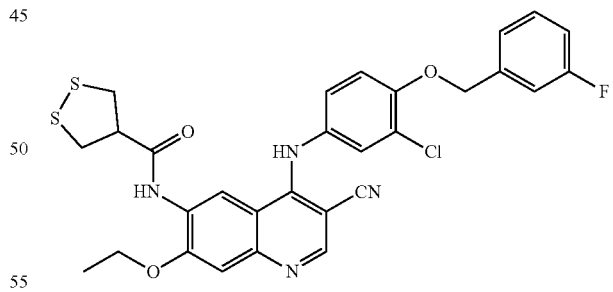

A mixture of N-(4-((3-chloro-4-((3-fluorobenzyl)oxy)phenyl)amino)-3-cyano-7-ethoxyquinolin-6-yl)-3-mercapto-2-(mercaptomethyl)propanamide (35 mg, 0.058 mmol) in DMSO (5 mL) was heated at 120° C. with stirring for 5 hours. The mixture was then cooled, poured into water and extracted with ethyl acetate (3×300 mL). The extracts were washed with water, dried over anhydrous Na$_2$SO$_4$ and concentrated at reduced pressure. The pure product was obtained by column chromatography on silica gel (100-200 mesh) eluting with 1% (v/v) methanol in dichloromethane to produce as pale brown solid (4.0 mg, yield 12%). $^1$H-NMR 400 MHz (DMSO-d6): δ 9.65 (s, 1H), 9.66 (s, 1H), 8.79 (s, 1H), 8.45 (s, 1H), 7.47-7.18 (m, 9H), 5.24 (s, 2H), 4.28 (q, J=6.8 Hz, 2H), 3.58-3.50 (m, 5H), 1.46 (t, J=6.8 Hz, 3H); MS (ES) m/e 595 [M+H]⁺.

Example 37: N-(4-((3-Chloro-4-((3-fluorobenzyl)oxy)phenyl)amino)-3-cyano-7-ethoxyquinolin-6-yl)-1,2-dithiolane-4-carboxamide

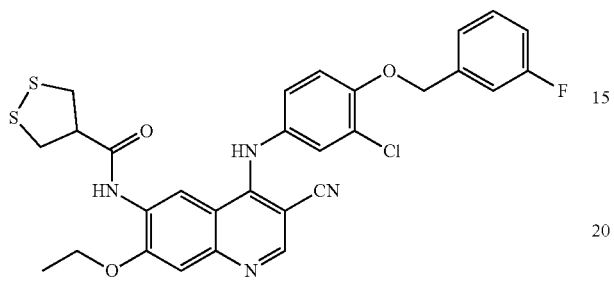

To a mixture of 4-((3-chloro-4-((3-fluorobenzyl)oxy)phenyl)amino)-6-amino-7-ethoxyquinoline-3-carbonitrile (0.51 g, 1.0 mmol) and asparagusic acid (1,2-dithiolan-4-carboxylic acid) (0.17 g, 1.0 mmol) in N-methylpyrrolidone (6 mL) was added 1-(3-dimethylaminopropyl)-3-ethylcarbodiimide hydrochloride (0.58 g, 3.08 mmol) and stirred for 2 hours at room temperature under dark condition. The mixture was cooled, poured into water and extracted with ethyl acetate (3×300 mL). The combined extracts were washed with water, dried over anhydrous Na₂SO₄, filtered and concentrated at reduced pressure. The pure product was obtained by column chromatography on silica gel (100-200 mesh) eluting with 2-3% (v/v) methanol in dichloromethane to produce the title compound as a yellow solid (0.18 g, yield 30%). ¹H-NMR 400 MHz (DMSO-d6): δ 9.65 (s, 1H), 9.66 (s, 1H), 8.79 (s, 1H), 8.45 (s, 1H), 7.47-7.18 (m, 9H), 5.24 (s, 2H), 4.28 (q, 2H, J=6.8 Hz, 2H), 3.58-3.50 (m, 5H), 1.46 (t, J=6.8 Hz, 3H); MS (ES) m/e 595 [M+H]⁺.

Example 38: 3,5-Bis(benzylthio)-N-(4-((3-chloro-4-fluorophenyl)amino)-3-cyano-7-ethoxyquinolin-6-yl)pentanamide

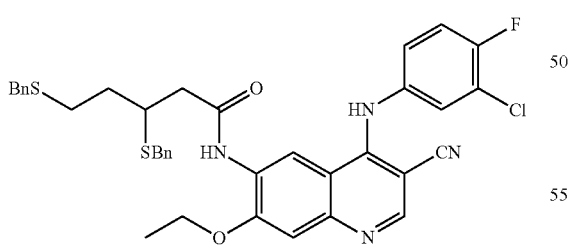

To a mixture of 4-((3-chloro-4-fluorophenyl)amino)-6-amino-7-ethoxyquinoline-3-carbonitrile (0.04 g, 0.12 mmol) and 3,5-bis(benzylthio)pentanoic acid (0.039 g, 0.12 mmol) in N-methylpyrrolidone (5 mL) was added 1-(3-dimethylaminopropyl)-3-ethylcarbodiimide hydrochloride (0.065 g, 0.34 mmol) and heated at 70° C. for 24 hours. The reaction mixture was then cooled, poured into cold water, a few drops of brine were added and stirred for 20 minutes. The solution was filtered and the resultant solid was dried under vacuum and purified by column chromatography on silica gel (100-200 mesh) eluting with 1-2% (v/v) methanol in dichloromethane to produce the desired product as pale brown solid (5.0 mg, yield 6.6%). ¹H-NMR 400 MHz (DMSO-d6): δ 9.23 (s, 1H), 8.81 (s, 1H), 8.22 (s, 1H), 7.31-7.20 (m, 13H), 7.02-7.00 (m, 1H), 4.23 (q, J=6.8 Hz, 2H), 3.77-3.76 (m, 2H), 3.66 (m, 2H), 3.16-3.12 (m, 2H), 2.78-2.72 (m, 2H), 1.86-1.84 (m, 1H), 1.74 (s, 3H), 1.47 (t, J=6.8 Hz, 3H); MS (ES) m/e 683 [M+H]⁺.

Example 39: N-(4-((3-Chloro-4-fluorophenyl)amino)-3-cyano-7-ethoxyquinolin-6-yl)-2-(1,2-dithiolan-3-yl)acetamide

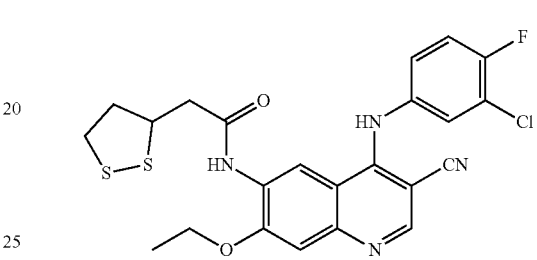

To a mixture of 6-amino-4-((3-chloro-4-fluorophenyl)amino)-7-ethoxyquinoline-3-carbonitrile (0.28 g, 0.79 mmol) and 2-(1,2-dithiolan-3-yl)acetic acid (0.13 g, 0.79 mmol) in N-methylpyrrolidone (5 mL) was added 1-(3-dimethylaminopropyl)-3-ethylcarbodiimide hydrochloride (0.46 g, 2.4 mmol) and stirred for 2 hours at room temperature under dark condition. The mixture was cooled, poured into water and extracted with ethyl acetate (3×300 mL). The combined extracts were washed with water, dried over anhydrous Na₂SO₄, filtered and concentrated at reduced pressure. The pure product was obtained by column chromatography on silica gel (100-200 mesh) eluting with 2-3% (v/v) methanol in dichloromethane to produce the title compound as a yellow solid (0.12 g, yield 31%). ¹H NMR 400 MHz (DMSO-d6): δ 9.0 (s, 1H), 8.6 (s, 1H), 8.25 (s, 1H), 7.70-7.40 (m, 5H), 4.30 (q, 2H), 4.10 (m, 1H), 3.21 (m, 2H), 2.91 (m, 2H), 2.62 (m, 1H), 2.1 (m, 1H), 1.52 (t, 3H); MS (ES) m/e 503 [M+H]⁺.

Example 40: N-(4-((3-Chloro-4-((3-fluorobenzyl)oxy)phenyl)amino)-3-cyano-7-ethoxyquinolin-6-yl)-2-(1,2-dithiolan-3-yl)acetamide

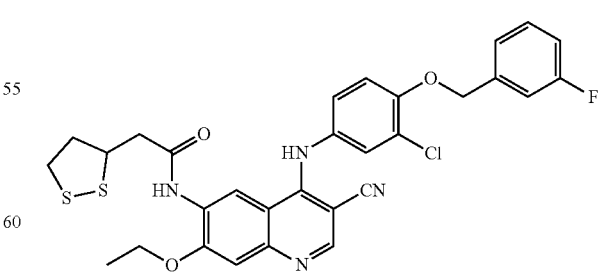

To a mixture of 4-((3-chloro-4-((3-fluorobenzyl)oxy)phenyl)amino)-6-amino-7-ethoxyquinoline-3-carbonitrile (0.11 g, 0.22 mmol) and 2-(1,2-dithiolan-3-yl)acetic acid (0.35 g, 2.2 mmol) in N-methylpyrrolidone (8 mL) was added 1-(3- dimethylaminopropyl)-3-ethylcarbodiimide hydrochloride (0.42 g, 2.16 mmol) and the reaction mixture was heated at 70° C. for 2 hours. The mixture was cooled and poured into cold water and extracted with ethyl acetate (3×300 mL). The combined extracts were washed with water, dried over anhydrous Na$_2$SO$_4$, filtered and concentrated at reduced pressure. The pure product was obtained by column chromatography on silica gel (100-200 mesh) eluting with 2-3% (v/v) methanol in dichloromethane to produce as pale brown solid (53 mg, yield 37%). $^1$H-NMR 400 MHz (DMSO-d6): δ 9.66 (b s, 1H), 9.64 (s, 1H), 8.79 (s, 1H), 8.45 (s, 1H), 7.91 (s, 1H), 7.47-7.18 (m, 7H), 5.24 (s, 2H), 4.28 (q, J=6.8 Hz, 2H), 3.58-3.50 (m, 5H), 2.95 (m, 2H), 1.47 (t, J=6.8 Hz, 3H); MS (ES) m/e 595 [M+H]$^+$.

Example 41: N-(4-((3-Chloro-4-fluorophenyl)amino)-3-cyano-7-ethoxyquinolin-6-yl)-3-(1,2-dithiolan-3-yl)propanamide

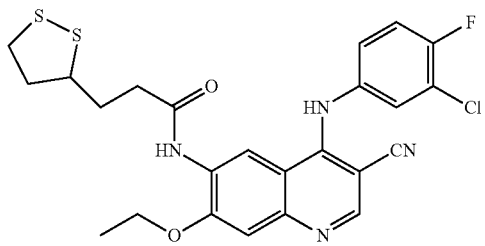 [SMILES: CCOc1cc2ncc(C#N)c(Nc3ccc(F)c(Cl)c3)c2cc1NC(=O)CCC1CCSS1]

To a mixture of 6-amino-4-((3-chloro-4-fluorophenyl)amino)-7-ethoxyquinoline-3-carbonitrile (0.36 g, 1.07 mmol) and 3-(1,2-dithiolan-3-yl)propanoic acid (0.21 g, 1.07 mmol) in N-methylpyrrolidone (6 mL) was added 1-(3-dimethylaminopropyl)-3-ethylcarbodiimide hydrochloride (0.58 g, 3.08 mmol) and the reaction mixture was stirred for 2 hours at room temperature under dark condition. The mixture was then cooled, poured into water and extracted with ethyl acetate (3×300 mL). The combined extracts were washed with water, dried over anhydrous Na$_2$SO$_4$, filtered and concentrated at reduced pressure. The pure product was obtained by column chromatography on silica gel (100-200 mesh) eluting with 2-3% (v/v) methanol in dichloromethane to produce the title compound as a yellow solid (0.17 g, yield 30%). $^1$H-NMR 400 MHz (DMSO-d6): δ 9.96 (s, 1H), 9.76 (s, 1H), 8.58 (s, 1H), 7.91 (s, 1H), 7.43 (s, 1H), 7.38 (s, 1H), 7.39-7.25 (m, 3H), 4.20 (q, J=6.8 Hz, 2H), 2.59-2.48 (m, 2H), 2.34 (m, 1H), 2.10 (t, 2H), 1.91-1.96 (m, 3H), 1.71 (m, 1H), 1.37 (t, J=6.8 Hz, 3H).

Example 42: N-(4-(3-Chloro-4-fluorophenylamino)-3-cyano-7-ethoxyquinolin-6-yl)-5-(1,2-dithiolan-3-yl)pentanamide

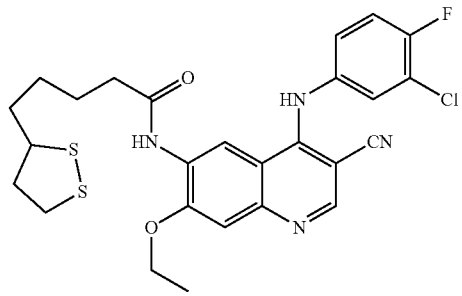 [SMILES: CCOc1cc2ncc(C#N)c(Nc3ccc(F)c(Cl)c3)c2cc1NC(=O)CCCCC1CCSS1]

To a solution of lipoic acid (930 mg, 4.50 mmol) in dichloromethane (10 mL) was added N—N-dimethylformamide (2 drops) and oxalyl chloride (0.50 mL, 5.4 mmol) at room temperature and the solution was stirred for 30 min. To this was added a solution of 4-((3-chloro-4-fluorophenyl)amino)-6-amino-7-ethoxyquinoline-3-carbonitrile (530 mg, 1.5 mmol) in dichloromethane (10 mL) and Et$_3$N (0.80 mL, 5.7 mmol) and the mixture was stirred at room temperature for 30 minutes. The dichloromethane layer was separated, washed with water and dried over Na$_2$SO$_4$ and filtered. Evaporation of solvents in vacuo gave a crude residue which was purified by column chromatography twice using 60-80% Ethyl acetate/hexanes as eluent to afford the desired product (110 mg, 13.0%) as an off white/yellowish solid. $^1$H NMR (400 MHz, DMSO-d6): δ 9.0 (s, 1H), 8.6 (s, 1H), 8.1 (s, 1H), 7.5 (s, 1H), 7.4 (s, 1H), 7.2-7.1 (m, 3H), 4.3 (q, 2H), 3.6 (m, 1H), 3.2 (m, 2H), 2.5 (m, 3H), 1.9 (m, 1H), 1.8-1.7 (m, 4H), 1.6 (m, 5H). HPLC 94.6%

Example 43: N-(4-(3-Chloro-4-fluorophenylamino)-3-cyano-7-ethoxyquinolin-6-yl)-5-(1,2-dithiolan-3-yl)pentanamide

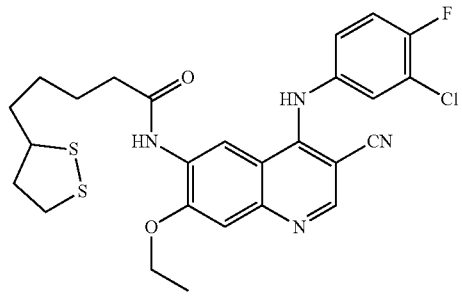 [SMILES: CCOc1cc2ncc(C#N)c(Nc3ccc(F)c(Cl)c3)c2cc1NC(=O)CCCCC1CCSS1]

To a solution of lipoic acid (0.29 g, 1.4 mmol) in N—N-dimethylformamide (10 ml) was added 4-((3-chloro-4-fluorophenyl)amino)-6-amino-7-ethoxyquinoline-3-carbonitrile (0.5 g, 1.4 mmol), EDC (3 eq) and stirred for 2-3 hours at room temperature under dark condition. Completion of reaction was monitored by TLC. The reaction mixture was poured in to ice cold-water (100 mL) and the precipitated solid was extracted with dichloromethane (200 mL) and the combined organic layer was washed with water (100 mL). The combined organic layer was dried over Na$_2$SO$_4$, filtered and concentrated. The crude product was purified over a column of silica gel (mobile phase: 50% Ethyl acetate-hexanes) to afford 0.17 g (31%) of the desired product as a yellow solid. ¹H NMR 400 MHz (CDCl3): δ 9.0 (s, 1H), 8.6 (s, 1H), 8.1 (s, 1H), 7.5 (s, 1H), 7.4 (s, 1H), 7.2-7.1 (m, 3H), 4.3 (q, 2H), 3.6 (m, 1H), 3.2 (m, 2H), 2.5 (m, 3H), 1.9 (m, 1H), 1.8-1.7 (m, 4H), 1.6 (m, 5H). ESI-Mass: m/e 545 [M+H]⁺.

Example 44: N-(4-(3-Chloro-4-((3-fluorobenzyloxy)phenylamino)-3-cyano-7-ethoxyquinolin-6-yl)-5-(1,2-dithiolan-3-yl)pentanamide

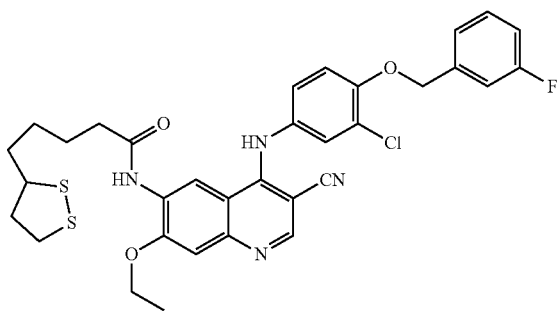 [SMILES: CCOc1cc2ncc(C#N)c(Nc3ccc(OCc4cccc(F)c4)c(Cl)c3)c2cc1NC(=O)CCCCC1CCSS1]

To a solution of lipoic acid (2.10 g, 10.2 mmol) in dichloromethane (20 mL) was added N—N-dimethylformamide (2 drops) and oxalyl chloride (0.90 mL, 10.2 mmol) at room temperature and the solution was stirred for 30 minutes. The reaction mixture was then concentrated in vacuo and was dissolved in dichloromethane (20 mL). From this solution 15 mL (7.6 mmol) was added to a solution of 6-amino-4-((3-chloro-4-(3-fluorobenzyloxy)phenylamino)-7-ethoxyquinoline-3-carbonitrile (785 mg, 1.70 mmol) in dichloromethane (20 mL) and Et₃N (1.90 mL, 13.6 mmol) and stirred at room temperature for 2 hours. The dichloromethane layer was separated, washed with water, dried over Na₂SO₄ and filtered. Evaporation of solvents in vacuo gave a crude residue which was purified by column chromatography twice using 60-100% Ethyl acetate/hexanes as eluent to afford the desired product (88 mg, 13%) as a yellowish semi-solid: ¹H-NMR 300 MHz (DMSO-d6): δ 10.02 (s, 1H), 9.77 (s, 1H), 8.82 (s, 1H), 8.47 (s, 1H), 7.42 (s, 1H), 7.39 (s, 1H), 7.35-6.95 (m, 6H), 5.20 (s, 2H), 4.31 (q, J=6.8 Hz, 2H), 3.20-3.11 (m, 3H), 2.95 (m, 2H), 2.50 (m, 1H), 1.90 (m, 2H), 1.80 (m, 2H), 1.47 (t, J=6.8 Hz, 3H), 1.34 (m, 2H); HPLC 93.3%.

Example 45: 5-Acetamido-2-nitrobenzoic acid

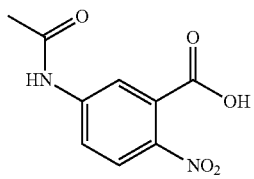 [SMILES: CC(=O)Nc1ccc([N+](=O)[O-])c(C(=O)O)c1]

To a stirred solution of 5-amino-2-nitrobenzoic acid (1.0 g, 5.49 mmol) in dichloromethane (15 mL) at 0° C. was added acetyl chloride (0.39 mL, 5.49 mmol) followed by addition of triethylamine (0.76 mL, 5.49 mmol) with stirring for 1 hour at room temperature. The reaction mixture was then quenched with water and extracted with ethyl acetate (3×200 mL) and the combined organic layer was dried over anhydrous Na₂SO₄, filtered and concentrated and dried under vacuum to give 0.92 g (76%) desired product as a white solid. ¹H NMR 400 MHz (DMSO-d6): δ 13.78 (s, 1H), 10.59 (s, 1H), 7.97 (m, 2H), 7.84 (m, 1H), 2.11 (s, 3H); MS (ES) m/e 225 [M+1]⁺.

Example 46: Phenyl 3-acetamido-2-nitrobenzoate

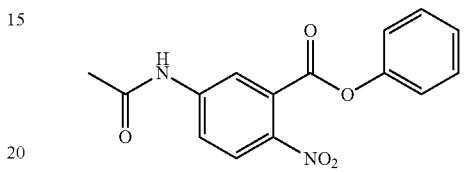

To a stirred mixture of 5-acetamido-2-nitrobenzoic acid (0.92 g, 4.13 mmol) in dichloromethane (10 mL) at 0° C. was added phenol (0.46 g, 4.95 mmol) followed by addition of N,N'-dicyclohexylcarbodiimide (1.27 g, 6.16 mmol) and 4-pyrrolidinopyridine (0.091 g, 0.62 mmol). The reaction mixture was stirred at room temperature for 12 hours then the reaction mixture was filtered through celite. The filtrate was concentrated and the desired product was isolated by column chromatography at 2% methanol in dichloromethane to give 1.2 g (97%) as a white solid. ¹H NMR 400 MHz (DMSO-d6): δ 10.75 (s, 1H), 8.23 (m, 2H), 7.95 (d, J=2.8 Hz, 1H), 7.53 (m, 2H), 7.29 (m, 3H); MS (ES) m/e 299 [M+1].

Example 47: Phenyl 5-acetamido-2-aminobenzoate

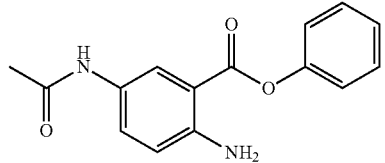 [SMILES: CC(=O)Nc1ccc(N)c(C(=O)Oc2ccccc2)c1]

To a solution of phenyl 3-acetamido-2-nitrobenzoate (1.2 g, 4.00 mmol) in methanol (20 mL) was carefully added 10% Pd/C (0.2 g) and was vigorously stirred at 30° C. under hydrogen pressure at 60 psi for 6 hours. The reaction mixture was filtered using celite and the filtrate was concentrated and dried under vacuum to furnish the desired product (1.0 g, yield 92%). ¹H NMR 400 MHz (DMSO-d6): δ 9.71 (s, 1H), 8.11 (d, J=2.4 Hz, 1H), 7.54 (m, 3H), 7.31-7.20 (m, 3H), 6.79-6.77 (d, J=8.8 Hz, 1H), 6.5 (s, 2H), 5.5 (d, J=7.6 Hz, 2H) 1.98 (s, 3H); MS (ES) m/e 271 [M+1]⁺.

Example 48: Phenyl (E)-5-acetamido-2-((2-cyanovinyl) amino) benzoate

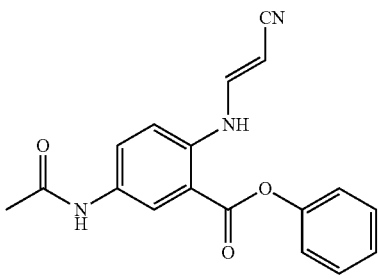 [SMILES: CC(=O)Nc1ccc(N/C=C/C#N)c(C(=O)Oc2ccccc2)c1]

To a slurry solution of phenyl 5-acetamido-2-aminobenzoate (1 g, 3.70 mmol) in acetic acid (10 mL) was added (E)-3-morpholinoacrylonitrile (0.79 g, 5.55 mmol) and the reaction mixture was stirred at room temperature for 2 hours. The reaction mixture was quenched with water and filtered and the resultant solid was dried under vacuum to give 1.0 g (71%) of the desired product. $^1$H NMR 400 MHz (DMSO-d6): δ 10.38 (d, J=12.8 Hz, 1H), 10.12 (s, 1H), 10.10 (s, 1H), 8.40 (m, 1H), 7.6 (m, 1H), 7.44 (m, 5H), 5.58 (d, J=8.4 Hz, 1H), 5.15 (d, J=13.6 Hz, 1H) 2.04 (s, 3H); MS (ES) m/e 322 [M+1]$^+$.

Example 49: N-(3-Cyano-4-hydroxyquinolin-6-yl)acetamide

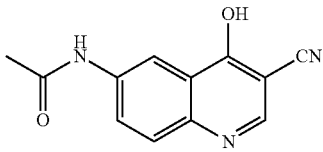 [SMILES: CC(=O)Nc1ccc2ncc(C#N)c(O)c2c1]

To a stirred solution of phenyl (E)-5-acetamido-2-((2-cyanovinyl) amino) benzoate (5.0 g, 15.57 mmol) in dry DMSO (30 mL) was added NaH (60%), (1.12 g, 23.36 mmol) at 0° C. and stirred at room temperature for 2 hours. The reaction mixture was quenched with water and acidified with 6N HCl to ~pH 6. The precipitated solid was filtered, dried under vacuum to give 2.5 g (71%) of desired product. $^1$H NMR 400 MHz (DMSO-d6): δ 12.78 (s, 1H), 10.26 (s, 1H), 8.64 (s, 1H), 8.37 (d, J=2 Hz, 1H), 7.98 (m, 1H), 7.60 (d, J=8.8 Hz, 1H), 2.07 (s, 3H); MS (ES) m/e 228 [M+1]$^+$.

Example 50: N-(4-Chloro-3-cyanoquinolin-6-yl)acetamide

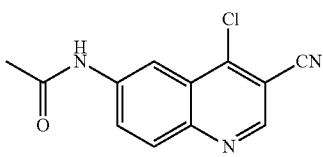 [SMILES: CC(=O)Nc1ccc2ncc(C#N)c(Cl)c2c1]

To a solution of N-(3-cyano-4-hydroxyquinolin-6-yl) acetamide (1.5 g, 6.60 mmol) in dioxane (50 mL) were added phosphorus oxychloride (5.05 mL, 33.03 mmol) dropwise at 0° C. and dimethylaminopyridine (0.40 g, 3.33 mmol), The reaction mixture was heated 100° C. for 3 hours, then cooled and concentrated, poured into water. A solution of saturated sodium carbonate was added resulting in a precipitate which was filtered and dried to give 1.5 g (93%) as solid. MS (ES) m/e 252 [M+1]$^+$.

Example 51: 2-Methyl-5-(2-methyl-4-nitrophenoxy)pyridine

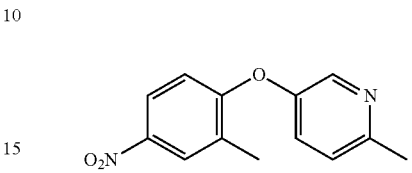

A mixture of 1-fluoro-2-methyl-4-nitrobenzene (1 g, 6.4 mmol), 6-methylpyridin-3-ol (0.77 g, 7.09 mmol), CS$_2$CO$_3$ (2.5 g, 7.7 mmol) and N—N-dimethylformamide (10 mL) was heated to 110° C. for 4 hours. The reaction mixture was cooled to room temperature and then quenched with water, extracted with ethyl acetate (3×200 mL). The combined organic layers were dried over anhydrous Na$_2$SO$_4$, filtered, concentrated and dried under vacuum to give 1.2 g (80%). $^1$H NMR 400 MHz (DMSO-d6): δ 8.33 (d, J=3.2 Hz, 1H), 8.25 (d, J=2.4 Hz, 1H), 8.06 (m, 1H), 7.52 (m, 1H), 7.33 (m, 1H), 6.86 (d, J=9.2 Hz, 1H) 2.50 (s, 3H), 2.39 (s, 3H); MS (ES) m/e 245 [M+1]$^+$.

Example 52: 3-Methyl-4-((6-methylpyridin-3-yl)oxy)aniline

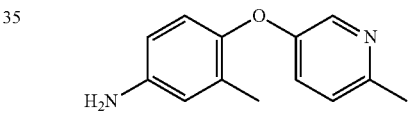

A solution of 2-methyl-5-(2-methyl-4-nitrophenoxy) pyridine (1.2 g, 4.9 mmol), 10% Pd/C (0.2 g), in methanol (20 mL) was vigorously stirred at 30° C. under hydrogen pressure at 60 psi for 12 hours. The reaction mixture was filtered using celite and the filtrate was concentrated and dried under vacuum to provide the product (0.8 g, yield 91%). $^1$H-NMR 400 MHz (DMSO-d6): δ 7.16 (m, 1H), 7.02 (dd, J$_1$=2.8 Hz, J$_2$=8.8 Hz, 1H), 6.6 (m, 1H), 6.6 (m, 1H), 6.4 (m, 1H), 5.00 (bs, 2H), 2.49 (s, 3H), 1.97 (s, 3H); MS (ES) m/e 215 [M+1]$^+$.

Example 53: N-(3-Cyano-4-((3-methyl-4-((6-methylpyridin-3-yl)oxy)phenyl)amino)quinolin-6-yl)acetamide

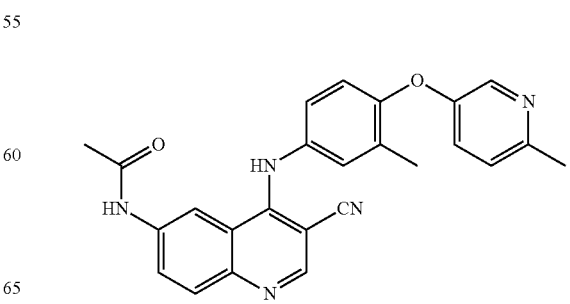

To a solution of N-(4-chloro-3-cyanoquinolin-6-yl) acetamide (0.4 g, 1.79 mmol) and 3-methyl-4-((6-methylpyridin-3-yl)oxy) aniline (0.46 g, 2.15 mmol), in isopropanol (20 mL) 3-methyl-4-((6-methylpyridin-3-yl)oxy) aniline (0.46 g, 2.15 mmol) was heated in a sealed tube at 150° C. for 12 hours. The reaction mixture was cooled and solvents were evaporated to give a reside which was washed with diethyl ether, filtered and dried to give 1.0 g of crude desired product as a white solid. MS (ES): m/e 424 [M+1]$^+$.

Example 54: 6-Amino-4-((3-methyl-4-((6-methyl-pyridin-3-yl)oxy)phenyl)amino)quinoline-3-carbonitrile

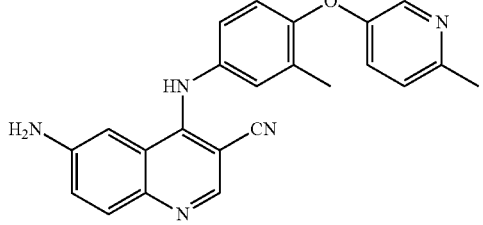

To a stirred solution of N-(3-cyano-4-((3-methyl-4-((6-methylpyridin-3-yl)oxy)phenyl)amino) quinolin-6-yl) acetamide (0.9 g, 2.13 mmol) in methanol (20 mL) was added KOH (0.36 g, 6.38 mmol) and heated for 60 hours at 70° C. After cooling, the solvent was removed and the residue was poured into ice water to furnish a precipitate which was filtered and dried to give 0.6 g (75%) as a solid. MS (ES): m/e 382 [M+1]$^+$.

Example 55: N-(3-Cyano-4-((3-methyl-4-((6-methylpyridin-3-yl)oxy)phenyl)amino)quinolin-6-yl)-2-(1,2-dithiolan-3-yl)acetamide

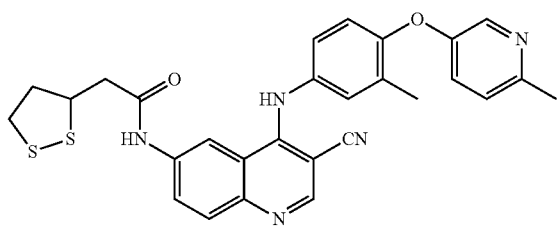 [SMILES: Cc1ccc(Oc2ccc(Nc3c(C#N)cnc4ccc(NC(=O)CC5CCSS5)cc34)cc2C)cn1]

To a solution of 2-(1,2-dithiolan-3-yl)acetyl chloride, prepared from 2-(1,2-dithiolan-3-yl)acetic acid (0.8 g, 4.8 mmol) and oxalyl chloride (1.84 mL, 14.6 mmol) in presence of catalytic amount N—N-dimethylformamide in dichloromethane (5 mL) and tetrahydrofuran (5 mL) at 0° C. was added a mixture of 6-amino-4-((3-methyl-4-((6-methylpyridin-3-yl)oxy)phenyl) amino)quinoline-3-carbonitrile (300 mg, 0.78 mmol)) and N, N-diisopropylethylamine (2.4 ml, 14.17 mmol) in N—N-dimethylformamide (5 mL) and tetrahydrofuran (10 mL) and the resultant solution was stirred for 1 hour. The solvents were then evaporated and poured into water, filtered and dried to afford a crude solid which was purified by preparative HPLC column: ODS-3V (250*4.6*5.0μ); mobile phase A 0.01 M ammonium acetate, B acetonitrile, flow rate 1 mL/min to give 8 mg of pure title compound. $^1$H NMR 400 MHz (DMSO-d6) δ 10.38 (s, 1H), 9.79 (s, 1H), 8.76 (s, 1H), 8.50 (s, 3H), 8.18 (s, 1H), 7.91-7.79 (m, 2H), 7.26-7.14 (m, 4H), 6.99 (m, 1H), 4.10 (s, 1H), 2.93-2.75 (m, 3H), 2.50 (m, 3H), 2.42 (s, 3H), 2.15 (s, 3H); LCMS m/e: 528 [M+1]$^+$.

Example 56: S,S'-(2-((3-Cyano-4-((3-methyl-4-((6-methylpyridin-3-yl)oxy)phenyl)amino) quinolin-6-yl)carbamoyl)propane-1,3-diyl)diethanethioate

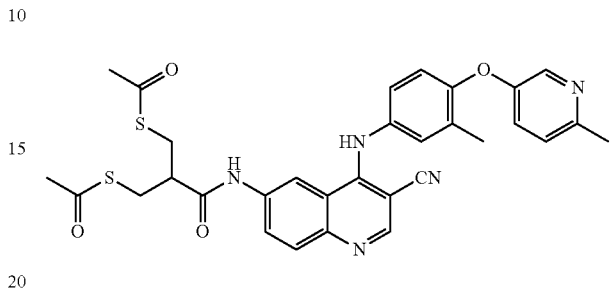

To a mixture of 6-amino-4-((3-methyl-4-((6-methylpyridin-3-yl)oxy)phenyl)amino)quinoline-3-carbonitrile (300 mg, 0.79 mmol) and S,S'-(2-(chlorocarbonyl)propane-1,3-diyl) diethanethioate (prepared from 3-(acetylthio)-2-((acetylthio)methyl)propanoic acid (1.3 g, 5.51 mmol) and oxalylchloride (0.96 mL, 7.62 mmol in dichloromethane (20 mL) and tetrahydrofuran (10 mL) was added N,N-diisopropylethylamine (2.4 mL, 14.2 mmol) at 0° C., and stirred at room temperature for 1 hour. The reaction mixture was concentrated and poured into water and extracted with ethyl acetate (3×100 mL). The organic extracts were washed with water, dried over anhydrous Na$_2$SO$_4$, filtered and concentrated at reduced pressure to furnish an oil which was purified by preparative HPLC column ACE C-8 (250*4.6*5.0μ); mobile phase A: 0.1% TFA, B: acetonitrile, flow rate 1 mL/min to give the title compound (9 mg, 2%). $^1$H NMR 400 MHz (DMSO-d6) δ 10.48 (s, 1H), 9.80 (s, 1H), 8.75 (s, 1H), 8.51 (s, 1H), 8.18 (s, 1H), 7.92-7.80 (m, 2H), 7.25-6.99 (m, 5H), 2.50-2.40 (m, 5H), 2.42 (s, 6H), 2.34 (s, 3H), 2.15 (s, 3H); LCMS m/e: 600 [M+1]$^+$.

Example 57: N-(3-Cyano-4-((3-methyl-4-((6-methylpyridin-3-yl)oxy)phenyl)amino)quinolin-6-yl)-1,2-dithiolane-4-carboxamide

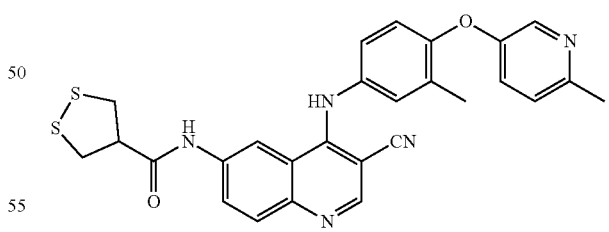

A mixture of S,S'-(2-((3-cyano-4-((3-methyl-4-((6-methylpyridin-3-yl)oxy)phenyl)amino) quinolin-6-yl)carbamoyl)propane-1,3-diyl)diethanethioate (17 mg 0.028 mmol) in methanolic ammonia (3 mL) at room temperature was stirred for 30 minutes. Evaporation of solvents gave an oil which was triturated with diethyl ether to afford a solid which was dried in vacuum (8 mg, 62%). $^1$H-NMR (DMSO-d6): δ 10.56 (s, 1H), 8.78 (s, 1H), 8.50 (s, 1H), 8.48 (s, 1H), 7.92-7.81 (m, 3H), 7.24-6.98 (m, 5H), 2.67-2.50 (m, 5H), 2.50 (s, 3H), 2.15 (s, 3H); LCMS m/e: 514 [M+1]$^+$.

Example 58: N-(4-((3-Chloro-4-((3-fluorobenzyl)oxy)phenyl)amino)-3-cyanoquinolin-6-yl)acetamide

Example 60: S,S'-(2-((4-((3-Chloro-4-((3-fluorobenzyl)oxy)phenyl)amino)-3-cyanoquinolin-6-yl)carbamoyl)propane-1,3-diyl)diethanethioate

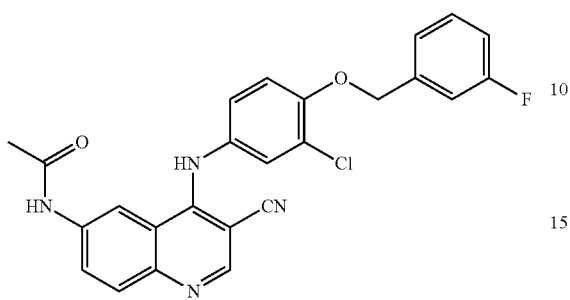

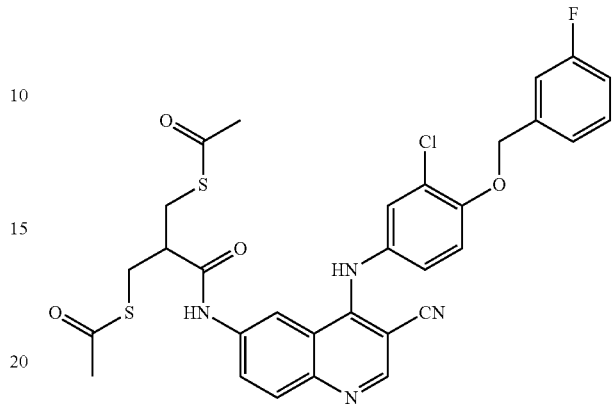

To a solution of N-(4-chloro-3-cyanoquinolin-6-yl)acetamide (1.0 g, 4.08 mmol) in isopropanol (20 mL) was added 3-chloro-4-(3-fluorobenzyl)oxyaniline (1.02 g, 4.08 mmol) and poured into a sealed tube for heating at 150° C. for 12 hours. The reaction mixture was cooled and solvents were evaporated to give a residue which was washed with diethyl ether, filtered and dried to give 2.0 g of crude desired product as solid. MS (ES) m/e 461 [M+1]$^+$.

Example 59: -Amino-4-((-3-Chloro-4-((3-flurobenzyl)oxy)phenyl)amino)quinolone-3-carbonitrile

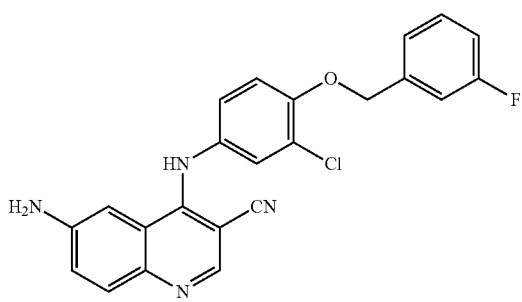 [SMILES: N#Cc1cnc2ccc(N)cc2c1Nc1ccc(OCc2cccc(F)c2)c(Cl)c1]

To a stirred solution of 6-amino-4-((-3-chloro-4-((3-flurobenzyl)oxy)phenyl)amino)quinolone-3-carbonitrile (1.9 g, 4.13 mmol) in methanol (35 mL) was added 2N HCl (25 mL) and heated at 70° C. for 12 hours. From the reaction mixture solvent was removed, poured into water and made basic to ~pH 8 with aqueous NaHCO$_3$ and precipitated solid was filtered and dried to give 0.8 g (47%) as a white solid. MS (ES): m/e 419 [M+1]$^+$.

To a mixture of 6-amino-4-((-3chloro-4-((3-flurobenzyl)oxy)phenyl)amino)quinolone-3-carbonitrile (300 mg, 0.71 mmol) and S,S'-(2-(chlorocarbonyl)propane-1,3-diyl)diethanethioate (prepared from 3-(acetylthio)-2-((acetylthio)methyl)propanoic acid (1.3 g, 5.02 mmol) and oxalylchloride (0.96 mL, 7.6 mmol in dichloromethane (15 mL) and tetrahydrofuran (10 mL) was added N,N-diisopropylethylamine (N,N-diisopropylethylamine, 2.4 mL, 7.0 mmol) at 0° C., and the reaction mixture was stirred at room temperature for 1 hour. The reaction mixture was concentrated and poured into water and then extracted with ethyl acetate (3×100 mL). The combined organic extracts were washed with water concentrated and dried anhydrous Na$_2$SO$_4$, filtered, and concentrated at reduced pressure to give the crude product as pale brown solid (400 mg). The pure compound was obtained by preparative HPLC column C-18 (250*4.6*5.0μ); mobile phase A: 0.1% TFA, B: acetonitrile, flow rate 1 mL/min to give to give 12 mg of the title compound. $^1$H NMR 400 MHz (DMSO-d6) δ 10.48 (s, 1H), 9.73 (s, 1H), 8.72 (d, J=2 Hz, 1H), 8.50 (s, 1H), 7.92-7.89 (m, 1H), 7.83-7.82 (m, 1H), 7.46 (m, 2H), 7.34 (m, 3H), 7.24 (m, 2H), 5.25 (s, 2H), 2.35 (s, 6H), 3.20 (m, 4H), 3.04 (m, 1H); LCMS m/e: 637 [M+1]$^+$.

Example 61: N-(4-((3-Chloro-4-((3-fluorobenzyl)oxy)phenyl)amino)-3-cyanoquinolin-6-yl)-1,2-dithiolane-4-carboxamide

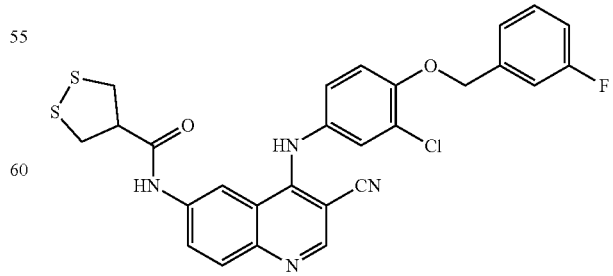

To a solution containing 6-amino-4-((3-chloro-4-((3-fluorobenzyl)oxy)phenyl)amino) quinoline-3-carbonitrile (0.25 g, 0.60 mmol) and 1,2-dithiolane-4-carboxylic acid (0.62 g, 4.19 mmol) in N-methylpyrrolidone (10 mL) was added 1-(3-dimethylaminopropyl)-3-ethylcarbodiimide hydrochloride (0.8 g, 4.19 mmol) and heated for 12 hours at 90° C. The reaction mixture was cooled and poured into water to form a precipitate which was filtered, dried and purified by column chromatography eluting with 2-3% methanol in dichloromethane to give the desired compound (120 mg, 37%). ¹H NMR 400 MHz (DMSO-d6): δ 10.54 (s, 1H), 9.73 (s, 1H), 8.75 (d, J=6.8 Hz, 1H), 8.50 (s, 1H), 7.92-7.90 (m, 1H) 7.82-7.80 (m, 1H), 7.49-7.41 (m, 2H), 7.34-7.30 (m, 2H), 7.26-7.15 (m, 3H), 5.25 (s, 1H), 3.57-3.44 (m, 3H), 3.37-3.32 (m, 2H); MS (ES) m/e 551 [M+1]⁺.

Example 62: N-(4-((3-Chloro-4-((3-fluorobenzyl)oxy)phenyl)amino)-3-cyanoquinolin-6-yl)-2-(1,2-dithiolan-3-yl)acetamide

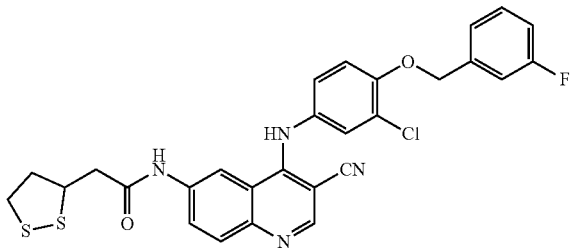 [SMILES: N#Cc1cnc2ccc(NC(=O)CC3CCSS3)cc2c1Nc1ccc(OCc2cccc(F)c2)c(Cl)c1]

A solution of 6-amino-4-((3-chloro-4-((3-fluorobenzyl)oxy)phenyl)amino)quinoline-3-carbonitrile (300 mg, 0.72 mmol) and 2-(1,2-dithiolan-3-yl)acetyl chloride (prepared from 2-(1,2-dithiolan-3-yl)acetic acid (0.96 g, 5.02 mmol) and oxalyl chloride (0.92 mL, 10.53 mmol) in dichloromethane (10 mL) and tetrahydrofuran (10 mL) was added N,N-diisopropylethylamine (1.27 mL, 7.17 mmol) and at 0° C. and the reaction was stirred for 2 hours at room temperature. The solvents were then evaporated, poured into water and extracted with 5% methanol in dichloromethane (2×100 mL). The organic extracts were combined, washed with water, dried over anhydrous Na₂SO₄, filtered and concentrated at reduced pressure. The title compound was isolated by column chromatography eluting with 5% methanol in dichloromethane followed by preparative HPLC: column symmetry C-18 (250*4.6*5.0µ); mobile phase A: 0.1% TFA, B: acetonitrile, flow rate 1 mL/min to afford title compound as a white solid (30 mg, 8%). ¹H NMR 400 MHz (DMSO-d6): δ 10.38 (s, 1H), 9.71 (s, 1H), 8.72 (d, J=1.2 Hz, 1H), 8.49 (s, 1H), 7.91-7.79 (m, 2H), 7.48-7.16 (m, 7H), 5.25 (s, 2H), 4.10-4.06 (m, 1H), 3.31-2.93 (m, 3H), 2.91-2.74 (m, 2H), 2.07 (m, 1H); LCMS m/e: 565[M+1]⁺.

Example 63: (E)-3-Morpholinoacrylonitrile

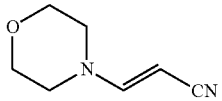

A mixture of morpholine (15.0 g, 172 mmol), 2-cyanoacetic acid (14.7 g, 172 mmol) and triethylorthoformate (28.6 ml, 172 mmol) was heated at 140° C. for 2 hours. The reaction mixture was concentrated under reduced pressure, diluted with dichloromethane and washed with water and saturated sodium bicarbonate solutions. The organic phase was dried over anhydrous Na₂SO₄, filtered and concentrated at reduced pressure to give the desired product (15 g, yield: 63%). ¹H-NMR (DMSO-d6): δ 7.15 (d, J=14.0 Hz, 1H), 4.14 (d, J=14.0 Hz, 1H), 3.56 (t, J=4.8 Hz, 4H), 3.15 (t, J=4.8 Hz, 4H); MS (ES) m/e 139 [M+H]⁺.

Example 64: (R)-(2,2-Dimethyl-1,3-dioxolan-4-yl)methyl methanesulfonate

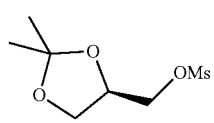

To a stirred solution of (S)-(2,2-dimethyl-1,3-dioxolan-4-yl)methanol (2.0 g, 15 mmol) in dichloromethane (60 mL) at 0° C. were added triethylamine (2.5 mL, 18 mmol) and methanesulfonyl chloride (1.3 mL, 17 mmol) and stirred at room temperature for 12 hours. The reaction mixture was concentrated, poured into water and made basic with sodium bicarbonate solution. This solution was then extracted with ethyl acetate (3×200 mL) and the organic layer was dried over anhydrous Na₂SO₄, filtered and concentrated in vacuo to give an oil. The desired product was obtained by column chromatography on silica gel using 20% ethyl acetate in hexanes as the eluent to give 3.0 g (100%). ¹H-NMR (DMSO-d6): δ 4.33-4.23 (m, 2H), 4.16-4.12 (m, 1H), 4.03 (dd, J₁=8.8 Hz, J₂=6.8 Hz, 1H), 3.71 (dd, J₁=8.4 Hz, J₂=6.0 Hz, 1H), 3.21 (s, 3H), 1.35 (s, 3H), 1.28 (s, 3H); MS (ES) m/e 211 [M+H]⁺.

Example 65: (S)-(2,2-Dimethyl-1,3-dioxolan-4-yl)methyl methanesulfonate

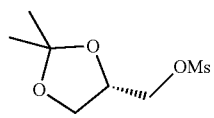

To a stirred solution of (R)-(2,2-dimethyl-1,3-dioxolan-4-yl)methanol (2.0 g, 15 mmol) in dichloromethane (60 mL) at 0° C. were added triethylamine (2.5 mL, 18 mmol) and methanesulfonyl chloride (1.3 mL, 17 mmol) and stirred at room temperature for 12 hours. The reaction mixture was concentrated, poured into water and made basic with sodium bicarbonate solution. This solution was then extracted with ethyl acetate (3×200 mL) and the organic layer was dried over anhydrous Na₂SO₄, filtered and concentrated in vacuo to give an oil. The desired product was obtained by column chromatography on silica gel using 20% ethyl acetate in hexanes as the eluent to give 3.0 g (100%). ¹H-NMR (DMSO-d6): δ 4.33-4.23 (m, 2H), 4.16-4.12 (m, 1H), 4.03 (dd, J₁=8.8 Hz, J₂=6.8 Hz, 1H), 3.71 (dd, J₁=8.4 Hz, J₂=6.0 Hz, 1H), 3.21 (s, 3H), 1.35 (s, 3H), 1.28 (s, 3H); MS (ES) m/e 211 [M+H]⁺.

Example 66: 3-Acetamido-4-methoxybenzoic acid

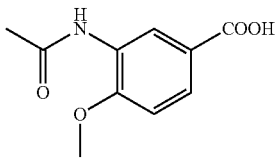

To a stirred solution of 3-amino-4-methoxybenzoic acid (4.17 g, 24.9 mmol) in dichloromethane (40 mL) at 0° C. were added acetyl chloride (1.77 mL, 24.9 mmol) and triethylamine (3.30 mL, 24.9 mmol). The solution was stirred at room temperature for 1 hours and then quenched with water, extracted with dichloromethane (3×200 mL) and the combined organic layer was dried over anhydrous $Na_2SO_4$, filtered, concentrated in vacuo and dried under vacuum to give 4.5 g (88%) desired product as solid. $^1$H-NMR (DMSO-d6): δ 12.60 (s, 1H), 9.23 (s, 1H), 8.55 (d, J=2 Hz, 1H), 7.68 (dd, $J_1$=8.8 Hz, $J_2$=2 Hz, 1H), 7.12 (d, J=8.8 Hz, 1H), 3.89 (s, 3H), 2.09 (s, 3H); MS (ES) m/e 210 $[M+H]^+$.

Example 67: Phenyl 3-acetamido-4-methoxybenzoate

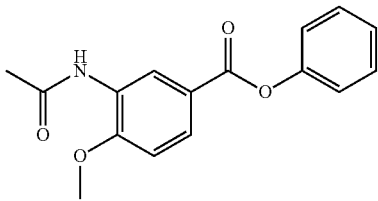 [SMILES: COc1ccc(C(=O)Oc2ccccc2)cc1NC(C)=O]

To a stirred mixture of 3-acetamido-4-methoxybenzoic acid (2.40 g, 11.5 mmol) in dichloromethane (50 mL) at 0° C. were added phenol (1.29 g, 13.7 mmol), N,N'-dicyclohexylcarbodiimide (3.55 g, 17.2 mmol) and 4-pyrrolidinopyridine (0.254 g, 1.72 mmol). The reaction mixture was stirred at room temperature for 12 hours, then filtered through celite and concentrated in vacuo. The product was isolated by column chromatography on silica gel using 30% ethyl acetate in petroleum ether to give 2.5 g (78%) as a solid. $^1$H-NMR (DMSO-d6): δ 9.39 (s, 1H), 8.74 (d, J=2 Hz, 1H), 7.76 (dd, $J_1$=8.8 Hz, $J_2$=2 Hz, 1H), 7.49-7.45 (m, 2H), 7.30-7.22 (m, 4H), 3.95 (s, 3H), 2.12 (s, 3H); MS (ES) m/e 286 $[M+H]^+$.

Example 68: Phenyl 5-acetamido-4-methoxy-2-nitrobenzoate

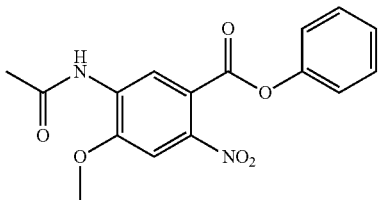 [SMILES: COc1cc([N+](=O)[O-])c(C(=O)Oc2ccccc2)cc1NC(C)=O]

To a stirred mixture of phenyl 3-acetamido-4-methoxybenzoate (2.50 g, 8.77 mmol) in dichloromethane (30 mL) at 0° C. was added fuming nitric acid (3.1 mL). The reaction mixture was stirred at room temperature for 2 hours. The reaction mixture was quenched with water and extracted with dichloromethane (2×500 mL) and the organic layer was dried over anhydrous $Na_2SO_4$, filtered, concentrated and washed with aqueous $NaHCO_3$ to give 2.5 g (86%) of the desired product as solid. $^1$H-NMR (DMSO-d6): δ 9.79 (s, 1H), 8.76 (s, 1H), 7.80 (s, 1H), 7.49-7.47 (m, 2H), 7.35-7.23 (s, 3H), 4.05 (s, 3H), 2.19 (s, 3H); MS (ES) m/e 329 $[M-H]^+$.

Example 69: Phenyl 5-acetamido-2-amino-4-methoxybenzoate

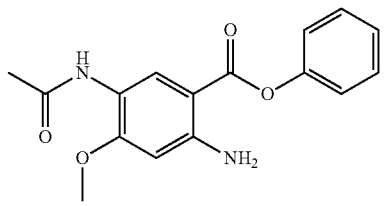 [SMILES: COc1cc(N)c(C(=O)Oc2ccccc2)cc1NC(C)=O]

The mixture of phenyl 5-acetamido-4-methoxy-2-nitrobenzoate (2.50 g, 7.57 mmol), 10% Pd/C (0.8 g), in methanol (100 mL) was vigorously stirred at 30° C. under hydrogen pressure at 60 psi for 2 hours. The reaction mixture was filtered using celite the filtrate was concentrated and dried under vacuum to provide the product (2.0 g, yield 88%). $^1$H-NMR (DMSO-d6): δ 8.99 (s, 1H), 8.22 (s, 1H), 7.46-7.42 (m, 2H), 7.29-7.17 (s, 3H), 6.73 (s, 1H), 6.42 (s, 1H), 3.81 (s, 3H), 2.00 (s, 3H); MS (ES) m/e 301 $[M+H]^+$.

Example 70: Phenyl (E)-5-acetamido-2-((2-cyanovinyl)amino)-4-methoxybenzoate

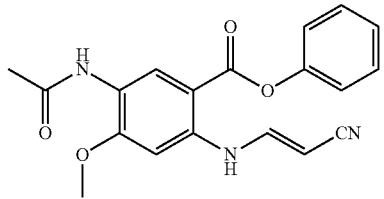 [SMILES: COc1cc(N/C=C/C#N)c(C(=O)Oc2ccccc2)cc1NC(C)=O]

To a slurry solution of phenyl 5-acetamido-2-amino-4-methoxybenzoate (2.0 g, 6.6 mmol) in acetic acid (20 mL) was added (E)-3-morpholinoacrylonitrile (1.37 g, 9.90 mmol) and the reaction mixture was stirred at room temperature for 2 hours, quenched with water and filtered over celite. Solvents were removed in vacuo and the residual solid was dried under vacuum to give 1.42 g (60%) desired product. $^1$H-NMR (DMSO-d6): δ 10.64 (d, J=12.4 Hz, 1H), 9.28 (s, 1H), 8.71 (s, 1H), 8.12-8.07 (m, 1H), 7.50-7.46 (m, 2H), 7.35-7.26 (m, 3H), 7.12 (s, 1H), 4.67 (d, J=8.4 Hz, 1H), 4.00 (s, 3H), 2.07 (s, 3H); MS (ES) m/e 352 $[M+H]^+$.

Example 71: N-(3-Cyano-4-hydroxy-7-methoxyquinolin-6-yl)acetamide

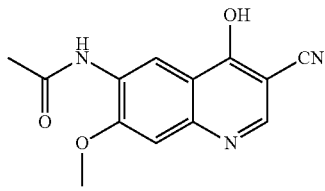 [SMILES: COc1cc2ncc(C#N)c(Cl)c2cc1NC(C)=O]

To a stirred solution of phenyl (E)-5-acetamido-2-((2-cyanovinyl)amino)-4-methoxybenzoate (1.50 g, 4.27 mmol) in DMSO (10 mL) was added a slurry of 60% NaH, (0.37 g, 6.4 mmol) at 0° C. and stirred at room temperature for 2 hours. The reaction mixture was then carefully quenched with water and acidified with 6N HCl to bring to ~pH 6. The precipitated solid was filtered, dried under vacuum to give 0.75 g (75%) of desired product. $^1$H-NMR (DMSO-d6): δ 12.58 (bs, 1H), 9.37 (s, 1H), 8.71 (s, 1H), 8.60 (s, 1H), 7.07 (s, 1H), 3.95 (s, 3H), 2.13 (s, 3H); MS (ES) m/e 258 [M+H]$^+$.

Example 72: N-(3-Cyano-4-chloro-7-methoxyquinolin-6-yl)acetamide

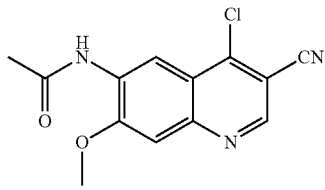

To a solution of N-(3-cyano-4-hydroxy-7-methoxyquinolin-6-yl)acetamide (0.20 g, 7.8 mmol) in toluene (8 mL) were added phosphorus oxychloride (0.30 mL, 1.9 mmol) dropwise at 0° C. and triethylamine (0.027 mL, 0.19 mmol), The reaction mixture was heated to 100° C. for 3 hours, then concentrated, poured carefully into water followed by the addition of sodium carbonate solution to make the solution basic. The solution was then extracted with ethyl acetate (3×100 mL) and the organic layer was dried over anhydrous Na$_2$SO$_4$, filtered, concentrated in vacuo to give an oil which was purified by column chromatography on silica gel using 2% methanol in dichloromethane as an eluent to give 0.20 g (93%) as an off white-solid. $^1$H-NMR (DMSO-d6): δ 9.73 (s, 1H), 9.12 (s, 1H), 9.01 (s, 1H), 7.62 (s, 1H), 4.10 (s, 3H), 2.23 (s, 3H); MS (ES) m/e 276 [M+H]$^+$.

Example 73: N-(3-Cyano-4-chloro-7-hydroxyquinolin-6-yl)acetamide

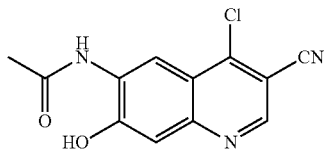 [SMILES: CC(=O)Nc1cc2c(Cl)c(C#N)cnc2cc1O]

To a stirred solution of N-(3-cyano-4-chloro-7-methoxyquinolin-6-yl)acetamide (0.027 g, 0.10 mmol) in 1,2 dichloroethane (5 mL) was added BBr$_3$ (0.29 mL, 3.1 mmol) at 0° C. and the reaction mixture was heated at 100° C. for 5 hours. The reaction mixture was cooled and solvents were evaporated under vacuum, quenched carefully with water and the obtained solid was filtered, dried under vacuum to give 0.02 g (80%) of desired product. $^1$H-NMR (DMSO-d6): δ 12.00 (bs, 1H), 9.65 (s, 1H), 9.11 (s, 1H), 8.93 (s, 1H), 7.44 (s, 1H), 2.23 (s, 3H); MS (ES) m/e 260 [M–H]$^+$.

Example 74: N-(4-((3-Chloro-4-((3-fluorobenzyl)oxy)phenyl)amino)-3-cyano-7-hydroxyquinolin-6-yl)acetamide

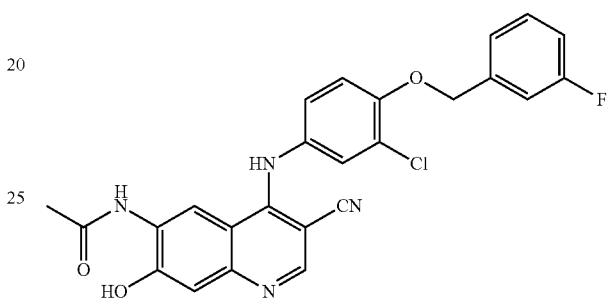

A solution of N-(3-cyano-4-chloro-7-hydroxyquinolin-6-yl)acetamide (0.010 g, 0.038 mmol) and 3-chloro-4-((3-fluorobenzyl)oxy)aniline (0.010 g, 0.042 mmol) and isopropyl alcohol (5 mL) in a sealed tube was heated at 150° C. for 12 hours. The reaction mixture was then cooled and solvents were evaporated in vacuo to give a crude solid which was washed with diethyl ether (5 mL) and dried under vacuum to afford a pale brown solid (10 mg, 56%). $^1$H-NMR (DMSO-d6): δ 12.50 (bs, 1H), 11.32 (s, 1H), 9.50 (s, 1H), 8.87 (s, 1H), 8.54 (s, 1H), 7.45 (s, 1H), 7.41-7.20 (m, 7H), 5.25 (s, 2H), 2.15 (s, 3H); MS (ES) m/e 477 [M+H]$^+$.

Example 75: (S)—N-(4-((3-Chloro-4-((3-fluorobenzyl)oxy)phenyl)amino)-3-cyano-7-((2,2-dimethyl-1,3-dioxolan-4-yl)methoxy)quinolin-6-yl)acetamide

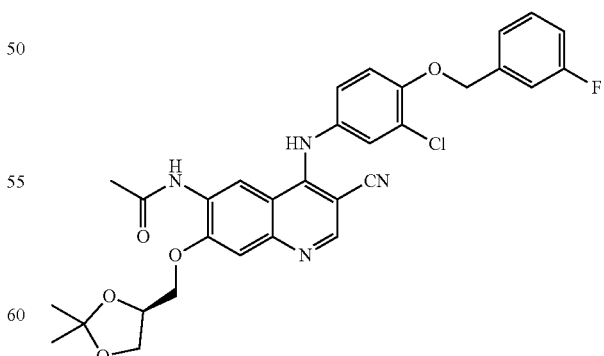

To a solution of N-(4-((3-chloro-4-((3-fluorobenzyl)oxy)phenyl)amino)-3-cyano-7-hydroxyquinolin-6-yl)acetamide (0.16 g, 0.34 mmol) in N—N-dimethylformamide (5 mL) was added Cs$_2$CO$_3$ (0.33 g, 1.01 mmol). After stirring for 10 minutes at room temperature, (R)-(2,2-dimethyl-1,3-dioxolan-4-yl)methyl methanesulfonate (0.11 g, 0.50 mmol) was added and the reaction mixture was heated at 90° C. for 12 h. The mixture was cooled, poured into water and extracted with ethyl acetate (3×50 mL). The combined extracts were washed with water, dried over anhydrous $Na_2SO_4$, filtered, concentrated at reduced pressure to produce the desired product (20 mg). $^1$H-NMR (DMSO-d6): δ 9.61 (s, 1H), 9.28 (s, 1H), 8.77 (s, 1H), 8.48 (s, 1H), 7.45 (s, 1H), 7.42-7.21 (m, 7H), 5.25 (s, 2H), 4.42-4.40 (m, 1H), 4.33 (d, J=5.2 Hz, 2H), 4.19-4.17 (m, 1H), 3.90-3.87 (m, 1H), 2.16 (s, 3H), 1.24 (s, 3H), 1.23 (s, 3H); MS (ES) m/e 591 [M+H]$^+$.

Example 76: (R)—N-(4-((3-Chloro-4-((3-fluorobenzyl)oxy)phenyl)amino)-3-cyano-7-((2,2-dimethyl-1,3-dioxolan-4-yl)methoxy)quinolin-6-yl)acetamide

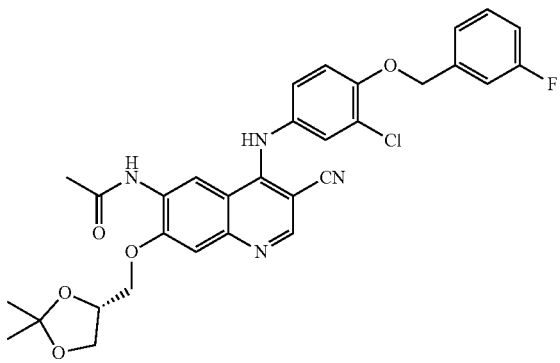 [SMILES: CC(=O)Nc1cc2c(Nc3ccc(OCc4cccc(F)c4)c(Cl)c3)c(C#N)cnc2cc1OC[C@@H]1COC(C)(C)O1]

To a solution of N-(4-((3-chloro-4-((3-fluorobenzyl)oxy)phenyl)amino)-3-cyano-7-hydroxyquinolin-6-yl)acetamide (0.16 g, 0.34 mmol) in N—N-dimethylformamide (5 mL) was added $Cs_2CO_3$ (0.327 g, 1.01 mmol). After stirring for 10 minutes at room temperature, (S)-(2,2-dimethyl-1,3-dioxolan-4-yl)methyl methanesulfonate (0.11 g, 0.50 mmol) was added and the reaction mixture was heated at 90° C. for 12 hours. The mixture was cooled, poured into water and extracted with ethyl acetate (3×50 mL). The combined extracts were washed with water, dried over anhydrous $Na_2SO_4$, filtered, concentrated at reduced pressure to produce the desired product (20 mg). $^1$H-NMR (DMSO-d6): δ 9.61 (s, 1H), 9.28 (s, 1H), 8.77 (s, 1H), 8.48 (s, 1H), 7.45 (s, 1H), 7.42-7.21 (m, 7H), 5.25 (s, 2H), 4.42-4.40 (m, 1H), 4.33 (d, J=5.2 Hz, 2H), 4.19-4.17 (m, 1H), 3.90-3.87 (m, 1H), 2.16 (s, 3H), 1.24 (s, 3H), 1.23 (s, 3H); MS (ES) m/e 591 [M+H]$^+$.

Example 77: (S)-6-Amino-4-((3-chloro-4-((3-fluorobenzyl)oxy)phenyl)amino)-7-((2,2-dimethyl-1,3-dioxolan-4-yl)methoxy)quinoline-3-carbonitrile

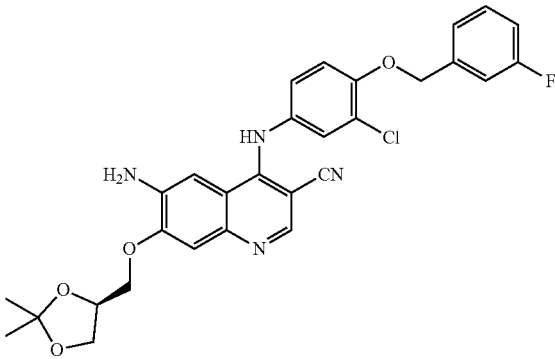 [SMILES: CC1(C)OC[C@H](COc2cc3ncc(C#N)c(Nc4ccc(OCc5cccc(F)c5)c(Cl)c4)c3cc2N)O1]

To a stirred solution of (S)—N-(4-((3-chloro-4-((3-fluorobenzyl)oxy)phenyl)amino)-3-cyano-7-((2,2-dimethyl-1,3-dioxolan-4-yl)methoxy)quinolin-6-yl)acetamide (2.73 g, 4.5 mmol) in methanol (30 mL) was added KOH (2.73 g, 4.5 mmol) and heated at 70° C. for 60 hours. After cooling, the solvent was evaporated in vacuo and the residue was poured into water, acidified with 2N HCl to bring the solution to ~pH 6. The aqueous mixture was then extracted with ethyl acetate (2×100 mL), washed with water, dried over anhydrous $Na_2SO_4$, filtered and concentrated at reduced pressure to produce 500 mg of the desired crude product. $^1$H-NMR (DMSO-d6): δ 9.14 (s, 1H), 8.76 (s, 1H), 8.31 (s, 1H), 8.47 (s, 1H), 7.47-7.06 (m, 7H), 5.76 (s, 2H), 5.25 (s, 2H), 4.54-4.51 (t, J=5.2 Hz, 1H), 4.22-4.19 (m, 3H), 3.90-3.88 (m, 1H), 1.39 (s, 6H); LCMS m/e 549 [M+H]$^+$.

Example 78: (R)-6-Amino-4-((3-chloro-4-((3-fluorobenzyl)oxy)phenyl)amino)-7-((2,2-dimethyl-1,3-dioxolan-4-yl)methoxy)quinoline-3-carbonitrile

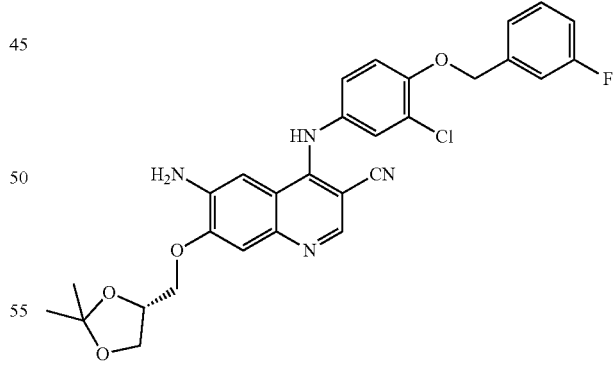

To a stirred solution of (R)—N-(4-((3-chloro-4-((3-fluorobenzyl)oxy)phenyl)amino)-3-cyano-7-((2,2-dimethyl-1,3-dioxolan-4-yl)methoxy)quinolin-6-yl)acetamide (4.0 g, 6.7 mmol) in methanol (40 mL) was added KOH (1.13 g, 20.3 mmol) and heated at 70° C. for 60 hours. After cooling, the solvent was evaporated in vacuo and the residue was poured into water, acidified with 2N HCl to bring the solution to ~pH 6. The aqueous mixture was then extracted with ethyl acetate (2×100 mL), washed with water, dried over anhydrous Na₂SO₄, filtered and concentrated at reduced pressure to produce 900 mg of the desired crude product (24%). ¹H-NMR (DMSO-d6): δ 9.14 (s, 1H), 8.76 (s, 1H), 8.31 (s, 1H), 8.47 (s, 1H), 7.47-7.06 (m, 7H), 5.76 (s, 2H), 5.25 (s, 2H), 4.54-4.51 (t, J=5.2 Hz, 1H), 4.22-4.19 (m, 3H), 3.90-3.88 (m, 1H), 1.39 (s, 6H); LCMS m/e 549 [M+H]⁺.

Example 79: N-(4-((3-Chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3-yl)acetamide

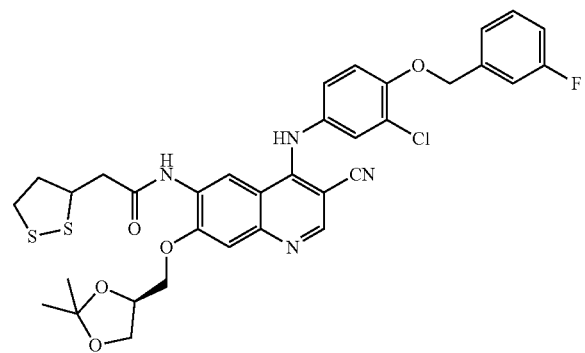 [SMILES: CC1(C)OC[C@H](COc2cc3ncc(C#N)c(Nc4ccc(OCc5cccc(F)c5)c(Cl)c4)c3cc2NC(=O)CC2CCSS2)O1]

To a mixture of (S)-6-amino-4-((3-chloro-4-((3-fluorobenzyl)oxy)phenyl)amino)-7-((2,2-dimethyl-1,3-dioxolan-4-yl)methoxy)quinoline-3-carbonitrile (0.35 g, 0.64 mmol) and 2-(1,2-dithiolan-3-yl)acetic acid (0.52 g, 3.2 mmol) in N-methylpyrrolidone (10 mL) was added 1-(3-dimethylaminopropyl)-3-ethylcarbodiimide hydrochloride (0.6 g, 3.19 mmol) and the reaction mixture was heated at 80° C. for 12 hours. The mixture was then cooled, poured into water and extracted with ethyl acetate (3×300 mL). The combined extracts were washed with water, dried over anhydrous Na₂SO₄, filtered and concentrated at reduced pressure to give the desired product (400 mg, crude), which was used in the next step without further purification. MS (ES) m/e 695 [M+H]⁺.

Example 80: N-(4-((3-Chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3R-yl)acetamide and N-(4-((3-chloro-4-((3-fluorobenzyl)oxy)phenyl)amino)-3-cyano-7-(((S)-2,2-dimethyl-1,3-dioxolan-4-yl) methoxy)quinolin-6-yl)-2-(1,2-dithiolan-3S-yl)acetamide

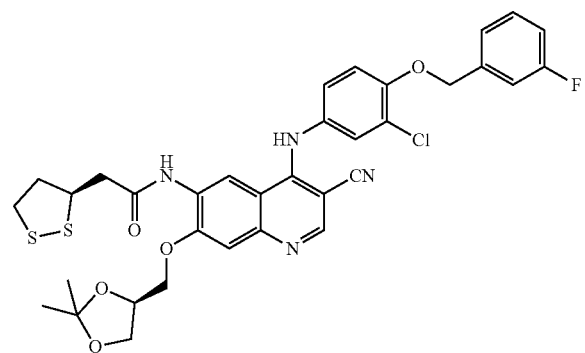

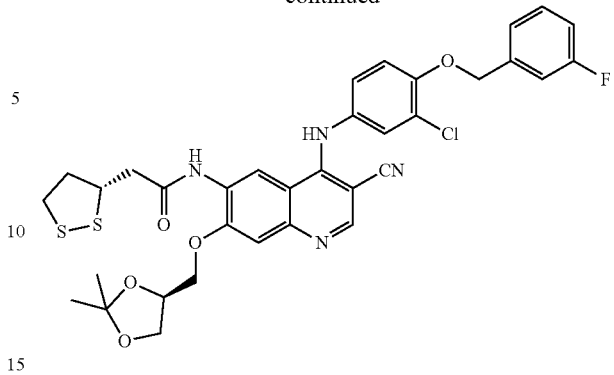

Alternatively, the diastereomeric mixture containing the two title compounds was separated chiral HPLC techniques to give two diastereomers peak 1, retention time 8.15 min (20 mg) and peak 2 retention time 9.42 min (21 mg) column: Chiralpak-IA (250*20*5.0µ), mobile phase-A: n-hexanes (0.1% DEA), mobile phase-B: ethanol, method: isocratic: 50:50 (A:B), flow rate: 15.0 mL/min, diluent: mobile phase: dichloromethane, sample loading: 12 mg/inj, run time: 25 min/inj.

¹H-NMR 400 MHz (DMSO-d6): δ 9.64 (s, 1H), 9.39-9.34 (m, 1H), 8.77 (s, 1H), 8.48 (s, 1H), 7.49-7.18 (m, 12H), 5.25 (s, 1H), 4.55-4.52 (m, 1H), (m, 1H), 4.27 (d, J=5.2 Hz, 2H), 4.19-4.17 (m, 1H), 3.28-3.24 (m, 1H), 3.18-3.14 (m, 1H), 2.92-2.81 (m, 2H), 2.07 (s, 1H), 1.39 (s, 3H), 1.33 (s, 3H); LCMS m/e: 695 [M+1]⁺. Peak 2 ¹H-NMR 400 MHz (DMSO-d6): δ 9.64 (s, 1H), 9.39-9.34 (m, 1H), 8.77 (s, 1H), 8.48 (s, 1H), 7.49-7.18 (m, 12H), 5.25 (s, 1H), 4.55-4.52 (m, 1H), 4.27 (d, J=5.2 Hz, 2H), 4.19-4.17 (m, 1H), 3.28-3.24 (m, 1H), 3.18-3.14 (m, 1H), 2.92-2.81 (m, 2H), 2.07 (s, 1H), 1.39 (s, 3H), 1.33 (s, 3H); LCMS m/e: 695 [M+1]⁺.

Example 81: N-(4-((3-Chloro-4-((3-fluorobenzyl)oxy)phenyl)amino)-3-cyano-7-((R)-2,3-dihydroxypropoxy)quinolin-6-yl)-2-(1,2-dithiolan-3S-yl) acetamide

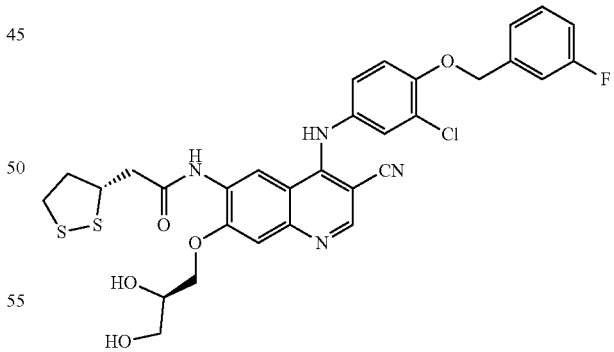

To a mixture of N-(4-((3-chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3S-yl)acetamide (peak 1 example 79) (18 mg, 0.025 mmol) in methanolic hydrochloric acid (5 mL) was stirred at room temperature for 15 min. The reaction mixture was concentrated and poured into water and the aqueous layer was extracted with 10% methanol in dichloromethane (3×50 mL). The combined organic extracts were washed with water, dried over anhydrous Na$_2$SO$_4$, filtered and concentrated at reduced pressure to give the desired product (10 mg, yield: 62.5%): $^1$H-NMR 400 MHz (DMSO-d6): δ 9.63 (s, 1H), 9.40 (s, 1H), 8.91 (s, 1H), 8.47 (s, 1H), 7.41-7.22 (m, 8H), 5.25 (s, 2H), 5.20 (s, 1H), 4.26 (m, 1H), 4.17-4.04 (m, 3H), 3.54-3.32 (m, 3H), 3.16-2.89 (m, 4H), 2.05 (m, 2H); LCMS m/e: 655 [M]$^+$. Chiral HPLC retention time 17.3 minutes, column: Chiralpak-IA (250*20*5.0μ), mobile phase-A: n-hexanes (0.1% DEA), mobile phase-B: ethanol, method: isocratic: 80:20 (A:B), flow rate: 1.0 mL/min, diluent: mobile phase: dichloromethane, sample loading: 12 mg/inj, run time: 25 min/inj.

Example 82: N-(4-((3-Chloro-4-((3-fluorobenzyl)oxy)phenyl)amino)-3-cyano-7-((R)-2,3-dihydroxypropoxy)quinolin-6-yl)-2-(1,2-dithiolan-3-yl)acetamide Example 83: N-(4-((3-Chloro-4-((3-fluorobenzyl)oxy)phenyl)amino)-3-cyano-7-((R)-2,3-dihydroxypropoxy)quinolin-6-yl)-2-(1,2-dithiolan-3-yl)acetamide Chiral HPLC separation method

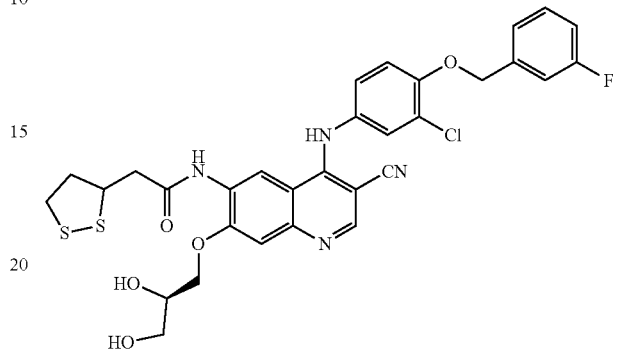

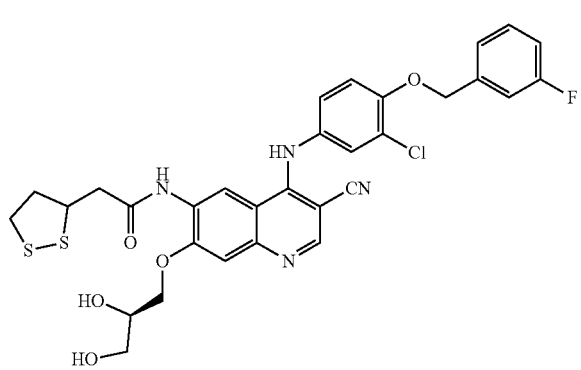 [SMILES: N#Cc1cnc2cc(OC[C@H](O)CO)c(NC(=O)CC3CCSS3)cc2c1Nc1ccc(OCc2cccc(F)c2)c(Cl)c1]

To a mixture of N-(4-((3-chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3-yl)acetamide (peak 2, example 79) (18 mg, 0.025 mmol) in methanolic hydrochloric acid (5 mL) was stirred at room temperature for 15 min. The reaction mixture was then concentrated and poured into water. The aqueous layer was extracted with 10% methanol in dichloromethane (3×50 mL) and the combined organic extracts were washed with water, dried over anhydrous Na$_2$SO$_4$, filtered and concentrated at reduced pressure to give the desired product (10 mg, yield: 63%) $^1$H-NMR 400 MHz (DMSO-d6): δ 9.63 (s, 1H), 9.40 (s, 1H), 8.91 (s, 1H), 8.47 (s, 1H), 7.41-7.22 (m, 8H), 5.25 (s, 2H), 5.20 (s, 1H), 4.26 (m, 1H), 4.17-4.04 (m, 3H), 3.54-3.32 (m, 3H), 3.16-2.89 (m, 4H), 2.05 (m, 2H); LCMS m/e: 655 [M]$^+$. Chiral HPLC retention time 15.4 minutes, column: Chiralpak-IA (250*20*5.0μ), mobile phase-A: n-hexanes (0.1% DEA), mobile phase-B: ethanol, method: isocratic: 50:50 (A:B), flow rate: 15.0 mL/min, diluent: mobile phase: dichloromethane, sample loading: 12 mg/inj, run time: 30 min/inj.

To a mixture of N-(4-((3-chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3-yl)acetamide (0.4 g, 0.57 mmol) in acetone (10 mL) was added 1M aqueous hydrochloric acid (4 mL) and stirred at 70° C. for 6 hours. The reaction mixture was concentrated in vacuo, poured into water and extracted with ethyl acetate (3×200 mL). The combined extracts were washed with water, dried over anhydrous Na$_2$SO$_4$, filtered and concentrated at reduced pressure to give 170 mg of diastereomeric mixture. The diastereomers were separated by preparative chiral HPLC conditions Chiralpak-IA (250*20*5.0μ), mobile phase-A: n-hexanes (0.1% DEA), mobile phase-B: ethanol, method: isocratic: 80:20 (A:B), flow rate: 15.0 mL/min, diluent: mobile phase: dichloromethane, sample loading: 10 mg/inj, run time: 30 min/inj. to give the title compound: N-(4-((3-chloro-4-((3-fluorobenzyl)oxy)phenyl)amino)-3-cyano-7-((R)-2,3-dihydroxypropoxy)quinolin-6-yl)-2-(1,2-dithiolan-3S-yl)acetamide (1.65 mg, retention time 17.3 min) and: N-(4-((3-chloro-4-((3-fluorobenzyl)oxy)phenyl)amino)-3-cyano-7-((R)-2,3-dihydroxypropoxy)quinolin-6-yl)-2-(1,2-dithiolan-3R-yl)acetamide (1 mg, retention time 15.4 minutes) together with a 1:1 mixture (35 mg, 9.3%) $^1$H-NMR 400 MHz (DMSO-d6): δ 8.92 (s, 1H), 8.47 (s, 1H), 7.47-7.44 (m, 1H), 7.38 (s, 1H), 7.34-7.22 (m, 6H), 5.25 (s, 2H), 4.28-4.26 (m, 1H), 4.13-4.04 (m, 3H), 3.54-3.53 (m, 2H), 3.27-3.14 (m, 3H), 2.98-2.89 (m, 3H), 2.09-2.02 (m, 2H); MS (ES) m/e 655 [M+H]$^+$.

Example 84: N-(4-((3-Chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,2-dithiolan-3R-yl)acetamide and N-(4-((3-chloro-4-((3-fluorobenzyl)oxy)phenyl)amino)-3-cyano-7-(((R)-2,2-dimethyl-1,3-dioxolan-4-yl) methoxy)quinolin-6-yl)-2-(1,2-dithiolan-3S-yl)acetamide

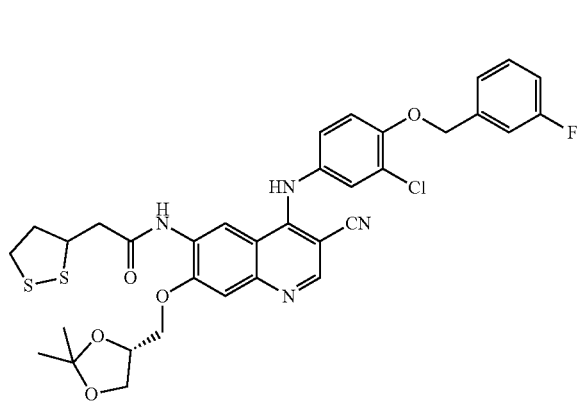 [SMILES: CC1(C)OC[C@@H](COc2cc3ncc(C#N)c(Nc4ccc(OCc5cccc(F)c5)c(Cl)c4)c3cc2NC(=O)CC2CCSS2)O1]

To a mixture of (R)-6-amino-4-((3-chloro-4-((3-fluorobenzyl)oxy)phenyl)amino)-7-((2,2-dimethyl-1,3-dioxolan-4-yl)methoxy)quinoline-3-carbonitrile (0.5 g, 0.9 mmol) and 2-(1,2-dithiolan-3-yl)acetic acid (1.34 g, 80 mmol) in N-methylpyrrolidone (25 mL) was added 1-(3-dimethylaminopropyl)-3-ethylcarbodiimide hydrochloride (1.56 g, 8.0 mmol) and the reaction mixture was heated at 80° C. for 12 hours. The mixture was then cooled, poured into water and extracted with ethyl acetate (3×500 mL). The combined organic extracts were washed with water, dried over anhydrous Na$_2$SO$_4$, filtered and concentrated at reduced pressure to give the desired product (400 mg, crude). This crude product was further separated by chiral preparative chiral HPLC methods: conditions Chiralpak-IA (250*20*5.0µ), mobile phase-A: n-hexanes (0.1% DEA), mobile phase-B: isopropanol, method: isocratic: 50:50 (A:B), flow rate: 15.0 mL/min, diluent: mobile phase: dichloromethane, sample loading: 10 mg/inj, run time: 30 min/inj. to give peak 1 (12 mg, retention time 11.6 minutes) $^1$H-NMR 400 MHz (DMSO-d6): δ 9.64 (s, 1H), 9.39 (s, 1H), 8.77 (s, 1H), 8.48 (s, 1H), 7.45 (s, 1H), 7.44-7.40 (m, 1H), 7.39-7.34 (m, 1H), 7.32-7.24 (m, 2H), 7.23-7.16 (m, 3H), 5.25 (s, 2H), 4.55-4.52 (m, 1H), 4.27 (d, J=5.2 Hz, 2H), 4.17-4.13 (m, 1H), 4.07-4.03 (m, 1H), 3.95-3.92 (m, 1H), 3.51 (s, 1H), 3.27-3.22 (m, 1H), 3.18-3.12 (m, 1H), 2.92-2.85 (m, 1H), 2.08-2.02 (m, 2H), 1.38 (s, 3H), 1.33 (s, 3H); LCMS m/e: 695 [M]$^+$, and peak 2 (25 mg, retention time 14.4 minutes) $^1$H-NMR (DMSO-d6): δ 9.23 (s, 1H), 8.69 (s, 1H), 8.15 (s, 1H), 7.48-7.43 (m, 1H), 7.34-7.30 (m, 3H), 7.29-7.15 (m, 4H), 7.14-7.10 (m, 1H), 5.18 (s, 2H), 4.52-4.49 (m, 1H), 4.19-4.18 (m, 3H), 4.06-4.02 (m, 1H), 3.94-3.91 (m, 1H), 3.52 (s, 2H), 2.08-2.01 (m, 4H), 1.39 (s, 3H), 1.32 (s, 3H); LCMS m/e: 695 [M]$^+$, corresponding to N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,2-dithiolan-3R-yl)acetamide and N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,2-dithiolan-3S-yl) acetamide.

Example 85: N-(4-((3-Chloro-4-((3-fluorobenzyl)oxy)phenyl)amino)-3-cyano-7-((S)-2,3-dihydroxypropoxy)quinolin-6-yl)-2-(1,2-dithiolan-3R-yl)acetamide

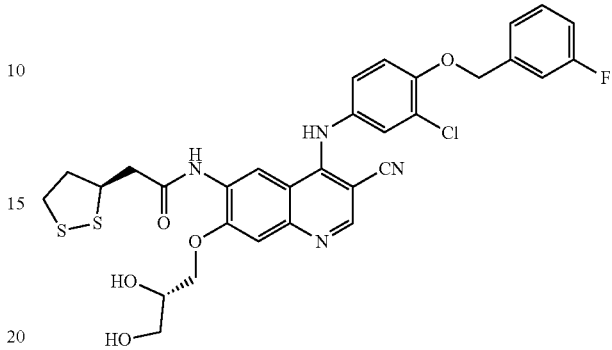

To a mixture of N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,2-dithiolan-3R-yl)acetamide (10 mg, 0.01 mmol) in methanolic hydrochloric acid (5 mL) and stirred at room temperature for 15 min. The reaction mixture was concentrated in vacuo, poured into water and extracted with 10% methanol in dichloromethane (3×50 mL). The combined extracts were washed with water, dried over anhydrous Na$_2$SO$_4$, filtered and concentrated at reduced pressure. The desired product was isolated as an off white (9 mg, 95%) $^1$H-NMR 400 MHz (DMSO-d6): δ 10.8 (s, br, 1H), 9.53 (s, 1H), 9.08 (s, 1H), 8.88 (s, 1H), 7.58-7.21 (m, 8H), 5.30 (s, 2H), 4.26 (m, 1H), 4.17-4.04 (m, 3H), 3.54-3.32 (m, 4H), 3.16-2.89 (m, 4H), 2.05 (m, 2H); LCMS m/e: 655 [M]$^+$. 4. Chiral HPLC conditions Chiralpak-IA (250*20*5.0µ), mobile phase-A: n-hexanes (0.1% DEA), mobile phase-B: ethanol, method: isocratic: 80:20 (A:B), flow rate: 15.0 mL/min, diluent: mobile phase: dichloromethane, sample loading: 10 mg/inj, run time: 30 min/inj. retention time 16.6 minutes.

Example 86: N-(4-((3-Chloro-4-((3-fluorobenzyl)oxy)phenyl)amino)-3-cyano-7-((S)-2,3-dihydroxypropoxy)quinolin-6-yl)-2-(1,2-dithiolan-3S-yl)acetamide

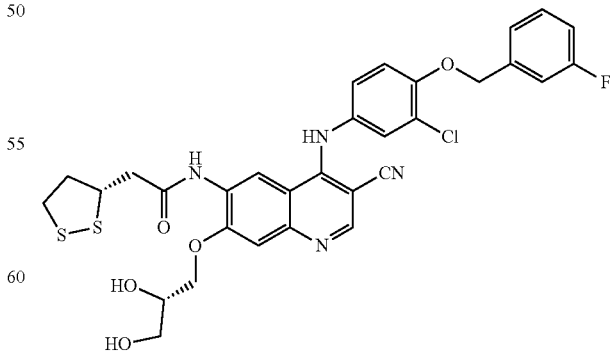

To a mixture of N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,2-dithiolan-3S-yl)acetamide (peak 2 example 57, 21 mg, 0.02 mmol) in methanolic hydrochloric acid (8 mL) and stirred at room temperature for 15 min. The reaction mixture was concentrated in vacuo, poured into water and extracted with 10% methanol in dichloromethane (3×80 mL). The combined extracts were washed with water, dried over anhydrous $Na_2SO_4$, filtered and concentrated at reduced pressure. The desired product was isolated as an off white (16 mg, 84%) $^1$H-NMR 400 MHz (DMSO-d6) δ 9.52 (m, 2H), 9.08 (s, 1H), 8.84 (s, 1H), 7.44-7.07 (m, 8H), 5.16 (s, 2H), 4.15 (m, 1H), 4.04-3.98 (m, 3H), 2.96-2.87 (m, 4H), 2.66-2.50 (m, 4H), 1.86 (m, 2H); LCMS m/e: 655 [M]$^+$. Chiral HPLC conditions Chiralpak-IA (250*20*5.0μ), mobile phase-A: n-hexanes (0.1% DEA), mobile phase-B: ethanol, method: isocratic: 80:20 (A:B), flow rate: 15.0 mL/min, diluent: mobile phase: dichloromethane, sample loading: 10 mg/inj, run time: 30 min/inj. retention time 14.0 minutes.

Example 87: N-(4-((3-Chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,1-dioxido-1,2-dithiolan-3R-yl)acetamide and N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,1-dioxido-1,2-dithiolan-3S-yl)acetamide The chromatographic separation in example 83 produced the mixture of the title compounds

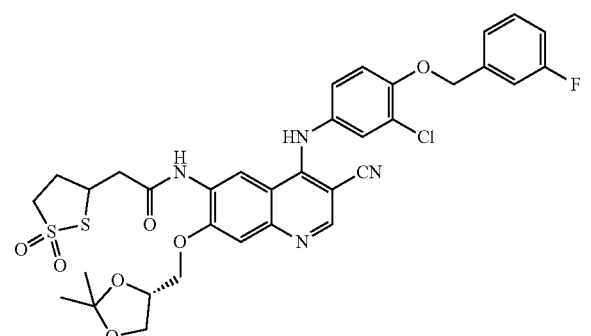

$^1$H-NMR 400 MHz (DMSO-d6): (s, 2H), 9.96 (s, 1H), 9.40 (s, 1H), 8.80 (s, 1H), 8.42 (s, 1H), 7.62-7.20 (m, 7H), 5.3 (s, 2H), 4.62-4.51 (m, 2H), 4.20 (s, 2H), 3.40 (m, 7H), 1.22 (m, 7H); LCMS m/e: 727[M]$^+$.

Example 88: N-(4-((3-Chloro-4-((3-fluorobenzyl)oxy)phenyl)amino)-3-cyano-7-((S)-2,3-dihydroxypropoxy)quinolin-6-yl)-2-(1,1-dioxido-1,2-dithiolan-3R-yl)acetamide and N-(4-((3-chloro-4-((3-fluorobenzyl)oxy)phenyl)amino)-3-cyano-7-((S)-2,3-dihydroxypropoxy)quinolin-6-yl)-2-(1,1-dioxido-1,2-dithiolan-3S-yl)acetamide

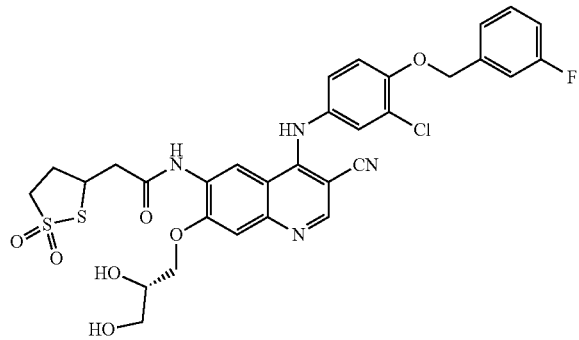 [SMILES: N#Cc1cnc2cc(OC[C@@H](O)CO)c(NC(=O)CC3CCS(=O)(=O)S3)cc2c1Nc1ccc(OCc2cccc(F)c2)c(Cl)c1]

A mixture of N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,1-dioxido-1,2-dithiolan-3-yl)acetamide diastereomeric mixture (20 mg), 0.02 mmol) and hydrochloric acid (5 mL) in methanol was stirred at room temperature for 15 minutes. The reaction mixture was concentrated and poured into water and the aqueous layer was extracted with 10% methanol in dichloromethane (3×50 mL). The combined organic extracts were washed with water, dried over anhydrous $Na_2SO_4$, concentrated at reduced pressure to give the desired product (10 mg, yield: 55%). $^1$H-NMR 400 MHz (DMSO-d6): δ 9.55 (m, 2H), 8.83 (s, 1H), 8.15 (s, 1H), 7.44-7.07 (m, 8H), 5.20 (s, 2H), 4.19-4.04 (m, 2H), 3.91 (m, 1H), 3.50 (m, 2H), 2.96-2.87 (m, 3H), 2.66-2.50 (m, 4H), 1.86 (m, 2H); LCMS m/e: 686 [M−1]$^+$.

Example 89: (S)—N-(4-((3-Chloro-4-((3-fluorobenzyl)oxy)phenyl)amino)-3-cyano-7-((2,2-dimethyl-1,3-dioxolan-4-yl)methoxy)quinolin-6-yl)-2-(1,2-dithiolan-4-yl)acetamide

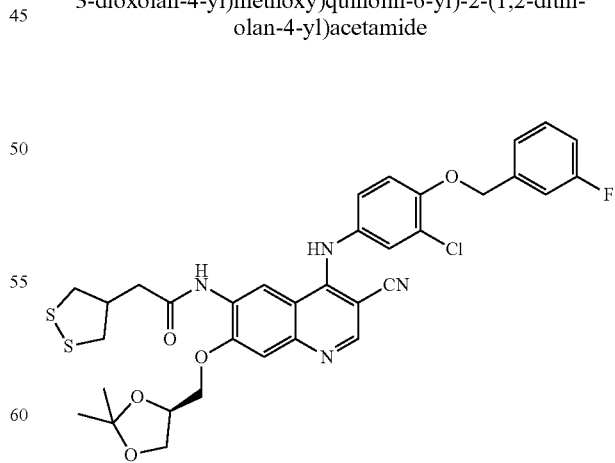

To a mixture of (S)-6-amino-4-((3-chloro-4-((3-fluorobenzyl)oxy)phenyl)amino)-7-((2,2-dimethyl-1,3-dioxolan-4-yl)methoxy)quinoline-3-carbonitrile (0.2 g, 0.36 mmol) and 2-(1,2-dithiolan-4-yl)acetic acid (0.59 g, 3.64 mmol) in N-methylpyrrolidone (5 mL) was added 1-(3-dimethylaminopropyl)-3-ethylcarbodiimide hydrochloride (0.70 g, 3.64 mmol) and the reaction mixture was heated at 90° C. for 12 hours. After cooling, the reaction mixture was poured into ice water and the precipitated solid was filtered and dried and was further purified by preparative HPLC column ACE C-8 (250*4.6*5.0μ); mobile phase A: 0.1% TFA, B: acetonitrile, flow rate 1 mL/min to give the title compound as a white solid (57 mg, yield 23%). $^1$H NMR (DMSO-d6): δ 9.61 (s, 1H), 9.43 (s, 1H), 8.70 (s, 1H), 8.48 (s, 1H), 7.44-7.23 (m, 8H), 5.25 (s, 2H), 4.50 (s, 1H), 4.27-4.26 (m, 2H), 4.14 (m, 1H), 3.90 (m, 1H), 3.36 (m, 2H), 3.023-2.98 (m, 2H), 2.69 (m, 1H), 2.19 (m, 1H), 1.90 (m, 1H), 1.39 (s, 6H); MS (ES) m/e 695 [M+1]$^+$.

Example 90: (R)—N-(4-((3-Chloro-4-((3-fluorobenzyl)oxy)phenyl)amino)-3-cyano-7-(2,3-dihydroxypropoxy)quinolin-6-yl)-2-(1,2-dithiolan-4-yl)acetamide

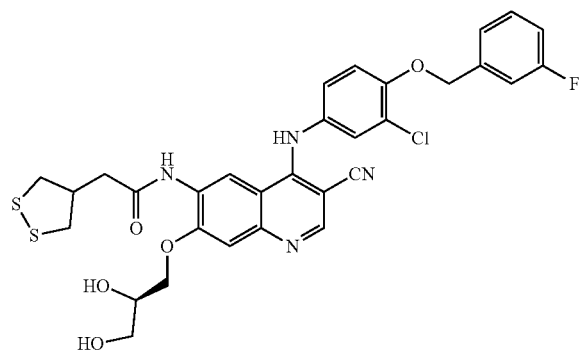 [SMILES: N#Cc1cnc2cc(OC[C@H](O)CO)c(NC(=O)CC3CSSC3)cc2c1Nc1ccc(OCc2cccc(F)c2)c(Cl)c1]

To a solution of (S)—N-(4-((3-chloro-4-((3-fluorobenzyl)oxy)phenyl)amino)-3-cyano-7-((2,2-dimethyl-1,3-dioxolan-4-yl)methoxy)quinolin-6-yl)-2-(1,2-dithiolan-4-yl)acetamide (40 mg, 0.06 mmol) in methanol (5 mL) was added methanolic. HCl (5 mL) and stirring was continued for 30 minutes at room temperature. Then reaction mixture was then concentrated and poured into water and The aqueous mixture was extracted with 10% methanol in dichloromethane (2×100 mL) and the organic layer was washed with water, dried over anhydrous Na$_2$SO$_4$, filtered and concentrated at reduced pressure to provide a crude solid which was further washed with diethyl ether and dried to provide the title compound (37 mg, yield: 98%). $^1$H NMR 400 MHz (DMSO-d6): δ 9.80 (s, 1H), 9.60 (s, 1H), 8.90 (s, 1H), 8.50 (s, 1H), 7.38 (m, 5H), 7.24 (m, 3H), 5.26 (s, 2H), 5.19 (s, 1H), 4.60 (s, 1H), 4.30 (m, 1H), 4.10 (m, 1H), 3.90 (m, 1H), 3.39 (m, 3H), 3.02 (m, 3H), 2.70 (m, 3H); MS (ES) m/e 656 [M+1]$^+$.

Example 91: (R)—N-(4-((3-Chloro-4-((3-fluorobenzyl)oxy)phenyl)amino)-3-cyano-7-((2,2-dimethyl-1,3-dioxolan-4-yl)methoxy)quinolin-6-yl)-2-(1,2-dithiolan-4-yl) acetamide

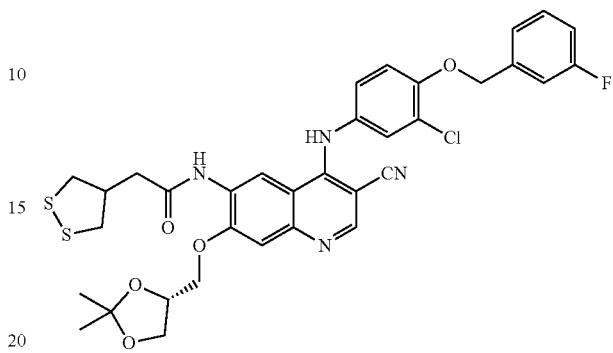

To a solution of ((R)-6-amino-4-((3-chloro-4-((3-fluorobenzyl)oxy)phenyl)amino)-7-((2,2-dimethyl-1,3-dioxolan-4-yl)methoxy)quinoline-3-carbonitrile (0.2 g, 0.36 mmol) and 2-(1,2-dithiolan-4-yl)acetic acid (0.59 g, 3.64 mmol) in N-methylpyrrolidone (5 mL) was added 1-(3-dimethylaminopropyl)-3-ethylcarbodiimide hydrochloride (0.70 g, 3.64 mmol) and the reaction mixture was heated for 12 hours at 90° C. After cooling, the reaction mixture was poured into ice water and the formed solid was filtered and dried to that crude was purified by preparative HPLC column ACE C-8 (250*4.6*5.0μ); mobile phase A: 0.1% TFA, B: acetonitrile, flow rate 1 mL/min to give the title compound (90 mg, yield 36%). $^1$H NMR (DMSO-d6): δ 9.63 (s, 1H), 9.47 (s, 1H), 8.70 (s, 1H), 8.48 (s, 1H), 7.49 (m, 3H), 7.34 (m, 5H), 5.25 (s, 2H), 4.52 (m, 1H), 4.23 (m, 3H), 3.93 (m, 1H), 3.30 (m, 1H), 3.09 (m, 2H), 2.15 (m, 2H), 1.93 (m, 2H), 1.49 (s, 6H); MS (ES) m/e 696 [M+1]$^+$.

Example 92: (S)—N-(4-((3-Chloro-4-((3-fluorobenzyl)oxy)phenyl)amino)-3-cyano-7-(2,3-dihydroxypropoxy)quinolin-6-yl)-2-(1,2-dithiolan-4-yl)acetamide

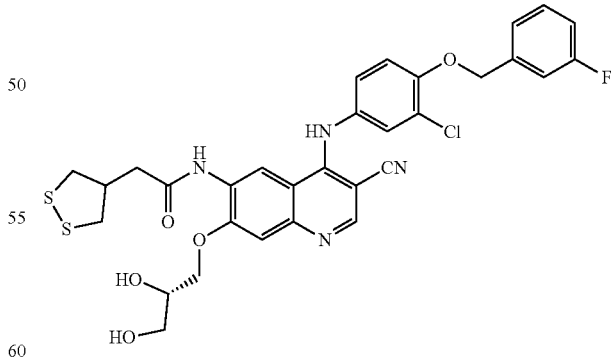

To a solution of (R)—N-(4-((3-chloro-4-((3-fluorobenzyl)oxy)phenyl)amino)-3-cyano-7-((2,2-dimethyl-1,3-dioxolan-4-yl)methoxy)quinolin-6-yl)-2-(1,2-dithiolan-4-yl) acetamide (80 mg, 0.12 mmol) in methanol (5 mL) was added methanolic HCl (5 mL) and was stirred for 30 minutes at room temperature. The reaction mixture was concentrated and poured into water and extracted with 10% methanol in dichloromethane (2×100 mL). and the combined extracts were washed with water, dried over anhydrous $Na_2SO_4$, filtered, concentrated at reduced pressure, further washed with diethyl ether and dried to furnish the title compound (60 mg, yield: 80%). $^1$H NMR 400 MHz (DMSO-d6): δ 9.65 (s, 1H), 9.44 (s, 1H), 8.87 (s, 1H), 8.49 (s, 1H), 7.49-7.17 (m, 8H), 5.25 (s, 2H), 5.20 (d, J=4.8 Hz, 1H), 4.80 (s, 1H), 4.28-4.24 (m, 1H), 4.10-4.07 (m, 1H), 3.93 (s, 1H), 3.53 (m, 2H), 3.28 (m, 1H), 3.02 (m, 2H), 2.68 (m, 2H), 2.33 (m, 1H), 1.91 (m, 1H); LCMS m/e: 653 (M−1).

Example 93: (S)—S,S'-(2-((4-((3-Chloro-4-((3-fluorobenzyl)oxy)phenyl)amino)-3-cyano-7-((2,2-dimethyl-1,3-dioxolan-4-yl)methoxy)quinolin-6-yl)carbamoyl)propane-1,3-diyl) diethanethioate

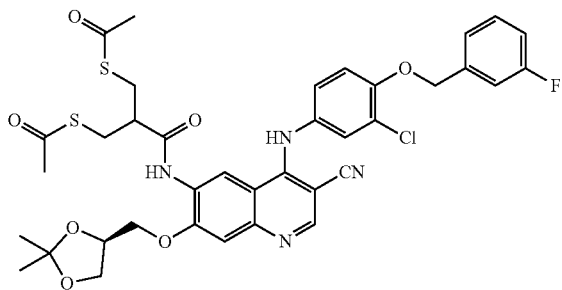 [SMILES: CC(=O)SCC(CSC(C)=O)C(=O)Nc1cc2c(Nc3ccc(OCc4cccc(F)c4)c(Cl)c3)c(C#N)cnc2cc1OC[C@H]1COC(C)(C)O1]

To a mixture of (S)-6-amino-4-((3-chloro-4-((3-fluorobenzyl)oxy)phenyl)amino)-7-((2,2-dimethyl-1,3-dioxolan-4-yl)methoxy)quinoline-3-carbonitrile (200 mg, 0.36 mmol) and S,S'-(2-(chlorocarbonyl)propane-1,3-diyl)diethanethioate (prepared from 3-(acetylthio)-2-((acetylthio)methyl)propanoic acid (0.6 g, 2.54 mmol) and oxalyl chloride (0.48 mL, 3.81 mmol)) in dichloromethane (15 mL) and tetrahydrofuran (10 mL) was added (N,N-diisopropylethylamine, 0.75 ml, 4.38 mmol) at 0° C., and the reaction mixture was warmed to room temperature and stirred for 1 hour. The reaction mixture was then concentrated, poured into water, extracted with ethyl acetate (3×100 mL) and the combined organic extracts were washed with water, dried over anhydrous $Na_2SO_4$, filtered and concentrated to give an oil which was further purified by column chromatography eluting with 1% methanol in dichloromethane to furnish the title compound (90 mg, 33.3%). LCMS m/e: 765 [M−1]$^+$.

Example 94: (R)—S,S'-(2-((4-((3-Chloro-4-((3-fluorobenzyl)oxy)phenyl)amino)-3-cyano-7-(2,3-dihydroxypropoxy)quinolin-6-yl)carbamoyl)propane-1,3-diyl)diethanethioate

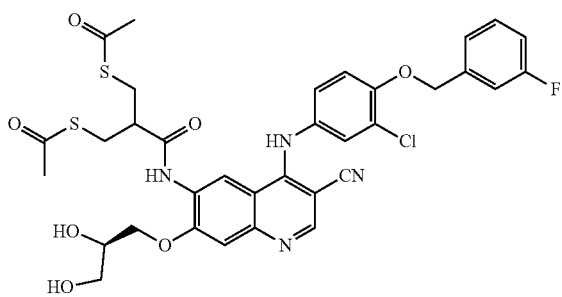 [SMILES: CC(=O)SCC(CSC(C)=O)C(=O)Nc1cc2c(Nc3ccc(OCc4cccc(F)c4)c(Cl)c3)c(C#N)cnc2cc1OC[C@H](O)CO]

A solution of (S)—S,S'-(2-((4-((3-chloro-4-((3-fluorobenzyl)oxy)phenyl)amino)-3-cyano-7-((2,2-dimethyl-1,3-dioxolan-4-yl)methoxy)quinolin-6-yl)carbamoyl)propane-1,3-diyl)diethanethioate (90 mg, 0.12 mmol) in methanolic HCl (5 mL) was stirred for 30 minutes at room temperature. Then reaction mixture was concentrated, poured into water and extracted with 10% methanol in dichloromethane (2×100 mL). The combined extracts were washed with water, dried over anhydrous $Na_2SO_4$, filtered and concentrated at reduced pressure and further purified by preparative HPLC: column ACE C-8 (250*4.6*5.0 microns); mobile phase A: 0.1% TFA, B: acetonitrile, flow rate 1 mL/min to give SAB312 (23 mg, 28%). $^1$H NMR (DMSO-d6): δ 9.64 (s, 1H), 9.44 (s, 1H), 8.85 (s, 1H), 8.48 (s, 1H), 7.47 (d, J=6.4 Hz, 1H), 7.43-7.18 (m, 7H), 5.25 (s, 2H), 5.1 (d, J=5.2 Hz, 1H), 4.75 (t, J=6 HZ, 1H), 4.28 (m, 1H), 4.13 (t, J=6.4 Hz, 1H), 3.95 (d, J=3.6 HZ, 1H), 3.56 (t, J=5.6 Hz, 2H), 3.19-3.06 (m, 5H), 2.39-2.30 (m, 6H); MS (ES) m/e 728 [M+1]$^+$.

Example 95: (R)—N-(4-((3-Chloro-4-((3-fluorobenzyl)oxy)phenyl)amino)-3-cyano-7-(2,3-dihydroxypropoxy)quinolin-6-yl)-1,2-dithiolane-4-carboxamide

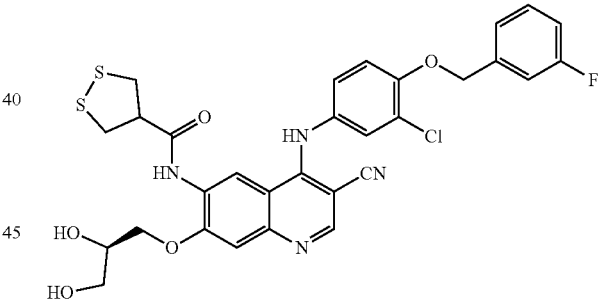

A solution of (R)—S,S'-(2-((4-((3-Chloro-4-((3-fluorobenzyl)oxy)phenyl)amino)-3-cyano-7-(2,3-dihydroxypropoxy)quinolin-6-yl)carbamoyl)propane-1,3-diyl)diethanethioate (14.8 mg, 0.20 mmol) in methanolic ammonia (5 mL) was stirred for 30 minutes at room temperature followed by evaporation of solvents under reduced pressure. The residue was washed with diethyl ether, filtered and dried in vacuum to furnish the title compound (9.5 mg, 73%). $^1$H NMR (DMSO-d6): δ 9.57 (s, 1H), 9.04 (s, 1H), 8.85 (s, 1H), 8.47 (m, 1H), 7.49-7.16 (m, 8H), 5.25 (s, 2H), 5.14 (d, J=5.2 Hz, 1H), 4.77 (m, 2H), 4.29 (m, 1H), 4.14-3.95 (m, 2H), 3.62-3.56 (m, 4H), 2.86 (m, 2H); MS (ES) m/e 643 [M+1]$^+$.

Example 96: (R)—S,S'-(2-((4-((3-Chloro-4-((3-fluorobenzyl)oxy)phenyl)amino)-3-cyano-7-((2,2-dimethyl-1,3-dioxolan-4-yl)methoxy)quinolin-6-yl)carbamoyl)propane-1,3-diyl)diethanethioate

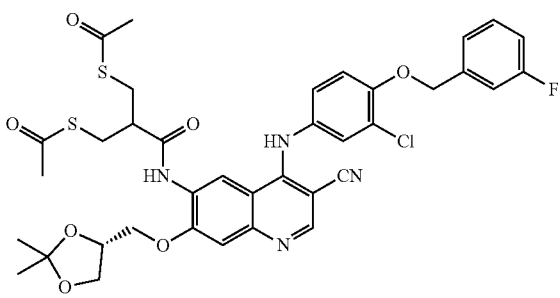 [SMILES: CC(=O)SCC(CSC(C)=O)C(=O)Nc1cc2c(Nc3ccc(OCc4cccc(F)c4)c(Cl)c3)c(C#N)cnc2cc1OC[C@@H]1COC(C)(C)O1]

To a mixture of (R)-6-amino-4-((3-chloro-4-((3-fluorobenzyl)oxy)phenyl)amino)-7-((2,2-dimethyl-1,3-dioxolan-4-yl)methoxy)quinoline-3-carbonitrile (230 mg, 0.42 mmol) and S,S'-(2-(chlorocarbonyl)propane-1,3-diyl)diethanethioate (prepared from 3-(acetylthio)-2-((acetylthio)methyl)propanoic acid (0.99 g, 4.19 mmol) and oxalyl chloride (0.56 mL, 6.29 mmol) in dichloromethane (10 mL) and tetrahydrofuran (5 mL) was added N,N-diisopropylethylamine (0.85 mL, 5.04 mmol) was stirred at 0° C. for 1 hour. The reaction mixture was concentrated, poured into water and extracted with ethyl acetate (3×100 mL). The combined extracts was washed with water, dried over anhydrous Na$_2$SO$_4$, filtered and concentrated at reduced pressure to provide a residue which was purified by column chromatography eluting with 1-2% methanol in dichloromethane to furnish the title compound (200 mg, 62.5%). $^1$H NMR 400 MHz (DMSO-d6) δ 9.69 (s, 1H), 9.49 (s, 1H), 8.74 (s, 1H), 8.49 (s, 1H), 7.73-7.16 (m, 8H), 5.25 (s, 2H), 4.51 (m, 1H), 4.31 (m, 4H), 4.16 (m, 2H), 3.88 (m, 1H), 3.14-3.06 (m, 2H), 1.96 (s, 6H), 1.33 (s, 6H); LCMS m/e: 768 [M+1]$^+$.

Example 97: (S)—S,S'-(2-((4-((3-Chloro-4-((3-fluorobenzyl)oxy)phenyl)amino)-3-cyano-7-(2,3-dihydroxypropoxy)quinolin-6-yl)carbamoyl)propane-1,3-diyl)diethanethioate

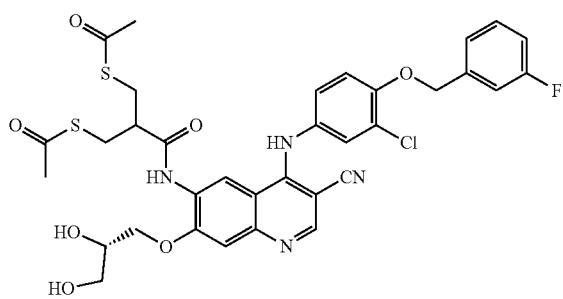 [SMILES: CC(=O)SCC(CSC(C)=O)C(=O)Nc1cc2c(Nc3ccc(OCc4cccc(F)c4)c(Cl)c3)c(C#N)cnc2cc1OC[C@@H](O)CO]

To a solution of (R)—S,S'-(2-((4-((3-chloro-4-((3-fluorobenzyl)oxy)phenyl)amino)-3-cyano-7-((2,2-dimethyl-1,3-dioxolan-4-yl)methoxy)quinolin-6-yl)carbamoyl)propane-1,3-diyl)diethanethioate (200 mg, 0.26 mmol) in methanol (5 mL) was added a solution of methanolic HCl (5 mL) and stirred room temperature for 30 minutes. Then reaction mixture was concentrated in vacuo, poured into water and extracted with 10% methanol in dichloromethane (2×100 mL). The organic extracts were washed with water, dried over anhydrous Na$_2$SO$_4$, filtered and concentrated at reduced pressure and the crude was purified by preparative HPLC: column YMC Triart (250*4.6*5.0μ); mobile phase A: 0.01 M ammonium acetate, B: acetonitrile, flow rate 1 mL/min to give the title compound (20 mg, 10%). $^1$H NMR (DMSO-d6): δ 10.30 (s, 1H), 9.51 (s, 1H), 8.93 (s, 1H), 8.80 (s, 1H), 7.49-7.18 (m, 8H), 5.30 (m, 1H), 5.27 (s, 2H), 4.30-4.26 (m, 1H), 4.15-4.11 (m, 1H), 3.97-3.95 (m, 1H), 3.56-3.54 (m, 3H), 3.43-3.06 (m, 5H), 2.40 (s, 6H); MS (ES) m/e 726 [M−1]$^+$.

Example 98: (S)—N-(4-((3-Chloro-4-((3-fluorobenzyl)oxy)phenyl)amino)-3-cyano-7-(2,3dihydroxypropoxy)quinolin-6-yl)-1,2-dithiolane-4-carboxamide

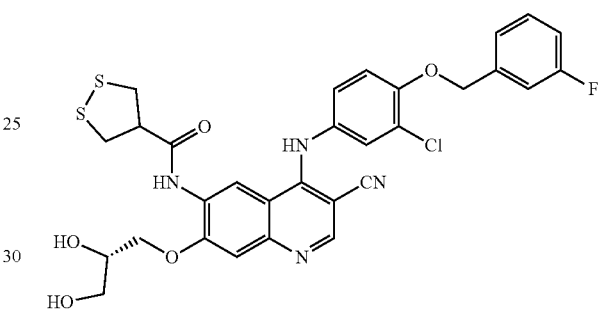

A solution of (S)—S,S'-(2-((4-((3-chloro-4-((3-fluorobenzyl)oxy)phenyl)amino)-3-cyano-7-(2,3-dihydroxypropoxy)quinolin-6-yl)carbamoyl)propane-1,3-diyl)diethanethioate (10 mg, 0.013 mmol) in methanolic ammonia (3 mL) was stirred for 30 minutes at room temperature followed by evaporation of solvents in vacuo. The residue was washed with diethyl ether, filtered and dried under vacuum to furnish the title compound (6 mg, 75%). $^1$H NMR 400 MHz (DMSO-d6): δ 9.80 (s, 1H), 9.58 (s, 1H), 8.87 (s, 1H), 8.51 (s, 1H), 7.47-6.94 (m, 8H), 5.25 (s, 2H), 5.20 (m, 1H), 4.80 (m, 1H), 4.26 (m, 1H), 4.12-3.90 (m, 2H), 3.59 (m, 3H), 2.32 (m, 1H), 2.08 (m, 1H), 1.50-1.20 (m, 2H); MS (ES) m/e 639 [M−1]$^+$.

Example 99: N-(4-Hydroxy-7-methoxyquinazolin-6-yl)acetamide

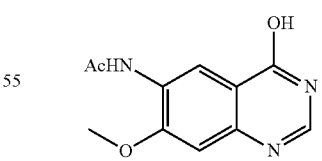

To a stirred solution of phenyl 5-acetamido-2-amino-4-methoxybenzoate (17 g, 56.7 mmol) in 2-methoxyethanol (170 mL) was added formimidamide acetate (29.5 g, 283.3 mmol) and was refluxed for 12 hours. After cooling, another portion of formimidamide acetate (14.75 g, 141.7 mmol) was added and reflux was continued for additional 12 hours. The reaction mixture was cooled, and filter the solid and washed with di ethyl ether dried under vacuum to give the title compound (10 g, 76%) ¹H NMR (DMSO-d6): 12.04 (s, 1H), 9.36 (s, 1H), 8.74 (s, 1H), 7.99 (s, 1H), 7.17 (s, 1H), 3.98 (s, 3H), 2.14 (s, 3H); MS (ES) m/e 234 [M+1]⁺.

Example 100:
N-(4-Chloro-7-methoxyquinazolin-6-yl)acetamide

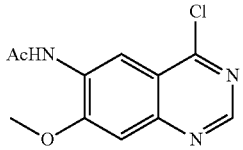 [SMILES: COc1cc2ncnc(Cl)c2cc1NC(C)=O]

To a solution of N-(4-chloro-7-methoxyquinazolin-6-yl) acetamide (2.0 g, 8.58 mmol) in toluene (30 mL) were added phosphorus oxychloride (3.28 mL, 21.45 mmol) and triethylamine (0.3 mL, 2.15 mmol) dropwise at 0° C. The reaction mixture was heated 120° C. for 6 hours then cooled, concentrated in vacuo, poured into water and made basic with the addition of saturated sodium bicarbonate solution. The resultant solid was filtered, dried under vacuum and purified by column chromatography eluting with 2% methanol in dichloromethane to give 1.0 g (47%) as a white solid. LCMS m/e: 252 [M+1]⁺.

Example 101: N-(7-Methoxy-4-((3-methyl-4-((6-methylpyridin-3-yl)oxy)phenyl)amino) quinazolin-6-yl)acetamide

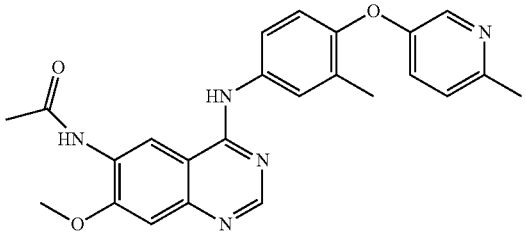 [SMILES: COc1cc2ncnc(Nc3ccc(Oc4ccc(C)nc4)c(C)c3)c2cc1NC(C)=O]

A solution containing N-(4-chloro-7-methoxyquinazolin-6-yl)acetamide (0.6 g, 2.39 mmol) and 3-methyl-4-((6-methylpyridin-3-yl)oxy)aniline (0.61 g, 2.87 mmol), in isopropanol (30 mL) was placed in a sealed tube and heated for 12 hours at 150° C. After cooling, solvents were evaporated and the residue was washed with diethyl ether, filtered and dried to give 1.02 g of the title compound as a solid. ¹H NMR 400 MHz (DMSO-d6): δ 9.68 (s, 1H), 8.98 (s, 1H), 8.71 (s, 1H), 8.21 (m, 1H), 7.64 (m, 1H), 7.78 (m, 1H), 7.28-7.22 (m, 4H), 6.98 (d, J=8.4 Hz, 1H), 4.04 (s, 3H), 2.45 (s, 3H), 2.24 (s, 3H), 2.19 (s, 3H); MS (ES) m/e 430 [M+1]⁺.

Example 102: 7-Methoxy-N-4-(3-methyl-4-((6-methylpyridin-3-yl)oxy)phenyl)quinazoline-4,6-diamine

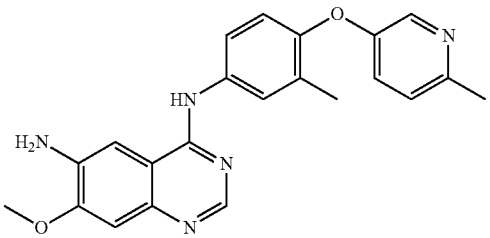

To stirred solution of N-(7-methoxy-4-((3-methyl-4-((6-methylpyridin-3-yl)oxy)phenyl)amino) quinazolin-6-yl)acetamide (1.02 g, 2.33 mmol) in methanol (20 mL) was added KOH (0.39 g, 6.99 mmol) and heated for 60 hours at 70° C. After cooling, the solvent was removed in vacuo, and the residue was poured into water and extracted with ethyl acetate (2×100 mL). The combined extracts were washed with water, dried over anhydrous Na₂SO₄, filtered and concentrated at reduced pressure to give a crude oil which was purified by column chromatography eluting with 3-5% methanol in dichloromethane to give the desired product (550 mg, 61%). ¹H NMR 400 MHz (DMSO-d6): δ 9.24 (s, 1H), 8.32 (s, 1H), 8.17 (d, J=2.8 Hz, 1H), 7.78 (d, J=2.4 Hz, 1H) 7.69 (m, 1H), 7.67 (d, J=2.8 Hz, 1H), 7.22-7.00 (m, 3H), 6.90 (d, J=8.8 Hz, 1H), 5.32 (bs, 1H), 3.96 (s, 3H), 2.45 (s, 3H), 2.15 (s, 3H); MS (ES) m/e 388 [M+1]⁺.

Example 103: S,S'-(2-((7-Methoxy-4-((3-methyl-4-((6-methylpyridin-3-yl)oxy)phenyl)amino) quinazolin-6-yl)carbamoyl)propane-1,3-diyl)diethanethioate

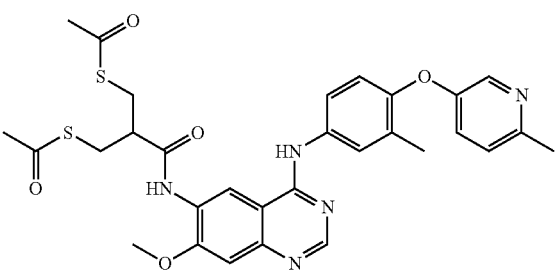 [SMILES: COc1cc2ncnc(Nc3ccc(Oc4ccc(C)nc4)c(C)c3)c2cc1NC(=O)C(CSC(C)=O)CSC(C)=O]

To a mixture of 7-methoxy-N-4-(3-methyl-4-((6-methylpyridin-3-yl)oxy)phenyl)quinazoline-4,6-diamine (200 mg, 0.516 mmol) and S,S'-(2-(chlorocarbonyl)propane-1,3-diyl) diethanethioate (prepared from 3-(acetylthio)-2-((acetylthio)methyl)propanoic acid (1.2 g, 5.16 mmol) and oxalyl chloride (0.96 mL, 7.62 mmol) in dichloromethane (20 mL) and tetrahydrofuran (10 mL) was added N,N-diisopropylethylamine (0.92 mL, 5.16 mmol) at 0° C., and stirred at room temperature for 1 hour. The reaction mixture was then concentrated, poured into water and extracted with dichloromethane (3×100 mL). The combined extracts were washed with water, dried over anhydrous Na₂SO₄, filtered and concentrated at reduced pressure to give an oil which was purified by preparative HPLC: column ACE C-8 (250*4.6*5.0µ); mobile phase A: 0.1% TFA, B: acetonitrile, flow rate 1 mL/min to give the title compound (13 mg, 4%).

¹H NMR 400 MHz (DMSO-d6): δ 9.71 (m, 2H), 8.81 (s, 1H), 8.47 (s, 1H), 8.18 (m, 1H), 7.70-7.62 (m, 2H), 7.25-7.18 (m, 3H), 6.93 (m, 1H), 4.00 (s, 3H), 3.31-3.10 (m, 5H), 2.43 (s, 3H), 2.35 (s, 6H), 2.20 (s, 3H); LCMS m/e: 606 [M+1]⁺.

Example 104: N-(7-Methoxy-4-((3-methyl-4-((6-methylpyridin-3-yl)oxy)phenyl)amino) quinazolin-6-yl)-1,2-dithiolane-4-carboxamide

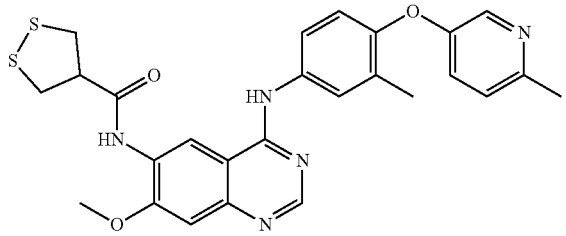 [SMILES: COc1cc2ncnc(Nc3ccc(Oc4ccc(C)nc4)c(C)c3)c2cc1NC(=O)C1CSSC1]

A solution of S,S'-(2-((7-methoxy-4-((3-methyl-4-((6-methylpyridin-3-yl)oxy)phenyl)amino)quinazolin-6-yl)carbamoyl)propane-1,3-diyl) diethanethioate (9 mg 0.018 mmol) in methanolic ammonia (4 mL) at room temperature was stirred for 30 minutes followed by evaporation of solvents and the residue was dried in vacuo to furnish the title compound (5 mg, 71%). ¹H NMR (DMSO-d6): δ 9.81 (s, 1H), 9.67 (s, 1H), 8.82 (s, 1H), 8.48 (s, 1H), 8.17 (d, J=2.4 Hz, 1H), 7.72-7.64 (m, 2H), 7.26-7.18 (m, 3H), 6.95 (d, J=8.8 Hz, 1H), 4.00 (s, 3H), 3.64-3.54 (m, 3H), 3.35-3.31 (m, 2H), 2.52 (s, 3H), 2.32 (s, 3H); MS (ES) m/e 518 [M–1]⁺.

Example 105: 2-(1,2-Dithiolan-3-yl)-N-(7-methoxy-4-((3-methyl-4-((6-methylpyridin-3-yl)oxy)phenyl) amino)quinazolin-6-yl)acetamide

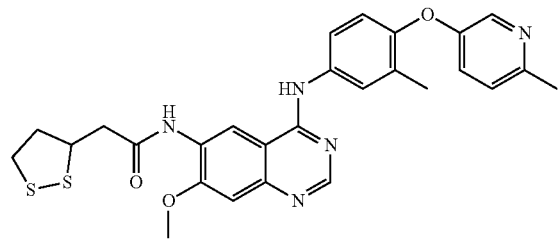 [SMILES: COc1cc2ncnc(Nc3ccc(Oc4ccc(C)nc4)c(C)c3)c2cc1NC(=O)CC1CCSS1]

To a mixture of 7-methoxy-N-4-(3-methyl-4-((6-methylpyridin-3-yl)oxy)phenyl)quinazoline-4,6-diamine (300 mg, 0.77 mmol) and 2-(1,2-dithiolan-3-yl)acetyl chloride (prepared from 2-(1,2-dithiolan-3-yl)acetic acid (0.8 g, 4.87 mmol) and oxalyl chloride (0.92 mL, 7.32 mmol) in N—N-dimethylformamide (5 mL) and tetrahydrofuran (5 mL) was added N,N-diisopropylethylamine (1.25 mL, 6.98 mmol) at 0° C. and stirred the at room temperature for 1 hour. The reaction mixture was then concentrated, poured into water and the precipitated solid was filtered, dried and purified by preparative HPLC: column ACE C-8 (250*4.6*5.0), mobile phase A: 0.1% TFA, B: acetonitrile, flow rate 1 mL/min to give the title compound (25 mg, 7%). ¹H NMR 400 MHz (DMSO-d6) δ 9.75 (s, 1H), 9.61 (s, 1H), 8.83 (s, 1H), 8.49 (s, 1H), 8.1 (d, J=2 Hz, 1H), 7.71 (s, 1H), 7.65 (d, J=8.8 Hz, 1H), 7.21 (m, 3H), 6.93 (d, J=8.8 Hz, 1H), 4.09 (m, 1H), 4.00 (s, 3H), 3.18 (m, 2H), 3.13 (m, 1H), 2.99 (m, 2H), 2.43 (s, 3H), 2.20 (s, 3H), 2.09 (s, 1H); LCMS m/e: 534 [M+1]⁺.

Example 106: N-(4-((3-Chloro-4-((3-fluorobenzyl) oxy)phenyl)amino)-7-methoxyquinazolin-6-yl)acetamide

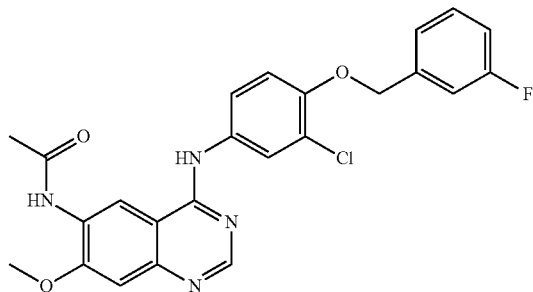 [SMILES: COc1cc2ncnc(Nc3ccc(OCc4cccc(F)c4)c(Cl)c3)c2cc1NC(C)=O]

To a solution of N-(4-chloro-7-methoxyquinazolin-6-yl)acetamide (1.0 g, 3.98 mmol) and 3-chloro-4-((3-fluorobenzyl)oxy)aniline (1.5 g, 5.98 mmol), in isopropanol (20 mL) in a sealed tube was refluxed for 12 hours at 150° C. Following cooling, the solvents were evaporated and the residue was washed with diethyl ether, filtered, washed with aqueous NaHCO₃, and dried in vacuo to furnish the desired compound (1.3 g, 72%). ¹H NMR 400 MHz (DMSO-d6): δ 9.74 (s, 1H), 9.57 (s, 1H), 8.78 (s, 1H), 8.75 (s, 1H), 8.50 (s, 1H), 7.95 (d, J=2.4 Hz, 1H), 7.68 (m, 1H), 7.48 (m, 1H), 7.34 (m, 2H), 7.21 (m, 1H), 7.18 (m, 1H), 5.25 (s, 2H), 4.00 (s, 3H), 2.15 (s, 3H); MS (ES) m/e 467 {M+1]⁺.

Example 107: N-4-(3-Chloro-4-((3-fluorobenzyl) oxy)phenyl)-7-methoxyquinazoline-4,6-diamine

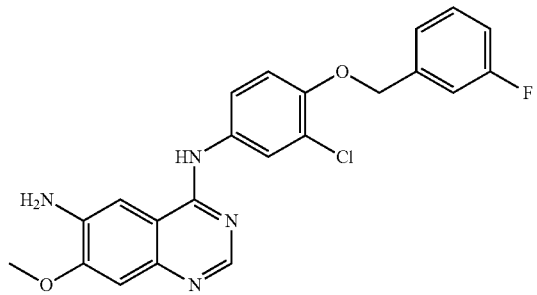 [SMILES: COc1cc2ncnc(Nc3ccc(OCc4cccc(F)c4)c(Cl)c3)c2cc1N]

To a stirred solution of N-(4-((3-chloro-4-((3-fluorobenzyl)oxy)phenyl)amino)-7-methoxyquinazolin-6-yl)acetamide (1.2 g, 2.78 mmol) in methanol (20 mL) was added a solution of 2N HCl (20 mL) and heated for 24 hours at 70° C. After cooling, the solvent was removed in vacuo and the residue was, poured into water, filtered and dried to furnish the title compound. (0.7 g, 70%). ¹H NMR 400 MHz (DMSO-d6): δ 10.22 (s, 1H), 8.57 (s, 1H), 8.54 (s, 1H), 7.90 (d, J=2.4 Hz, 1H), 7.62-7.59 (m, 1H), 7.48-7.34 (m, 2H), 7.34-7.13 (m, 6H), 5.76 (bs, 2H), 4.00 (s, 3H), (m, 2H); MS (ES) m/e 425 [M+1]⁺.

Example 108: N-(4-((3-Chloro-4-((3-fluorobenzyl)oxy)phenyl)amino)-7-methoxyquinazolin-6-yl)-2-(1,2-dithiolan-3-yl)acetamide

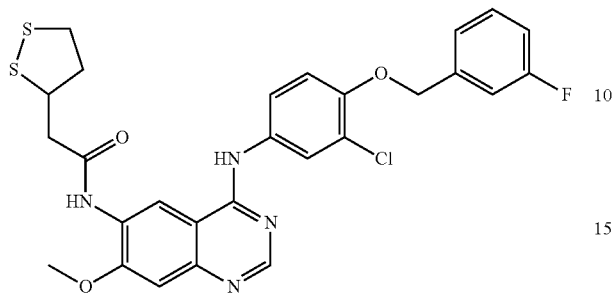

To a solution of N-4-(3-chloro-4-((3-fluorobenzyl)oxy)phenyl)-7-methoxyquinazoline-4,6-diamine (300 mg, 0.707 mmol) and 2-(1,2-dithiolan-3-yl)acetyl chloride (prepared from 2-(1,2-dithiolan-3-yl)acetic acid (0.8 g, 4.87 mmol) and oxalyl chloride (0.92 mL, 7.32 mmol) in N—N-dimethylformamide (5 mL) and tetrahydrofuran (5 mL) was added N,N-diisopropylethylamine (2.2 mL, 12.73 mmol) at 0° C. was stirred at room temperature for 1 hour. The reaction mixture was then concentrated and poured into water, filtered, dried and purified by preparative HPLC: column YMC Triart (250*4.6*5.0μ); mobile phase A: 0.01 M ammonium acetate, B: acetonitrile, flow rate 1 mL/min to give the desired compound (30 mg, 8%). $^1$H NMR 400 MHz (DMSO-d6) δ 9.69 (s, 1H), 9.60 (s, 1H), 8.80 (s, 1H), 8.47 (s, 1H), 7.94 (d, J=2 Hz, 1H), 7.68-7.66 (m, 1H), 7.48-7.44 (m, 1H), 7.34-7.16 (m, 5H), 5.25 (s, 2H), 4.06 (m, 1H), 3.99 (s, 3H), 3.25-3.15 (m, 3H), 2.99-2.88 (m, 3H); LCMS m/e: 571 [M+1]$^+$.

Example 109: S,S'-(2-((4-((3-Chloro-4-((3-fluorobenzyl)oxy)phenyl)amino)-7-methoxyquinazolin-6-yl)carbamoyl)propane-1,3-diyl)diethanethioate

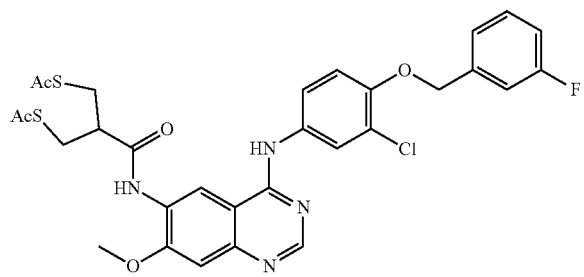

To a mixture of N-4-(3-chloro-4-((3-fluorobenzyl)oxyphenyl)-7-methoxyquinazoline-4,6-diamine (300 mg, 0.70 mmol) and S,S'-(2-(chlorocarbonyl)propane-1,3-diyl)diethanethioate (prepared from 3-(acetylthio)-2-((acetylthio)methyl)propanoic acid (1.3 g, 5.02 mmol) and oxalyl chloride (0.96 mL, 7.62 mmol) in N—N-dimethylformamide (5 mL) and tetrahydrofuran (5 mL) was added N,N-diisopropylethylamine (2.4 mL, 14.0 mmol) at 0° C. and stirred at room temperature for 1 hour. The reaction mixture was concentrated, poured into water and a precipitate was filtered, dried and purified by preparative HPLC; column ACE-C18 (250*4.6*5.0μ); mobile phase A: 0.1% TFA, B: acetonitrile, flow rate 1 mL/min to give 27 mg of the title compound. $^1$H NMR 400 MHz (DMSO-d6): δ 9.71 (d, J=13.2 Hz, 2H), 9.67 (s, 1H), 8.79 (s, 1H), 8.47 (s, 1H), 7.93 (m, 1H), 7.68-7.15 (m, 6H), 5.2 (s, 2H), 4.00 (s, 3H), 3.36-3.09 (m, 5H), 2.49-2.32 (m, 6H); LCMS m/e: 643 [M+1]$^+$.

Example 110: N-(4-((3-Chloro-4-((3-fluorobenzyl)oxy)phenyl)amino)-7-methoxyquinazolin-6-yl)-1,2-dithiolane-4-carboxamide

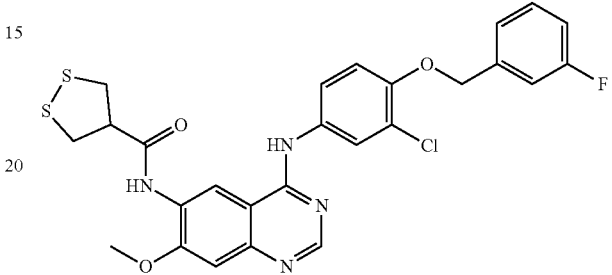

A solution of S,S'-(2-((4-((3-chloro-4-((3-fluorobenzyl)oxy)phenyl)amino)-7-methoxyquinazolin-6-yl)carbamoyl)propane-1,3-diyl)diethanethioate (20 mg, 0.031 mmol) in methanolic ammonia, was stirred at room temperature stirred for 30 minutes. The solvent was evaporated and the residual solid was dried, washed with diethyl ether and dried under vacuum to give the title compound (8 mg, 47%). $^1$H NMR 400 MHz (DMSO-d6) δ 9.81 (s, 1H), 9.68 (s, 1H), 8.80 (s, 1H), 8.48 (s, 3H), 7.95 (d, J=2.4 Hz, 1H), 7.69 (m, 1H), 7.49 (m, 1H), 7.3-7.1 (m, 5H), 5.24 (s, 2H), 4.01 (s, 3H), 3.59 (m, 4H), 3.4 (m 1H); LCMS m/e: 557 [M+1]$^+$.

Formulations

The present invention also relates to compositions or formulations which comprise the kinase inhibitors according to the present invention. In general, the compositions of the present invention comprise an effective amount of one or more 1,2-dithiolane and salts thereof according to the present invention which are effective for providing treatment or prevention of cancer such as cancer of the lung, head and neck, colon, kidney, ovaries, prostate, and breast, cancers of the skin such as melanoma, and cancer of the blood such as leukemia, lymphoma and myeloma; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known kinase inhibitors. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician.

The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds of the disclosure according to the present invention and one or more excipients; from about 0.01 mg to about 100 mg of one or more compounds of the disclosure according to the present invention and one or more excipients; and from about 0.1 mg to about 10 mg of one or more compounds of the disclosure according to the present invention; and one or more excipients.

Biological Testing

Various techniques are known in the art for testing compounds of this invention. In order that this invention described herein, the following biological assays are set forth. It should be noted that these examples are for illustrative purposes only and are not met to be limiting.

Representative compounds of this invention, when tested in the assays described below demonstrated a binding constant Kd (nM) activity level as set forth in Tables 15-17 wherein:

"A" refers to a Kd activity level of from 1 nM to 99 nM;
"B" refers to a Kd activity level of from 100 nM to 999 nM;
"C" refers to a Kd activity level of from 1000 nM to 10000 nM;
"D" refers to a Kd activity level of from >10000 nM.

EGFR WT refers to wild type EGFR; mutant EGFR enzymes having a single point mutation are indicated as EGFR listing the point mutation for example EGFR (L858R) refers to EGFR having a point mutation at amino acid 858 and mutant enzymes with amino acid sequence deletion are represented by del. Amino acids letter designation are used for example L refers to lysine, R to arginine and the like Kinase assays (Kd): KINOMEscan™ is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag.

For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 M non-biotinylated affinity ligand) and incubated at room temperature with shaking for 30 minutes. The kinase concentration in the eluates was measured by qPCR.

TABLE 15

Binding constant (Kd) of exemplary compounds of the disclosure

| Example | Compound Name | Kd Activity Level (EGFR WT) | Kd Activity Level (EGFR L858R) |
|---|---|---|---|
| 33 | N-(4-((3-chloro-4-fluorophenyl)amino)-3-cyano-7-ethoxyquinolin-6-yl)-1,2-dithiolane-3-carboxamide | A | A |
| 34 | S,S'-(2-((4-((3-chloro-4-((3-fluorobenzyl)oxy)phenyl)amino)-3-cyano-7-ethoxyquinolin-6-yl)carbamoyl)propane-1,3-diyl)diethanethioate | A | A |
| 36 | N-(4-((3-chloro-4-((3-fluorobenzyl)oxy)phenyl)amino)-3-cyano-7-ethoxyquinolin-6-yl)-1,2-dithiolane-4-carboxamide | A | A |
| 79 | N-(4-((3-chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3-yl)acetamide | A | A |
| 80 isomer 1 | N-(4-((3-chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3R-yl)acetamide | A | A |
| 80 isomer 2 | N-(4-((3-chloro-4-((3-fluorobenzyl)oxy)phenyl)amino)-3-cyano-7-(((S)-2,2-dimethyl-1,3-dioxolan-4-yl)methoxy)quinolin-6-yl)-2-(1,2-dithiolan-3S-yl)acetamide | A | A |
| 81 | N-(4-((3-chloro-4-((3-fluorobenzyl)oxy)phenyl)amino)-3-cyano-7-((R)-2,3-dihydroxypropoxy)quinolin-6-yl)-2-(1,2-dithiolan-3S-yl)acetamide | A | A |
| 82 | N-(4-((3-chloro-4-((3-fluorobenzyl)oxy)phenyl)amino)-3-cyano-7-((R)-2,3-dihydroxypropoxy)quinolin-6-yl)-2-(1,2-dithiolan-3R-yl)acetamide | A | A |
| 84 isomer 1 | N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,2-dithiolan-3S-yl)acetamide | A | A |
| 84 isomer 2 | N-(4-((3-chloro-4-((3-fluorobenzyl)oxy)phenyl)amino)-3-cyano-7-(((R)-2,2-dimethyl-1,3-dioxolan-4-yl)methoxy)quinolin-6-yl)-2-(1,2-dithiolan-3R-yl)acetamide | A | A |
| 85 | N-(4-((3-chloro-4-((3-fluorobenzyl)oxy)phenyl)amino)-3-cyano-7-((S)-2,3-dihydroxypropoxy)quinolin-6-yl)-2-(1,2-dithiolan-3R-yl)acetamide | A | A |
| 86 | N-(4-((3-chloro-4-((3-fluorobenzyl)oxy)phenyl)amino)-3-cyano-7-((S)-2,3-dihydroxypropoxy)quinolin-6-yl)-2-(1,2-dithiolan-3S-yl)acetamide | A | A |
| 94 | (R)-S,S'-(2-((4-((3-chloro-4-((3-fluorobenzyl)oxy)phenyl)amino)-3-cyano-7-(2,3-dihydroxypropoxy)quinolin-6-yl)carbamoyl)propane-1,3-diyl)diethanethioate | A | A |

TABLE 16

Binding constant (Kd) of exemplary compounds of the disclosure

| Example | Kd Activity Level (EGFR L858R/T790M) | Kd Activity Level (EGFR E746-A750del) | Kd Activity Level (EGFR S752-I759del) |
|---|---|---|---|
| 34 | D | B | B |
| 36 | D | A | A |
| 40 | D | A | A |
| 81 | D | A | A |
| 82 | D | A | A |
| 85 | D | A | A |

TABLE 16-continued

Binding constant (Kd) of exemplary compounds of the disclosure

| Example | Kd Activity Level (EGFR L858R/T790M) | Kd Activity Level (EGFR E746-A750del) | Kd Activity Level (EGFR S752-I759del) |
|---|---|---|---|
| 86 | D | A | A |
| 92 |   | A | A |

The Kd activity level of N-(4-((3-chloro-4-((3-fluorobenzyl)oxy)phenyl)amino)-3-cyano-7-ethoxyquinolin-6-yl)-2-(1,2-dithiolan-3-yl)acetamide (Example 40) in various mutant EGF receptors are reported in Table 17.

TABLE 17

| EGFR G719C | EGFR G719S | EGFR L861Q | EGFR L747-E749del, A750P | EGFR L747-S752del, P753S | EGFR L747-T750del Sins |
|---|---|---|---|---|---|
| A | A | A | A | A | A |

Representative compounds of this invention, when tested in the assays described below demonstrated a 50% inhibition $IC_{50}$ (nM) activity level as set forth in Table 18 wherein:

"A" refers to an $IC_{50}$ activity level of from 1 nM to 99 nM;
"B" refers to an $IC_{50}$ activity level of from 100 nM to 999 nM;
"C" refers to an $IC_{50}$ activity level of from 1000 nM to 10000 nM;
"D" refers to an $IC_{50}$ activity level of from >10000 nM.

Rabbit Reticulocyte Lysate Assay Design: KinaseSeeker is a homogeneous competition binding assay where the displacement of an active site dependent probe by an inhibitor is measured by a change in luminescence signal. Luminescence readout translates into a highly sensitive and robust assay with low background and minimal interference from test compounds.

10 mM stock solutions of test compounds were serially diluted in DMSO to make assay stocks. Prior to initiating $IC_{50}$ determinations, the test compounds were evaluated for false positive against split-luciferase.

Each test compound was screened in duplicate against target kinase i.e. EGFR (L858R) at 7 different concentrations. For kinase assays, Cfluc-kinase was translated along with Fos-Nfluc using a cell-free system (rabbit reticulocyte lysate) at 30° C. for 90 min. 24 uL aliquot of this lysate containing either 1 uL of DMSO (for no-inhibitor control) or compound solution in DMSO was incubated for 30 minutes at room temperature followed by 1 hour in presence of a kinase specific probe. 80 uL of luciferin assay reagent was added to each solution and luminescence was immediately measured on a luminometer.

The % Inhibition and % Activity Remaining was calculated using the following equation:

% Inhibition=[(ALU$_{Control}$−ALU$_{Sample}$)/ALU$_{Control}$]×100

% Activity Remaining=100−% Inhibition

The % Activity was plotted against compound concentration and the $IC_{50}$ was determined for each compound using a 7-point curve (Jester, B. W.; et. al. *J. Am. Chem. Soc.* 2010, 132, 11727-11735. Jester, B. W.; et. al. *J. Med. Chem.* 2012, 55, 1526-1537). Biological activity of representative compounds of the disclosure are described in Table 18.

TABLE 18

$IC_{50}$ Activity levels of exemplary compounds of the disclosure

| Entry | Example | EGFR L858R | EGFR WT | HER2 |
|---|---|---|---|---|
| 1 | 29 | B |   |   |
| 2 | 31 | B | B | B |
| 3 | 33 | A |   |   |
| 4 | 34 | A | B | B |
| 5 | 36 | A | B | B |
| 6 | 38 | C |   |   |
| 7 | 39 | B |   |   |
| 8 | 40 | A | B | B |
| 9 | 43 | B | B | B |
| 10 | 44 | A |   |   |
| 11 | 55 | D | D | D |
| 12 | 58 | D |   |   |
| 13 | 60 | A | B |   |
| 14 | 62 | A | B |   |
| 15 | 81 | A | B | B |
| 16 | 82 | A | B | B |
| 17 | 85 | A | B | B |
| 18 | 86 | A | B | B |
| 19 | 90 | A | B |   |
| 20 | 92 | A | B | B |
| 21 | 95 | A | B |   |
| 22 | 98 | A | B |   |
| 23 | 104 | B | B | B |
| 24 | 105 | A | B | A |
| 25 | 109 | A | A |   |
| 26 | 110 | A | A |   |

Representative compounds of this invention, when tested in the assays described below demonstrated a 50% inhibition $IC_{50}$ (nM) activity level as set forth in Table 19 wherein:

"A" refers to an $IC_{50}$ activity level of from 1 nM to 99 nM;
"B" refers to an $IC_{50}$ activity level of from 100 nM to 999 nM;
"C" refers to an $IC_{50}$ activity level of from 1000 nM to 10000 nM;
"D" refers to an $IC_{50}$ activity level of from >10000 nM Radioisotope Filter Binding Assay: In this assay format, it directly detects the true product without the use of modified substrates or coupling enzymes (Uitdehaag, J. C. et al. *Br. J. Pharmacol.* 2012, 166, 858-876; Hastie, C. J. et al. *Nat. Protoc.* 2006, 1, 968-971) according to equation 1.

$$\text{Substrate} + [\gamma\text{-}^{33}P] - ATP \rightarrow {}^{33}P\text{-Substrate} + ADP \quad \text{Equation 1}$$

The protocol calls for test compound of the invention to be incubated with kinase, substrate, cofactors, and radio-isotope-labeled ATP ($^{33}$P-gamma-ATP). The reaction mixtures are then spotted onto filter papers which bind the radioisotope labeled catalytic product. Unreacted phosphate is removed via washing. The reagents used include base reaction buffer; 20 mM Hepes (pH 7.5), 10 mM MgCl2, 1 mM EGTA, 0.02% Brij35, 0.02 mg/ml BSA, 0.1 mM Na$_3$VO$_4$, 2 mM DTT, 1% DMSO. The reaction procedure include the following steps: (1) prepare indicated substrate in freshly prepared base reaction buffer, (2) deliver any required cofactors to the substrate solution above, (3) deliver indicated kinase into the substrate solution and gently mix, (4) deliver compounds in DMSO into the kinase reaction mixture by Acoustic technology (Echo550; nanoliter range), incubate for 20 minutes at room temperature, (5) deliver $^{33}$P-ATP (specific activity 10 µCi/µL) into the reaction mixture to initiate the reaction, (6) incubate kinase reaction for 2 hours at room temperature, (7) reactions are spotted onto P81 ion exchange paper, (8) detect kinase activity by filter-binding method.

TABLE 19

IC$_{50}$ Activity levels of exemplary compounds of the disclosure

| Entry | Example | EGFR L858R | EGFR E746-A750del | EGFR WT | HER 2 | HER 4 |
|---|---|---|---|---|---|---|
| 1 | 61 | | | | | B |
| 2 | 62 | | | | | A |
| 3 | 90 | B | C | A | B | A |
| 4 | 92 | B | C | A | B | A |
| 5 | 95 | B | C | A | | |
| 6 | 98 | A | B | A | B | A |

What is claimed is:

1. A compound having formula (I):

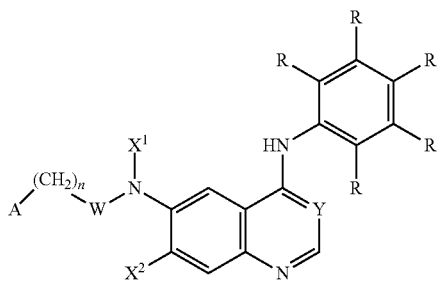

including enantiomers, diastereomers, and pharmaceutically acceptable salts thereof, wherein:

A is selected from the group consisting of

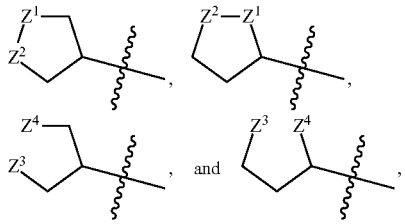

with the proviso that when A is

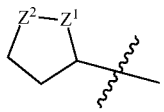

then Y cannot be N and $X^2$ cannot be H when Y is N;

$Z^1$ is selected from the group consisting of S, SO, and $SO_2$;

$Z^2$ is selected from the group consisting of S, SO, and $SO_2$;

$Z^3$ is selected from the group consisting of SH, SCOR$^1$, SO$_2$R$^2$, and SO$_3$H;

$Z^4$ is selected from the group consisting of SH, SCOR$^1$, SO$_2$R$^2$, and SO$_3$H;

n=0, 1, 2, 3, 4;

W is selected from the group consisting of CO and SO$_2$;

$X^1$ is selected from the group consisting of hydrogen, optionally substituted C$_{1-6}$ alkyl, and, optionally substituted C$_{1-6}$ alkoxy;

$X^2$ is selected from the group consisting of hydrogen, optionally substituted C$_{1-6}$ alkyl, OR$^3$,

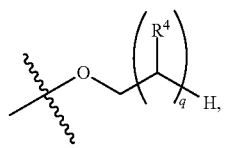

and the C$_{2-6}$ sugar alcohols such as ethylene glycol, glycerol, erythritol, threitol, arabitol, xylitol, ribitol, mannitol, galacitol frucitol, iditol, inositol, and sorbitol;

Y is selected from the group consisting of N and C—CN;

R is at each occurrence independently selected from the group consisting of hydrogen, C$_{1-6}$ alkyl, C$_{1-6}$ alkenyl, C$_{1-6}$ alkynyl, halogen, C$_{1-6}$ haloalkyl, C$_{3-7}$ cycloalkyl, cycloalkylalkyl, aryl, arylalkyl, heterocyclyl, heterocyclylalkyl, heteroaryl, heteroarylalkyl, alkoxyheteroarylalkyl,

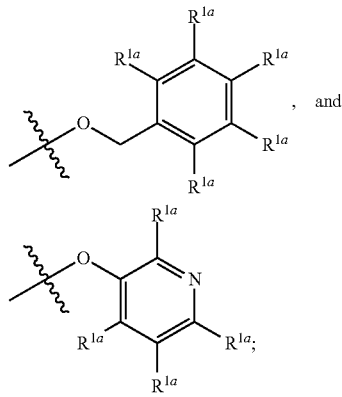

$R^{1a}$ is at each occurrence independently selected from the group consisting of hydrogen, halogen, C$_{1-6}$ alkyl, and C$_{1-6}$ alkoxy;

$R^1$ is at each occurrence independently selected from the group consisting of hydrogen, optionally substituted C$_{1-6}$ alkyl, and optionally substituted C$_{1-6}$ alkoxy;

$R^2$ is at each occurrence independently selected from the group consisting of hydrogen, optionally substituted C$_{1-6}$ alkyl, and optionally substituted C$_{1-6}$ alkoxy;

$R^3$ is an optionally substituted C$_{1-6}$ alkyl;

$R^4$ is at each occurrence independently selected from the group consisting of hydrogen, OH, and OR$^5$;

q=0, 1, 2, 3, 4, or 5;

$R^5$ is at each occurrence an optionally substituted C$_{1-6}$ alkyl;

two $R^5$ substituents can be joined together with the atoms to which they are bound to form a 5 to 6 membered ring.

2. The compound according to claim 1 having formula (II):

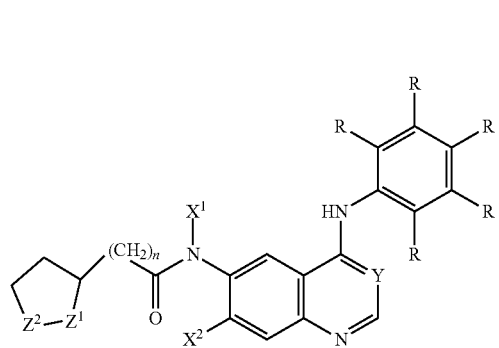

including enantiomers, diastereomers, and pharmaceutically acceptable salts thereof.

3. The compound according to claim 1 having formula (III):

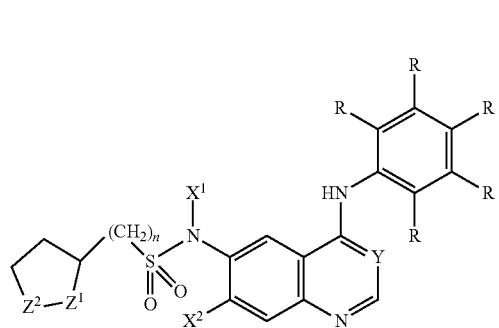

including pharmaceutically acceptable salts thereof.

4. The compound according to claim 1 having formula (IV):

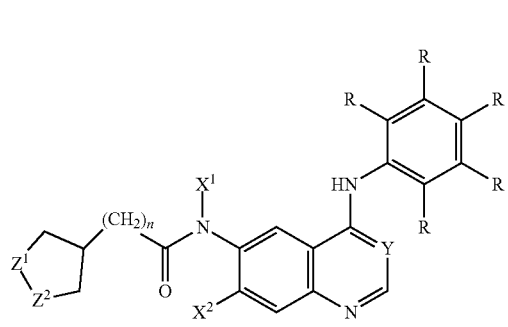

including enantiomers, diastereomers, and pharmaceutically acceptable salts thereof.

5. The compound according to claim 1 having formula (V):

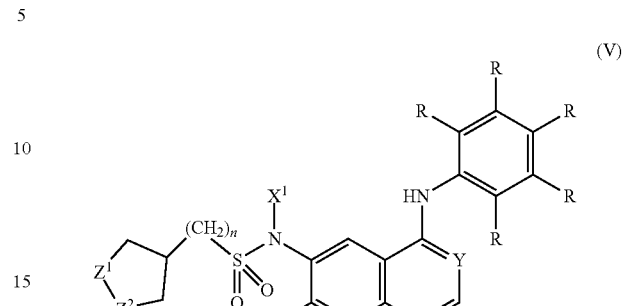

including pharmaceutically acceptable salts thereof.

6. The compound according to claim 1 having formula (VI):

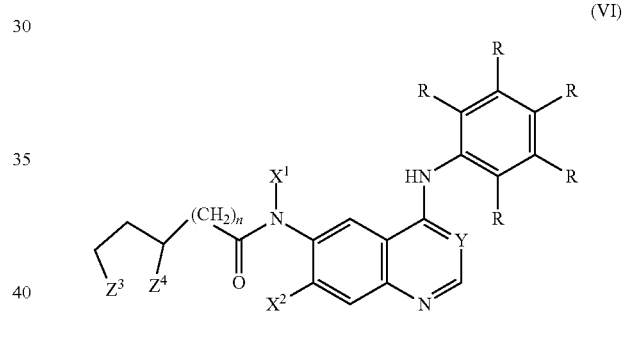

including pharmaceutically acceptable salts thereof.

7. The compound according to claim 1 having formula (VII):

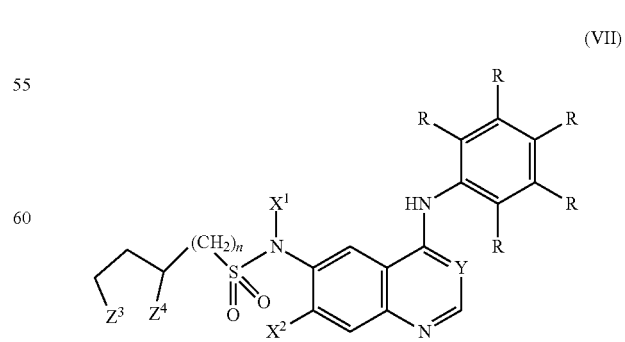

including pharmaceutically acceptable salts thereof.

8. The compound according to claim 1 having formula (VIII):

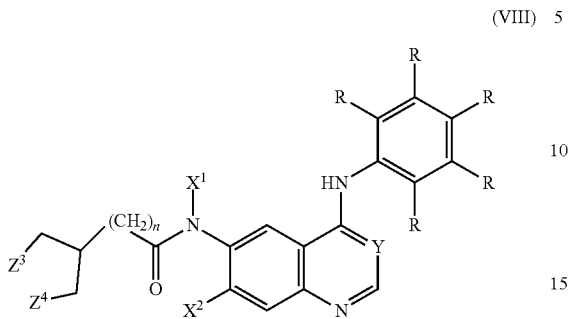

including enantiomers, diastereomers, and pharmaceutically acceptable salts thereof.

9. The compound according to claim 1 having formula (IX):

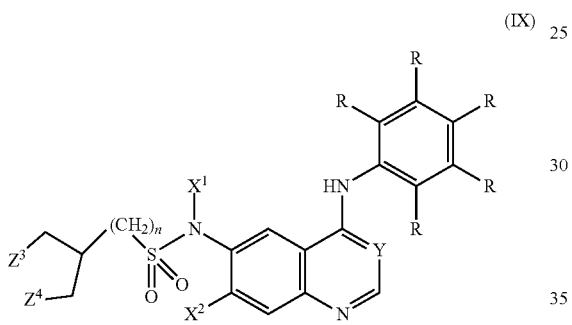

Including pharmaceutically acceptable salts thereof.

10. The compound according to claim 1 that is:

S,S'-(2-((4-(((3-chloro-4-fluorophenyl)amino)-3-cyano-7-ethoxyquinolin-6-yl)carbamoyl)propane-1,3-diyl)diethanethioate;

N-(4-((3-chloro-4-fluorophenyl)amino)-3-cyano-7-ethoxyquinolin-6-yl)-3-mercapto-2-(mercaptomethyl)propanamide;

N-(4-((3-chloro-4-fluorophenyl)amino)-3-cyano-7-ethoxyquinolin-6-yl)-1,2-dithiolane-4-carboxamide;

N-(4-((3-chloro-4-fluorophenyl)amino)-3-cyano-7-ethoxyquinolin-6-yl)-1,2-dithiolane-3-carboxamide;

S,S'-(2-((4-(3-chloro-4-((3-fluorobenzyl)oxy)phenyl)amino)-3-cyano-7-ethoxyquinolin-6-yl)carbomoyl)propane-1,3-diyl)diethanethioate;

N-(4-((3-chloro-4-((3-fluorobenzyl)oxy)phenyl)amino)-3-cyano-7-ethoxyquinolin-6-yl)-3-mercapto-2-(mercaptomethyl)propanamide;

N-(4-((3-chloro-4-((3-fluorobenzyl)oxy)phenyl)amino)-3-cyano-7-ethoxyquinolin-6-yl)-1,2-dithiolane-4-carboxamide;

N-(4-((3-chloro-4-fluorophenyl)amino)-3-cyano-7-ethoxyquinolin-6-yl)-2-(1,2-dithiolan-3-yl)acetamide;

N-(4-((3-chloro-4-((3-fluorobenzyl)oxy)phenyl)amino)-3-cyano-7-ethoxyquinolin-6-yl)-2-(1,2-dithiolan-3-yl)acetamide;

N-(4-((3-chloro-4-fluorophenyl)amino)-3-cyano-7-ethoxyquinolin-6-yl)-3-(1,2-dithiolan-3-yl)propanamide;

N-(4-(3-chloro-4-fluorophenylamino)-3-cyano-7-ethoxyquinolin-6-yl)-5-(1,2-dithiolan-3-yl)pentanamide;

N-(4-(3-chloro-4-((3-fluorobenzyloxy)phenylamino)-3-cyano-7-ethoxyquinolin-6-yl)-5-(1,2-dithiolan-3-yl)pentanamide;

N-(4-((3-chloro-4-fluorophenyl)amino)-3-cyano-7-ethoxyquinolin-6-yl)-1,2-dithiolane-4-carboxamide 1-oxide;

N-(4-((3-chloro-4-fluorophenyl)amino)-3-cyano-7-ethoxyquinolin-6-yl)-1,2-dithiolane-4-carboxamide 1,2-dioxide;

N-(4-((3-chloro-4-fluorophenyl)amino)-3-cyano-7-ethoxyquinolin-6-yl)-1,2-dithiolane-4-carboxamide 1,1-dioxide;

N-(4-((3-chloro-4-fluorophenyl)amino)-3-cyano-7-ethoxyquinolin-6-yl)-1,2-dithiolane-4-carboxamide 1,1,2-trioxide;

N-(4-((3-chloro-4-fluorophenyl)amino)-3-cyano-7-ethoxyquinolin-6-yl)-1,2-dithiolane-4-carboxamide 1,1,2,2-tetroxide;

N-(4-((3-chloro-4-fluorophenyl)amino)-3-cyano-7-ethoxyquinolin-6-yl)-2-(1-oxido-1,2-dithiolan-3-yl)acetamide;

N-(4-((3-chloro-4-fluorophenyl)amino)-3-cyano-7-ethoxyquinolin-6-yl)-2-(2-oxido-1,2-dithiolan-3-yl)acetamide;

N-(4-((3-chloro-4-fluorophenyl)amino)-3-cyano-7-ethoxyquinolin-6-yl)-2-(1,1-dioxido-1,2-dithiolan-3-yl)acetamide;

N-(4-((3-chloro-4-fluorophenyl)amino)-3-cyano-7-ethoxyquinolin-6-yl)-2-(1,2-dioxido-1,2-dithiolan-3-yl)acetamide;

N-(4-((3-chloro-4-fluorophenyl)amino)-3-cyano-7-ethoxyquinolin-6-yl)-2-(2,2-dioxido-1,2-dithiolan-3-yl)acetamide;

N-(4-((3-chloro-4-fluorophenyl)amino)-3-cyano-7-ethoxyquinolin-6-yl)-2-(1,1,2-trioxido-1,2-dithiolan-3-yl)acetamide;

N-(4-((3-chloro-4-fluorophenyl)amino)-3-cyano-7-ethoxyquinolin-6-yl)-2-(1,2,2-trioxido-1,2-dithiolan-3-yl)acetamide;

N-(4-((3-chloro-4-fluorophenyl)amino)-3-cyano-7-ethoxyquinolin-6-yl)-2-(1,1,2,2-tetroxido-1,2-dithiolan-3-yl)acetamide;

N-(4-((3-chloro-4-fluorophenyl)amino)-3-cyano-7-ethoxyquinolin-6-yl)-4-(1,2-dithiolan-3-yl)butanamide;

N-(4-((3-chloro-4-fluorophenyl)amino)-3-cyano-7-ethoxyquinolin-6-yl)-5-(1,2-dithiolan-3-yl)pentanamide;

N-(4-((3-chloro-4-fluorophenyl)amino)-3-cyano-7-ethoxyquinolin-6-yl)-1,2-dithiolane-4-sulfonamide;

N-(4-((3-chloro-4-fluorophenyl)amino)-3-cyano-7-ethoxyquinolin-6-yl)-1,2-dithiolane-4-sulfonamide 1-oxide;

N-(4-((3-chloro-4-fluorophenyl)amino)-3-cyano-7-ethoxyquinolin-6-yl)-1,2-dithiolane-4-sulfonamide 1,1-dioxide;

N-(4-((3-chloro-4-fluorophenyl)amino)-3-cyano-7-ethoxyquinolin-6-yl)-1,2-dithiolane-3-sulfonamide;

N-(4-((3-chloro-4-fluorophenyl)amino)-3-cyano-7-ethoxyquinolin-6-yl)-1-(1,2-dithiolan-3-yl)methanesulfonamide;

N-(4-((3-chloro-4-fluorophenyl)amino)-3-cyano-7-ethoxyquinolin-6-yl)-1-(1-oxido-1,2-dithiolan-3-yl)methanesulfonamide;

N-(4-((3-chloro-4-fluorophenyl)amino)-3-cyano-7-ethoxyquinolin-6-yl)-1-(1,1-dioxido-1,2-dithiolan-3-yl)methanesulfonamide;

N-(4-((3-chloro-4-fluorophenyl)amino)-3-cyano-7-ethoxyquinolin-6-yl)-1-(2,2-dioxido-1,2-dithiolan-3-yl)methanesulfonamide;

N-(4-((3-chloro-4-fluorophenyl)amino)-3-cyano-7-ethoxyquinolin-6-yl)-1-(1,2-dithiolan-4-yl)methanesulfonamide;

N-(4-((3-chloro-4-fluorophenyl)amino)-3-cyano-7-ethoxyquinolin-6-yl)-2-(1,2-dithiolan-3-yl)ethane-1-sulfonamide;

N-(4-((3-chloro-4-fluorophenyl)amino)-3-cyano-7-ethoxyquinolin-6-yl)-2-(1,2-dithiolan-4-yl)ethane-1-sulfonamide;

N-(4-((3-chloro-4-fluorophenyl)amino)-3-cyano-7-ethoxyquinolin-6-yl)-3-(1,2-dithiolan-3-yl)propane-1-sulfonamide;

N-(4-((3-chloro-4-fluorophenyl)amino)-3-cyano-7-ethoxyquinolin-6-yl)-3-(1,2-dithiolan-4-yl)propane-1-sulfonamide;

N-(4-((3-chloro-4-fluorophenyl)amino)-3-cyano-7-ethoxyquinolin-6-yl)-4-(1,2-dithiolan-3-yl)butane-1-sulfonamide;

N-(4-((3-chloro-4-fluorophenyl)amino)-3-cyano-7-ethoxyquinolin-6-yl)-4-(1,2-dithiolan-4-yl)butane-1-sulfonamide;

N-(4-((3-chloro-4-fluorophenyl)amino)-7-ethoxyquinazolin-6-yl)-1,2-dithiolane-4-carboxamide;

N-(4-((3-chloro-4-fluorophenyl)amino)-7-ethoxyquinazolin-6-yl)-1,2-dithiolane-4-carboxamide 1-oxide;

N-(4-((3-chloro-4-fluorophenyl)amino)-7-ethoxyquinazolin-6-yl)-1,2-dithiolane-4-carboxamide 1,2-dioxide;

N-(4-((3-chloro-4-fluorophenyl)amino)-7-ethoxyquinazolin-6-yl)-1,2-dithiolane-4-carboxamide 1,1-dioxide;

N-(4-((3-chloro-4-fluorophenyl)amino)-7-ethoxyquinazolin-6-yl)-1,2-dithiolane-4-carboxamide 1,1,2-trioxide;

N-(4-((3-chloro-4-fluorophenyl)amino)-7-ethoxyquinazolin-6-yl)-1,2-dithiolane-4-carboxamide 1,1,2,2-tetroxide;

N-(4-((3-chloro-4-fluorophenyl)amino)-7-ethoxyquinazolin-6-yl)-2-(1,2-dithiolan-3-yl)acetamide;

N-(4-((3-chloro-4-fluorophenyl)amino)-7-ethoxyquinazolin-6-yl)-2-(1-oxido-1,2-dithiolan-3-yl)acetamide;

N-(4-((3-chloro-4-fluorophenyl)amino)-7-ethoxyquinazolin-6-yl)-2-(2-oxido-1,2-dithiolan-3-yl)acetamide;

N-(4-((3-chloro-4-fluorophenyl)amino)-7-ethoxyquinazolin-6-yl)-2-(1,1-dioxido-1,2-dithiolan-3-yl)acetamide;

N-(4-((3-chloro-4-fluorophenyl)amino)-7-ethoxyquinazolin-6-yl)-2-(2,2-dioxido-1,2-dithiolan-3-yl)acetamide;

N-(4-((3-chloro-4-fluorophenyl)amino)-7-ethoxyquinazolin-6-yl)-2-(1,2-dioxido-1,2-dithiolan-3-yl)acetamide;

N-(4-((3-chloro-4-fluorophenyl)amino)-7-ethoxyquinazolin-6-yl)-2-(1,1,2-trioxido-1,2-dithiolan-3-yl)acetamide;

N-(4-((3-chloro-4-fluorophenyl)amino)-7-ethoxyquinazolin-6-yl)-2-(1,2,2-trioxido-1,2-dithiolan-3-yl)acetamide;

N-(4-((3-chloro-4-fluorophenyl)amino)-7-ethoxyquinazolin-6-yl)-2-(1,1,2,2-tetroxido-1,2-dithiolan-3-yl)acetamide;

N-(4-((3-chloro-4-fluorophenyl)amino)-7-ethoxyquinazolin-6-yl)-3-(1,2-dithiolan-3-yl)propanamide;

N-(4-((3-chloro-4-fluorophenyl)amino)-7-ethoxyquinazolin-6-yl)-3-(1,2-dithiolan-4-yl)propanamide;

N-(4-((3-chloro-4-fluorophenyl)amino)-7-ethoxyquinazolin-6-yl)-4-(1,2-dithiolan-3-yl)butanamide;

N-(4-((3-chloro-4-fluorophenyl)amino)-7-ethoxyquinazolin-6-yl)-4-(1,2-dithiolan-4-yl)butanamide;

N-(4-((3-chloro-4-fluorophenyl)amino)-7-ethoxyquinazolin-6-yl)-5-(1,2-dithiolan-3-yl)pentanamide;

N-(4-((3-chloro-4-fluorophenyl)amino)-7-ethoxyquinazolin-6-yl)-5-(1,2-dithiolan-4-yl)pentanamide;

N-(4-((3-chloro-4-fluorophenyl)amino)-7-ethoxyquinazolin-6-yl)-1,2-dithiolane-4-sulfonamide;

N-(4-((3-chloro-4-fluorophenyl)amino)-7-ethoxyquinazolin-6-yl)-1,2-dithiolane-4-sulfonamide 1-oxide;

N-(4-((3-chloro-4-fluorophenyl)amino)-7-ethoxyquinazolin-6-yl)-1,2-dithiolane-4-sulfonamide 1,1-dioxide;

N-(4-((3-chloro-4-fluorophenyl)amino)-7-ethoxyquinazolin-6-yl)-1,2-dithiolane-3-sulfonamide;

N-(4-((3-chloro-4-fluorophenyl)amino)-7-ethoxyquinazolin-6-yl)-1-(1,2-dithiolan-3-yl)methanesulfonamide;

N-(4-((3-chloro-4-fluorophenyl)amino)-7-ethoxyquinazolin-6-yl)-1-(1-oxido-1,2-dithiolan-3-yl)methanesulfonamide;

N-(4-((3-chloro-4-fluorophenyl)amino)-7-ethoxyquinazolin-6-yl)-1-(2-oxido-1,2-dithiolan-3-yl)methanesulfonamide;

N-(4-((3-chloro-4-fluorophenyl)amino)-7-ethoxyquinazolin-6-yl)-1-(1,1-dioxido-1,2-dithiolan-3-yl)methanesulfonamide;

N-(4-((3-chloro-4-fluorophenyl)amino)-7-ethoxyquinazolin-6-yl)-1-(2,2-dioxido-1,2-dithiolan-3-yl)methanesulfonamide;

N-(4-((3-chloro-4-fluorophenyl)amino)-7-ethoxyquinazolin-6-yl)-1-(1,2-dithiolan-4-yl)methanesulfonamide;

N-(4-((3-chloro-4-fluorophenyl)amino)-7-ethoxyquinazolin-6-yl)-2-(1,2-dithiolan-3-yl)ethane-1-sulfonamide;

N-(4-((3-chloro-4-fluorophenyl)amino)-7-ethoxyquinazolin-6-yl)-2-(1,2-dithiolan-4-yl)ethane-1-sulfonamide;

N-(4-((3-chloro-4-fluorophenyl)amino)-7-ethoxyquinazolin-6-yl)-3-(1,2-dithiolan-3-yl)propane-1-sulfonamide;

N-(4-((3-chloro-4-fluorophenyl)amino)-7-ethoxyquinazolin-6-yl)-3-(1,2-dithiolan-4-yl)propane-1-sulfonamide;

N-(4-((3-chloro-4-fluorophenyl)amino)-7-ethoxyquinazolin-6-yl)-4-(1,2-dithiolan-3-yl)butane-1-sulfonamide;

N-(4-((3-chloro-4-fluorophenyl)amino)-7-ethoxyquinazolin-6-yl)-4-(1,2-dithiolan-4-yl)butane-1-sulfonamide;

N-(4-((3-chloro-4-((3-fluorobenzyl)oxy)phenyl)amino)-3-cyano-7-ethoxyquinolin-6-yl)-1,2-dithiolane-4-carboxamide 1-oxide;

N-(4-((3-chloro-4-((3-fluorobenzyl)oxy)phenyl)amino)-3-cyano-7-ethoxyquinolin-6-yl)-1,2-dithiolane-4-carboxamide 1,2-dioxide;

N-(4-((3-chloro-4-((3-fluorobenzyl)oxy)phenyl)amino)-3-cyano-7-ethoxyquinolin-6-yl)-1,2-dithiolane-4-carboxamide 1,1-dioxide;

N-(4-((3-chloro-4-((3-fluorobenzyl)oxy)phenyl)amino)-3-cyano-7-ethoxyquinolin-6-yl)-1,2-dithiolane-4-carboxamide 1,1,2-trioxide;

N-(4-((3-chloro-4-((3-fluorobenzyl)oxy)phenyl)amino)-3-cyano-7-ethoxyquinolin-6-yl)-1,2-dithiolane-4-carboxamide 1,1,2,2-tetraoxide;

N-(4-((3-chloro-4-((3-fluorobenzyl)oxy)phenyl)amino)-3-cyano-7-ethoxyquinolin-6-yl)-2-(1-oxido-1,2-dithiolan-3-yl)acetamide;

N-(4-((3-chloro-4-((3-fluorobenzyl)oxy)phenyl)amino)-3-cyano-7-ethoxyquinolin-6-yl)-2-(2-oxido-1,2-dithiolan-3-yl)acetamide;

N-(4-((3-chloro-4-((3-fluorobenzyl)oxy)phenyl)amino)-3-cyano-7-ethoxyquinolin-6-yl)-2-(1,1-dioxido-1,2-dithiolan-3-yl)acetamide;

N-(4-((3-chloro-4-((3-fluorobenzyl)oxy)phenyl)amino)-3-cyano-7-ethoxyquinolin-6-yl)-2-(1,2-dioxido-1,2-dithiolan-3-yl)acetamide;

N-(4-((3-chloro-4-((3-fluorobenzyl)oxy)phenyl)amino)-3-cyano-7-ethoxyquinolin-6-yl)-2-(2,2-dioxido-1,2-dithiolan-3-yl)acetamide;

N-(4-((3-chloro-4-((3-fluorobenzyl)oxy)phenyl)amino)-3-cyano-7-ethoxyquinolin-6-yl)-2-(1,1,2-trioxido-1,2-dithiolan-3-yl)acetamide;

N-(4-((3-chloro-4-((3-fluorobenzyl)oxy)phenyl)amino)-3-cyano-7-ethoxyquinolin-6-yl)-2-(1,2,2-trioxido-1,2-dithiolan-3-yl)acetamide;

N-(4-((3-chloro-4-((3-fluorobenzyl)oxy)phenyl)amino)-3-cyano-7-ethoxyquinolin-6-yl)-2-(1,1,2,2-tetraoxido-1,2-dithiolan-3-yl)acetamide;

N-(4-((3-chloro-4-((3-fluorobenzyl)oxy)phenyl)amino)-3-cyano-7-ethoxyquinolin-6-yl)-3-(1,2-dithiolan-3-yl)propanamide;

N-(4-((3-chloro-4-((3-fluorobenzyl)oxy)phenyl)amino)-3-cyano-7-ethoxyquinolin-6-yl)-3-(1,2-dithiolan-4-yl)propanamide;

N-(4-((3-chloro-4-((3-fluorobenzyl)oxy)phenyl)amino)-3-cyano-7-ethoxyquinolin-6-yl)-4-(1,2-dithiolan-3-yl)butanamide;

N-(4-((3-chloro-4-((3-fluorobenzyl)oxy)phenyl)amino)-3-cyano-7-ethoxyquinolin-6-yl)-4-(1,2-dithiolan-4-yl)butanamide;

N-(4-((3-chloro-4-((3-fluorobenzyl)oxy)phenyl)amino)-3-cyano-7-ethoxyquinolin-6-yl)-5-(1-oxido-1,2-dithiolan-3-yl)pentanamide;

N-(4-((3-chloro-4-((3-fluorobenzyl)oxy)phenyl)amino)-3-cyano-7-ethoxyquinolin-6-yl)-5-(2-oxido-1,2-dithiolan-3-yl)pentanamide;

N-(4-((3-chloro-4-((3-fluorobenzyl)oxy)phenyl)amino)-3-cyano-7-ethoxyquinolin-6-yl)-5-(1,2-dioxido-1,2-dithiolan-3-yl)pentanamide;

N-(4-((3-chloro-4-((3-fluorobenzyl)oxy)phenyl)amino)-3-cyano-7-ethoxyquinolin-6-yl)-5-(1,1-dioxido-1,2-dithiolan-3-yl)pentanamide;

N-(4-((3-chloro-4-((3-fluorobenzyl)oxy)phenyl)amino)-3-cyano-7-ethoxyquinolin-6-yl)-5-(2,2-dioxido-1,2-dithiolan-3-yl)pentanamide;

N-(4-((3-chloro-4-((3-fluorobenzyl)oxy)phenyl)amino)-3-cyano-7-ethoxyquinolin-6-yl)-5-(1,1,2-trioxido-1,2-dithiolan-3-yl)pentanamide;

N-(4-((3-chloro-4-((3-fluorobenzyl)oxy)phenyl)amino)-3-cyano-7-ethoxyquinolin-6-yl)-5-(1,2,2-trioxido-1,2-dithiolan-3-yl)pentanamide;

N-(4-((3-chloro-4-((3-fluorobenzyl)oxy)phenyl)amino)-3-cyano-7-ethoxyquinolin-6-yl)-5-(1,1,2,2-tetraoxido-1,2-dithiolan-3-yl)pentanamide;

N-(4-((3-chloro-4-((3-fluorobenzyl)oxy)phenyl)amino)-3-cyano-7-ethoxyquinolin-6-yl)-1,2-dithiolane-4-sulfonamide;

N-(4-((3-chloro-4-((3-fluorobenzyl)oxy)phenyl)amino)-3-cyano-7-ethoxyquinolin-6-yl)-1,2-dithiolane-3-sulfonamide;

N-(4-((3-chloro-4-((3-fluorobenzyl)oxy)phenyl)amino)-3-cyano-7-ethoxyquinolin-6-yl)-1-(1,2-dithiolan-3-yl)methanesulfonamide;

N-(4-((3-chloro-4-((3-fluorobenzyl)oxy)phenyl)amino)-3-cyano-7-ethoxyquinolin-6-yl)-1-(1-oxido-1,2-dithiolan-3-yl)methanesulfonamide;

N-(4-((3-chloro-4-((3-fluorobenzyl)oxy)phenyl)amino)-3-cyano-7-ethoxyquinolin-6-yl)-1-(2-oxido-1,2-dithiolan-3-yl)methanesulfonamide;

N-(4-((3-chloro-4-((3-fluorobenzyl)oxy)phenyl)amino)-3-cyano-7-ethoxyquinolin-6-yl)-1-(1,1-dioxido-1,2-dithiolan-3-yl)methanesulfonamide;

N-(4-((3-chloro-4-((3-fluorobenzyl)oxy)phenyl)amino)-3-cyano-7-ethoxyquinolin-6-yl)-1-(2,2-dioxido-1,2-dithiolan-3-yl)methanesulfonamide;

N-(4-((3-chloro-4-((3-fluorobenzyl)oxy)phenyl)amino)-3-cyano-7-ethoxyquinolin-6-yl)-2-(1,2-dithiolan-3-yl)ethanesulfonamide;

N-(4-((3-chloro-4-((3-fluorobenzyl)oxy)phenyl)amino)-3-cyano-7-ethoxyquinolin-6-yl)-2-(1,2-dithiolan-4-yl)ethanesulfonamide;

N-(4-((3-chloro-4-((3-fluorobenzyl)oxy)phenyl)amino)-3-cyano-7-ethoxyquinolin-6-yl)-3-(1,2-dithiolan-3-yl)propane-1-sulfonamide;

N-(4-((3-chloro-4-((3-fluorobenzyl)oxy)phenyl)amino)-3-cyano-7-ethoxyquinolin-6-yl)-3-(1,2-dithiolan-4-yl)propane-1-sulfonamide;

N-(4-((3-chloro-4-((3-fluorobenzyl)oxy)phenyl)amino)-3-cyano-7-ethoxyquinolin-6-yl)-4-(1,2-dithiolan-3-yl)butane-1-sulfonamide;

N-(4-((3-chloro-4-((3-fluorobenzyl)oxy)phenyl)amino)-3-cyano-7-ethoxyquinolin-6-yl)-4-(1,2-dithiolan-4-yl)butane-1-sulfonamide;

N-(4-((3-chloro-4-((3-fluorobenzyl)oxy)phenyl)amino)-7-ethoxyquinazolin-6-yl)-1,2-dithiolane-4-carboxamide;

N-(4-((3-chloro-4-((3-fluorobenzyl)oxy)phenyl)amino)-7-ethoxyquinazolin-6-yl)-1,2-dithiolane-4-carboxamide 1-oxide;

N-(4-((3-chloro-4-((3-fluorobenzyl)oxy)phenyl)amino)-7-ethoxyquinazolin-6-yl)-1,2-dithiolane-4-carboxamide 1,2-dioxide;

N-(4-((3-chloro-4-((3-fluorobenzyl)oxy)phenyl)amino)-7-ethoxyquinazolin-6-yl)-1,2-dithiolane-4-carboxamide 1,1-dioxide;

N-(4-((3-chloro-4-((3-fluorobenzyl)oxy)phenyl)amino)-7-ethoxyquinazolin-6-yl)-1,2-dithiolane-4-carboxamide 1,1,2-trioxide;

N-(4-((3-chloro-4-((3-fluorobenzyl)oxy)phenyl)amino)-7-ethoxyquinazolin-6-yl)-1,2-dithiolane-4-carboxamide 1,1,2,2-tetraoxide;

N-(4-((3-chloro-4-((3-fluorobenzyl)oxy)phenyl)amino)-7-ethoxyquinazolin-6-yl)-2-(1,2-dithiolan-3-yl)acetamide;

N-(4-((3-chloro-4-((3-fluorobenzyl)oxy)phenyl)amino)-7-ethoxyquinazolin-6-yl)-2-(1-oxido-1,2-dithiolan-3-yl)acetamide;

N-(4-((3-chloro-4-((3-fluorobenzyl)oxy)phenyl)amino)-7-ethoxyquinazolin-6-yl)-2-(2-oxido-1,2-dithiolan-3-yl)acetamide;

N-(4-((3-chloro-4-((3-fluorobenzyl)oxy)phenyl)amino)-7-ethoxyquinazolin-6-yl)-2-(1,1-dioxido-1,2-dithiolan-3-yl)acetamide;

N-(4-((3-chloro-4-((3-fluorobenzyl)oxy)phenyl)amino)-7-ethoxyquinazolin-6-yl)-2-(1,2-dioxido-1,2-dithiolan-3-yl)acetamide;

N-(4-((3-chloro-4-((3-fluorobenzyl)oxy)phenyl)amino)-7-ethoxyquinazolin-6-yl)-2-(2,2-dioxido-1,2-dithiolan-3-yl)acetamide;

N-(4-((3-chloro-4-((3-fluorobenzyl)oxy)phenyl)amino)-7-ethoxyquinazolin-6-yl)-2-(1,1,2-trioxido-1,2-dithiolan-3-yl)acetamide;

N-(4-((3-chloro-4-((3-fluorobenzyl)oxy)phenyl)amino)-7-ethoxyquinazolin-6-yl)-2-(1,2,2-trioxido-1,2-dithiolan-3-yl)acetamide;

N-(4-((3-chloro-4-((3-fluorobenzyl)oxy)phenyl)amino)-7-ethoxyquinazolin-6-yl)-2-(1,1,2,2-tetroxido-1,2-dithiolan-3-yl)acetamide;

N-(4-((3-chloro-4-((3-fluorobenzyl)oxy)phenyl)amino)-7-ethoxyquinazolin-6-yl)-3-(1,2-dithiolan-3-yl)propanamide;

N-(4-((3-chloro-4-((3-fluorobenzyl)oxy)phenyl)amino)-7-ethoxyquinazolin-6-yl)-3-(1,2-dithiolan-4-yl)propanamide;

N-(4-((3-chloro-4-((3-fluorobenzyl)oxy)phenyl)amino)-7-ethoxyquinazolin-6-yl)-4-(1,2-dithiolan-3-yl)butanamide;

N-(4-((3-chloro-4-((3-fluorobenzyl)oxy)phenyl)amino)-7-ethoxyquinazolin-6-yl)-4-(1,2-dithiolan-4-yl)butanamide;

N-(4-((3-chloro-4-((3-fluorobenzyl)oxy)phenyl)amino)-7-ethoxyquinazolin-6-yl)-5-(1,2-dithiolan-3-yl)pentanamide;

N-(4-((3-chloro-4-((3-fluorobenzyl)oxy)phenyl)amino)-7-ethoxyquinazolin-6-yl)-2-(1,2-dithiolan-4-yl)pentanamide;

N-(4-((3-chloro-4-((3-fluorobenzyl)oxy)phenyl)amino)-7-ethoxyquinazolin-6-yl)-1,2-dithiolane-4-sulfonamide;

N-(4-((3-chloro-4-((3-fluorobenzyl)oxy)phenyl)amino)-7-ethoxyquinazolin-6-yl)-1,2-dithiolane-4-sulfonamide 1-oxide;

N-(4-((3-chloro-4-((3-fluorobenzyl)oxy)phenyl)amino)-7-ethoxyquinazolin-6-yl)-1,2-dithiolane-4-sulfonamide 1,1-dioxide;

N-(4-((3-chloro-4-((3-fluorobenzyl)oxy)phenyl)amino)-7-ethoxyquinazolin-6-yl)-1,2-dithiolane-3-sulfonamide;

N-(4-((3-chloro-4-((3-fluorobenzyl)oxy)phenyl)amino)-7-ethoxyquinazolin-6-yl)-1-(1,2-dithiolan-3-yl)methanesulfonamide;

N-(4-((3-chloro-4-((3-fluorobenzyl)oxy)phenyl)amino)-7-ethoxyquinazolin-6-yl)-1-(1-oxido-1,2-dithiolan-3-yl)methanesulfonamide;

N-(4-((3-chloro-4-((3-fluorobenzyl)oxy)phenyl)amino)-7-ethoxyquinazolin-6-yl)-1-(2-oxido-1,2-dithiolan-3-yl)methanesulfonamide;

N-(4-((3-chloro-4-((3-fluorobenzyl)oxy)phenyl)amino)-7-ethoxyquinazolin-6-yl)-1-(1,1-dioxo-1,2-dithiolan-3-yl)methanesulfonamide N-(4-((3-chloro-4-((3-fluorobenzyl)oxy)phenyl)amino)-7-ethoxyquinazolin-6-yl)-1-(2,2-dioxo-1,2-dithiolan-3-yl)methanesulfonamide;

N-(4-((3-chloro-4-((3-fluorobenzyl)oxy)phenyl)amino)-7-ethoxyquinazolin-6-yl)-1-(1,2-dithiolan-4-yl)methanesulfonamide;

N-(4-((3-chloro-4-((3-fluorobenzyl)oxy)phenyl)amino)-7-ethoxyquinazolin-6-yl)-2-(1,2-dithiolan-3-yl)ethane-1-sulfonamide;

N-(4-((3-chloro-4-((3-fluorobenzyl)oxy)phenyl)amino)-7-ethoxyquinazolin-6-yl)-2-(1,2-dithiolan-4-yl)ethane-1-sulfonamide;

N-(4-((3-chloro-4-((3-fluorobenzyl)oxy)phenyl)amino)-7-ethoxyquinazolin-6-yl)-3-(1,2-dithiolan-3-yl)propane-1-sulfonamide;

N-(4-((3-chloro-4-((3-fluorobenzyl)oxy)phenyl)amino)-7-ethoxyquinazolin-6-yl)-3-(1,2-dithiolan-4-yl)propane-1-sulfonamide;

N-(4-((3-chloro-4-((3-fluorobenzyl)oxy)phenyl)amino)-7-ethoxyquinazolin-6-yl)-4-(1,2-dithiolan-3-yl)butane-1-sulfonamide;

N-(4-((3-chloro-4-((3-fluorobenzyl)oxy)phenyl)amino)-7-ethoxyquinazolin-6-yl)-4-(1,2-dithiolan-4-yl)butane-1-sulfonamide;

N-(4-((3-chloro-4-fluorophenyl)amino)-3-cyano-7-(2,3-dihydroxypropoxy)quinolin-6-yl)-1,2-dithiolane-3-carboxamide;

N-(4-((3-chloro-4-fluorophenyl)amino)-3-cyano-7-(2,3-dihydroxypropoxy)quinolin-6-yl)-1,2-dithiolane-3-carboxamide -1-oxide;

N-(4-((3-chloro-4-fluorophenyl)amino)-3-cyano-7-(2,3-dihydroxypropoxy)quinolin-6-yl)-1,2-dithiolane-3-carboxamide -1,1-dioxide;

N-(4-((3-chloro-4-fluorophenyl)amino)-3-cyano-7-(2,3-dihydroxypropoxy)quinolin-6-yl)-1,2-dithiolane-3-carboxamide -2-oxide;

N-(4-((3-chloro-4-fluorophenyl)amino)-3-cyano-7-(2,3-dihydroxypropoxy)quinolin-6-yl)-1,2-dithiolane-3-carboxamide -2,2-dioxide;

N-(4-((3-chloro-4-fluorophenyl)amino)-3-cyano-7-(2,3-dihydroxypropoxy)quinolin-6-yl)-2-(1,2-dithiolan-3-yl)acetamide;

N-(4-((3-chloro-4-fluorophenyl)amino)-3-cyano-7-(2,3-dihydroxypropoxy)quinolin-6-yl)-2-(1-oxido-1,2-dithiolan-3-yl)acetamide;

N-(4-((3-chloro-4-fluorophenyl)amino)-3-cyano-7-(2,3-dihydroxypropoxy)quinolin-6-yl)-2-(2-oxido-1,2-dithiolan-3-yl)acetamide;

N-(4-((3-chloro-4-fluorophenyl)amino)-3-cyano-7-(2,3-dihydroxypropoxy)quinolin-6-yl)-2-(1,1-dioxido-1,2-dithiolan-3-yl)acetamide;

N-(4-((3-chloro-4-fluorophenyl)amino)-3-cyano-7-(2,3-dihydroxypropoxy)quinolin-6-yl)-2-(2,2-dioxido-1,2-dithiolan-3-yl)acetamide;

N-(4-((3-chloro-4-fluorophenyl)amino)-3-cyano-7-(2,3-dihydroxypropoxy)quinolin-6-yl)-3-(1,2-dithiolan-3-yl)propanamide;

N-(4-((3-chloro-4-fluorophenyl)amino)-3-cyano-7-(2,3-dihydroxypropoxy)quinolin-6-yl)-3-(1-oxido-1,2-dithiolan-3-yl)propanamide;

N-(4-((3-chloro-4-fluorophenyl)amino)-3-cyano-7-(2,3-dihydroxypropoxy)quinolin-6-yl)-3-(2-oxido-1,2-dithiolan-3-yl)propanamide;

N-(4-((3-chloro-4-fluorophenyl)amino)-3-cyano-7-(2,3-dihydroxypropoxy)quinolin-6-yl)-3-(1,1-dioxido-1,2-dithiolan-3-yl)propanamide;

N-(4-((3-chloro-4-fluorophenyl)amino)-3-cyano-7-(2,3-dihydroxypropoxy)quinolin-6-yl)-3-(2,2-dioxido-1,2-dithiolan-3-yl)propanamide;

N-(4-((3-chloro-4-fluorophenyl)amino)-7-(2,3-dihydroxypropoxy)quinazolin-6-yl)-1,2-dithiolane-3-carboxamide;

N-(4-((3-chloro-4-fluorophenyl)amino)-7-(2,3-dihydroxypropoxy)quinazolin-6-yl)-1,2-dithiolane-3-carboxamide -1-oxide;
N-(4-((3-chloro-4-fluorophenyl)amino)-7-(2,3-dihydroxypropoxy)quinazolin-6-yl)-1,2-dithiolane-3-carboxamide -1,1-dioxide;
N-(4-((3-chloro-4-fluorophenyl)amino)-7-(2,3-dihydroxypropoxy)quinazolin-6-yl)-1,2-dithiolane-3-carboxamide -2-oxide;
N-(4-((3-chloro-4-fluorophenyl)amino)-7-(2,3-dihydroxypropoxy)quinazolin-6-yl)-1,2-dithiolane-3-carboxamide -2,2-dioxide;
N-(4-((3-chloro-4-fluorophenyl)amino)-7-(2,3-dihydroxypropoxy)quinazolin-6-yl)-2-(1,2-dithiolan-3-yl)acetamide;
N-(4-((3-chloro-4-fluorophenyl)amino)-7-(2,3-dihydroxypropoxy)quinazolin-6-yl)-2-(1-oxido-1,2-dithiolan-3-yl)acetamide;
N-(4-((3-chloro-4-fluorophenyl)amino)-7-(2,3-dihydroxypropoxy)quinazolin-6-yl)-2-(2-oxido-1,2-dithiolan-3-yl)acetamide;
N-(4-((3-chloro-4-fluorophenyl)amino)-7-(2,3-dihydroxypropoxy)quinazolin-6-yl)-2-(1,1-dioxido-1,2-dithiolan-3-yl)acetamide;
N-(4-((3-chloro-4-fluorophenyl)amino)-7-(2,3-dihydroxypropoxy)quinazolin-6-yl)-2-(2,2-dioxido-1,2-dithiolan-3-yl)acetamide;
N-(4-((3-chloro-4-fluorophenyl)amino)-7-(2,3-dihydroxypropoxy)quinazolin-6-yl)-3-(1,2-dithiolan-3-yl)propanamide;
N-(4-((3-chloro-4-fluorophenyl)amino)-7-(2,3-dihydroxypropoxy)quinazolin-6-yl)-3-(1-oxido-1,2-dithiolan-3-yl)propanamide;
N-(4-((3-chloro-4-fluorophenyl)amino)-7-(2,3-dihydroxypropoxy)quinazolin-6-yl)-3-(2-oxido-1,2-dithiolan-3-yl)propanamide;
N-(4-((3-chloro-4-fluorophenyl)amino)-7-(2,3-dihydroxypropoxy)quinazolin-6-yl)-3-(1,1-dioxido-1,2-dithiolan-3-yl)propanamide;
N-(4-((3-chloro-4-fluorophenyl)amino)-7-(2,3-dihydroxypropoxy)quinazolin-6-yl)-3-(2,2-dioxido-1,2-dithiolan-3-yl)propanamide;
N-(4-((3-chloro-4-((3-fluorobenzyl)oxy)phenyl)amino)-3-cyano-7-(2,3-dihydroxypropoxy)quinolin-6-yl)-1,2-dithiolane-3-carboxamide;
N-(4-((3-chloro-4-((3-fluorobenzyl)oxy)phenyl)amino)-3-cyano-7-(2,3-dihydroxypropoxy)quinolin-6-yl)-1,2-dithiolane-3-carboxamide -1-oxide;
N-(4-((3-chloro-4-((3-fluorobenzyl)oxy)phenyl)amino)-3-cyano-7-(2,3-dihydroxypropoxy)quinolin-6-yl)-1,2-dithiolane-3-carboxamide -1,1-dioxide;
N-(4-((3-chloro-4-((3-fluorobenzyl)oxy)phenyl)amino)-3-cyano-7-(2,3-dihydroxypropoxy)quinolin-6-yl)-1,2-dithiolane-3-carboxamide -2-oxide;
N-(4-((3-chloro-4-((3-fluorobenzyl)oxy)phenyl)amino)-3-cyano-7-(2,3-dihydroxypropoxy)quinolin-6-yl)-1,2-dithiolane-3-carboxamide -2,2-dioxide;
N-(4-((3-chloro-4-((3-fluorobenzyl)oxy)phenyl)amino)-3-cyano-7-(2,3-dihydroxypropoxy)quinolin-6-yl)-2-(1,2-dithiolan-3-yl)acetamide;
N-(4-((3-chloro-4-((3-fluorobenzyl)oxy)phenyl)amino)-3-cyano-7-(2,3-dihydroxypropoxy)quinolin-6-yl)-2-(1-oxido-1,2-dithiolan-3-yl)acetamide;
N-(4-((3-chloro-4-((3-fluorobenzyl)oxy)phenyl)amino)-3-cyano-7-(2,3-dihydroxypropoxy)quinolin-6-yl)-2-(2-oxido-1,2-dithiolan-3-yl)acetamide;
N-(4-((3-chloro-4-((3-fluorobenzyl)oxy)phenyl)amino)-3-cyano-7-(2,3-dihydroxypropoxy)quinolin-6-yl)-2-(1,1-dioxido-1,2-dithiolan-3-yl)acetamide;
N-(4-((3-chloro-4-((3-fluorobenzyl)oxy)phenyl)amino)-3-cyano-7-(2,3-dihydroxypropoxy)quinolin-6-yl)-2-(2,2-dioxido-1,2-dithiolan-3-yl)acetamide;
N-(4-((3-chloro-4-((3-fluorobenzyl)oxy)phenyl)amino)-3-cyano-7-(2,3-dihydroxypropoxy)quinolin-6-yl)-3-(1,2-dithiolan-3-yl)propanamide;
N-(4-((3-chloro-4-((3-fluorobenzyl)oxy)phenyl)amino)-3-cyano-7-(2,3-dihydroxypropoxy)quinolin-6-yl)-3-(1-oxido-1,2-dithiolan-3-yl)propanamide;
N-(4-((3-chloro-4-((3-fluorobenzyl)oxy)phenyl)amino)-3-cyano-7-(2,3-dihydroxypropoxy)quinolin-6-yl)-3-(2-oxido-1,2-dithiolan-3-yl)propanamide;
N-(4-((3-chloro-4-((3-fluorobenzyl)oxy)phenyl)amino)-3-cyano-7-(2,3-dihydroxypropoxy)quinolin-6-yl)-3-(1,1-dioxido-1,2-dithiolan-3-yl)propanamide;
N-(4-((3-chloro-4-((3-fluorobenzyl)oxy)phenyl)amino)-3-cyano-7-(2,3-dihydroxypropoxy)quinolin-6-yl)-3-(2,2-dioxido-1,2-dithiolan-3-yl)propanamide;
N-(4-((3-chloro-4-((3-fluorobenzyl)oxy)phenyl)amino)-7-(2,3-dihydroxypropoxy)quinazolin-6-yl)-1,2-dithiolane-3-carboxamide;
N-(4-((3-chloro-4-((3-fluorobenzyl)oxy)phenyl)amino)-7-(2,3-dihydroxypropoxy)quinazolin-6-yl)-1,2-dithiolane-3-carboxamide -1-oxide;
N-(4-((3-chloro-4-((3-fluorobenzyl)oxy)phenyl)amino)-7-(2,3-dihydroxypropoxy)quinazolin-6-yl)-1,2-dithiolane-3-carboxamide -1,1-dioxide;
N-(4-((3-chloro-4-((3-fluorobenzyl)oxy)phenyl)amino)-7-(2,3-dihydroxypropoxy)quinazolin-6-yl)-1,2-dithiolane-3-carboxamide -2-oxide;
N-(4-((3-chloro-4-((3-fluorobenzyl)oxy)phenyl)amino)-7-(2,3-dihydroxypropoxy)quinazolin-6-yl)-1,2-dithiolane-3-carboxamide -2,2-dioxide;
N-(4-((3-chloro-4-((3-fluorobenzyl)oxy)phenyl)amino)-7-(2,3-dihydroxypropoxy)quinazolin-6-yl)-2-(1,2-dithiolan-3-yl)acetamide;
N-(4-((3-chloro-4-((3-fluorobenzyl)oxy)phenyl)amino)-7-(2,3-dihydroxypropoxy)quinazolin-6-yl)-2-(1-oxido-1,2-dithiolan-3-yl)acetamide;
N-(4-((3-chloro-4-((3-fluorobenzyl)oxy)phenyl)amino)-7-(2,3-dihydroxypropoxy)quinazolin-6-yl)-2-(2-oxido-1,2-dithiolan-3-yl)acetamide;
N-(4-((3-chloro-4-((3-fluorobenzyl)oxy)phenyl)amino)-7-(2,3-dihydroxypropoxy)quinazolin-6-yl)-2-(1,1-dioxido-1,2-dithiolan-3-yl)acetamide;
N-(4-((3-chloro-4-((3-fluorobenzyl)oxy)phenyl)amino)-7-(2,3-dihydroxypropoxy)quinazolin-6-yl)-2-(2,2-dioxido-1,2-dithiolan-3-yl)acetamide;
N-(4-((3-chloro-4-((3-fluorobenzyl)oxy)phenyl)amino)-7-(2,3-dihydroxypropoxy)quinazolin-6-yl)-3-(1,2-dithiolan-3-yl)propanamide;
N-(4-((3-chloro-4-((3-fluorobenzyl)oxy)phenyl)amino)-7-(2,3-dihydroxypropoxy)quinazolin-6-yl)-3-(1-oxido-1,2-dithiolan-3-yl)propanamide;
N-(4-((3-chloro-4-((3-fluorobenzyl)oxy)phenyl)amino)-7-(2,3-dihydroxypropoxy)quinazolin-6-yl)-3-(2-oxido-1,2-dithiolan-3-yl)propanamide;
N-(4-((3-chloro-4-((3-fluorobenzyl)oxy)phenyl)amino)-7-(2,3-dihydroxypropoxy)quinazolin-6-yl)-3-(1,1-dioxido-1,2-dithiolan-3-yl)propanamide;
N-(4-((3-chloro-4-((3-fluorobenzyl)oxy)phenyl)amino)-7-(2,3-dihydroxypropoxy)quinazolin-6-yl)-3-(2,2-dioxido-1,2-dithiolan-3-yl)propanamide;
or a pharmaceutically acceptable form thereof.

11. A composition comprising an effective mutant EGFR modulating amount of at least one compound according to claim 1.

12. The composition according to claim 11, further comprising at least one excipient.

* * * * *